United States Patent [19]

Barnette et al.

[11] Patent Number: 5,500,438

[45] Date of Patent: Mar. 19, 1996

[54] ARTHROPODICIDAL ANILIDES

[75] Inventors: William E. Barnette, West Chester, Pa.; Charles R. Harrison, Newark, Del.; George P. Lahm, Wilmington, Del.; David W. Piotrowski, Bear, Del.; Keith D. Wing, Wilmington, Del.

[73] Assignee: E. I. Du Pont de Nemours and Company, Wilmington, Del.

[21] Appl. No.: 146,210

[22] PCT Filed: May 15, 1992

[86] PCT No.: PCT/US92/03880

§ 371 Date: Nov. 22, 1993

§ 102(e) Date: Nov. 22, 1993

[87] PCT Pub. No.: WO92/20682

PCT Pub. Date: Nov. 26, 1992

Related U.S. Application Data

[63] Continuation-in-part of Ser. No. 812,200, Dec. 20, 1991, abandoned, which is a continuation-in-part of Ser. No. 744,759, Aug. 14, 1991, abandoned, which is a continuation-in-part of Ser. No. 705,428, May 24, 1991, abandoned.

[51] Int. Cl.$^6$ ............... A01N 43/90; C07D 491/048
[52] U.S. Cl. ..................... 514/403; 548/359 S
[58] Field of Search ........... 348/359.5; 514/403

[56] References Cited

U.S. PATENT DOCUMENTS 4,971,821  11/1990  McIntyre.

FOREIGN PATENT DOCUMENTS

| | | |
|---|---|---|
| 0286346 | 10/1988 | European Pat. Off.. |
| 0377304 | 7/1990 | European Pat. Off.. |
| 0386892 | 9/1990 | European Pat. Off.. |
| WO90/07495 | 7/1990 | WIPO. |
| WO91/08207 | 6/1991 | WIPO. |

OTHER PUBLICATIONS

Tamura, Y. et al., *Synthesis*, (1977), pp. 1–17.
Vedejs, E., *J. Am. Chem. Soc.*, (1974), 96, pp. 5944, 5946.
Masui, M. et al, *Tetrahedron Lett.*, (1988), 29(23), pp. 2835–2838.
Davis, F. A. et al, *J. Org. Chem.*, (1986), 51, pp. 2402–2404.
Russell, G. et al, *J. Am. Chem. Soc.* (1985), 107, pp. 4175–4182.
Kende, A. S., Editor, *Org. Synth.*, (1985), 64, pp. 118–127.
Andreae, S. et al., *Synthesis*, (1991), pp. 327–341.
Caglioti, L. et al, *J. Org. Chem.*, (1973), 38, pp. 920–923.
House, H. O., *Modern Synthetic Reactions*, 1972, pp. 1–44.
Bedford, C. D. et al, *J. Med. Chem.*, (1986), 29, pp. 2174–2183.
House, H. O., *Modern Synthetic Reactions*, 1972, pp. 629–733.

*Primary Examiner*—Robert W. Ramsuer

[57] ABSTRACT

Substituted anilides of the formula

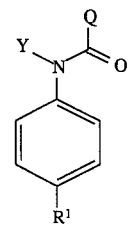

wherein
Q is one of

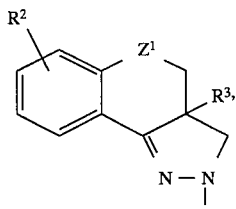

Q-1

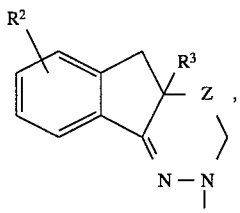

Q-2 and or

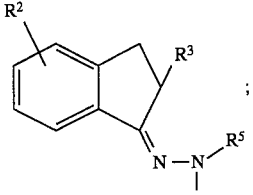

Q-3 and
$R^1$ to $R^5$, Y, Z and $Z^1$ are as defined in the text, arthropodicidal compositions containing such compounds; and a method for controlling arthropods by use of such compounds.

7 Claims, No Drawings

ARTHROPODICIDAL ANILIDES

RELATIONSHIP TO OTHER APPLICATIONS

This application is a continuation-in-part of U.S. patent application Ser. No. 07/812,200, filed Dec. 20, 1991, which in turn is a continuation-in-part of U.S. patent application Ser. No. 07/744,759, filed Aug. 14, 1991, which in turn is a continuation-in-part of U.S. patent application Ser. No. 07/705,428, filed May 24, 1991, all of which are now abandoned.

The substituted anilides of this invention are unknown in the art, with WO 90/07495 being perhaps the most relevant publication in this regard. The anilides of this invention include all geometric and stereoisomers, arthropodicidally suitable salts thereof, arthropodicidal compositions containing them and their use to control arthropods in agronomic and nonagronomic environments. The term "compounds" includes all such isomers and salts thereof. The compounds are:

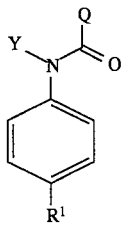

I wherein

Q is selected from the group

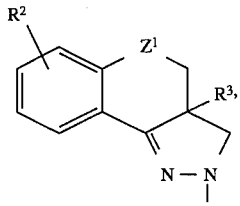

Q-1

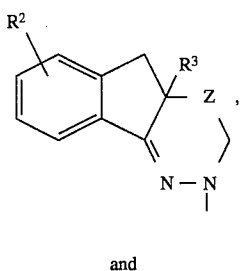

Q-2 and

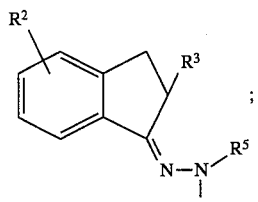

Q-3

$R^1$ is selected from the group Cl, Br, $CF_3$, $OCF_3$, $OCF_2H$ and $OSO_2CF_3$; $R^1$ being $OCF_3$ when Q is Q-3 and Y is $CH_3$, $CH_2CH_2CH_2CH_3$ or $CH_2Ph$;

$R^2$ is selected from the group H, F, Cl, Br, $CF_3$, $OCF_3$, $OCF_2H$ and $OCH_2CF_3$;

Y is selected from the group $C_1$–$C_6$ alkyl, $C_2$–$C_6$ alkenyl, $C_2$–$C_6$ alkynyl, $C_1$–$C_3$ alkylsulfonyl, $C_3$–$C_6$ cycloalkyl, $C_3$–$C_6$ cycloalkylalkyl, $NR^6R^7$, $N=CR^8R^9$, $OR^6$, $COR^4$, $CO_2R^4$ and $C_1$–$C_6$ alkyl substituted by a group selected from halogen, $C_1$–$C_3$ alkoxy, CN, $NO_2$, $S(O)_nR^4$, $COR^8$, $CO_2R^8$ and phenyl, the phenyl optionally substituted by a group selected from halogen, CN, $C_1$–$C_2$ alkyl, $C_1$–$C_2$ alkoxy, $C_1$–$C_2$ haloalkyl and $C_1$–$C_2$ haloalkoxy; Y being $NR^6R^7$, $N=CR^8R^9$ or $OR^6$ when Q is Q-2; and Y being other than $COR^4$ and $CO_2R^4$ when Q is Q-3;

$R^3$ is selected from the group $CO_2Me$, $CO_2Et$, Ph, 4-F-Ph, 4-Cl-Ph and $C_1$–$C_3$ alkyl;

$R^4$ is $C_1$–$C_3$ alkyl; $R^4$ being $C_2$–$C_3$ alkyl when Y is $COR^4$ or $CO_2R^4$, Q is Q-1 and $Z^1$ is O;

$R^5$ is selected from the group H and $C_1$–$C_3$ alkyl;

$R^6$ is selected from the group H, $C_1$–$C_4$ alkyl, $C_1$–$C_4$ haloalkyl, $C_2$–$C_4$ alkenyl, $C_2$–$C_4$ alkynyl, $SO_2NR^8R^9$, $SO_2R^{10}$, $COR^8$, $CONR^8R^9$, $CO_2R^8$, phenyl optionally substituted with halogen or $C_1$–$C_4$ alkoxy, and benzyl optionally substituted with halogen;

$R^7$ is selected from the group H, $C_1$–$C_4$ alkyl and $COR^8$;

$R^8$ is selected from the group H, $C_1$–$C_4$ alkyl, $C_1$–$C_4$ haloalkyl and phenyl optionally substituted by a group selected from halogen, CN, $NO_2$, $CF_3$ and $OCF_3$;

$R^9$ is selected from the group H and $C_1$–$C_4$ alkyl;

$R^8$ and $R^9$ can be taken together as $-CH_2CH_2CH_2-$, $-CH_2CH_2CH_2CH_2-$ and $-CH_2CH_2CH_2CH_2CH_2-$;

$R^{10}$ is selected from the group $C_1$–$C_4$ alkyl and $C_1$–$C_4$ haloalkyl;

$R^{11}$ is selected from the group H and $C_1$–$C_4$ alkyl; $R^{11}$ being H when Q is Q-1 and Y is $CH_3$ or $C(O)CH_3$;

Z is selected from the group $CH_2$, O, S and $NR^6$; and $Z^1$ is selected from the group O and $NR^{11}$.

Preferred for reasons including greater arthropodicidal efficacy are:

A) Compounds of Formula I wherein Q is Q-1;

B) Compounds of Formula I wherein Q is Q-2;

C) Compounds of Formula I wherein Q is Q-3;

D) Compounds of Preferred A wherein Y is $NR^6R^7$, $N=CR^8R^9$ or $OR^6$;

E) Compounds of Preferred D wherein $R^6$ is H or $C_1$–$C_3$ alkyl;

F) Compounds of Preferred A wherein Y is $CH_3$ or $CH_2CH_3$; and

G) Compounds of Preferred A wherein $R^3$ is $CO_2Me$.

Specifically preferred is Compound E:

H) methyl 2-[[-1-[4(trifluoromethyl)phenyl]-hydrazino]carbonyl]-2,3-dihydro-7-(trifluoromethyl)[1]benzopyrano[4,3-C]pyrazole-3a (4H)-carboxylate.

Specifically preferred are Compounds G:

I) methyl 2,3-dihydro-2-[[N-methyl-N-[4-(trifluoromethyl)phenyl] amino]carbonyl]-7-(trifluoromethyl)[1]benzopyrano[4,3-c]pyrazole-3a(4H)-carboxylate, J) methyl 7-chloro-2,3-dihydro-2-[[N-methyl-N-[4-(trifluoromethyl)phenyl] amino]carbonyl][1]benzopyrano[4,3-c]pyrazole-3a(4H)-carboxylate, K) methyl 2-[[N-(4-chlorophenyl)-N-methylamino]carbonyl]- 2,3-dihydro-7-(trifluoromethyl)-[1]benzopyrano[4,3-c]pyrazole-3a(4H)-carboxylate, L) methyl 2-[[N-(4-bromophenyl)-N-methylamino]-carbonyl] 2,3-dihydro-7-(trifluoromethyl)[1]benzopyrano[4,3-c]pyrazole-3a(4H)-carboxylate, and M) methyl 2,3-dihydro-2-[[N-methyl-N[4- (trifluoromethoxy)-phenyl] amino]carbonyl]-7-(trifluoromethyl)[1]benzopyrano[4,3-c]pyrazole-3a (4H)-carboxylate.

In the above definitions, the term "alkyl", used either alone or in compound words such as "haloalkyl" includes straight chain or branched alkyl such as methyl, ethyl, n-propyl, isopropyl, butyl, pentyl or the different hexyl isomers. Alkenyl includes straight chain or branched alkenes, such as 1-propenyl, 2-propenyl, 3-propenyl and the different hexenyl isomers. Alkynyl includes straight chain or branched chain alkynyl groups such as 1-pentynyl, 2-pentynyl, 3-pentynyl and the different hexynyl isomers. Alkoxy includes methoxy, ethoxy, n-propyloxy and isopropyloxy. The term "halogen", either alone or in compound words such as "haloalkyl", means fluorine, chlorine, bromine or iodine Further, when used in compound words such as "haloalkyl" said alkyl can be partially or fully substituted with halogen atoms, which can be the same or different. Examples of haloalkyl include $CH_2CH_2F$, $CF_2CF_3$ and $CH_2CHFCl$. The total number of carbon atoms in a substituent group is indicated by the $C_i$–$C_j$ prefix where i and j are numbers from 1 to 6. For example, $C_1$–$C_3$ alkoxy would designate methoxy through propoxy. The term "cycloalkyl" alone or in compound words such as "cyclohaloalkyl" includes cyclopropyl, cyclobutyl, cyclopentyl and cyclohexyl groups. Cycloalkylalkyl includes cyclopropylmethyl, cyclobutylmethyl, cyclopentylmethyl and cyclohexylmethyl groups.

DETAILS OF THE INVENTION

The preparation of Formula I (Q-1) compounds where Y is other than $NR^6R^7$ $N=CR^8R^9$ or $OR^6$ can be accomplished by the N-alkylation of Formula II (Q-1) derivatives. For example, Formula II (Q-1) derivatives are treated with a base such as sodium hydride, potassium hydride, potassium tert-butoxide, lithium diisopropyl amide and the like in an inert solvent such as ether, tetrahydrofuran, dioxane, dimethylformamide and dimethylsulfoxide. Subsequent treatment with an electrophilic reagent such as alkyl halides, dialkylsulfates, alkenyl halides, alkynyl halides, substituted alkyl halides, optionally substituted benzyl halides, alkylsulfonyl halides and the like will result in the formation of Formula I compounds as illustrated in Scheme 1.

SCHEME 1

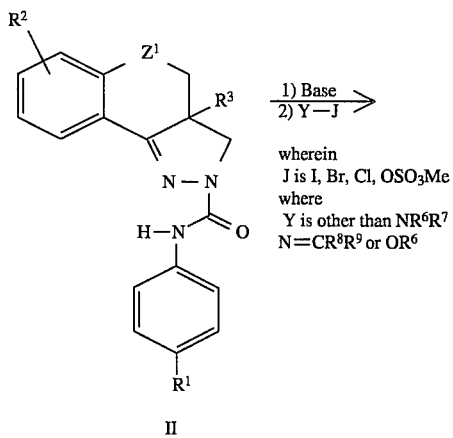

wherein
J is I, Br, Cl, $OSO_3Me$
where
Y is other than $NR^6R^7$
$N=CR^8R^9$ or $OR^6$ -continued
SCHEME 1

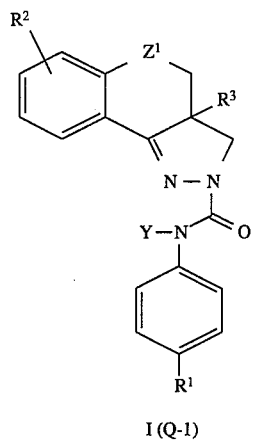

I (Q-1)

Formula I compounds where Y is $NR^6R^7$ can be prepared by the N-amination of Formula II derivatives. For example, Formula II derivatives are treated with a base such as sodium hydride, potassium hydride, potassium tert-butoxide, lithiumdiisopropyl amide and the like in an inert solvent such as ether, tetrahydrofuran dioxane, dimethylformamide and dimethylsulfoxide. Subsequent treatment of the anion with an electrophilic aminating reagent such as O-diphenylphosphinylhydroxylamine, hydroxylamine-O-sulfonic acid (HOSA), O-(2,4-dinitrophenyl)hydroxylamine, O-mesitylenesulfonylhydroxylamine (MSH), and the like will result in the formation of Formula I compounds where Y is $NR^6R^7$ as illustrated in Scheme 2. Methods for the preparation and use of such electrophilic aminating reagents can be found in *Synthesis* 1977, 1. For instance, amides, imides, pyrroles and other related compounds can be aminated by aminating reagents in good yields.

SCHEME 2

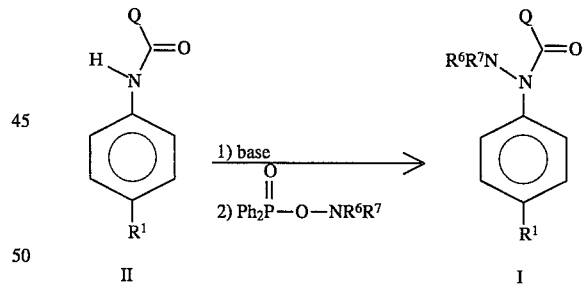

Alternatively, Formula I compounds can be prepared by coupling of the intermediate compounds of the Formula III with a compound of Formula IIIa in the presence of phosgene or a phosgene equivalent. Typical reaction conditions involve combination of a phosgene equivalent with the Formula III compound in a solvent such as tetrahydrofuran or chloroform followed by the addition of the Formula IIIa compound. This chemistry is depicted in Scheme 3.

SCHEME 3

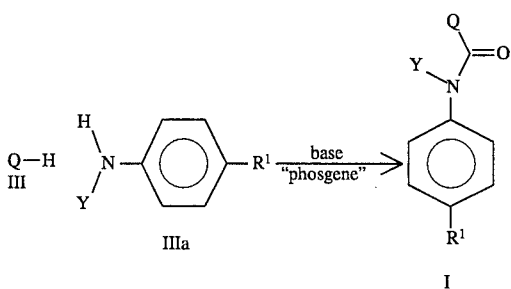

Compounds of Formula I where Y is $NH_2$, $NHR^7$ or OH can be further derivatized by standard alkylation, acylation, sulfonylation and related reactions by procedures well documented in the art. Furthermore, compounds of Formula I where Y is $NH_2$ can be condensed with aldehydes and ketones to form the corresponding hydrazone derivatives of Formula I. These procedures are also well documented in the art.

The preparation of Formula II (Q-1) derivatives is described in WO 90/10623, WO 88/0799 and WO 91/08207. For instance, tricyclic pyrazolines of Formula III (Q-1) can be condensed with equimolar amounts of isocyanates of Formula V to give Formula II (Q-1) compounds.

Compounds of Formula II (Q-2) where Z is O, S, $NR^6$ can be prepared by the reaction of Formula IV compounds with isocyanates of Formula V. Typical reactions involve the combination of equimolar amounts of IV and V in a conventional organic solvent such as, but not limited ethyl acetate, methylene chloride, chloroform, benzene or toluene. A base such as an alkali metal, tertiary amine, alkali metal alkoxide or metal hydride can be used. Scheme 4 illustrates this transformation.

SCHEME 4

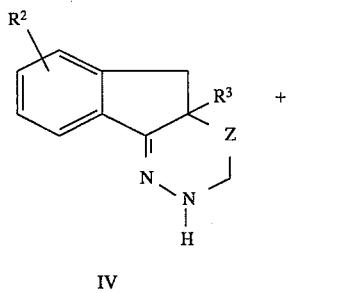

where Z is O, S, $NR^6$

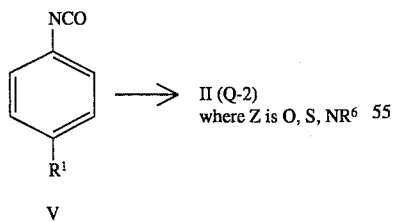

Alternatively, compounds of Formula II (Q-2), where Z is O or S, can be prepared by the reaction of semicarbazones of Formula VI with paraformaldehyde or other equivalents known to those skilled in the art. Typical reactions involve the combination of an excess in molar amounts of paraformaldehyde (1.1 equivalents to 40 equivalents) with I equivalent of a Formula VI compound optionally in the presence of less than one molar equivalent of an acid catalyst (0 equivalents to 0.9 equivalents). Typical acid catalysts include alkyl or aryl sulfonic acids (such as methyl, camphor or p-toluene sulfonic) and mineral acids (such as hydrochloric or sulfuric). Conventional polar organic solvents such as acetonitrile, dimethylformamide, tetrahydrofuran, methanol or ethanol can be used. The reaction temperature can vary from 0° C. to the reflux temperature of the particular solvent being used and the reaction is usually complete in less than 24 hours. Scheme 5 illustrates this transformation.

SCHEME 5

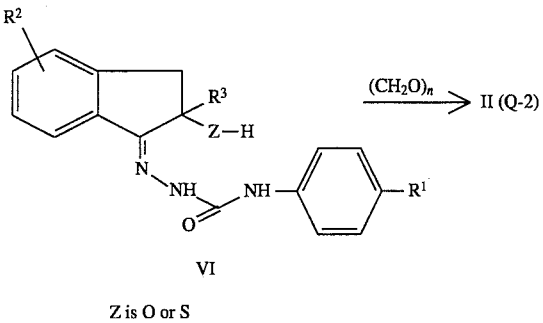

Z is O or S

Alternatively, compounds of Formula II (Q-2), where Z is O, S or $NR^6$, can be prepared by the reaction of compounds of Formula VI with compounds of Formula VII (see Scheme 6). Typical reactions involve combination of an excess in molar amounts of a Formula VII compound (1.1 equivalents to 5.0 equivlents) with one equivalent of a Formula VI compound in the presence of a base such as a tertiary amine (such as triethylamine, pyridine or DBU),an alkali metal, an alkali metal hydride or an alkali metal alkoxide or hydroxide (such as sodium methoxide, potassium-t-butoxide, sodium hydroxide or potassium hydroxide). Conventional polar organic solvents such as methanol, ethanol, propanol, dimethylformamide, THF, dichloromethane or acetonitrile can be used. The reaction temperatures can vary from 0° C. to the reflux temperature of the particular solvent being used and the reaction is usually complete in less than 24 hours.

Alternatively, when Z is $NR^6$ and $L^1$ and $L^2$ are taken together as $=NMe_2^{\oplus}I^{\ominus}$ the reaction can be performed in the absence of base in aprotic solvents such as THF, dioxane and the like. Equimolar amounts of VI and VII are used and the reaction is usually complete in 72 hours.

SCHEME 6

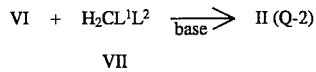

wherein:

$L^1L^2$ are Cl, Br, I, imidazole, or $L^1$ and $L^2$ may be taken together to equal $=O$, $=S$ or $=N(CH_3)_2^{\oplus}I^{\ominus}$ (where Z is $NR^6$).

Compounds of Formula IV can be prepared by the reaction of Formula VIII compounds with either compounds of Formula VII or a formaldehyde equivalent using methods analogous to those shown for the preparation of Formula II (Q-2) compounds in Schemes 5 and 6. The preparation of Formula IV compounds is shown in Scheme 7.

SCHEME 7

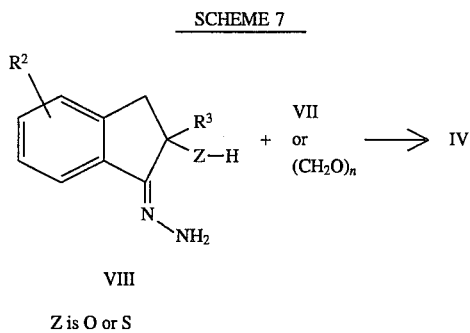

Z is O or S

Compounds of Formula VI can be prepared by the reaction of Formula VIII compounds with isocyanates of Formula V as shown in Scheme 8. Typical reactions involve the combination of equimolar amounts of VIII and V in the presence of i molar equivalent of water in a polar organic solvent such as tetrahydrofuran or dimethylformamide. The reaction is usually complete in less than 24 hours.

SCHEME 8

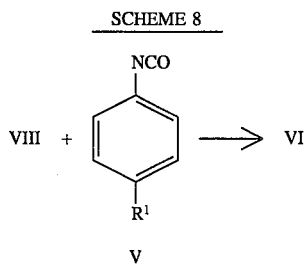

Alternatively, Formula VI compounds can be prepared by the reaction of compounds of Formula IX with semicarbazides of Formula X. Conditions for this reaction optionally include an acid catalyst such as hydrochloric, sulfuric or p-toluene sulfonic acid. Reaction temperatures can range from 0° to 150° C. with the reflux temperature of the solvent used generally preferred. Suitable solvents include, but are not limited to, methanol, ethanol, isopropanol, tetrahydrofuran and dioxane. Scheme 9 illustrates this transformation.

SCHEME 9

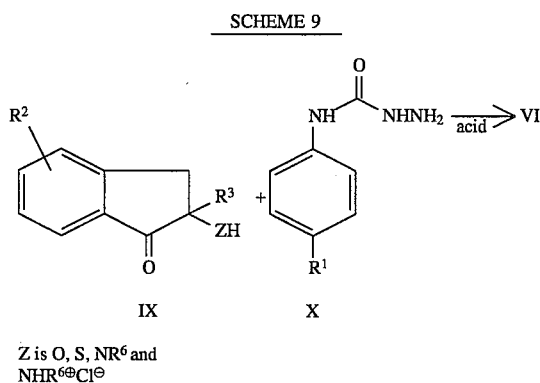

Z is O, S, $NR^6$ and $NHR^{6\oplus}Cl^{\ominus}$

The preparation of Formula VIII compounds can be accomplished by the reaction of Formula IX compounds with an excess of equivalents (1.1 to 10.0 equivalents) of hydrazine, hydrazine monohydrate, hydrazine acetate, hydrazine hydrochloride and the like. The reaction is conducted in an alcohol solvent such as methanol, ethanol, n-propanol, isopropanol, n-butanol and the like or acetic acid and the temperature is governed by the reflux temperature of the particular solvent. The reaction is generally complete in 24 hours. Scheme 10 illustrates this transformation.

SCHEME 10

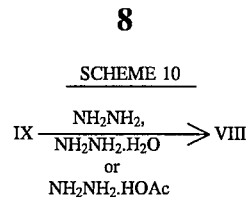

Compounds of Formula IX where Z is O can be prepared by the α-hydroxylation of ketones of Formula XI using procedures that are well-known to one skilled in the art. See, for instance, J. Am. Chem. Soc., 1974, 96, 5944; Tetrahedron Lett., 1988, 29, 2835; J. Org. Chem., 1986, 51, 2402. Scheme 11 illustrates this transformation.

SCHEME 11

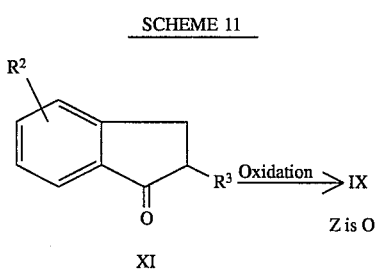

Numerous alternative procedures exist for the preparation of α-hydroxyketones of Formula IX (where Z is O) including the procedure whereby the silyl enol-ether derived from XI is treated with meta-chloroperoxybenzoic acid followed by de-silylation with fluoride (Org. Synth., 64, 118).

α-Keto sulfides of Formula IX where Z is S can be prepared from ketones of Formula XI using procedures known to the art such as treatment of XI with tetramethylthiuram disulfide followed by alkaline hydrolysis (J. Amer. Chem. Soc., 1985, 107, 4175).

α-Amino ketones of Formula IX where Z is $NR^6$ can be prepared from ketones of Formula XI using procedures known in the art such as treatment of ketones XI with cyclohexanespiro-3'-oxaziridine in the presence of base if necessary (Synthesis, 1991, 327).

Compounds where Z is $NHR^{6\oplus}Cl^{\ominus}$, can be prepared by the reaction of Formula XI compounds with compounds of the type XII using a procedure similar to those described in the art (Synthesis, 1991, 327). The conditions for this reaction are the combination of equimolar amounts of Formulae XI and XII derivatives in the presence of a base as a catalyst, such as, but not limited to, DABCO, DBU, sodium hydroxide and the like. Suitable solvents include, but are not limited to, toluene, dioxane and water. Scheme 12 illustrates this transformation.

SCHEME 12

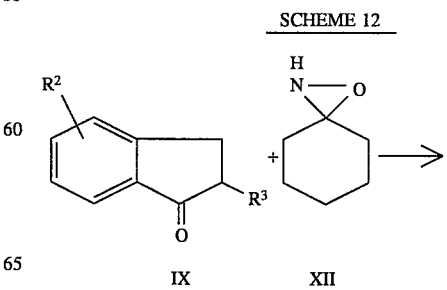

-continued
SCHEME 12

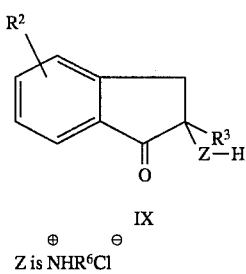

Z is NHR⁶Cl

The starting ketones of Formula XI are known in the art or can be obtained by methods analogous to known procedures. Those skilled in the art will recognize the Formula XI compounds to be indanones.

One skilled in the art will recognize that the transformation of Formula XI compounds into Formula IX compounds may require the use of protecting groups to prevent undesired side reactions of functionalities that may be sensitive to the reaction conditions (for example, an indoxyl nitrogen atom may require a protecting group to render it unreactive in an α-hydroxylation of the carbonyl group). Since numerous alternative synthetic methods for the preparations of Formula IX compounds exist, a further discussion of protecting-group chemistry will be omitted.

Semicarbazides of Formula X can be prepared using procedures well-known to those skilled in the art.

Compounds of Formula II (Q-2) where Z is CH₂ can be prepared by the reaction of Formula IV compounds with isocyanates of Formula V employing equimolar amounts of IV and V in a conventional organic solvent such as, but not limited to, ethyl acetate, methylene chloride, chloroform, benzene or toluene. A base such as an alkali metal, tertiary amine or metal hydride can be used. Scheme 13 illustrates this transformation.

SCHEME 13

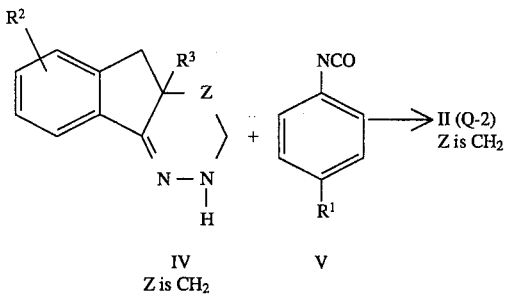

The preparation of Formula IV compounds where Z is CH₂ can be accomplished by the reaction of Formula XIII compounds with a reducing agent such as LiAlH₄ or BH₃ (see J. Org. Chem., 1973 38, 921). The typical reaction involves the combination of an excess in molar amounts of the reducing agent (1.1 equivalents to 5.0 equivalents) with 1 equivalent of a Formula XIII compound. Conventional aprotic organic solvents such as diethyl ether, tetrahydrofuran or 1,2-dimethoxyethane can be used. The reaction temperature can vary from 0° C. to the reflux temperature of the particular solvent being used and the reaction is usually complete in less than 24 hours. Scheme 14 illustrates this transformation.

SCHEME 14

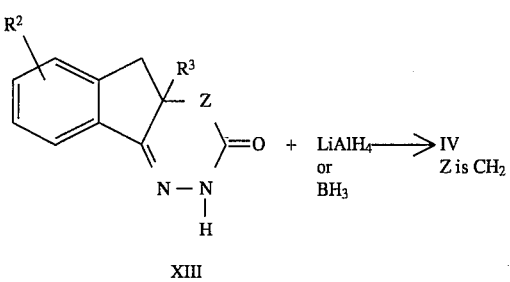

The preparation of Formula XIII compounds can be accomplished by the reaction of Formula XIV compounds with an excess of equivalents (1.1 to 10.0 equivalents) of hydrazine, hydrazine monohydrate, hydrazine acetate, hydrazine hydrochloride and the like. The reaction is conducted in an alcohol solvent such as methanol, ethanol, n-propanol, isopropanol, n-butanol and the like or acetic acid and the temperature is governed by the reflux temperature of the particular solvent. The reaction is generally complete in 24 hours. Scheme 15 illustrates this transformation. Alternatively, Formula XIII compounds can be prepared from Formula XIVa derivatives as described for the preparation of Formula VII compounds (Scheme 15).

SCHEME 15

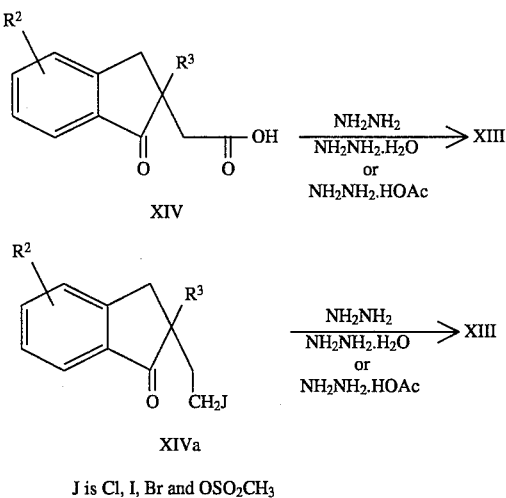

J is Cl, I, Br and OSO₂CH₃

Compounds of Formula XIV where R³ is equal to H can be prepared by the reduction of Formula XV compounds. This transformation can be effected by catalytic hydrogenation (House, Modern Synthetic Reactions, 1972, pp. 1–44) or more conveniently through the use of an excess of equivalents (1.5 to 4.0 equivalents) of zinc in refluxing acetic acid as solvent (J. Med. Chem., 1986 29, 2181). The reaction is usually complete in 24 hours. Scheme 16 illustrates this transformation.

SCHEME 16

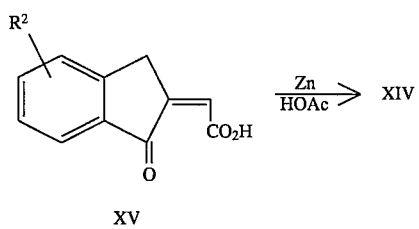

Compounds of Formula XV can be prepared by the reaction of Formula XI derivatives with Formula XVI compounds. One skilled in the art will recognize this reaction as an Aldol condensation (House, Modern Synthetic Reactions, 1972, pp.629–733) which is a well-known transformation; see Scheme 17.

SCHEME 17

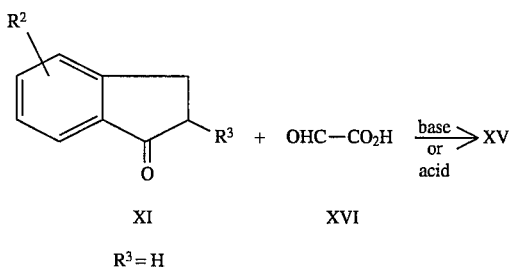

$R^3 = H$

Alternatively, compounds of Formula XIV can be prepared by hydrolysis of Formula XVII compounds. One skilled in the art will recognize this transformation as conventional and well-understood. Scheme 18 illustrates this common reaction.

SCHEME 18

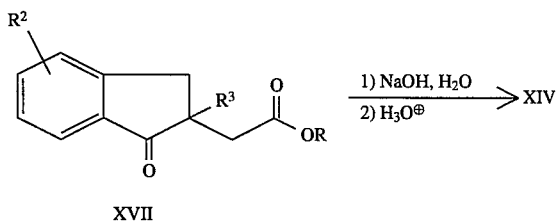

$R = C_1-C_4$ alkyl

Formula XVII compounds can be prepared by the alkylation of Formula XI derivatives with Formula XVIII compounds. The reaction can be accomplished by the reaction of equimolar amounts of Formula XI and XVIII compounds in the presence of a base such as an alkali metal, tertiary amine, metal hydride and the like in a conventional organic solvent such as, but not limited to, ether, tetrahydrofuran, 1,2-dimethoxyethane, dimethylformamide, dimethylsulfoxide, methanol, ethanol and propanol. The reaction is usually conducted at temperatures between 0° C. and the reflux temperature of the solvent utilized. The reaction is usually complete in 48 hours. Scheme 19 (reaction A) illustrates this transformation.

Additionally, the ketone XI serves as a useful intermediate for compounds of Formula XIVa. Formula XIVa compounds can be prepared by the alkylation of Formula XI derivatives with Formula XVIIIa compounds. The reaction can be accomplished by the reaction of one equivalent of Formula XI compounds and one to ten equivalents of Formula XVIIIa compounds in the presence of a base such as an alkali metal, tertiary amine, metal hydride and the like in a conventional organic solvent such as, but not limited to, ether, tetrahydrofuran, 1,2-dimethoxyethane, dimethylformamide, dimethylsulfoxide, methanol, ethanol and propanol. The reaction is usually conducted at temperatures between 0° C. and the reflux temperature of the solvent utilized. The reaction is usually complete in 48 hours. Scheme 19 (reaction B) illustrates this transformation.

SCHEME 19

A.

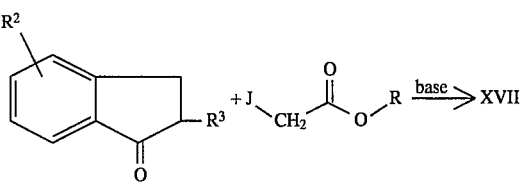

XI     XVIII
$J = Cl, Br, I$
$R = C_1-C_4$ alkyl

B.

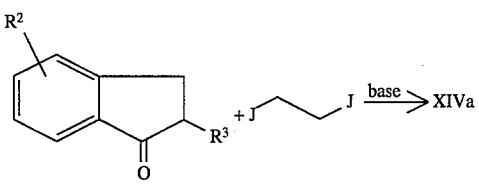

XI     XVIIIa
$J = Cl, Br, I$

The starting ketones of Formula XI are known in the art or can be obtained by methods analogous to known procedures.

The preparation of Formula II (Q-3) derivatives is described in WO 90/07495.

The following Examples serve to further illustrate the invention.

EXAMPLE 1

Methyl
2,3-dihydro-2-[[N-methyl-N-[4-(trifluoromethyl)
phenyl]
amino]carbonyl]-7-(trifluoromethyl)[1]benzopyrano
[4,3-c]pyrazole-3a (4H)-carboxylate To a mixture of 60% sodium hydride (0.19 g, 4.75 mmol) in 10 mL of dimethylformamide was added methyl 2,3-dihydro-7-(trifluoromethyl)-2-[[[4-(trifluoromethyl)phenyl] amino]carbonyl]-[1]benzopyrano[4,3-c]pyrazole- 3a(4H)-carboxylate (1.0 g, 2.05 mmol) in one portion. The color of the reaction turned yellow and the evolution of hydrogen gas was noted. After 10 minutes, methyl iodide (0.3 mL, 4.78 mmol) was added in one portion via syringe and the mixture was then heated at 50° C. for one hour. After this time, TLC showed near completion of the reaction, with only a faint trace of residual starting compound. After cooling to room temperature overnight, the mixture was partitioned between 5% aqueous sodium bicarbonate and ether, the aqueous extracts were washed with ether and the combined ether extracts were dried over magnesium sulfate and concentrated to 1.47 g of a pale green, oily solid. Chromatography on silica gel (1:1 ethyl acetate:hexane) afforded 1.12 g of a clear colorless oil which set up to a white solid. Trituration with cold methanol afforded 0.28 g of a white solid, m.p. 105°–111° C. The filtrate was concentrated and triturated with cold hexane to afford a second crop of 0.38 g of white solid, m.p. 107°–110° C. $^1$H NMR of both crops were identical.

$^1$H NMR (CDCl$_3$) δ3.47 (s, 3H), 3.76 (s,3H), 3.90 (d, 1H), 4.09 (d, 1H), 4.15 (d, 1H), 5.00 (d, 1H), 7.13 (s, 3H), 7.32 (d, 2H), 7.62 (d, 2H).

EXAMPLE 2

Methyl 2-[[-1-[4-(trifluoromethyl)phenyl]hydrazino]carbonyl]-2,3-dihydro-7-(trifluoromethyl)[1]benzopyrano[4,3-c]pyrazole-3a (4H)-carboxylate To a mixture of 60% sodium hydride (0.16 g, 4 mmol) in 10 mL of dimethylformamide was added methyl 2,3-dihydro- 7-(trifluoromethyl)2-[[[4-(trifluoromethyl)phenyl]amino]carbonyl]-[1]benzopyrano[4,3-c]pyrazole- 3a(4H)]-carboxylate (1.0 g, 2.05 mmol) at 0° C. in one portion. The color of the reaction turned yellow and the evolution of hydrogen gas was noted. The reaction was warmed to ambient temperature over 30 minutes, then O-diphenylphosphinylhydroxylamine (0.75 g, 3.20 mmol) was added in one portion resulting in a white suspension. An extra 10 ml portion of dimethylformamide was added and the reaction was stirred for one hour. After this time the mixture was partitioned between saturated aqueous sodium bicarbonate and ether, the aqueous phase was extracted with ether. The combined ether extracts were dried over anhydrous magnesium sulfate, filtered, and concentrated under vacuum. The residue was purified by chromatography on silica gel (40% ethyl acetate/hexane) to afford an oily product. Trituration with ether and hexanes afforded 0.37 g of a white solid, m.p. 118°–121° C.

$^1$H NMR (CDCl$_3$) δ7.64–7.50 (m, 5H), 7.22–7.19 (m, 2H), 5.2 (bs, 2H), 5.05 (d, 1H), 4.35 (d, 1H), 4.18 (d, 1H), 3.95 (d, 1H), 3.79 (s, 3H).

EXAMPLE 3

Step A: 5-Fluoro-2-(4-fluorophenyl)-2,3-dihydro-1H-inden-1-one

To a solution of 50.0 g (0.324 mol) 4-fluorophenylacetic acid in 68 ml of methanol was added 1.2 g (6.5 mmol) of p-toluenesulfonic acid. The solution was heated at reflux overnight and then cooled to room temperature and partitioned between dichloromethane and saturated sodium bicarbonate. The dichloromethane layer was washed with saturated sodium bicarbonate, dried over magnesium sulfate, filtered and concentrated to afford 43.7 g of a clear, colorless oil.

To a solution of 5.7 g (0.14 mol) of 60% sodium hydride in 120 ml of dimethylformamide under nitrogen was added 30.0 g (0.162 mol) of the crude methyl 4-fluorophenylacetate dropwise such that hydrogen evolution was moderate and the temperature of the reaction was maintained at less than 50° C. Once hydrogen evolution had ceased, a solution of 33.2 g (0.162 mol) of 3-fluorobenzylbromide in 30 ml of dimethylformamide was added very cautiously such that the reaction temperature was maintained at less than 60° C. The reaction was maintained at 50°to 60° C. with stirring overnight after which time it was partitioned between 5% aqueous NaHCO$_3$ and diethyl ether, the aqueous extracts were washed five times with ether and the combined organic extracts were then washed with water. The ether extracts were dried over magnesium sulfate, filtered and concentrated to afford 31.9 g of a yellow oil.

The crude product was combined with 300 ml of methanol, 40 ml of water and 20 ml of 50% aqueous sodium hydroxide and refluxed overnight. After this time, the reaction was concentrated and the crude residue partitioned between water and ether. The aqueous extracts were acidified with 1M hydrochloric acid and extracted three times with ether. The ether extracts were dried over magnesium sulfate, filtered and concentrated to 28.7 g of a yellow oil.

The crude product (27.4 g, 0.104 mol) was combined with 32 ml of thionyl chloride and then heated at reflux for 3 hours. Thionyl chloride was removed by concentration at reduced pressure and then the mixture was concentrated several times from carbon tetrachloride. The residue was combined with 130 ml of dichloroethane, cooled under nitrogen to 0° C., and 15.3 g of aluminum trichloride was then added. After stirring overnight the reaction was poured onto a mixture of ice in 1N hydrochloric acid, extracted three times with ether and chromatographed on silica gel (10% ethyl acetate/hexane) to afford 8.6 g of product.

$^1$H NMR (CDCl$_3$) δ7.82 (dd, 1H), 7.25–6.95 (m, 6H), 3.90 (dd, 1H), 3.68 (dd, 1H), 3.21 (dd, 1H).

Step B: 5-Fluoro-2-(4-fluorophenyl)-2,3-dihydro-2-hydroxy-1H-inden-1-one

A solution of 7.0 g (0.029 moles) of the product obtained from Step A and 69 mL of toluene was added with stirring to a mixture of 5.7 g (0.034 moles) of triethylphosphite, 0.33 g (0.0014 moles) of benzyltriethylammonium chloride, 344 mL of toluene and 167 mL of 50% aqueous sodium hydroxide solution. A steady stream of air was introduced into the vigorously stirred reaction mixture at room temperature for 1 hour. The resulting mixture was partitioned between hexane/ether and water and the aqueous layer was extracted three times with ether. The combined organic layers were washed twice with water, three times with saturated aqueous sodium bisulfite solution, dried over magnesium sulfate and concentrated. The resulting crude product was triturated several times with hexanes to afford 2.93 g of a pale yellow solid.

$^1$H NMR (CDCl$_3$) δ7.83 (dd, 1H), 7.32–7.15 (m, 4H), 6.99 (apparent t, 2H), 3.56 (s, 2H), 3.2 (bs, 1H).

Step C: 2-[5-Fluoro-2-(4-fluorophenyl)-2,3-dihydro-2-hydroxy- 1H-inden-1-ylidene]-N-[4-bromophenyl]hydrazinecarboxamide A solution of 2.8 g (0.0108 moles) of the product obtained from Step B, 0.78 mL (0.016 moles) of hydrazine monohydrate and 15 mL of methanol was heated at reflux for 3 hours. The resulting solution was partitioned between water and methylene chloride and the aqueous layer was extracted with methylene chloride. The combined organic layers were washed with water, dried over magnesium sulfate, filtered and concentrated, to afford 3.0 g of a yellow solid.

A solution of 0.8 g of the above product, 0.58 g (0.0029 moles) of 4-bromophenyl isocyanate, 8 mL of tetrahydrofuran and 1 drop of water was stirred at room temperature for two hours then 50 ml of hexane was added. After 15 minutes, a precipitate formed. The solid was filtered to afford 1.17 g of a pale yellow solid, m.p. 235°–237° C.

$^1$H NMR (d$_6$-DMSO) δ9.42 (s, 1H), 9.23 (s, 1H), 8.03 (t, 1H), 7.59 (d, 2H), 7.44 (d, 2H),7.4–7.1 (m, 7H), 3.53 (d, 1H), 3.3 (d, overlapping with DMSO, 1H).

Step D: 7-Fluoro-4a-(4-fluorophenyl)-4a,5-dihydro-N-[4-bromophenyl]-indeno[ 1,2-e]-[1,3,4]oxadiazine-2(3H)-carboxamide A mixture of 0.80 g (0.0017 moles) of the product obtained in Step C, 0.25 g (0.0027 moles) of paraformaldehyde, 50 mg of p-toluene sulfonic acid monohydrate and 45 mL of acetonitrile was refluxed for 30 minutes. The resulting mixture was partitioned between chloroform and saturated aqueous sodium bicarbonate and the aqueous layer was extracted three times with chloroform. The combined organic layers were dried over magnesium sulfate and concentrated to give a yellow solid. The solid was triturated with methanol/water, and dried under vacuum to afford 0.57 g of a yellow solid, m.p. 208°–209° C.

$^1$H NMR (CDCl$_3$) δ8.41 (bs, 1H), 7.75 (dd, 1H), 7.43 (apparent q, 4H), 7.32–7.22 (m, 2H), 7.15–6.92 (m, 4H), 5.75 (d, 1H), 4.52 (d, 1H), 3.48 (ABq, 2H).

Step E: 7-Fluoro-4a-(4-fluorophenyl)-4a,5-dihydroindeno[1,2,3]-[1,3,4]oxadiazine-2(3H)-carboxylic acid 1-(4-bromophenyl)hydrazide To a mixture of 60% sodium hydride (0.16 g, 4 mmol) in 10 mL of dimethylformamide was added N-(4-bromophenyl)- 7-fluoro-4a-(4-fluorophenyl)4a,5-dihydroindeno[1,2-e][1,3,4]oxadiazole-2(3H)-carboxamide (1.0 g, 2.07 mmol) at 0° C. in one portion. The color of the reaction turned yellow and the evolution of hydrogen was noted. The reaction was warmed to ambient temperature over 20 minutes, then O-diphenylphosphoylhydroxylamine (0.73 g, 3.10 mmol) was added in one portion to give a heterogeneous reaction mixture. After the hour, the mixture was partitioned between saturated sodium bicarbonate and ether and the aqueous phase was extracted with ether. The combined ether extracts were washed with water and brine, dried over magnesium sulfate, filtered and concentrated under vacuum. The residue was purified by chromatography on silica gel (40% ethyl acetate/hexane) to give 0.43 g of a yellow solid, m.p. 175°–180° C.

$^1$H NMR (CDCl$_3$) δ7.5–6.8 (m, 11H), 5.5 (d, 1H), 4.7 (bs, 2H), 4.65 (d, 1H), 3.4 (ABq, 2H).

By the procedures described herein or through obvious modifications thereof, the compounds of Tables 1–23 can be prepared.

GENERAL STRUCTURES FOR COMPOUNDS OF TABLES 1–14

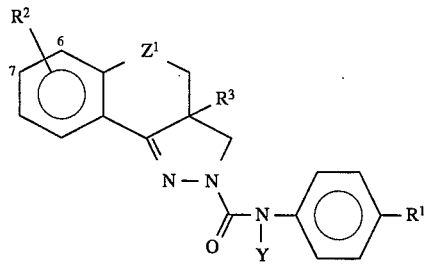

Table

| | | |
|---|---|---|
| 1 | R$^3$ = CO$_2$Me | Z$^1$ = O |
| 2 | R$^3$ = CO$_2$Et | Z$^1$ = O |
| 3 | R$^3$ = Me | Z$^1$ = O |
| 4 | R$^3$ = n-Pr | Z$^1$ = O |
| 5 | R$^3$ = i-Pr | Z$^1$ = O |
| 6 | R$^3$ = Ph | Z$^1$ = O |
| 7 | R$^3$ = 4-F-Ph | Z$^1$ = O |
| 8 | R$^3$ = 4-Cl-Ph | Z$^1$ = O |
| 9 | Z$^1$ = O | |
| 10 | Z$^1$ = O | |

GENERAL STRUCTURES FOR COMPOUNDS OF TABLES 1–14

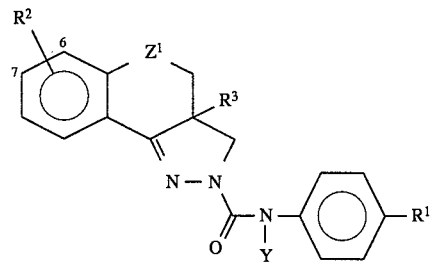

Table

| | |
|---|---|
| 11 | Z$^1$ = NH |
| 12 | Z$^1$ = N—Me |
| 13 | Z$^1$ = N—H |
| 14 | Z$^1$ = N—Me |

GENERAL STRUCTURES FOR TABLES 15–18

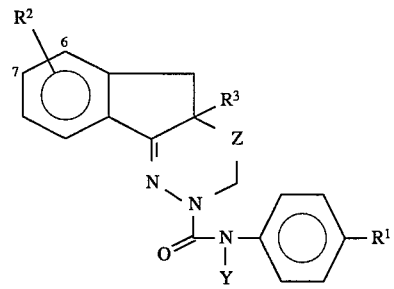

Table

| | |
|---|---|
| 15 | Z = O |
| 16 | Z = NH |
| 17 | Z = N—Me |
| 18 | Z = CH$_2$ |
| 19 | Z = O |

GENERAL STRUCTURES FOR TABLES 20–23

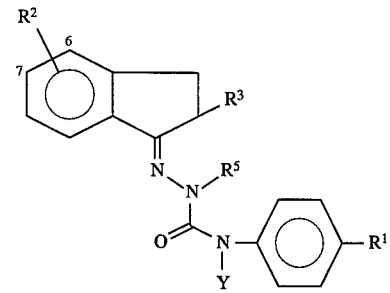

Table

| | |
|---|---|
| 20 | R$^5$ = H |
| 21 | R$^5$ = Me |
| 22 | R$^5$ = H |
| 23 | R$^5$ = Me |

TABLE 1

| $R^1$ | $R^2$ | Y | $R^1$ | $R^2$ | Y |
|---|---|---|---|---|---|
| Cl | H | Me | Cl | 6-$CF_3$ | Me |
| Br | H | Me | Br | 6-$CF_3$ | Me |
| $CF_3$ | H | Me | $CF_3$ | 6-$CF_3$ | Me |
| $OCF_3$ | H | Me | $OCF_3$ | 6-$CF_3$ | Me |
| $OSO_2CF_3$ | H | Me | $OSO_2CF_3$ | 6-$CF_3$ | Me |
| Cl | H | Et | Cl | 6-$CF_3$ | Et |
| Br | H | Et | Br | 6-$CF_3$ | Et |
| $CF_3$ | H | Et | $CF_3$ | 6-$CF_3$ | Et |
| $OCF_3$ | H | Et | $OCF_3$ | 6-$CF_3$ | Et |
| $OSO_2CF_3$ | H | Et | $OSO_2CF_3$ | 6-$CF_3$ | Et |
| Cl | 6-Cl | Me | Cl | 7-Cl | Me |
| Br | 6-Cl | Me | Br | 7-Cl | Me |
| $CF_3$ | 6-Cl | Me | $CF_3$ | 7-Cl | Me |
| $OCF_3$ | 6-Cl | Me | $OCF_3$ | 7-Cl | Me |
| $OSO_2CF_3$ | 6-Cl | Me | $OSO_2CF_3$ | 7-Cl | Me |
| Cl | 6-Cl | Et | Cl | 7-Cl | Et |
| Br | 6-Cl | Et | Br | 7-Cl | Et |
| $CF_3$ | 6-Cl | Et | $CF_3$ | 7-Cl | Et |
| $OCF_3$ | 6-Cl | Et | $OCF_3$ | 7-Cl | Et |
| $OSO_2CF_3$ | 6-Cl | Et | $OSO_2CF_3$ | 7-Cl | Et |
| Cl | 6-F | Me | Cl | 7-F | Me |
| Br | 6-F | Me | Br | 7-F | Me |
| $CF_3$ | 6-F | Me | $CF_3$ | 7-F | Me |
| $OCF_3$ | 6-F | Me | $OCF_3$ | 7-F | Me |
| $OSO_2CF_3$ | 6-F | Me | $OSO_2CF_3$ | 7-F | Me |
| Cl | 6-F | Et | Cl | 7-F | Et |
| Br | 6-F | Et | Br | 7-F | Et |
| $CF_3$ | 6-F | Et | $CF_3$ | 7-F | Et |
| $OCF_3$ | 6-F | Et | $OCF_3$ | 7-F | Et |
| $OSO_2CF_3$ | 6-F | Et | $OSO_2CF_3$ | 7-F | Et |
| Cl | 7-$CF_3$ | Me | $OCF_3$ | 7-$CF_3$ | $(CH_2)_2OMe$ |
| Br | 7-$CF_3$ | Me | $CF_3$ | 7-$CF_3$ | $CH_2SMe$ |
| $CF_3$ | 7-$CF_3$ | Me | $OCF_3$ | 7-$CF_3$ | $CH_2SMe$ |
| $OCF_3$ | 7-$CF_3$ | Me | $CF_3$ | 7-$CF_3$ | $CH_2CO_2Me$ |
| $OSO_2CF_3$ | 7-$CF_3$ | Me | $OCF_3$ | 7-$CF_3$ | $CH_2CO_2Me$ |
| Cl | 7-$CF_3$ | Et | $CF_3$ | 7-$CF_3$ | $CH_2Ph$ |
| Br | 7-$CF_3$ | Et | $OCF_3$ | 7-$CF_3$ | $CH_2Ph$ |
| $CF_3$ | 7-$CF_3$ | Et | $CF_3$ | 7-$CF_3$ | allyl |
| $OCF_3$ | 7-$CF_3$ | Et | $OCF_3$ | 7-$CF_3$ | allyl |
| $OSO_2CF_3$ | 7-$CF_3$ | Et | $CF_3$ | 6-F | $CO_2Et$ |
| $CF_3$ | 7-Cl | $CH_2CN$ | $OCF_3$ | 6-F | $CO_2Et$ |
| $OCF_3$ | 7-Cl | $CH_2CN$ | Cl | 6-F | $CO_2Et$ |
| $CF_3$ | 7-Cl | $CH_2OMe$ | Br | 6-F | $CO_2Et$ |
| $OCF_3$ | 7-Cl | $CH_2OMe$ | $CF_3$ | 6-Cl | $CO_2Et$ |
| $CF_3$ | 7-Cl | $(CH_2)_2OMe$ | $OCF_3$ | 6-Cl | $CO_2Et$ |
| $OCF_3$ | 7-Cl | $(CH_2)_2OMe$ | Cl | 6-Cl | $CO_2Et$ |
| $CF_3$ | 7-Cl | $CH_2SMe$ | Br | 6-Cl | $CO_2Et$ |
| $OCF_3$ | 7-Cl | $CH_2SMe$ | $CF_3$ | 7-F | $CO_2Et$ |
| $CF_3$ | 7-Cl | $CH_2CO_2Me$ | $OCF_3$ | 7-F | $CO_2Et$ |
| $OCF_3$ | 7-Cl | $CH_2CO_2Me$ | Cl | 7-F | $CO_2Et$ |
| $CF_3$ | 7-Cl | $CH_2Ph$ | Br | 7-F | $CO_2Et$ |
| $OCF_3$ | 7-Cl | $CH_2Ph$ | $CF_3$ | 7-Cl | $CO_2Et$ |
| $CF_3$ | 7-Cl | allyl | $OCF_3$ | 7-Cl | $CO_2Et$ |
| $OCF_3$ | 7-Cl | allyl | Cl | 7-Cl | $CO_2Et$ |
| $CF_3$ | 7-$CF_3$ | $CH_2CN$ | Br | 7-Cl | $CO_2Et$ |
| $OCF_3$ | 7-$CF_3$ | $CH_2CN$ | $CF_3$ | 7-$CF_3$ | $CO_2Et$ |
| $CF_3$ | 7-$CF_3$ | $CH_2OMe$ | $OCF_3$ | 7-$CF_3$ | $CO_2Et$ |
| $OCF_3$ | 7-$CF_3$ | $CH_2OMe$ | Cl | 7-$CF_3$ | $CO_2Et$ |
| $CF_3$ | 7-$CF_3$ | $(CH_2)_2OMe$ | Br | 7-$CF_3$ | $CO_2Et$ |
| $CF_3$ | 6-F | $CO_2n$—Pr | | | |
| $OCF_3$ | 6-F | $CO_2n$—Pr | | | |
| Cl | 6-F | $CO_2n$—Pr | | | |
| Br | 6-F | $CO_2n$—Pr | | | |
| $CF_3$ | 6-Cl | $CO_2n$—Pr | | | |
| $OCF_3$ | 6-Cl | $CO_2n$—Pr | | | |
| Cl | 6-Cl | $CO_2n$—Pr | | | |
| Br | 6-Cl | $CO_2n$—Pr | | | |
| $CF_3$ | 7-F | $CO_2n$—Pr | | | |
| $OCF_3$ | 7-F | $CO_2n$—Pr | | | |
| Cl | 7-F | $CO_2n$—Pr | | | |
| Br | 7-F | $CO_2n$—Pr | | | |
| $CF_3$ | 7-Cl | $CO_2n$—Pr | | | |
| $OCF_3$ | 7-Cl | $CO_2n$—Pr | | | |
| Cl | 7-Cl | $CO_2n$—Pr | | | |
| Br | 7-Cl | $CO_2n$—Pr | | | |
| $CF_3$ | 7-$CF_3$ | $CO_2n$—Pr | | | |
| $OCF_3$ | 7-$CF_3$ | $CO_2n$—Pr | | | |

TABLE 1-continued

| R¹ | R² | Y |
|---|---|---|
| Cl | 7-CF₃ | CO₂n—Pr |
| Br | 7-CF₃ | CO₂n—Pr |

TABLE 2

| R¹ | R² | Y | R¹ | R² | Y |
|---|---|---|---|---|---|
| Cl | H | Me | Cl | 6-CF₃ | Me |
| Br | H | Me | Br | 6-CF₃ | Me |
| CF₃ | H | Me | CF₃ | 6-CF₃ | Me |
| OCF₃ | H | Me | OCF₃ | 6-CF₃ | Me |
| OSO₂CF₃ | H | Me | OSO₂CF₃ | 6-CF₃ | Me |
| Cl | H | Et | Cl | 6-CF₃ | Et |
| Br | H | Et | Br | 6-CF₃ | Et |
| CF₃ | H | Et | CF₃ | 6-CF₃ | Et |
| OCF₃ | H | Et | OCF₃ | 6-CF₃ | Et |
| OSO₂CF₃ | H | Et | OSO₂CF₃ | 6-CF₃ | Et |
| Cl | 6-Cl | Me | Cl | 7-Cl | Me |
| Br | 6-Cl | Me | Br | 7-Cl | Me |
| CF₃ | 6-Cl | Me | CF₃ | 7-Cl | Me |
| OCF₃ | 6-Cl | Me | OCF₃ | 7-Cl | Me |
| OSO₂CF₃ | 6-Cl | Me | OSO₂CF₃ | 7-Cl | Me |
| Cl | 6-Cl | Et | Cl | 7-Cl | Et |
| Br | 6-Cl | Et | Br | 7-Cl | Et |
| CF₃ | 6-Cl | Et | CF₃ | 7-Cl | Et |
| OCF₃ | 6-Cl | Et | OCF₃ | 7-Cl | Et |
| OSO₂CF₃ | 6-Cl | Et | OSO₂CF₃ | 7-Cl | Et |
| Cl | 6-F | Me | Cl | 7-F | Me |
| Br | 6-F | Me | Br | 7-F | Me |
| CF₃ | 6-F | Me | CF₃ | 7-F | Me |
| OCF₃ | 6-F | Me | OCF₃ | 7-F | Me |
| OSO₂CF₃ | 6-F | Me | OSO₂CF₃ | 7-F | Me |
| Cl | 6-F | Et | Cl | 7-F | Et |
| Br | 6-F | Et | Br | 7-F | Et |
| CF₃ | 6-F | Et | CF₃ | 7-F | Et |
| OCF₃ | 6-F | Et | OCF₃ | 7-F | Et |
| OSO₂CF₃ | 6-F | Et | OSO₂CF₃ | 7-F | Et |
| Cl | 7-CF₃ | Me | OCF₃ | 7-CF₃ | (CH₂)₂OMe |
| Br | 7-CF₃ | Me | CF₃ | 7-CF₃ | CH₂SMe |
| CF₃ | 7-CF₃ | Me | OCF₃ | 7-CF₃ | CH₂SMe |
| OCF₃ | 7-CF₃ | Me | CF₃ | 7-CF₃ | CH₂CO₂Me |
| OSO₂CF₃ | 7-CF₃ | Me | OCF₃ | 7-CF₃ | CH₂CO₂Me |
| Cl | 7-CF₃ | Et | CF₃ | 7-CF₃ | CH₂Ph |
| Br | 7-CF₃ | Et | OCF₃ | 7-CF₃ | CH₂Ph |
| CF₃ | 7-CF₃ | Et | CF₃ | 7-CF₃ | allyl |
| OCF₃ | 7-CF₃ | Et | OCF₃ | 7-CF₃ | allyl |
| OSO₂CF₃ | 7-CF₃ | Et | | | |
| CF₃ | 7-Cl | CH₂CN | | | |
| OCF₃ | 7-Cl | CH₂CN | | | |
| CF₃ | 7-Cl | CH₂OMe | | | |
| OCF₃ | 7-Cl | CH₂OMe | | | |
| CF₃ | 7-Cl | (CH₂)₂OMe | | | |
| OCF₃ | 7-Cl | (CH₂)₂OMe | | | |
| CF₃ | 7-Cl | CH₂SMe | | | |
| OCF₃ | 7-Cl | CH₂SMe | | | |
| CF₃ | 7-Cl | CH₂CO₂Me | | | |
| OCF₃ | 7-Cl | CH₂CO₂Me | | | |
| CF₃ | 7-Cl | CH₂Ph | | | |
| OCF₃ | 7-Cl | CH₂Ph | | | |
| CF₃ | 7-Cl | allyl | | | |
| OCF₃ | 7-Cl | allyl | | | |
| CF₃ | 7-CF₃ | CH₂CN | | | |
| OCF₃ | 7-CF₃ | CH₂CN | | | |
| CF₃ | 7-CF₃ | CH₂OMe | | | |
| OCF₃ | 7-CF₃ | CH₂OMe | | | |
| CF₃ | 7-CF₃ | (CH₂)₂OMe | | | |

TABLE 3

| R¹ | R² | Y | R¹ | R² | Y |
|---|---|---|---|---|---|
| Cl | H | Me | Cl | 6-CF₃ | Me |
| Br | H | Me | Br | 6-CF₃ | Me |
| CF₃ | H | Me | CF₃ | 6-CF₃ | Me |

TABLE 3-continued

| R¹ | R² | Y | R¹ | R² | Y |
|---|---|---|---|---|---|
| OCF₃ | H | Me | OCF₃ | 6-CF₃ | Me |
| OSO₂CF₃ | H | Me | OSO₂CF₃ | 6-CF₃ | Me |
| Cl | H | Et | Cl | 6-CF₃ | Et |
| Br | H | Et | Br | 6-CF₃ | Et |
| CF₃ | H | Et | CF₃ | 6-CF₃ | Et |
| OCF₃ | H | Et | OCF₃ | 6-CF₃ | Et |
| OSO₂CF₃ | H | Et | OSO₂CF₃ | 6-CF₃ | Et |
| Cl | 6-Cl | Me | Cl | 7-Cl | Me |
| Br | 6-Cl | Me | Br | 7-Cl | Me |
| CF₃ | 6-Cl | Me | CF₃ | 7-Cl | Me |
| OCF₃ | 6-Cl | Me | OCF₃ | 7-Cl | Me |
| OSO₂CF₃ | 6-Cl | Me | OSO₂CF₃ | 7-Cl | Me |
| Cl | 6-Cl | Et | Cl | 7-Cl | Et |
| Br | 6-Cl | Et | Br | 7-Cl | Et |
| CF₃ | 6-Cl | Et | CF₃ | 7-Cl | Et |
| OCF₃ | 6-Cl | Et | OCF₃ | 7-Cl | Et |
| OSO₂CF₃ | 6-Cl | Et | OSO₂CF₃ | 7-Cl | Et |
| Cl | 6-F | Me | Cl | 7-F | Me |
| Br | 6-F | Me | Br | 7-F | Me |
| CF₃ | 6-F | Me | CF₃ | 7-F | Me |
| OCF₃ | 6-F | Me | OCF₃ | 7-F | Me |
| OSO₂CF₃ | 6-F | Me | OSO₂CF₃ | 7-F | Me |
| Cl | 6-F | Et | Cl | 7-F | Et |
| Br | 6-F | Et | Br | 7-F | Et |
| CF₃ | 6-F | Et | CF₃ | 7-F | Et |
| OCF₃ | 6-F | Et | OCF₃ | 7-F | Et |
| OSO₂CF₃ | 6-F | Et | OSO₂CF₃ | 7-F | Et |
| Cl | 7-CF₃ | Me | OCF₃ | 7-CF₃ | (CH₂)₂OMe |
| Br | 7-CF₃ | Me | CF₃ | 7-CF₃ | CH₂SMe |
| CF₃ | 7-CF₃ | Me | OCF₃ | 7-CF₃ | CH₂SMe |
| OCF₃ | 7-CF₃ | Me | CF₃ | 7-CF₃ | CH₂CO₂Me |
| OSO₂CF₃ | 7-CF₃ | Me | OCF₃ | 7-CF₃ | CH₂CO₂Me |
| Cl | 7-CF₃ | Et | CF₃ | 7-CF₃ | CH₂Ph |
| Br | 7-CF₃ | Et | OCF₃ | 7-CF₃ | CH₂Ph |
| CF₃ | 7-CF₃ | Et | CF₃ | 7-CF₃ | allyl |
| OCF₃ | 7-CF₃ | Et | OCF₃ | 7-CF₃ | allyl |
| OSO₂CF₃ | 7-CF₃ | Et | | | |
| CF₃ | 7-Cl | CH₂CN | | | |
| OCF₃ | 7-Cl | CH₂CN | | | |
| CF₃ | 7-Cl | CH₂OMe | | | |
| OCF₃ | 7-Cl | CH₂OMe | | | |
| CF₃ | 7-Cl | (CH₂)₂OMe | | | |
| OCF₃ | 7-Cl | (CH₂)₂OMe | | | |
| CF₃ | 7-Cl | CH₂SMe | | | |
| OCF₃ | 7-Cl | CH₂SMe | | | |
| CF₃ | 7-Cl | CH₂CO₂Me | | | |
| OCF₃ | 7-Cl | CH₂CO₂Me | | | |
| CF₃ | 7-Cl | CH₂Ph | | | |
| OCF₃ | 7-Cl | CH₂Ph | | | |
| CF₃ | 7-Cl | allyl | | | |
| OCF₃ | 7-Cl | allyl | | | |
| CF₃ | 7-CF₃ | CH₂CN | | | |
| OCF₃ | 7-CF₃ | CH₂CN | | | |
| CF₃ | 7-CF₃ | CH₂OMe | | | |
| OCF₃ | 7-CF₃ | CH₂OMe | | | |
| CF₃ | 7-CF₃ | (CH₂)₂OMe | | | |

TABLE 4

| R¹ | R² | Y | R¹ | R² | Y |
|---|---|---|---|---|---|
| Cl | H | Me | Cl | 6-CF₃ | Me |
| Br | H | Me | Br | 6-CF₃ | Me |
| CF₃ | H | Me | CF₃ | 6-CF₃ | Me |
| OCF₃ | H | Me | OCF₃ | 6-CF₃ | Me |
| OSO₂CF₃ | H | Me | OSO₂CF₃ | 6-CF₃ | Me |
| Cl | H | Et | Cl | 6-CF₃ | Et |
| Br | H | Et | Br | 6-CF₃ | Et |
| CF₃ | H | Et | CF₃ | 6-CF₃ | Et |
| OCF₃ | H | Et | OCF₃ | 6-CF₃ | Et |
| OSO₂CF₃ | H | Et | OSO₂CF₃ | 6-CF₃ | Et |
| Cl | 6-Cl | Me | Cl | 7-Cl | Me |
| Br | 6-Cl | Me | Br | 7-Cl | Me |
| CF₃ | 6-Cl | Me | CF₃ | 7-Cl | Me |
| OCF₃ | 6-Cl | Me | OCF₃ | 7-Cl | Me |

TABLE 4-continued

| R¹ | R² | Y | R¹ | R² | Y |
|---|---|---|---|---|---|
| OSO₂CF₃ | 6-Cl | Me | OSO₂CF₃ | 7-Cl | Me |
| Cl | 6-Cl | Et | Cl | 7-Cl | Et |
| Br | 6-Cl | Et | Br | 7-Cl | Et |
| CF₃ | 6-Cl | Et | CF₃ | 7-Cl | Et |
| OCF₃ | 6-Cl | Et | OCF₃ | 7-Cl | Et |
| OSO₂CF₃ | 6-Cl | Et | OSO₂CF₃ | 7-Cl | Et |
| Cl | 6-F | Me | Cl | 7-F | Me |
| Br | 6-F | Me | Br | 7-F | Me |
| CF₃ | 6-F | Me | CF₃ | 7-F | Me |
| OCF₃ | 6-F | Me | OCF₃ | 7-F | Me |
| OSO₂CF₃ | 6-F | Me | OSO₂CF₃ | 7-F | Me |
| Cl | 6-F | Et | Cl | 7-F | Et |
| Br | 6-F | Et | Br | 7-F | Et |
| CF₃ | 6-F | Et | CF₃ | 7-F | Et |
| OCF₃ | 6-F | Et | OCF₃ | 7-F | Et |
| OSO₂CF₃ | 6-F | Et | OSO₂CF₃ | 7-F | Et |
| Cl | 7-CF₃ | Me | OCF₃ | 7-CF₃ | (CH₂)₂OMe |
| Br | 7-CF₃ | Me | CF₃ | 7-CF₃ | CH₂SMe |
| CF₃ | 7-CF₃ | Me | OCF₃ | 7-CF₃ | CH₂SMe |
| OCF₃ | 7-CF₃ | Me | CF₃ | 7-CF₃ | CH₂CO₂Me |
| OSO₂CF₃ | 7-CF₃ | Me | OCF₃ | 7-CF₃ | CH₂CO₂Me |
| Cl | 7-CF₃ | Et | CF₃ | 7-CF₃ | CH₂Ph |
| Br | 7-CF₃ | Et | OCF₃ | 7-CF₃ | CH₂Ph |
| CF₃ | 7-CF₃ | Et | CF₃ | 7-CF₃ | allyl |
| OCF₃ | 7-CF₃ | Et | OCF₃ | 7-CF₃ | allyl |
| OSO₂CF₃ | 7-CF₃ | Et | | | |
| CF₃ | 7-Cl | CH₂CN | | | |
| OCF₃ | 7-Cl | CH₂CN | | | |
| CF₃ | 7-Cl | CH₂OMe | | | |
| OCF₃ | 7-Cl | CH₂OMe | | | |
| CF₃ | 7-Cl | (CH₂)₂OMe | | | |
| OCF₃ | 7-Cl | (CH₂)₂OMe | | | |
| CF₃ | 7-Cl | CH₂SMe | | | |
| OCF₃ | 7-Cl | CH₂SMe | | | |
| CF₃ | 7-Cl | CH₂CO₂Me | | | |
| OCF₃ | 7-Cl | CH₂CO₂Me | | | |
| CF₃ | 7-Cl | CH₂Ph | | | |
| OCF₃ | 7-Cl | CH₂Ph | | | |
| CF₃ | 7-Cl | allyl | | | |
| OCF₃ | 7-Cl | allyl | | | |
| CF₃ | 7-CF₃ | CH₂CN | | | |
| OCF₃ | 7-CF₃ | CH₂CN | | | |
| CF₃ | 7-CF₃ | CH₂OMe | | | |
| OCF₃ | 7-CF₃ | CH₂OMe | | | |
| CF₃ | 7-CF₃ | (CH₂)₂OMe | | | |

TABLE 5

| R¹ | R² | Y | R¹ | R² | Y |
|---|---|---|---|---|---|
| Cl | H | Me | Cl | 6-CF₃ | Me |
| Br | H | Me | Br | 6-CF₃ | Me |
| CF₃ | H | Me | CF₃ | 6-CF₃ | Me |
| OCF₃ | H | Me | OCF₃ | 6-CF₃ | Me |
| OSO₂CF₃ | H | Me | OSO₂CF₃ | 6-CF₃ | Me |
| Cl | H | Et | Cl | 6-CF₃ | Et |
| Br | H | Et | Br | 6-CF₃ | Et |
| CF₃ | H | Et | CF₃ | 6-CF₃ | Et |
| OCF₃ | H | Et | OCF₃ | 6-CF₃ | Et |
| OSO₂CF₃ | H | Et | OSO₂CF₃ | 6-CF₃ | Et |
| Cl | 6-Cl | Me | Cl | 7-Cl | Me |
| Br | 6-Cl | Me | Br | 7-Cl | Me |
| CF₃ | 6-Cl | Me | CF₃ | 7-Cl | Me |
| OCF₃ | 6-Cl | Me | OCF₃ | 7-Cl | Me |
| OSO₂CF₃ | 6-Cl | Me | OSO₂CF₃ | 7-Cl | Me |
| Cl | 6-Cl | Et | Cl | 7-Cl | Et |
| Br | 6-Cl | Et | Br | 7-Cl | Et |
| CF₃ | 6-Cl | Et | CF₃ | 7-Cl | Et |
| OCF₃ | 6-Cl | Et | OCF₃ | 7-Cl | Et |
| OSO₂CF₃ | 6-Cl | Et | OSO₂CF₃ | 7-Cl | Et |
| Cl | 6-F | Me | Cl | 7-F | Me |
| Br | 6-F | Me | Br | 7-F | Me |
| CF₃ | 6-F | Me | CF₃ | 7-F | Me |
| OCF₃ | 6-F | Me | OCF₃ | 7-F | Me |
| OSO₂CF₃ | 6-F | Me | OSO₂CF₃ | 7-F | Me |

TABLE 5-continued

| R¹ | R² | Y | R¹ | R² | Y |
|---|---|---|---|---|---|
| Cl | 6-F | Et | Cl | 7-F | Et |
| Br | 6-F | Et | Br | 7-F | Et |
| CF₃ | 6-F | Et | CF₃ | 7-F | Et |
| OCF₃ | 6-F | Et | OCF₃ | 7-F | Et |
| OSO₂CF₃ | 6-F | Et | OSO₂CF₃ | 7-F | Et |
| Cl | 7-CF₃ | Me | OCF₃ | 7-CF₃ | (CH₂)₂OMe |
| Br | 7-CF₃ | Me | CF₃ | 7-CF₃ | CH₂SMe |
| CF₃ | 7-CF₃ | Me | OCF₃ | 7-CF₃ | CH₂SMe |
| OCF₃ | 7-CF₃ | Me | CF₃ | 7-CF₃ | CH₂CO₂Me |
| OSO₂CF₃ | 7-CF₃ | Me | OCF₃ | 7-CF₃ | CH₂CO₂Me |
| Cl | 7-CF₃ | Et | CF₃ | 7-CF₃ | CH₂Ph |
| Br | 7-CF₃ | Et | OCF₃ | 7-CF₃ | CH₂Ph |
| CF₃ | 7-CF₃ | Et | CF₃ | 7-CF₃ | allyl |
| OCF₃ | 7-CF₃ | Et | OCF₃ | 7-CF₃ | allyl |
| OSO₂CF₃ | 7-CF₃ | Et | | | |
| CF₃ | 7-Cl | CH₂CN | | | |
| OCF₃ | 7-Cl | CH₂CN | | | |
| CF₃ | 7-Cl | CH₂OMe | | | |
| OCF₃ | 7-Cl | CH₂OMe | | | |
| CF₃ | 7-Cl | (CH₂)₂OMe | | | |
| OCF₃ | 7-Cl | (CH₂)₂OMe | | | |
| CF₃ | 7-Cl | CH₂SMe | | | |
| OCF₃ | 7-Cl | CH₂SMe | | | |
| CF₃ | 7-Cl | CH₂CO₂Me | | | |
| OCF₃ | 7-Cl | CH₂CO₂Me | | | |
| CF₃ | 7-Cl | CH₂Ph | | | |
| OCF₃ | 7-Cl | CH₂Ph | | | |
| CF₃ | 7-Cl | allyl | | | |
| OCF₃ | 7-Cl | allyl | | | |
| CF₃ | 7-CF₃ | CH₂CN | | | |
| OCF₃ | 7-CF₃ | CH₂CN | | | |
| CF₃ | 7-CF₃ | CH₂OMe | | | |
| OCF₃ | 7-CF₃ | CH₂OMe | | | |
| CF₃ | 7-CF₃ | (CH₂)₂OMe | | | |

TABLE 6

| R¹ | R² | Y | R¹ | R² | Y |
|---|---|---|---|---|---|
| Cl | H | Me | Cl | 6-CF₃ | Me |
| Br | H | Me | Br | 6-CF₃ | Me |
| CF₃ | H | Me | CF₃ | 6-CF₃ | Me |
| OCF₃ | H | Me | OCF₃ | 6-CF₃ | Me |
| OSO₂CF₃ | H | Me | OSO₂CF₃ | 6-CF₃ | Me |
| Cl | H | Et | Cl | 6-CF₃ | Et |
| Br | H | Et | Br | 6-CF₃ | Et |
| CF₃ | H | Et | CF₃ | 6-CF₃ | Et |
| OCF₃ | H | Et | OCF₃ | 6-CF₃ | Et |
| OSO₂CF₃ | H | Et | OSO₂CF₃ | 6-CF₃ | Et |
| Cl | 6-Cl | Me | Cl | 7-Cl | Me |
| Br | 6-Cl | Me | Br | 7-Cl | Me |
| CF₃ | 6-Cl | Me | CF₃ | 7-Cl | Me |
| OCF₃ | 6-Cl | Me | OCF₃ | 7-Cl | Me |
| OSO₂CF₃ | 6-Cl | Me | OSO₂CF₃ | 7-Cl | Me |
| Cl | 6-Cl | Et | Cl | 7-Cl | Et |
| Br | 6-Cl | Et | Br | 7-Cl | Et |
| CF₃ | 6-Cl | Et | CF₃ | 7-Cl | Et |
| OCF₃ | 6-Cl | Et | OCF₃ | 7-Cl | Et |
| OSO₂CF₃ | 6-Cl | Et | OSO₂CF₃ | 7-Cl | Et |
| Cl | 6-F | Me | Cl | 7-F | Me |
| Br | 6-F | Me | Br | 7-F | Me |
| CF₃ | 6-F | Me | CF₃ | 7-F | Me |
| OCF₃ | 6-F | Me | OCF₃ | 7-F | Me |
| OSO₂CF₃ | 6-F | Me | OSO₂CF₃ | 7-F | Me |
| Cl | 6-F | Et | Cl | 7-F | Et |
| Br | 6-F | Et | Br | 7-F | Et |
| CF₃ | 6-F | Et | CF₃ | 7-F | Et |
| OCF₃ | 6-F | Et | OCF₃ | 7-F | Et |
| OSO₂CF₃ | 6-F | Et | OSO₂CF₃ | 7-F | Et |
| Cl | 7-CF₃ | Me | OCF₃ | 7-CF₃ | (CH₂)₂OMe |
| Br | 7-CF₃ | Me | CF₃ | 7-CF₃ | CH₂SMe |
| CF₃ | 7-CF₃ | Me | OCF₃ | 7-CF₃ | CH₂SMe |
| OCF₃ | 7-CF₃ | Me | CF₃ | 7-CF₃ | CH₂CO₂Me |
| OSO₂CF₃ | 7-CF₃ | Me | OCF₃ | 7-CF₃ | CH₂CO₂Me |
| Cl | 7-CF₃ | Et | CF₃ | 7-CF₃ | CH₂Ph |

TABLE 6-continued

| R¹ | R² | Y | R¹ | R² | Y |
|---|---|---|---|---|---|
| Br | 7-CF₃ | Et | OCF₃ | 7-CF₃ | CH₂Ph |
| CF₃ | 7-CF₃ | Et | CF₃ | 7-CF₃ | allyl |
| OCF₃ | 7-CF₃ | Et | OCF₃ | 7-CF₃ | allyl |
| OSO₂CF₃ | 7-CF₃ | Et | CF₃ | 7-CF₃ | OMe |
| CF₃ | 7-Cl | CH₂CN | OCF₃ | 7-Cl | OMe |
| OCF₃ | 7-Cl | CH₂CN | | | |
| CF₃ | 7-Cl | CH₂OMe | | | |
| OCF₃ | 7-Cl | CH₂OMe | | | |
| CF₃ | 7-Cl | (CH₂)₂OMe | | | |
| OCF₃ | 7-Cl | (CH₂)₂OMe | | | |
| CF₃ | 7-Cl | CH₂SMe | | | |
| OCF₃ | 7-Cl | CH₂SMe | | | |
| CF₃ | 7-Cl | CH₂CO₂Me | | | |
| OCF₃ | 7-Cl | CH₂CO₂Me | | | |
| CF₃ | 7-Cl | CH₂Ph | | | |
| OCF₃ | 7-Cl | CH₂Ph | | | |
| CF₃ | 7-Cl | allyl | | | |
| OCF₃ | 7-Cl | allyl | | | |
| CF₃ | 7-Cl | OMe | | | |
| OCF₃ | 7-Cl | OMe | | | |
| CF₃ | 7-CF₃ | CH₂CN | | | |
| OCF₃ | 7-CF₃ | CH₂CN | | | |
| CF₃ | 7-CF₃ | CH₂OMe | | | |
| OCF₃ | 7-CF₃ | CH₂OMe | | | |
| CF₃ | 7-CF₃ | (CH₂)₂OMe | | | |

TABLE 7

| R¹ | R² | Y | R¹ | R² | Y |
|---|---|---|---|---|---|
| Cl | H | Me | Cl | 6-CF₃ | Me |
| Br | H | Me | Br | 6-CF₃ | Me |
| CF₃ | H | Me | CF₃ | 6-CF₃ | Me |
| OCF₃ | H | Me | OCF₃ | 6-CF₃ | Me |
| OSO₂CF₃ | H | Me | OSO₂CF₃ | 6-CF₃ | Me |
| Cl | H | Et | Cl | 6-CF₃ | Et |
| Br | H | Et | Br | 6-CF₃ | Et |
| CF₃ | H | Et | CF₃ | 6-CF₃ | Et |
| OCF₃ | H | Et | OCF₃ | 6-CF₃ | Et |
| OSO₂CF₃ | H | Et | OSO₂CF₃ | 6-CF₃ | Et |
| Cl | 6-Cl | Me | Cl | 7-Cl | Me |
| Br | 6-Cl | Me | Br | 7-Cl | Me |
| CF₃ | 6-Cl | Me | CF₃ | 7-Cl | Me |
| OCF₃ | 6-Cl | Me | OCF₃ | 7-Cl | Me |
| OSO₂CF₃ | 6-Cl | Me | OSO₂CF₃ | 7-Cl | Me |
| Cl | 6-Cl | Et | Cl | 7-Cl | Et |
| Br | 6-Cl | Et | Br | 7-Cl | Et |
| CF₃ | 6-Cl | Et | CF₃ | 7-Cl | Et |
| OCF₃ | 6-Cl | Et | OCF₃ | 7-Cl | Et |
| OSO₂CF₃ | 6-Cl | Et | OSO₂CF₃ | 7-Cl | Et |
| Cl | 6-F | Me | Cl | 7-F | Me |
| Br | 6-F | Me | Br | 7-F | Me |
| CF₃ | 6-F | Me | CF₃ | 7-F | Me |
| OCF₃ | 6-F | Me | OCF₃ | 7-F | Me |
| OSO₂CF₃ | 6-F | Me | OSO₂CF₃ | 7-F | Me |
| Cl | 6-F | Et | Cl | 7-F | Et |
| Br | 6-F | Et | Br | 7-F | Et |
| CF₃ | 6-F | Et | CF₃ | 7-F | Et |
| OCF₃ | 6-F | Et | OCF₃ | 7-F | Et |
| OSO₂CF₃ | 6-F | Et | OSO₂CF₃ | 7-F | Et |
| Cl | 7-CF₃ | Me | OCF₃ | 7-CF₃ | (CH₂)₂OMe |
| Br | 7-CF₃ | Me | CF₃ | 7-CF₃ | CH₂SMe |
| CF₃ | 7-CF₃ | Me | OCF₃ | 7-CF₃ | CH₂SMe |
| OCF₃ | 7-CF₃ | Me | CF₃ | 7-CF₃ | CH₂CO₂Me |
| OSO₂CF₃ | 7-CF₃ | Me | OCF₃ | 7-CF₃ | CH₂CO₂Me |
| Cl | 7-CF₃ | Et | CF₃ | 7-CF₃ | CH₂Ph |
| Br | 7-CF₃ | Et | OCF₃ | 7-CF₃ | CH₂Ph |
| CF₃ | 7-CF₃ | Et | CF₃ | 7-CF₃ | allyl |
| OCF₃ | 7-CF₃ | Et | OCF₃ | 7-CF₃ | allyl |
| OSO₂CF₃ | 7-CF₃ | Et | | | |
| CF₃ | 7-Cl | CH₂CN | | | |
| OCF₃ | 7-Cl | CH₂CN | | | |
| CF₃ | 7-Cl | CH₂OMe | | | |
| OCF₃ | 7-Cl | CH₂OMe | | | |
| CF₃ | 7-Cl | (CH₂)₂OMe | | | |

TABLE 7-continued

| R¹ | R² | Y |
|---|---|---|
| OCF₃ | 7-Cl | (CH₂)₂OMe |
| CF₃ | 7-Cl | CH₂SMe |
| OCF₃ | 7-Cl | CH₂SMe |
| CF₃ | 7-Cl | CH₂CO₂Me |
| OCF₃ | 7-Cl | CH₂CO₂Me |
| CF₃ | 7-Cl | CH₂Ph |
| OCF₃ | 7-Cl | CH₂Ph |
| CF₃ | 7-Cl | allyl |
| OCF₃ | 7-Cl | allyl |
| CF₃ | 7-CF₃ | CH₂CN |
| OCF₃ | 7-CF₃ | CH₂CN |
| CF₃ | 7-CF₃ | CH₂OMe |
| OCF₃ | 7-CF₃ | CH₂OMe |
| CF₃ | 7-CF₃ | (CH₂)₂OMe |

TABLE 8

| R¹ | R² | Y | R¹ | R² | Y |
|---|---|---|---|---|---|
| Cl | H | Me | Cl | 6-CF₃ | Me |
| Br | H | Me | Br | 6-CF₃ | Me |
| CF₃ | H | Me | CF₃ | 6-CF₃ | Me |
| OCF₃ | H | Me | OCF₃ | 6-CF₃ | Me |
| OSO₂CF₃ | H | Me | OSO₂CF₃ | 6-CF₃ | Me |
| Cl | H | Et | Cl | 6-CF₃ | Et |
| Br | H | Et | Br | 6-CF₃ | Et |
| CF₃ | H | Et | CF₃ | 6-CF₃ | Et |
| OCF₃ | H | Et | OCF₃ | 6-CF₃ | Et |
| OSO₂CF₃ | H | Et | OSO₂CF₃ | 6-CF₃ | Et |
| Cl | 6-Cl | Me | Cl | 7-Cl | Me |
| Br | 6-Cl | Me | Br | 7-Cl | Me |
| CF₃ | 6-Cl | Me | CF₃ | 7-Cl | Me |
| OCF₃ | 6-Cl | Me | OCF₃ | 7-Cl | Me |
| OSO₂CF₃ | 6-Cl | Me | OSO₂CF₃ | 7-Cl | Me |
| Cl | 6-Cl | Et | Cl | 7-Cl | Et |
| Br | 6-Cl | Et | Br | 7-Cl | Et |
| CF₃ | 6-Cl | Et | CF₃ | 7-Cl | Et |
| OCF₃ | 6-Cl | Et | OCF₃ | 7-Cl | Et |
| OSO₂CF₃ | 6-Cl | Et | OSO₂CF₃ | 7-Cl | Et |
| Cl | 6-F | Me | Cl | 7-F | Me |
| Br | 6-F | Me | Br | 7-F | Me |
| CF₃ | 6-F | Me | CF₃ | 7-F | Me |
| OCF₃ | 6-F | Me | OCF₃ | 7-F | Me |
| OSO₂CF₃ | 6-F | Me | OSO₂CF₃ | 7-F | Me |
| Cl | 6-F | Et | Cl | 7-F | Et |
| Br | 6-F | Et | Br | 7-F | Et |
| CF₃ | 6-F | Et | CF₃ | 7-F | Et |
| OCF₃ | 6-F | Et | OCF₃ | 7-F | Et |
| OSO₂CF₃ | 6-F | Et | OSO₂CF₃ | 7-F | Et |
| Cl | 7-CF₃ | Me | OCF₃ | 7-CF₃ | (CH₂)₂OMe |
| Br | 7-CF₃ | Me | CF₃ | 7-CF₃ | CH₂SMe |
| CF₃ | 7-CF₃ | Me | OCF₃ | 7-CF₃ | CH₂SMe |
| OCF₃ | 7-CF₃ | Me | CF₃ | 7-CF₃ | CH₂CO₂Me |
| OSO₂CF₃ | 7-CF₃ | Me | OCF₃ | 7-CF₃ | CH₂CO₂Me |
| Cl | 7-CF₃ | Et | CF₃ | 7-CF₃ | CH₂Ph |
| Br | 7-CF₃ | Et | OCF₃ | 7-CF₃ | CH₂Ph |
| CF₃ | 7-CF₃ | Et | CF₃ | 7-CF₃ | allyl |
| OCF₃ | 7-CF₃ | Et | OCF₃ | 7-CF₃ | allyl |
| OSO₂CF₃ | 7-CF₃ | Et | CF₃ | 7-CF₃ | OMe |
| CF₃ | 7-Cl | CH₂CN | OCF₃ | 7-CF₃ | OMe |
| OCF₃ | 7-Cl | CH₂CN | | | |
| CF₃ | 7-Cl | CH₂OMe | | | |
| OCF₃ | 7-Cl | CH₂OMe | | | |
| CF₃ | 7-Cl | (CH₂)₂OMe | | | |
| OCF₃ | 7-Cl | (CH₂)₂OMe | | | |
| CF₃ | 7-Cl | CH₂SMe | | | |
| OCF₃ | 7-Cl | CH₂SMe | | | |
| CF₃ | 7-Cl | CH₂CO₂Me | | | |
| OCF₃ | 7-Cl | CH₂CO₂Me | | | |
| CF₃ | 7-Cl | CH₂Ph | | | |
| OCF₃ | 7-Cl | CH₂Ph | | | |
| CF₃ | 7-Cl | allyl | | | |
| OCF₃ | 7-Cl | allyl | | | |
| CF₃ | 7-Cl | OMe | | | |
| OCF₃ | 7-Cl | OMe | | | |

TABLE 8-continued

| $R^1$ | $R^2$ | Y | $R^1$ | $R^2$ | Y |
|---|---|---|---|---|---|
| $CF_3$ | 7-$CF_3$ | $CH_2CN$ | | | |
| $OCF_3$ | 7-$CF_3$ | $CH_2CN$ | | | |
| $CF_3$ | 7-$CF_3$ | $CH_2OMe$ | | | |
| $OCF_3$ | 7-$CF_3$ | $CH_2OMe$ | | | |
| $CF_3$ | 7-$CF_3$ | $(CH_2)_2OMe$ | | | |

TABLE 9

| $R^1$ | $R^2$ | $R^3$ | Y | $R^1$ | $R^2$ | $R^3$ | Y |
|---|---|---|---|---|---|---|---|
| Br | 6-F | $CO_2Me$ | $NH_2$ | $CF_3$ | 6-F | $CO_2Me$ | $NH_2$ |
| Br | 6-F | $CO_2Et$ | $NH_2$ | $CF_3$ | 6-F | $CO_2Et$ | $NH_2$ |
| Br | 6-F | Me | $NH_2$ | $CF_3$ | 6-F | Me | $NH_2$ |
| Br | 6-F | n—Pr | $NH_2$ | $CF_3$ | 6-F | n—Pr | $NH_2$ |
| Br | 6-F | i—Pr | $NH_2$ | $CF_3$ | 6-F | i—Pr | $NH_2$ |
| Br | 6-F | 4-F-Ph | $NH_2$ | $CF_3$ | 6-F | 4-F—Ph | $NH_2$ |
| Br | 7-F | $CO_2Me$ | $NH_2$ | $CF_3$ | 7-F | $CO_2Me$ | $NH_2$ |
| Br | 7-F | $CO_2Et$ | $NH_2$ | $CF_3$ | 7-F | $CO_2Et$ | $NH_2$ |
| Br | 7-F | Me | $NH_2$ | $CF_3$ | 7-F | Me | $NH_2$ |
| Br | 7-tr | n—Pr | $NH_2$ | $CF_3$ | 7-F | n—Pr | $NH_2$ |
| Br | 7-F | i—Pr | $NH_2$ | $CF_3$ | 7-F | i—Pr | $NH_2$ |
| Br | 7-F | 4-F—Ph | $NH_2$ | $CF_3$ | 7-F | 4-F—Ph | $NH_2$ |
| Br | 7-Cl | $CO_2Me$ | $NH_2$ | $CF_3$ | 7-Cl | $CO_2Me$ | $NH_2$ |
| Br | 7-Cl | $CO_2Et$ | $NH_2$ | $CF_3$ | 7-Cl | $CO_2Et$ | $NH_2$ |
| Br | 7-Cl | Me | $NH_2$ | $CF_3$ | 7-Cl | Me | $NH_2$ |
| Br | 7-Cl | n—Pr | $NH_2$ | $CF_3$ | 7-Cl | n—Pr | $NH_2$ |
| Br | 7-Cl | i—Pr | $NH_2$ | $CF_3$ | 7-Cl | i—Pr | $NH_2$ |
| Br | 7-Cl | 4-F—Ph | $NH_2$ | $CF_3$ | 7-Cl | 4-F—Ph | $NH_2$ |
| Br | 7-$CF_3$ | $CO_2Me$ | $NH_2$ | $CF_3$ | 7-$CF_3$ | $CO_2Me$ | $NH_2$ |
| Br | 7-$CF_3$ | $CO_2Et$ | $NH_2$ | $CF_3$ | 7-$CF_3$ | $CO_2Et$ | $NH_2$ |
| Br | 7-$CF_3$ | Me | $NH_2$ | $CF_3$ | 7-$CF_3$ | Me | $NH_2$ |
| Br | 7-$CF_3$ | n—Pr | $NH_2$ | $CF_3$ | 7-$CF_3$ | n—Pr | $NH_2$ |
| Br | 7-$CF_3$ | i—Pr | $NH_2$ | $CF_3$ | 7-$CF_3$ | i—Pr | $NH_2$ |
| Br | 7-$CF_3$ | 4-F—Ph | $NH_2$ | $CF_3$ | 7-$CF_3$ | 4-F—Ph | $NH_2$ |
| $OCF_3$ | 6-F | $CO_2Me$ | $NH_2$ | Br | 6-F | $CO_2Me$ | $NH_2$ |
| $OCF_3$ | 6-F | $CO_2Et$ | $NH_2$ | Br | 6-F | $CO_2Et$ | $NH_2$ |
| $OCF_3$ | 6-F | Me | $NH_2$ | Br | 6-F | Me | $NH_2$ |
| $OCF_3$ | 6-F | n—Pr | $NH_2$ | Br | 6-F | n—Pr | $NH_2$ |
| $OCF_3$ | 6-F | i—Pr | $NH_2$ | Br | 6-F | i—Pr | $NH_2$ |
| $OCF_3$ | 6-F | 4-F—Ph | $NH_2$ | Br | 6-F | 4-F—Ph | $NH_2$ |
| $OCF_3$ | 7-F | $CO_2Me$ | $NH_2$ | Br | 7-F | $CO_2Me$ | NHMe |
| $OCF_3$ | 7-F | $CO_2Et$ | $NH_2$ | Br | 7-F | $CO_2Et$ | NHMe |
| $OCF_3$ | 7-F | Me | $NH_2$ | Br | 7-F | Me | NHMe |
| $OCF_3$ | 7-F | n—Pr | $NH_2$ | Br | 7-F | n—Pr | NHMe |
| $OCF_3$ | 7-F | i—Pr | $NH_2$ | Br | 7-F | i—Pr | NHMe |
| $OCF_3$ | 7-F | 4-F—Ph | $NH_2$ | Br | 7-F | 4-F—Ph | NHMe |
| $OCF_3$ | 7-Cl | $CO_2Me$ | $NH_2$ | Br | 7-Cl | $CO_2Me$ | NHMe |
| $OCF_3$ | 7-Cl | $CO_2Et$ | $NH_2$ | Br | 7-Cl | $CO_2Et$ | NHMe |
| $OCF_3$ | 7-Cl | Me | $NH_2$ | Br | 7-Cl | Me | NHMe |
| $OCF_3$ | 7-Cl | n—Pr | $NH_2$ | Br | 7-Cl | n—Pr | NHMe |
| $OCF_3$ | 7-Cl | i—Pr | $NH_2$ | Br | 7-Cl | i—Pr | NHMe |
| $OCF_3$ | 7-Cl | 4-F—Ph | $NH_2$ | Br | 7-Cl | 4-F—Ph | NHMe |
| $OCF_3$ | 7-$CF_3$ | $CO_2Me$ | $NH_2$ | Br | 7-$CF_3$ | $CO_2Me$ | NHMe |
| $OCF_3$ | 7-$CF_3$ | $CO_2Et$ | $NH_2$ | Br | 7-$CF_3$ | $CO_2Et$ | NHMe |
| $OCF_3$ | 7-$CF_3$ | Me | $NH_2$ | Br | 7-$CF_3$ | Me | NHMe |
| $OCF_3$ | 7-$CF_3$ | n—Pr | $NH_2$ | Br | 7-$CF_3$ | n—Pr | NHMe |
| $OCF_3$ | 7-$CF_3$ | i—Pr | $NH_2$ | Br | 7-$CF_3$ | i—Pr | NHMe |
| $OCF_3$ | 7-$CF_3$ | 4-F—Ph | $NH_2$ | Br | 7-$CF_3$ | 4-F—Ph | NHMe |
| $CF_3$ | 6-F | $CO_2Me$ | NHMe | $OCF_3$ | 6-F | $CO_2Me$ | NHMe |
| $CF_3$ | 6-F | $CO_2Et$ | NHMe | $OCF_3$ | 6-F | $CO_2Et$ | NHMe |
| $CF_3$ | 6-F | Me | NHMe | $OCF_3$ | 6-F | Me | NHMe |
| $CF_3$ | 6-F | n—Pr | NHMe | $OCF_3$ | 6-F | n—Pr | NHMe |
| $CF_3$ | 6-F | i—Pr | NHMe | $OCF_3$ | 6-F | i—Pr | NHMe |
| $CF_3$ | 6-F | 4-F—Ph | NHMe | $OCF_3$ | 6-F | 4-F—Ph | NHMe |
| $CF_3$ | 7-F | $CO_2Me$ | NHMe | $OCF_3$ | 7-F | $CO_2Me$ | NHMe |
| $CF_3$ | 7-F | $CO_2Et$ | NHMe | $OCF_3$ | 7-F | $CO_2Et$ | NHMe |
| $CF_3$ | 7-F | Me | NHMe | $OCF_3$ | 7-F | Me | NHMe |
| $CF_3$ | 7-F | n—Pr | NHMe | $OCF_3$ | 7-F | n—Pr | NHMe |
| $CF_3$ | 7-F | i—Pr | NHMe | $OCF_3$ | 7-F | i—Pr | NHMe |
| $CF_3$ | 7-F | 4-F—Ph | NHMe | $OCF_3$ | 7-F | 4-F—Ph | NHMe |
| $CF_3$ | 7-Cl | $CO_2Me$ | NHMe | $OCF_3$ | 7-Cl | $CO_2Me$ | NHMe |
| $CF_3$ | 7-Cl | $CO_2Et$ | NHMe | $OCF_3$ | 7-Cl | $CO_2Et$ | NHMe |
| $CF_3$ | 7-Cl | Me | NHMe | $OCF_3$ | 7-Cl | Me | NHMe |
| $CF_3$ | 7-Cl | n—Pr | NHMe | $OCF_3$ | 7-Cl | n—Pr | NHMe |
| $CF_3$ | 7-Cl | i—Pr | NHMe | $OCF_3$ | 7-Cl | i—Pr | NHMe |

TABLE 9-continued

| R¹ | R² | R³ | Y | R¹ | R² | R³ | Y |
|---|---|---|---|---|---|---|---|
| CF₃ | 7-Cl | 4-F—Ph | NHMe | OCF₃ | 7-Cl | 4-F—Ph | NHMe |
| CF₃ | 7-CF₃ | CO₂Me | NHMe | OCF₃ | 7-CF₃ | CO₂Me | NHMe |
| CF₃ | 7-CF₃ | CO₂Et | NHMe | OCF₃ | 7-CF₃ | CO₂Et | NHMe |
| CF₃ | 7-CF₃ | MO | NHMe | OCF₃ | 7-CF₃ | Me | NHMe |
| CF₃ | 7-CF₃ | n—Pr | NHMe | OCF₃ | 7-CF₃ | n—Pr | NHMe |
| CF₃ | 7-CF₃ | i—Pr | NHHe | OCF₃ | 7-CF₃ | i—Pr | NHMe |
| CF₃ | 7-CF₃ | 4-F—Ph | NHMe | OCF₃ | 7-CF₃ | 4-F—Ph | NHMe |
| Br | 6-F | CO₂Me | NHCHO | CF₃ | 6-F | CO₂Me | NHCHO |
| Br | 6-F | CO₂Et | NHCHO | CF₃ | 6-F | CO₂Et | NHCHO |
| Br | 6-F | Me | NHCHO | CF₃ | 6-F | Me | NHCHO |
| Br | 6-F | n—Pr | NHCHO | CF₃ | 6-F | n—Pr | NHCHO |
| Br | 6-F | i—Pr | NHCHO | CF₃ | 6-F | i—Pr | NHCHO |
| Br | 6-F | 4-F—Ph | NHCHO | CF₃ | 6-F | 4-F—Ph | NHCHO |
| Br | 7-F | CO₂Me | NHCHO | CF₃ | 7-F | CO₂Me | NHCH |
| Br | 7-F | CO₂Et | NHCHO | CF₃ | 7-F | CO₂Et | NHCHO |
| Br | 7-F | Me | NHCHO | CF₃ | 7-F | Me | NHCHO |
| Br | 7-F | n—Pr | NHCHO | CF₃ | 7-F | n—Pr | NHCHO |
| Br | 7-F | i—Pr | NHCHO | CF₃ | 7-F | i—Pr | NHCHO |
| Br | 7-F | 4-F—Ph | NHCHO | CF₃ | 7-F | 4-F—Ph | NHCHO |
| Br | 7-Cl | CO₂Me | NHCHO | CF₃ | 7-Cl | CO₂Me | NHCHO |
| Br | 7-Cl | CO₂Et | NHCHO | CF₃ | 7-Cl | CO₂Et | NHCHO |
| Br | 7-Cl | Me | NHCHO | CF₃ | 7-Cl | Me | NHCHO |
| Br | 7-Cl | n—Pr | NHCHO | CF₃ | 7-Cl | n—Pr | NHCHO |
| Br | 7-Cl | i—Pr | NHCHO | CF₃ | 7-Cl | i—Pr | NHCHO |
| Br | 7-Cl | 4-F—Ph | NHCHO | CF₃ | 7-Cl | 4-F—Ph | NHCHO |
| Br | 7-CF₃ | CO₂Me | NHCHO | CF₃ | 7-CF₃ | CO₂Me | NHCHO |
| Br | 7-CF₃ | CO₂Et | NHCHO | CF₃ | 7-CF₃ | CO₂Et | NHCHO |
| Br | 7-CF₃ | Me | NHCHO | CF₃ | 7-CF₃ | Me | NHCHO |
| Br | 7-CF₃ | n—Pr | NHCHO | CF₃ | 7-CF₃ | n—Pr | NHCHO |
| Br | 7-CF₃ | i—Pr | NHCHO | CF₃ | 7-CF₃ | i—Pr | NHCHO |
| Br | 7-CF₃ | 4-F—Ph | NHCHO | CF₃ | 7-CF₃ | 4-F—Ph | NHCHO |
| OCF₃ | 6-F | CO₂Me | NHCHO | Br | 6-F | CO₂Me | NH(CO)Me |
| OCF₃ | 6-F | CO₂Et | NHCHO | Br | 6-F | CO₂Et | NH(CO)Me |
| OCF₃ | 6-F | Me | NHCHO | ar | 6-F | Me | NH(CO)Me |
| OCF₃ | 6-F | n—Pr | NHCHO | Br | 6-F | n—Pr | NH(CO)Me |
| OCF₃ | 6-F | i—Pr | NHCHO | Br | 6-F | i—Pr | NH(CO)Me |
| OCF₃ | 6-F | 4-F—Ph | NHCHO | Br | 6-F | 4-F—Ph | NH(CO)Me |
| OCF₃ | 7-F | CO₂Me | NHCHO | Br | 7-F | CO₂Men | NH(CO)Me |
| OCF₃ | 7-F | CO₂Et | NHCHO | Br | 7-F | CO₂Et | NH(CO)Me |
| OCF₃ | 7-F | Me | NHCHO | Br | 7-F | Me | NH(CO)Me |
| OCF₃ | 7-F | n—Pr | NHCHO | Br | 7-F | n—Pr | NH(CO)Me |
| OCF₃ | 7-F | i—Pr | NHCHO | Br | 7-F | i—Pr | NH(CO)Me |
| OCF₃ | 7-F | 4-F—Ph | NHCHO | Br | 7-F | 4-F—Ph | NH(CO)Me |
| OCF₃ | 7-Cl | CO₂Me | NHCHO | Br | 7-Cl | CO2Me | NH(CO)Me |
| OCF₃ | 7-Cl | CO₂Et | NHCHO | Br | 7-Cl | CO₂Et | NH(CO)Me |
| OCF₃ | 7-Cl | Me | NHCHO | Br | 7-Cl | Me | NH(CO)Me |
| OCF₃ | 7-Cl | n—Pr | NHCHO | Br | 7-Cl | n—Pr | NH(CO)Me |
| OCF₃ | 7-Cl | i—Pr | NHCHO | Br | 7-Cl | i—Pr | NH(CO)Me |
| OCF₃ | 7-Cl | 4-F—Ph | NHCHO | Br | 7-Cl | 4-F—Ph | NH(CO)Me |
| OCF₃ | 7-CF₃ | CO₂Me | NHCHO | Br | 7-CF₃ | CO₂Me | NH(CO)Me |
| OCF₃ | 7-CF₃ | CO₂Et | NHCHO | Br | 7-CF₃ | CO₂Et | NH(CO)Me |
| OCF₃ | 7-CF₃ | Me | NHCHO | Bz | 7-CF₃ | Me | NH(CO)Me |
| OCF₃ | 7-CF₃ | n—Pr | NHCHO | Br | 7-CF₃ | n—Pr | NH(CO)Me |
| OCF₃ | 7-CF₃ | i—Pr | NHCHO | Br | 7-CF₃ | i—Pr | NH(CO)Me |
| OCF₃ | 7-CF₃ | 4-F—Ph | NHCHO | Br | 7-CF₃ | 4-F—Ph | NH(CO)Me |
| CF₃ | 6-F | CO₂Me | NH(CO)Me | OCF₃ | 6-F | CO₂Me | NH(CO)Me |
| CF₃ | 6-F | CO₂Et | NH(CO)Me | OCF₃ | 6-F | CO₂Et | NH(CO)Me |
| CF₃ | 6-F | Me | NH(CO)Me | OCF₃ | 6-F | Me | NH(CO)Me |
| CF₃ | 6-F | n—Pr | NH(CO)Me | OCF₃ | 6-F | n—Pr | NH(CO)Me |
| CF₃ | 6-F | i—Pr | NH(CO)Me | OCF₃ | 6-F | i—Pr | NH(CO)Me |
| CF₃ | 6-F | 4-F—Ph | NH(CO)Me | OCF₃ | 6-F | 4-F—Ph | NH(CO)Me |
| CF₃ | 7-F | CO₂Me | NH(CO)Me | OCF₃ | 7-F | CO₂Me | NH(CO)Me |
| CF₃ | 7-F | CO₂Et | NH(CO)Me | OCF₃ | 7-F | CO₂Et | NH(CO)Me |
| CF₃ | 7-F | Me | NH(CO)Me | OCF₃ | 7-F | Me | NH(CO)Me |
| CF₃ | 7-F | n—Pr | NH(CO)Me | OCF₃ | 7-F | n—Pr | NH(CO)Me |
| CF₃ | 7-F | i—Pr | NH(CO)Me | OCF₃ | 7-F | i—Pr | NH(CO)Me |
| CF₃ | 7-F | 4-F—Ph | NH(CO)Me | OCF₃ | 7-F | 4-F—Ph | NH(CO)Me |
| CF₃ | 7-Cl | CO₂Me | NH(CO)Me | OCF₃ | 7-Cl | CO₂Me | NH(CO)Me |
| CF₃ | 7-Cl | CO₂Et | NH(CO)Me | OCF₃ | 7-Cl | CO₂Et | NH(CO)Me |
| CF₃ | 7-Cl | Me | NH(CO)Me | OCF₃ | 7-Cl | Me | NH(CO)Me |
| CF₃ | 7-Cl | n—Pr | NH(CO)Me | OCF₃ | 7-Cl | n—Pr | NH(CO)Me |
| CF₃ | 7-Cl | i—Pr | NH(CO)Me | OCF₃ | 7-Cl | i—Pr | NH(CO)Me |
| CF₃ | 7-Cl | 4-F—Ph | NH(CO)Me | OCF₃ | 7-Cl | 4-F—Ph | NH(CO)Me |
| CF₃ | 7-CF₃ | CO₂Me | NH(CO)Me | OCF₃ | 7-CF₃ | CO₂Me | NH(CO)Me |
| CF₃ | 7-CF₃ | CO₂Et | NH(CO)Me | OCF₃ | 7-CF₃ | CO₂Et | NH(CO)Me |
| CF₃ | 7-CF₃ | Me | NH(CO)Me | OCF₃ | 7-CF₃ | Me | NH(CO)Me |
| CF₃ | 7-CF₃ | n—Pr | NH(CO)Me | OCF₃ | 7-CF₃ | n—Pr | NH(CO)Me |

TABLE 9-continued

| R¹ | R² | R³ | Y | R¹ | R² | R³ | Y |
|---|---|---|---|---|---|---|---|
| CF₃ | 7-CF₃ | i—Pr | NH(CO)Me | OCF₃ | 7-CF₃ | i—Pr | NH(CO)Me |
| CF₃ | 7-CF₃ | 4-F—Ph | NH(CO)Me | OCF₃ | 7-CF₃ | 4-F—Ph | NH(CO)Me |
| Br | 6-F | CO₂Me | NH(CO)NHMe | CF₃ | 6-F | CO₂Me | NH(CO)NHMe |
| Br | 6-F | CO₂Et | NH(CO)NHMe | CF₃ | 6-F | CO₂Et | NH(CO)NHMe |
| Br | 6-F | Me | NH(CO)NHMe | CF₃ | 6-F | Me | NH(CO)NHMe |
| Br | 6-F | n—Pr | NH(CO)NHMe | CF₃ | 6-F | n—Pr | NH(CO)NHMe |
| Br | 6-F | i—Pr | NH(CO)NHMe | CF₃ | 6-F | i—Pr | NH(CO)NHMe |
| Br | 6-F | 4-F—Ph | NH(CO)NHMe | CF₃ | 6-F | 4-F—Ph | NH(CO)NHMe |
| Br | 7-F | CO₂Me | NH(CO)NHMe | CF₃ | 7-F | CO₂Me | NH(CO)NHMe |
| Br | 7-F | CO₂Et | NH(CO)NHMe | CF₃ | 7-F | CO₂Et | NH(CO)NHMe |
| Br | 7-F | Me | NH(CO)NHMe | CF₃ | 7-F | Me | NH(CO)NHMe |
| Br | 7-F | n—Pr | NH(CO)NHMe | CF₃ | 7-F | n—Pr | NH(CO)NHMe |
| Br | 7-F | i—Pr | NH(CO)NHMe | CF₃ | 7-F | i—Pr | NH(CO)NHMe |
| Br | 7-F | 4-F—Ph | NH(CO)NHMe | CF₃ | 7-F | 4-F—Ph | NH(CO)NHMe |
| Br | 7-Cl | CO₂Me | NH(CO)NHMe | CF₃ | 7-Cl | CO₂Me | NH(CO)NHMe |
| Br | 7-Cl | CO₂Et | NH(CO)MHMe | CF₃ | 7-Cl | CO₂Et | NH(CO)NHMe |
| Br | 7-Cl | Me | NH(CO)MHMe | CF₃ | 7-Cl | Me | NH(CO)NHMe |
| Br | 7-Cl | n—Pr | NH(CO)NHMe | CF₃ | 7-Cl | n—Pr | NH(CO)NHMe |
| Br | 7-Cl | i—Pr | NH(CO)NHMe | CF₃ | 7-Cl | i—Pr | NH(CO)NHMe |
| Br | 7-Cl | 4-F—Ph | NH(CO)NHMe | CF₃ | 7-Cl | 4-F—Ph | NH(CO)NHMe |
| Br | 7-CF₃ | CO₂Me | NH(CO)NHMe | CF₃ | 7-CF₃ | CO₂Me | NH(CO)NHMe |
| Br | 7-CF₃ | CO₂Et | NH(CO)NHMe | CF₃ | 7-CF₃ | CO₂Et | NH(CO)NHMe |
| Br | 7-CF₃ | Me | NH(CO)NHMe | CF₃ | 7-CF₃ | Me | NH(CO)NHMe |
| Br | 7-CF₃ | n—Pr | NH(CO)NHMe | CF₃ | 7-CF₃ | n—Pr | NH(CO)NHMe |
| Br | 7-CF₃ | i—Pr | NH(CO)NHMe | CF₃ | 7-CF₃ | i—Pr | NH(CO)NHMe |
| Br | 7-CF₃ | 4-F—Ph | NH(CO)NHMe | CF₃ | 7-CF₃ | 4-F—Ph | NH(CO)NHMe |
| OCF₃ | 6-F | CO₂Me | NH(CO)NHMe | Br | 6-F | CO₂Me | N=CH₂ |
| OCF₃ | 6-F | CO₂Et | NH(CO)NHMe | Br | 6-F | CO₂Et | N=CH₂ |
| OCF₃ | 6-F | Me | NH(CO)NHMe | Br | 6-F | Me | N=CH₂ |
| OCF₃ | 6-F | n—Pr | NH(CO)NHMe | Br | 6-F | n—Pr | N=CH₂ |
| OCF₃ | 6-F | i—Pr | NH(CO)NHMe | Br | 6-F | i—Pr | N=CH₂ |
| OCF₃ | 6-F | 4-F—Ph | NH(CO)NHMe | Br | 6-F | 4-F—Ph | N=CH₂ |
| OCF₃ | 7-F | CO₂Me | NH(CO)NHMe | Br | 7-F | CO₂Me | N=CH₂ |
| OCF₃ | 7-F | CO₂Et | NH(CO)NHMe | Br | 7-F | CO₂Et | N=CH₂ |
| OCF₃ | 7-F | Me | NH(CO)NHMe | Br | 7-F | Me | N=CH₂ |
| OCF₃ | 7-F | n—Pr | NH(CO)NHMe | Br | 7-F | n—Pr | N=CH₂ |
| OCF₃ | 7-F | i—Pr | NH(CO)NHMe | Br | 7-F | i—Pr | N=CH₂ |
| OCF₃ | 7-F | 4-F—Ph | NH(CO)NHMe | Br | 7-F | 4-F—Ph | N=CH₂ |
| OCF₃ | 7-Cl | CO₂Me | NH(CO)NHMe | Br | 7-Cl | CO₂Me | N=CH₂ |
| OCF₃ | 7-Cl | CO₂Et | NH(CO)NHMe | Br | 7-Cl | CO₂Et | N=CH₂ |
| OCF₃ | 7-Cl | Me | NH(CO)NHMe | Br | 7-Cl | Me | N=CH₂ |
| OCF₃ | 7-Cl | n—Pr | NH(CO)NHMe | Br | 7-Cl | n—Pr | N=CH₂ |
| OCF₃ | 7-Cl | i—Pr | NH(CO)NHMe | Br | 7-Cl | i—Pr | N=CH₂ |
| OCF₃ | 7-Cl | 4-F—Ph | NH(CO)NHMe | Br | 7-Cl | 4-F—Ph | N=CH₂ |
| OCF₃ | 7-CF₃ | CO₂Me | NH(CO)NHMe | Br | 7-CF₃ | CO₂Me | N=CH₂ |
| OCF₃ | 7-CF₃ | CO₂Et | NH(CO)NHMe | Br | 7-CF₃ | CO₂Et | N=CH₂ |
| OCF₃ | 7-CF₃ | Me | NH(CO)NHMe | Br | 7-CF₃ | Me | N=CH₂ |
| OCF₃ | 7-CF₃ | n—Pr | NH(CO)NHMe | Br | 7-CF₃ | n—Pr | N=CH₂ |
| OCF₃ | 7-CF₃ | i—Pr | NH(CO)NHMe | Br | 7-CF₃ | i—Pr | N=CH₂ |
| OCF₃ | 7-CF₃ | 4-F—Ph | NH(CO)NHMe | Br | 7-CF₃ | 4-F—Ph | N=CH₂ |
| CF₃ | 6-F | CO₂Me | N=CH₂ | OCF₃ | 6-F | CO₂Me | N=CH₂ |
| CF₃ | 6-F | CO₂Et | N=CH₂ | OCF₃ | 6-F | CO₂Et | N=CH₂ |
| CF₃ | 6-T | Me | N=CH₂ | OCF₃ | 6-F | Me | N=CH₂ |
| CF₃ | 6-F | n—Pr | N=CH₂ | OCF₃ | 6-F | n—Pr | N=CH₂ |
| CF₃ | 6-F | i—Pr | N=CH₂ | OCF₃ | 6-F | i—Pr | N=CH₂ |
| CF₃ | 6-F | 4-F—Ph | N=CH₂ | OCF₃ | 6-F | 4-F—Ph | N=CH₂ |
| CF₃ | 7-F | CO₂Me | N=CH₂ | OCF₃ | 7-F | CO₂Me | N=CH₂ |
| CF₃ | 7-F | CO₂Et | N=CH₂ | OCF₃ | 7-F | CO₂Et | N=CH₂ |
| CF₃ | 7-F | Me | N=CH₂ | OCF₃ | 7-F | Me | N=CH₂ |
| CF₃ | 7-F | n—Pr | N=CH₂ | OCF₃ | 7-F | n—Pr | N=CH₂ |
| CF₃ | 7-F | i—Pr | N=CH₂ | OCF₃ | 7-F | i—Pr | N=CH₂ |
| CF₃ | 7-F | 4-F—Ph | N=CH₂ | OCF₃ | 7-F | 4-F—Ph | N=CH₂ |
| CF₃ | 7-Cl | CO₂Me | N=CH₂ | OCF₃ | 7-Cl | CO₂Me | N=CH₂ |
| CF₃ | 7-Cl | CO₂Et | N=CH₂ | OCF₃ | 7-Cl | CO₂Et | N=CH₂ |
| CF₃ | 7-Cl | Me | N=CH₂ | OCF₃ | 7-Cl | Me | N=CH₂ |
| CF₃ | 7-Cl | n—Pr | N=CH₂ | OCF₃ | 7-Cl | n—Pr | N=CH₂ |
| CF₃ | 7-Cl | i—Pr | N=CH₂ | OCF₃ | 7-C | i—Pr | N=CH₂ |
| CF₃ | 7-Cl | 4-F—Ph | N=CH₂ | OCF₃ | 7-Cl | 4-F—Ph | N=CH₂ |
| CF₃ | 7-CF₃ | CO₂Me | N=CH₂ | OCF₃ | 7-CF₃ | CO₂Me | N=CH₂ |
| CF₃ | 7 CF₃ | CO₂Et | N=CH₂ | OCF₃ | 7-CF₃ | CO₂Et | N=CH₂ |
| CF₃ | 7-CF₃ | Me | N=CH₂ | OCF₃ | 7-CF₃ | Me | N=CH₂ |
| CF₃ | 7-CF₃ | n—Pr | N=CH₂ | OCF₃ | 7-CF₃ | n—Pr | N=CH₂ |
| CF₃ | 7-CF₃ | i—Pr | N=CH₂ | OCF₃ | 7-CF₃ | i—Pr | N=CH₂ |
| CF₃ | 7-CF₃ | 4-F—Ph | N=CH₂ | OCF₃ | 7-CF₃ | 4-F—Ph | N=CH₂ |
| Br | 6-F | CO₂Me | N=CH₂ | CF₃ | 6-F | CO₂Me | N=CMe₂ |
| Br | 6-F | CO₂Et | N=CH₂ | CF₃ | 6-F | CO₂Et | N=CMe₂ |
| Br | 6-F | Me | N=CH₂ | CF₃ | 6-F | Me | N=CMe₂ |

TABLE 9-continued

| $R^1$ | $R^2$ | $R^3$ | Y | $R^1$ | $R^2$ | $R^3$ | Y |
|---|---|---|---|---|---|---|---|
| Br | 6-F | n—Pr | N=CH$_2$ | CF$_3$ | 6-F | n—Pr | N=CMe$_2$ |
| Br | 6-F | i—Pr | N=CH$_2$ | CF$_3$ | 6-F | i—Pr | N=CMe$_2$ |
| Br | 6-F | 4-F—Ph | N=CH$_2$ | CF$_3$ | 6-F | 4-F—Ph | N=CMe$_2$ |
| Br | 7-F | CO$_2$Me | N=CH$_2$ | CF$_3$ | 7-F | CO$_2$Me | N=CMe$_2$ |
| Br | 7-F | CO$_2$Et | N=CH$_2$ | CF$_3$ | 7-F | CO$_2$Et | N=CMe$_2$ |
| Br | 7-F | Me | N=CH$_2$ | CF$_3$ | 7-F | Me | N=CMe$_2$ |
| Br | 7-F | n—Pr | N=CH$_2$ | CF$_3$ | 7-F | n—Pr | N=CMe$_2$ |
| Br | 7-F | i—Pr | N=CH$_2$ | CF$_3$ | 7-F | i—Pr | N=CMe$_2$ |
| Br | 7-F | 4-F—Ph | N=CH$_2$ | CF$_3$ | 7-F | 4-F—Ph | N=CMe$_2$ |
| Br | 7-Cl | CO$_2$Me | N=CH$_2$ | CF$_3$ | 7-Cl | CO$_2$Me | N=CMe$_2$ |
| Br | 7-Cl | CO$_2$Et | N=CH$_2$ | CF$_3$ | 7-Cl | CO$_2$Et | N=CMe$_2$ |
| Br | 7-Cl | Me | N=CH$_2$ | CF$_3$ | 7-Cl | Me | N=CMe$_2$ |
| Br | 7-Cl | n—Pr | N=CH$_2$ | CF$_3$ | 7-Cl | n—Pr | N=CMe$_2$ |
| Br | 7-Cl | i—Pr | N=CH$_2$ | CF$_3$ | 7-Cl | i—Pr | N=CMe$_2$ |
| Br | 7-Cl | 4-F—Ph | N=CH$_2$ | CF$_3$ | 7-Cl | 4-F—Ph | N=CMe$_2$ |
| Br | 7-CF$_3$ | CO$_2$Me | N=CH$_2$ | CF$_3$ | 7-CF$_3$ | CO$_2$Me | N=CMe$_2$ |
| Br | 7-CF$_3$ | CO$_2$Et | N=CH$_2$ | CF$_3$ | 7-CF$_3$ | CO$_2$Et | N=CMe$_2$ |
| Br | 7-CF$_3$ | Me | N=CH$_2$ | CF$_3$ | 7-CF$_3$ | Me | N=CMe$_2$ |
| Br | 7-CF$_3$ | n—Pr | N=CH$_2$ | CF$_3$ | 7-CF$_3$ | n—Pr | N=CMe$_2$ |
| Br | 7-CF$_3$ | i—Pr | N=CH$_2$ | CF$_3$ | 7-CF$_3$ | i—Pr | N=CMe$_2$ |
| Br | 7-CF$_3$ | 4-F—Ph | N=CH$_2$ | CF$_3$ | 7-CF$_3$ | 4-F—Ph | N=CMe$_2$ |
| OCF$_3$ | 6-F | CO$_2$Me | N=CMe$_2$ | Br | 6-F | CO$_2$Me | N=CHPh |
| OCF$_3$ | 6-F | CO$_2$Et | N=CMe$_2$ | Br | 6-F | CO$_2$Et | N=CHPh |
| OCF$_3$ | 6-F | Me | N=CMe$_2$ | Br | 6-F | Me | N=CHPh |
| OCF$_3$ | 6-F | n—Pr | N=CMe$_2$ | Br | 6-F | n—Pr | N=CHPh |
| OCF$_3$ | 6-F | i—Pr | N=CMe$_2$ | Br | 6-F | i—Pr | N=CHPh |
| OCF$_3$ | 6-F | 4-F—Ph | N=CMe$_2$ | Br | 6-F | 4-F—Ph | N=CHPh |
| OCF$_3$ | 7-F | CO$_2$Me | N=CMe$_2$ | Br | 7-F | CO$_2$Me | N=CHPh |
| OCF$_3$ | 7-F | CO$_2$Et | N=CMe$_2$ | Br | 7-F | CO$_2$Et | N=CHPh |
| OCF$_3$ | 7-F | Me | N=CMe$_2$ | Br | 7-F | Me | N=CHPh |
| OCF$_3$ | 7-F | n—Pr | N=CMe$_2$ | Br | 7-F | n—Pr | N=CHPh |
| OCF$_3$ | 7-F | i—Pr | N=CMe$_2$ | Br | 7-F | i—Pr | N=CHPh |
| OCF$_3$ | 7-F | 4-F—Ph | N=CMe$_2$ | Br | 7-F | 4-F—Ph | N=CHPh |
| OCF$_3$ | 7-Cl | CO$_2$Me | N=CMe$_2$ | Br | 7-Cl | CO$_2$Me | N=CHPh |
| OCF$_3$ | 7-Cl | CO$_2$Et | N=CMe$_2$ | Br | 7-Cl | CO$_2$Et | N=CHPh |
| OCF$_3$ | 7-Cl | Me | N=CMe$_2$ | Br | 7-Cl | Me | N=CHPh |
| OCF$_3$ | 7-Cl | n—Pr | N=CMe$_2$ | Br | 7-Cl | n—Pr | N=CHPh |
| OCF$_3$ | 7-Cl | i—Pr | N=CMe$_2$ | Br | 7-Cl | i—Pr | N=CHPh |
| OCF$_3$ | 7-Cl | 4-F—Ph | N=CMe$_2$ | Br | 7-Cl | 4-F—Ph | N=CHPh |
| OCF$_3$ | 7-CF$_3$ | CO$_2$Me | N=CMe$_2$ | Br | 7-CF$_3$ | CO$_2$Me | N=CHPh |
| OCF$_3$ | 7-CF$_3$ | CO$_2$Et | N=CMe$_2$ | Br | 7-CF$_3$ | CO$_2$Et | N=CHPh |
| OCF$_3$ | 7-CF$_3$ | Me | N=CMe$_2$ | Br | 7-CF$_3$ | Me | N=CHPh |
| OCF$_3$ | 7-CF$_3$ | n—Pr | N=CMe$_2$ | Br | 7-CF$_3$ | n—Pr | N=CHPh |
| OCF$_3$ | 7-CF$_3$ | i—Pr | N=CMe$_2$ | Br | 7-CF$_3$ | i—Pr | N=CHPh |
| OCF$_3$ | 7-CF$_3$ | 4-F—Ph | N=CMe$_2$ | Br | 7-CF$_3$ | 4-F—Ph | N=CHPh |
| CF$_3$ | 6-F | CO$_2$Me | N=CHPh | OCF$_3$ | 6-F | CO$_2$Me | N=CHPh |
| CF$_3$ | 6-F | CO$_2$Et | N=CHPh | OCF$_3$ | 6-F | CO$_2$Et | N=CHPh |
| CF$_3$ | 6-F | Me | N=CHPh | OCF$_3$ | 6-F | Me | N=CHPh |
| CF$_3$ | 6-F | n—Pr | N=CHPh | OCF$_3$ | 6-F | n—Pr | N=CHPh |
| CF$_3$ | 6-F | i—Pr | N=CHPh | OCF$_3$ | 6-F | i—Pr | N=CHPh |
| CF$_3$ | 6-F | 4-F—Ph | N=CHPh | OCF$_3$ | 6-F | 4-F—Ph | N=CHPh |
| CF$_3$ | 7-F | CO$_2$Me | N=CHPh | OCF$_3$ | 7-F | CO$_2$Me | N=CHPh |
| CF$_3$ | 7-F | CO$_2$Et | N=CHPh | OCF$_3$ | 7-F | CO$_2$Et | N=CHPh |
| CF$_3$ | 7-F | Me | N=CHPh | OCF$_3$ | 7-F | Me | N=CHPh |
| CF$_3$ | 7-F | n—Pr | N=CHPh | OCF$_3$ | 7-F | n—Pr | N=CHPh |
| CF$_3$ | 7-F | i—Pr | N=CHPh | OCF$_3$ | 7-F | i—Pr | N=CHPh |
| CF$_3$ | 7-F | 4-F—Ph | N=CHPh | OCF$_3$ | 7-F | 4-F—Ph | N=CHPh |
| CF$_3$ | 7-Cl | CO$_2$Me | N=CHPh | OCF$_3$ | 7-Cl | CO$_2$Me | N=CHPh |
| CF$_3$ | 7-Cl | CO$_2$Et | N=CHPh | OCF$_3$ | 7-Cl | CO$_2$Et | N=CHPh |
| CF$_3$ | 7-Cl | Me | N=CHPh | OCF$_3$ | 7-Cl | Me | N=CHPh |
| CF$_3$ | 7-Cl | n—Pr | N=CHPh | OCF$_3$ | 7-Cl | n—Pr | N=CHPh |
| CF$_3$ | 7-Cl | i—Pr | N=CHPh | OCF$_3$ | 7-Cl | i—Pr | N=CHPh |
| CF$_3$ | 7-Cl | 4-F—Ph | N=CHPh | OCF$_3$ | 7-Cl | 4-F—Ph | N=CHPh |
| CF$_3$ | 7-CF$_3$ | CO$_2$Me | N=CHPh | OCF$_3$ | 7-CF$_3$ | CO$_2$Me | N=CHPh |
| CF$_3$ | 7-CF$_3$ | CO$_2$Et | N=CHPh | OCF$_3$ | 7-CF$_3$ | CO$_2$Et | N=CHPh |
| CF$_3$ | 7-CF$_3$ | Me | N=CHPh | OCF$_3$ | 7-CF$_3$ | Me | N=CHPh |
| CF$_3$ | 7-CF$_3$ | n—Pr | N=CHPh | OCF$_3$ | 7-CF$_3$ | n—Pr | N=CHPh |
| CF$_3$ | 7-CF$_3$ | i—Pr | N=CHPh | OCF$_3$ | 7-CF$_3$ | i—Pr | N=CHPh |
| CF$_3$ | 7-CF$_3$ | 4-F—Ph | N=CHPh | OCF$_3$ | 7-CF$_3$ | 4-F—Ph | N=CHPh |
| Br | 6-F | CO$_2$Me | NH(CO)CF$_3$ | CF$_3$ | 6-F | CO$_2$Me | NH(CO)CF$_3$ |
| Br | 6-F | CO$_2$Et | NH(CO)CF$_3$ | CF$_3$ | 6-F | CO$_2$Et | NH(CO)CF$_3$ |
| Br | 6-F | Me | NH(CO)CF$_3$ | CF$_3$ | 6-F | Me | NH(CO)CF$_3$ |
| Br | 6-F | n—Pr | NH(CO)CF$_3$ | CF$_3$ | 6-F | n—Pr | NH(CO)CF$_3$ |
| Br | 6-F | i—Pr | NH(CO)CF$_3$ | CF$_3$ | 6-F | i—Pr | NH(CO)CF$_3$ |
| Br | 6-F | 4-F—Ph | NH(CO)CF$_3$ | CF$_3$ | 6-F | 4-F—Ph | NH(CO)CF$_3$ |
| Br | 7-F | CO$_2$Me | NH(CO)CF$_3$ | CF$_3$ | 7-F | CO$_2$Me | NH(CO)CF$_3$ |
| Br | 7-F | CO$_2$Et | NH(CO)CF$_3$ | CF$_3$ | 7-F | CO$_2$Et | NH(CO)CF$_3$ |

TABLE 9-continued

| R¹ | R² | R³ | Y | R¹ | R² | R³ | Y |
|---|---|---|---|---|---|---|---|
| Br | 7-F | Me | NH(CO)CF₃ | CF₃ | 7-F | Me | NH(CO)CF₃ |
| Br | 7-F | n—Pr | NH(CO)CF₃ | CF₃ | 7-F | n—Pr | NH(CO)CF₃ |
| Br | 7-F | i—Pr | NH(CO)CF₃ | CF₃ | 7-F | i—Pr | NH(CO)CF₃ |
| Br | 7-F | 4-F—Ph | NH(CO)CF₃ | CF₃ | 7-F | 4-F—Ph | NH(CO)CF₃ |
| Br | 7-Cl | CO₂Me | NH(CO)CF₃ | CF₃ | 7-Cl | CO₂Me | NH(CO)CF₃ |
| Br | 7-Cl | CO₂Et | NH(CO)CF₃ | CF₃ | 7-Cl | CO₂Et | NH(CO)CF₃ |
| Br | 7-Cl | Me | NH(CO)CF₃ | CF₃ | 7-Cl | Me | NH(CO)CF₃ |
| Br | 7-Cl | n—Pr | NH(CO)CF₃ | CF₃ | 7-Cl | n—Pr | NH(CO)CF₃ |
| Br | 7-Cl | i—Pr | NH(CO)CF₃ | CF₃ | 7-Cl | i—Pr | NH(CO)CF₃ |
| Br | 7-Cl | 4-F—Ph | NH(CO)CF₃ | CF₃ | 7-Cl | 4-F—Ph | NH(CO)CF₃ |
| Br | 7-CF₃ | CO₂Me | NH(CO)CF₃ | CF₃ | 7-CF₃ | CO₂Me | NH(CO)CF₃ |
| Br | 7-CF₃ | CO₂Et | NH(CO)CF₃ | CF₃ | 7-CF₃ | CO₂Et | NH(CO)CF₃ |
| Br | 7-CF₃ | Me | NH(CO)CF₃ | CF₃ | 7-CF₃ | Me | NH(CO)CF₃ |
| Br | 7-CF₃ | n—Pr | NH(CO)CF₃ | CF₃ | 7-CF₃ | n—Pr | NH(CO)CF₃ |
| Br | 7-CF₃ | i—Pr | NH(CO)CF₃ | CF₃ | 7-CF₃ | i—Pr | NH(CO)CF₃ |
| Br | 7-CF₃ | 4-F—Ph | NH(CO)CF₃ | CF₃ | 7-CF₃ | 4-F—Ph | NH(CO)CF₃ |
| OCF₃ | 6-F | CO₂Me | NH(CO)CF₃ | Br | 6-F | CO₂Me | OH |
| OCF₃ | 6-F | CO₂Et | NH(CO)CF₃ | Br | 6-F | CO₂Et | OH |
| OCF₃ | 6-F | Me | NH(CO)CF₃ | Br | 6-F | Me | OH |
| OCF₃ | 6-F | n—Pr | NH(CO)CF₃ | Br | 6-F | n—Pr | OH |
| OCF₃ | 6-F | i—Pr | NH(CO)CF₃ | Br | 6-F | i—Pr | OH |
| OCF₃ | 6-F | 4-F—Ph | NH(CO)CF₃ | Br | 6-F | 4-F—Ph | OH |
| OCF₃ | 7-F | CO₂Me | NH(CO)CF₃ | Br | 7-F | CO₂Me | OH |
| OCF₃ | 7-F | CO₂Et | NH(CO)CF₃ | Br | 7-F | CO₂Et | OH |
| OCF₃ | 7-F | Me | NH(CO)CF₃ | Br | 7-F | Me | OH |
| OCF₃ | 7-F | n—Pr | NH(CO)CF₃ | Br | 7-F | n—Pr | OH |
| OCF₃ | 7-F | i—Pr | NH(CO)CF₃ | Br | 7-F | i—Pr | OH |
| OCF₃ | 7-F | 4-F—Ph | NH(CO)CF₃ | Br | 7-F | 4-F—Ph | OH |
| OCF₃ | 7-Cl | CO₂Me | NH(CO)CF₃ | Br | 7-Cl | CO₂Me | OH |
| OCF₃ | 7-Cl | CO₂Et | NH(CO)CF₃ | Br | 7-Cl | CO₂Et | OH |
| OCF₃ | 7-Cl | Me | NH(CO)CF₃ | Br | 7-Cl | Me | OH |
| OCF₃ | 7-Cl | n—Pr | NH(CO)CF₃ | Br | 7-Cl | n—Pr | OH |
| OCF₃ | 7-Cl | i—Pr | NH(CO)CF₃ | Br | 7-Cl | i—Pr | OH |
| OCF₃ | 7-Cl | 4-F—Ph | NH(CO)CF₃ | Br | 7-Cl | 4-F—Ph | OH |
| OCF₃ | 7-CF₃ | CO₂Me | NH(CO)CF₃ | Br | 7-CF₃ | CO₂Me | OH |
| OCF₃ | 7-CF₃ | CO₂Et | NH(CO)CF₃ | Br | 7-CF₃ | CO₂Et | OH |
| OCF₃ | 7-CF₃ | Me | NH(CO)CF₃ | Br | 7-CF₃ | Me | OH |
| OCF₃ | 7-CF₃ | n—Pr | NH(CO)CF₃ | Br | 7-CF₃ | n—Pr | OH |
| OCF₃ | 7-CF₃ | i—Pr | NH(CO)CF₃ | Br | 7-CF₃ | i—Pr | OH |
| OCF₃ | 7-CF₃ | 4-F—Ph | NH(CO)CF₃ | Br | 7-CF₃ | 4-F—Ph | OH |
| CF₃ | 6-F | CO₂Me | OH | OCF₃ | 6-F | CO₂Me | OH |
| CF₃ | 6-F | CO₂Et | OH | OCF₃ | 6-F | CO₂Et | OH |
| CF₃ | 6-F | Me | OH | OCF₃ | 6-F | Me | OH |
| CF₃ | 6-F | n—Pr | OH | OCF₃ | 6-F | n—Pr | OH |
| CF₃ | 6-F | i—Pr | OH | OCF₃ | 6-F | i—Pr | OH |
| CF₃ | 6-F | 4-F—Ph | OH | OCF₃ | 6-F | 4-F—Ph | OH |
| CF₃ | 7-F | CO₂Me | OH | OCF₃ | 7-F | CO₂Me | OH |
| CF₃ | 7-F | CO₂Et | OH | OCF₃ | 7-F | CO₂Et | OH |
| CF₃ | 7-F | Me | OH | OCF₃ | 7-r | Me | OH |
| CF₃ | 7-F | n—Pr | OH | OCF₃ | 7-F | n—Pr | OH |
| CF₃ | 7-F | i—Pr | OH | OCF₃ | 7-F | i—Pr | OH |
| CF₃ | 7-F | 4-F—Ph | OH | OCF₃ | 7-F | 4-F—Ph | OH |
| CF₃ | 7-Cl | CO₂Me | OH | OCF₃ | 7-Cl | CO₂Me | OH |
| CF₃ | 7-Cl | CO₂Et | OH | OCF₃ | 7-Cl | CO₂Et | OH |
| CF₃ | 7-Cl | Me | OH | OCF₃ | 7-Cl | Me | OH |
| CF₃ | 7-Cl | n—Pr | OH | OCF₃ | 7-Cl | n—Pr | OH |
| CF₃ | 7-Cl | i—Pr | OH | OCF₃ | 7-Cl | i—Pr | OH |
| CF₃ | 7-Cl | 4-F—Ph | OH | OCF₃ | 7-Cl | 4-F—Ph | OH |
| CF₃ | 7-CF₃ | CO₂Me | OH | OCF₃ | 7-CF₃ | CO₂Me | OH |
| CF₃ | 7-CF₃ | CO₂Et | OH | OCF₃ | 7-CF₃ | CO₂Et | OH |
| CF₃ | 7-CF₃ | Me | OH | OCF₃ | 7-CF₃ | Me | OH |
| CF₃ | 7-CF₃ | n—Pr | OH | OCF₃ | 7-CF₃ | n—Pr | OH |
| CF₃ | 7-CF₃ | i—Pr | OH | OCF₃ | 7-CF₃ | i—Pr | OH |
| CF₃ | 7-CF₃ | 4-F—Ph | OH | OCF₃ | 7-CF₃ | 4-F—Ph | OH |
| Br | 6-F | CO₂Me | OMe | CF₃ | 6-F | CO₂Me | OMe |
| Br | 6-F | CO₂Et | OMe | CF₃ | 6-F | CO₂Et | OMe |
| Br | 6-F | Me | OMe | CF₃ | 6-F | Me | OMe |
| Br | 6-F | n—Pr | OMe | CF₃ | 6-F | n—Pr | OMe |
| Br | 6-F | i—Pr | OMe | CF₃ | 6-F | i—Pr | OMe |
| Br | 6-F | 4-F—Ph | OMe | CF₃ | 6-F | 4-F—Ph | OMe |
| Br | 7-F | CO₂Me | OMe | CF₃ | 7-F | CO₂Me | OMe |
| Br | 7-F | CO₂Et | OMe | CF₃ | 7-F | CO₂Et | OMe |
| Br | 7-F | Me | OMe | CF₃ | 7-F | Me | OMe |
| Br | 7-F | n—Pr | OMe | CF₃ | 7-F | n—Pr | OMe |
| Br | 7-F | i—Pr | OMe | CF₃ | 7-F | i—Pr | OMe |
| Br | 7-F | 4-F—Ph | OMe | CF₃ | 7-F | 4-F—Ph | OMe |
| Br | 7-Cl | CO₂Me | OMe | CF₃ | 7-Cl | CO₂Me | OMe |

TABLE 9-continued

| R¹ | R² | R³ | Y | R¹ | R² | R³ | Y |
|---|---|---|---|---|---|---|---|
| Br | 7-Cl | CO₂Et | OMe | CF₃ | 7-Cl | CO₂Et | OMe |
| Br | 7-Cl | Me | OMe | CF₃ | 7-Cl | Me | OMe |
| Br | 7-Cl | n—Pr | OMe | CF₃ | 7-Cl | n—Pr | OMe |
| Br | 7-Cl | i—Pr | OMe | CF₃ | 7-Cl | i—Pr | OMe |
| Br | 7-Cl | 4-F—Ph | OMe | CF₃ | 7-Cl | 4-F—Ph | OMe |
| Br | 7-CF₃ | CO₂Me | OMe | CF₃ | 7-CF₃ | CO₂Me | OMe |
| Br | 7-CF₃ | CO₂Et | OMe | CF₃ | 7-CF₃ | CO₂Et | OMe |
| Br | 7-CF₃ | Me | OMe | CF₃ | 7-CF₃ | Me | OMe |
| Br | 7-CF₃ | n—Pr | OMe | CF₃ | 7-CF₃ | n—Pr | OMe |
| Br | 7-CF₃ | i—Pr | OMe | CF₃ | 7-CF₃ | i—Pr | OMe |
| Br | 7-CF₃ | 4-F—Ph | OMe | CF₃ | 7-CF₃ | 4-F—Ph | OMe |
| OCF₃ | 6-F | CO₂Me | OMe | Br | 6-F | CO₂Me | OCH₂Ph |
| OCF₃ | 6-F | CO₂Et | OMe | Br | 6-F | CO₂Et | OCH₂Ph |
| OCF₃ | 6-F | Me | OMe | Br | 6-F | Me | OCH₂Ph |
| OCF₃ | 6-F | n—Pr | OMe | Br | 6-F | n—Pr | OCH₂Ph |
| OCF₃ | 6-F | i—Pr | OMe | Br | 6-F | i—Pr | OCH₂Ph |
| OCF₃ | 6-F | 4-F—Ph | OMe | Br | 6-F | 4-F—Ph | OCH₂Ph |
| OCF₃ | 7-F | CO₂Me | OMe | Br | 7-F | CO₂Me | OCH₂Ph |
| OCF₃ | 7-F | CO₂Et | OMe | Br | 7-F | CO₂Et | OCH₂Ph |
| OCF₃ | 7-F | Me | OMe | Br | 7-F | Me | OCH₂Ph |
| OCF₃ | 7-F | n—Pr | OMe | Br | 7-F | n—Pr | OCH₂Ph |
| OCF₃ | 7-F | i—Pr | OMe | Br | 7-F | i—Pr | OCH₂Ph |
| OCF₃ | 7-F | 4-F—Ph | OMe | Br | 7-F | 4-F—Ph | OCH₂Ph |
| OCF₃ | 7-Cl | CO₂Me | OMe | Br | 7-Cl | CO₂Me | OCH₂Ph |
| OCF₃ | 7-Cl | CO₂Et | OMe | Br | 7-Cl | CO₂Et | OCH₂Ph |
| OCF₃ | 7-Cl | Me | OMe | Br | 7-Cl | Me | OCH₂Ph |
| OCF₃ | 7-Cl | n—Pr | OMe | Br | 7-Cl | n—Pr | OCH₂Ph |
| OCF₃ | 7-Cl | i—Pr | OMe | Br | 7-Cl | i—Pr | OCH₂Ph |
| OCF₃ | 7-Cl | 4-F—Ph | OMe | Br | 7-Cl | 4-F—Ph | OCH₂Ph |
| OCF₃ | 7-CF₃ | CO₂Me | OMe | Br | 7-CF₃ | CO₂Me | OCH₂Ph |
| OCF₃ | 7-CF₃ | CO₂Et | OMe | Br | 7-CF₃ | CO₂Et | OCH₂Ph |
| OCF₃ | 7-CF₃ | Me | OMe | Br | 7-CF₃ | Me | OCH₂Ph |
| OCF₃ | 7-CF₃ | n—Pr | OMe | Br | 7-CF₃ | n—Pr | OCH₂Ph |
| OCF₃ | 7-CF₃ | i—Pr | OMe | Br | 7-CF₃ | i—Pr | OCH₂Ph |
| OCF₃ | 7-CF₃ | 4-F—Ph | OMe | Br | 7-CF₃ | 4-F—Ph | OCH₂Ph |
| CF₃ | 6-F | CO₂Me | OCH₂Ph | OCF₃ | 6-F | CO₂Me | OCH₂Ph |
| CF₃ | 6-F | CO₂Et | OCH₂Ph | OCF₃ | 6-F | CO₂Et | OCH₂Ph |
| CF₃ | 6-F | Me | OCH₂Ph | OCF₃ | 6-F | Me | OCH₂Ph |
| CF₃ | 6-F | n—Pr | OCH₂Ph | OCF₃ | 6-F | n—Pr | OCH₂Ph |
| CF₃ | 6-F | i—Pr | OCH₂Ph | OCF₃ | 6-F | i—Pr | OCH₂Ph |
| CF₃ | 6-F | 4-F—Ph | OCH₂Ph | OCF₃ | 6-F | 4-F—Ph | OCH₂Ph |
| CF₃ | 7-F | CO₂Me | OCH₂Ph | OCF₃ | 7-F | CO₂Me | OCH₂Ph |
| CF₃ | 7-F | CO₂Et | OCH₂Ph | OCF₃ | 7-F | CO₂Et | OCH₂Ph |
| CF₃ | 7-F | Me | OCH₂Ph | OCF₃ | 7-F | Me | OCH₂Ph |
| CF₃ | 7-F | n—Pr | OCH₂Ph | OCF₃ | 7-F | n—Pr | OCH₂Ph |
| CF₃ | 7-F | i—Pr | OCH₂Ph | OCF₃ | 7-F | i—Pr | OCH₂Ph |
| CF₃ | 7-F | 4-F—Ph | OCH₂Ph | OCF₃ | 7-F | 4-F—Ph | OCH₂Ph |
| CF₃ | 7-Cl | CO₂Me | OCH₂Ph | OCF₃ | 7-Cl | CO₂Me | OCH₂Ph |
| CF₃ | 7-Cl | CO₂Et | OCH₂Ph | OCF₃ | 7-Cl | CO₂Et | OCH₂Ph |
| CF₃ | 7-Cl | Me | OCH₂Ph | OCF₃ | 7-Cl | Me | OCH₂Ph |
| CF₃ | 7-Cl | n—Pr | OCH₂Ph | OCF₃ | 7-Cl | n—Pr | OCH₂Ph |
| CF₃ | 7-Cl | i—Pr | OCH₂Ph | OCF₃ | 7-Cl | i—Pr | OCH₂Ph |
| CF₃ | 7-Cl | 4-F—Ph | OCH₂Ph | OCF₃ | 7-Cl | 4-F—Ph | OCH₂Ph |
| CF₃ | 7-CF₃ | CO₂Me | OCH₂Ph | OCF₃ | 7-CF₃ | CO₂Me | OCH₂Ph |
| CF₃ | 7-CF₃ | CO₂Et | OCH₂Ph | OCF₃ | 7-CF₃ | CO₂Et | OCH₂Ph |
| CF₃ | 7-CF₃ | Me | OCH₂Ph | OCF₃ | 7-CF₃ | Me | OCH₂Ph |
| CF₃ | 7-CF₃ | n—Pr | OCH₂Ph | OCF₃ | 7-CF₃ | n—Pr | OCH₂Ph |
| CF₃ | 7-CF₃ | i—Pr | OCH₂Ph | OCF₃ | 7-CF₃ | i—Pr | OCH₂Ph |
| CF₃ | 7-CF₃ | 4-F—Ph | OCH₂Ph | OCF₃ | 7-CF₃ | 4-F—Ph | OCH₂Ph |

TABLE 10

| R¹ | R² | R³ | Y | R¹ | R² | R³ | Y |
|---|---|---|---|---|---|---|---|
| CF₃ | 7-CF₃ | CO₂Me | NHSO₂Me | CF₃ | 7-CF₃ | CO₂Me | NMe(CHO) |
| OCF₃ | 7-CF₃ | CO₂Me | NHSO₂Me | OCF₃ | 7-CF₃ | CO₂Me | NMe(CHO) |
| CF₃ | 7-Cl | i—Pr | NHSO₂Me | CF₃ | 7-Cl | i—Pr | NMe(CHO) |
| OCF₃ | 7-Cl | i—Pr | NHSO₂Me | OCF₃ | 7-Cl | i—Pr | NMe(CHO) |
| CF₃ | 7-CF₃ | 4-F—Ph | NHSO₂Me | CF₃ | 7-CF₃ | 4-F—Ph | NMe(CHO) |
| OCF₃ | 7-CF₃ | 4-F—Ph | NHSO₂Me | OCF₃ | 7-CF₃ | 4-F—Ph | NHe(CHO) |
| CF₃ | 7-CF₃ | CO₂Me | NHSO₂Ph | CF₃ | 7-CF₃ | CO₂Me | NMe(CO)ME |
| OCF₃ | 7-CF₃ | CO₂Me | NHSO₂Ph | OCF₃ | 7-CF₃ | CO₂Me | NMe(CO)ME |
| CF₃ | 7-Cl | i—Pr | NHSO₂Ph | CF₃ | 7-Cl | i—Pr | NMe(CO)Me |
| OCF₃ | 7-Cl | i—Pr | NHSO₂Ph | OCF₃ | 7-Cl | i—Pr | NMe(CO)Me |
| CF₃ | 7-CF₃ | 4-F—Ph | NHSO₂Ph | CF₃ | 7-CF₃ | 4-F—Ph | NME(CO)Me |

TABLE 10-continued

| R¹ | R² | R³ | Y | R¹ | R² | R³ | Y |
|---|---|---|---|---|---|---|---|
| OCF₃ | 7-CF₃ | 4-F—Ph | NHSO₂Ph | OCF₃ | 7-CF₃ | 4-F—Ph | NME(CO)Me |
| CF₃ | 7-CF₃ | CO₂Me | NH(CO)NHPh | CF₃ | 7-CF₃ | CO₂Me | O(CO)Me |
| OCF₃ | 7-CF₃ | CO₂Me | NH(CO)NHPh | OCF₃ | 7-CF₃ | CO₂Me | O(CO)ME |
| CF₃ | 7-Cl | i—Pr | NH(CO)NHPh | CF₃ | 7-Cl | i—Pr | O(CO)Me |
| OCF₃ | 7-Cl | i—Pr | NH(CO)NHPh | OCF₃ | 7-Cl | i—Pr | O(CO)Me |
| CF₃ | 7-CF₃ | 4-F—Ph | NH(CO)NHPh | CF₃ | 7-CF₃ | 4-F—Ph | O(CO)Me |
| OCF₃ | 7-CF₃ | 4-F—Ph | NH(CO)NHPh | OCF₃ | 7-CF₃ | 4-F—Ph | O(CO)Me |
| CF₃ | 7-CF₃ | CO₂Me | N=CHMe | CF₃ | 7-CF₃ | CO₂Me | O(CO)OMe |
| OCF₃ | 7-CF₃ | CO₂Me | N=CHMe | OCF₃ | 7-CF₃ | CO₂Me | O(Co)OMe |
| CF₃ | 7-Cl | i—Pr | N=CHMe | CF₃ | 7-Cl | i—Pr | O(CO)OMe |
| OCF₃ | 7-Cl | i—Pr | N=CHMe | OCF₃ | 7-Cl | i—Pr | O(CO)OMe |
| CF₃ | 7-CF₃ | 4-F—Ph | N=CHMe | CF₃ | 7-CF₃ | 4-F—Ph | O(CO)OMe |
| OCF₃ | 7-CF₃ | 4-F—Ph | N=CHMe | OCF₃ | 7-CF₃ | 4-F—Ph | O(CO)OMe |
| CF₃ | 7-CF₃ | CO₂Me | O(CO)NHMe | CF₃ | 7-CF₃ | CO₂Me | NHCH₂Ph |
| OCF₃ | 7-CF₃ | CO₂Me | O(CO)NHMe | OCF₃ | 7-F₃ | CO₂Me | NHCH₂Ph |
| CF₃ | 7-Cl | i—Pr | O(CO)NHMe | CF₃ | 7-Cl | i—Pr | NHCH₂Ph |
| OCF₃ | 7-Cl | i—Pr | O(CO)NHMe | OCF₃ | 7-Cl | i—Pr | NHCH₂Ph |
| CF₃ | 7-CF₃ | 4-F—Ph | O(CO)NHMe | CF₃ | 7-CF₃ | 4-F—Ph | NHCH₂Ph |
| OCF₃ | 7-CF₃ | 4-F—Ph | O(CO)NHMe | OCF₃ | 7-CF₃ | 4-F—Ph | NHCH₂Ph |
| CF₃ | 7-CF₃ | CO₂Me | NMe₂ | CF₃ | 7-CF₃ | CO₂Me | NHPh |
| OCF₃ | 7-CF₃ | CO₂Me | NMe₂ | OCF₃ | 7-CF₃ | CO₂Me | NHPh |
| CF₃ | 7-Cl | i—Pr | NMe₂ | CF₃ | 7-Cl | i—Pr | NHPh |
| OCF₃ | 7-Cl | i—Pr | NMe₂ | OCF₃ | 7-Cl | i—Pr | NHPh |
| CF₃ | 7-CF₃ | 4-F—Ph | NMe₂ | CF₃ | 7-CF₃ | 4-F—Ph | NHPh |
| OCF₃ | 7-CF₃ | 4-F—Ph | NMe₂ | OCF₃ | 7-CF₃ | 4-F—Ph | NHPh |
| CF₃ | 7-CF₃ | CO₂Me | NHEt | CF₃ | 7-CF₃ | CO₂Me | NH(CO)Et |
| OCF₃ | 7-CF₃ | CO₂Me | NHEt | OCF₃ | 7-CF₃ | CO₂Me | NH(CO)Et |
| CF₃ | 7-Cl | i—Pr | NHEt | CF₃ | 7-Cl | i—Pr | NH(CO)Et |
| OCF₃ | 7-Cl | i—Pr | NHEt | OCF₃ | 7-Cl | i—Pr | NH(CO)Et |
| CF₃ | 7-CF₃ | 4-F—Ph | NHEt | CF₃ | 7-CF₃ | 4-F—Ph | NH(CO)Et |
| OCF₃ | 7-CF₃ | 4-F—Ph | NHEt | OCF₃ | 7-CF₃ | 4-F—Ph | NH(CO)Et |
| CF₃ | 7-CF₃ | CO₂Me | NHiPr | CF₃ | 7-CF₃ | CO₂Me | NH(CO)Ph |
| OCF₃ | 7-CF₃ | CO₂Me | NHiPr | OCF₃ | 7-CF₃ | CO₂Me | NH(CO)Ph |
| CF₃ | 7-Cl | i—Pr | NHiPr | CF₃ | 7-Cl | i—Pr | NH(CO)Ph |
| OCF₃ | 7-Cl | i—Pr | NHiPr | OCF₃ | 7-Cl | i—Pr | NH(CO)Ph |
| CF₃ | 7-CF₃ | 4-F—Ph | NHiPr | CF₃ | 7-CF₃ | 4-F—Ph | NH(CO)Ph |
| OCF₃ | 7-CF₃ | 4-F—Ph | NHiPr | OCF₃ | 7-CF₃ | 4-F—Ph | NH(CO)Ph |
| CF₃ | 7-CF₃ | CO₂Me | NHCO₂Me | CF₃ | 7-CF₃ | CO₂Me | NHSO₂NHMe |
| OCF₃ | 7-CF₃ | CO₂Me | NHCO₂Me | OCF₃ | 7-CF₃ | CO₂Me | NHSO₂NHMe |
| CF₃ | 7-Cl | i—Pr | NHCO₂Me | CF₃ | 7-Cl | i—Pr | NHSO₂NHMe |
| OCF₃ | 7-Cl | i—Pr | NHCO₂Me | OCF₃ | 7-Cl | i—Pr | NHSO₂NHMe |
| CF₃ | 7-CF₃ | 4-F—Ph | NHCO₂Me | CF₃ | 7-CF₃ | 4-F—Ph | NHSO₂NHMe |
| OCF₃ | 7-CF₃ | 4-F—Ph | NHCO₂Me | OCF₃ | 7CF₃ | 4-F—Ph | NHSO₂NHMe |
| CF₃ | 7-CF₃ | CO₂Me | NHCO₂Et | CF₃ | 7-CF₃ | CO₂Me | NH(4-F—Ph) |
| OCF₃ | 7-CF₃ | CO₂Me | NHCO₂Et | OCF₃ | 7-CF₃ | CO₂Me | NH(4-F—Ph) |
| CF₃ | 7-Cl | i—Pr | NHCO₂Et | CF₃ | 7-Cl | i—Pr | NH(4-F—Ph) |
| OCF₃ | 7-Cl | i—Pr | NHCO₂Et | OCF₃ | 7-Cl | i—Pr | NH(4-F—Ph) |
| CF₃ | 7-CF₃ | 4-F—Ph | NHCO₂Et | CF₃ | 7-CF₃ | 4-F—Ph | NH(4-F—Ph) |
| OCF₃ | 7-CF₃ | 4-F—Ph | NHCO₂Et | OCF₃ | 7-CF₃ | 4-F—Ph | NH(4-F—Ph) |
| CF₃ | 7-CF₃ | CO₂Me | NHSO₂NH₂ | CF₃ | 7-CF₃ | CO₂Me | NH(4-MeO—Ph) |
| OCF₃ | 7-CF₃ | CO₂Me | NHSO₂NH₂ | OCF₃ | 7-CF₃ | CO₂Me | NH(4-MeO—Ph) |
| CF₃ | 7-Cl | i—Pr | NHSO₂NH₂ | CF₃ | 7-Cl | i—Pr | NH(4-MeO—Ph) |
| OCF₃ | 7-Cl | i—Pr | NHSO₂NH₂ | OCF₃ | 7-Cl | i—Pr | NH(4-MeO—Ph) |
| CF₃ | 7-CF₃ | 4-F—Ph | NHSO₂NH₂ | CF₃ | 7-CF₃ | 4-F—Ph | NH(4-MeO—Ph) |
| OCF₃ | 7-CF₃ | 4-F—Ph | NHSO₂NH₂ | OCF₃ | 7-CF₃ | 4-F—Ph | NH(4-MeO—Ph) |
| CF₃ | 7-CF₃ | CO₂Me | NHSO₂NHPh | CF₃ | 7-CF₃ | CO₂Me | NHCH₂C≡CH |
| OCF₃ | 7-CF₃ | CO₂Me | NHSO₂NHPh | OCF₃ | 7-CF₃ | CO₂Me | NHCH₂C≡CH |
| CF₃ | 7-Cl | i—Pr | NHSO₂NHPh | CF₃ | 7-Cl | i—Pr | NHCH₂C≡CH |
| OCF₃ | 7-Cl | i—Pr | NHSO₂NHPh | OCF₃ | 7-Cl | i—Pr | NHCH₂C≡CH |
| CF₃ | 7-CF₃ | 4-F—Ph | NHSO₂NHPh | CF₃ | 7-CF₃ | 4-F—Ph | NHCH₂C≡CH |
| OCF₃ | 7-CF₃ | 4-F—Ph | NHSO₂NHPh | OCF₃ | 7-CF₃ | 4-F—Ph | NHCH₂C≡CH |

TABLE 11

| R¹ | R² | R³ | Y | R¹ | R² | R³ | Y |
|---|---|---|---|---|---|---|---|
| Br | 6-F | CO₂Me | NH₂ | CF₃ | 6-F | CO₂Me | NH₂ |
| Br | 6-F | CO₂Et | NH₂ | CF₃ | 6-F | CO₂Et | NH₂ |
| Br | 6-F | Me | NH₂ | CF₃ | 6-F | Me | NH₂ |
| Br | 6-F | n-Pr | NH₂ | CF₃ | 6-F | n-Pr | NH₂ |
| Br | 6-F | i-Pr | NH₂ | CF₃ | 6-F | i-Pr | NH₂ |
| Br | 6-F | 4-F-Ph | NH₂ | CF₃ | 6-F | 4-F-Ph | NH₂ |
| Br | 7-F | CO₂Me | NH₂ | CF₃ | 7-F | CO₂Me | NH₂ |
| Br | 7-F | CO₂Et | NH₂ | CF₃ | 7-F | CO₂Et | NH₂ |
| Br | 7-F | Me | NH₂ | CF₃ | 7-F | Me | NH₂ |

TABLE 11-continued

| R¹ | R² | R³ | Y | R¹ | R² | R³ | Y |
|---|---|---|---|---|---|---|---|
| Br | 7-F | n-Pr | $NH_2$ | $CF_3$ | 7-F | n-Pr | $NH_2$ |
| Br | 7-F | i-Pr | $NH_2$ | $CF_3$ | 7-F | i-Pr | $NH_2$ |
| Br | 7-F | 4-F-Ph | $NH_2$ | $CF_3$ | 7-F | 4-F-Ph | $NH_2$ |
| Br | 7-Cl | $CO_2Me$ | $NH_2$ | $CF_3$ | 7-Cl | $CO_2Me$ | $NH_2$ |
| Br | 7-Cl | $CO_2Et$ | $NH_2$ | $CF_3$ | 7-Cl | $CO_2Et$ | $NH_2$ |
| Br | 7-Cl | Me | $NH_2$ | $CF_3$ | 7-Cl | Me | $NH_2$ |
| Br | 7-Cl | n-Pr | $NH_2$ | $CF_3$ | 7-Cl | n-Pr | $NH_2$ |
| Br | 7-Cl | i-Pr | $NH_2$ | $CF_3$ | 7-Cl | i-Pr | $NH_2$ |
| Br | 7-Cl | 4-F-Ph | $NH_2$ | $CF_3$ | 7-Cl | 4-F-Ph | $NH_2$ |
| Br | 7-$CF_3$ | $CO_2Me$ | $NH_2$ | $CF_3$ | 7-$CF_3$ | $CO_2Me$ | $NH_2$ |
| Br | 7-$CF_3$ | $CO_2Et$ | $NH_2$ | $CF_3$ | 7-$CF_3$ | $CO_2Et$ | $NH_2$ |
| Br | 7-$CF_3$ | Me | $NH_2$ | $CF_3$ | 7-$CF_3$ | Me | $NH_2$ |
| Br | 7-$CF_3$ | n-Pr | $NH_2$ | $CF_3$ | 7-$CF_3$ | n-Pr | $NH_2$ |
| Br | 7-$CF_3$ | i-Pr | $NH_2$ | $CF_3$ | 7-$CF_3$ | i-Pr | $NH_2$ |
| Br | 7-$CF_3$ | 4-F-Ph | $NH_2$ | $CF_3$ | 7-$CF_3$ | 4-F-Ph | $NH_2$ |
| $OCF_3$ | 6-F | $CO_2Me$ | $NH_2$ | Br | 6-F | $CO_2Me$ | NHMe |
| $OCF_3$ | 6-F | $CO_2Et$ | $NH_2$ | Br | 6-F | $CO_2Et$ | NHMe |
| $OCF_3$ | 6-F | Me | $NH_2$ | Br | 6-F | Me | NHMe |
| $OCF_3$ | 6-F | n-Pr | $NH_2$ | Br | 6-F | n-Pr | NHMe |
| $OCF_3$ | 6-F | i-Pr | $NH_2$ | Br | 6-F | i-Pr | NHMe |
| $OCF_3$ | 6-F | 4-F-Ph | $NH_2$ | Br | 6-F | 4-F-Ph | NHMe |
| $OCF_3$ | 7-F | $CO_2Me$ | $NH_2$ | Br | 7-F | $CO_2Me$ | NHMe |
| $OCF_3$ | 7-F | $CO_2Et$ | $NH_2$ | Br | 7-F | $CO_2Et$ | NHMe |
| $OCF_3$ | 7-F | Me | $NH_2$ | Br | 7-F | Me | NHMe |
| $OCF_3$ | 7-F | n-Pr | $NH_2$ | Br | 7-F | n-Pr | NHMe |
| $OCF_3$ | 7-F | i-Pr | $NH_2$ | Br | 7-F | i-Pr | NHMe |
| $OCF_3$ | 7-F | 4-F-Ph | $NH_2$ | Br | 7-F | 4-F-Ph | NHMe |
| $OCF_3$ | 7-Cl | $CO_2Me$ | $NH_2$ | Br | 7-Cl | $CO_2Me$ | NHMe |
| $OCF_3$ | 7-Cl | $CO_2Et$ | $NH_2$ | Br | 7-Cl | $CO_2Et$ | NHMe |
| $OCF_3$ | 7-Cl | Me | $NH_2$ | Br | 7-Cl | Me | NHMe |
| $OCF_3$ | 7-Cl | n-Pr | $NH_2$ | Br | 7-Cl | n-Pr | NHMe |
| $OCF_3$ | 7-Cl | i-Pr | $NH_2$ | Br | 7-Cl | i-Pr | NHMe |
| $OCF_3$ | 7-Cl | 4-F-Ph | $NH_2$ | Br | 7-Cl | 4-F-Ph | NHMe |
| $OCF_3$ | 7-$CF_3$ | $CO_2Me$ | $NH_2$ | Br | 7-$CF_3$ | $CO_2Me$ | NHMe |
| $OCF_3$ | 7-$CF_3$ | $CO_2Et$ | $NH_2$ | Br | 7-$CF_3$ | $CO_2Et$ | NHMe |
| $OCF_3$ | 7-$CF_3$ | Me | $NH_2$ | Br | 7-$CF_3$ | Me | NHMe |
| $OCF_3$ | 7-$CF_3$ | n-Pr | $NH_2$ | Br | 7-$CF_3$ | n-Pr | NHMe |
| $OCF_3$ | 7-$CF_3$ | i-Pr | $NH_2$ | Br | 7-$CF_3$ | i-Pr | NHMe |
| $OCF_3$ | 7-$CF_3$ | 4-F-Ph | $NH_2$ | Br | 7-$CF_3$ | 4-F-Ph | NHMe |
| $CF_3$ | 6-F | $CO_2Me$ | NHMe | $OCF_3$ | 6-F | $CO_2Me$ | NHMe |
| $CF_3$ | 6-F | $CO_2Et$ | NHMe | $OCF_3$ | 6-F | $CO_2Et$ | NHMe |
| $CF_3$ | 6-F | Me | NHMe | $OCF_3$ | 6-F | Me | NHMe |
| $CF_3$ | 6-F | n-Pr | NHMe | $OCF_3$ | 6-F | n-Pr | NHMe |
| $CF_3$ | 6-F | i-Pr | NHMe | $OCF_3$ | 6-F | i-Pr | NHMe |
| $CF_3$ | 6-F | 4-F-Ph | NHMe | $OCF_3$ | 6-F | 4-F-Ph | NHMe |
| $CF_3$ | 7-F | $CO_2Me$ | NHMe | $OCF_3$ | 7-F | $CO_2Me$ | NHMe |
| $CF_3$ | 7-F | $CO_2Et$ | NHMe | $OCF_3$ | 7-F | $CO_2Et$ | NHMe |
| $CF_3$ | 7-F | Me | NHMe | $OCF_3$ | 7-F | Me | NHMe |
| $CF_3$ | 7-F | n-Pr | NHMe | $OCF_3$ | 7-F | n-Pr | NHMe |
| $CF_3$ | 7-F | i-Pr | NHMe | $OCF_3$ | 7-F | i-Pr | NHMe |
| $CF_3$ | 7-F | 4-F-Ph | NHMe | $OCF_3$ | 7-F | 4-F-Ph | NHMe |
| $CF_3$ | 7-Cl | $CO_2Me$ | NHMe | $OCF_3$ | 7-Cl | $CO_2Me$ | NHMe |
| $CF_3$ | 7-Cl | $CO_2Et$ | NHMe | $OCF_3$ | 7-Cl | $CO_2Et$ | NHMe |
| $CF_3$ | 7-Cl | Me | NHMe | $OCF_3$ | 7-Cl | Me | NHMe |
| $CF_3$ | 7-Cl | n-Pr | NHMe | $OCF_3$ | 7-Cl | n-Pr | NHMe |
| $CF_3$ | 7-Cl | i-Pr | NHMe | $OCF_3$ | 7-Cl | i-Pr | NHMe |
| $CF_3$ | 7-Cl | 4-F-Ph | NHMe | $OCF_3$ | 7-Cl | 4-F-Ph | NHMe |
| $CF_3$ | 7-$CF_3$ | $CO_2Me$ | NHMe | $OCF_3$ | 7-$CF_3$ | $CO_2Me$ | NHMe |
| $CF_3$ | 7-$CF_3$ | $CO_2Et$ | NHMe | $OCF_3$ | 7-$CF_3$ | $CO_2Et$ | NHMe |
| $CF_3$ | 7-$CF_3$ | Me | NHMe | $OCF_3$ | 7-$CF_3$ | Me | NHMe |
| $CF_3$ | 7-$CF_3$ | n-Pr | NHMe | $OCF_3$ | 7-$CF_3$ | n-Pr | NHMe |
| $CF_3$ | 7-$CF_3$ | i-Pr | NHMe | $OCF_3$ | 7-$CF_3$ | i-Pr | NHMe |
| $CF_3$ | 7-$CF_3$ | 4-F-Ph | NHMe | $OCF_3$ | 7-$CF_3$ | 4-F-Ph | NHMe |
| Br | 6-F | $CO_2Me$ | NHCHO | $CF_3$ | 6-F | $CO_2Me$ | NHCHO |
| Br | 6-F | $CO_2Et$ | NHCHO | $CF_3$ | 6-F | $CO_2Et$ | NHCHO |
| Br | 6-F | Me | NHCHO | $CF_3$ | 6-F | Me | NHCHO |
| Br | 6-F | n-Pr | NHCHO | $CF_3$ | 6-F | n-Pr | NHCHO |
| Br | 6-F | i-Pr | NHCHO | $CF_3$ | 6-F | i-Pr | NHCHO |
| Br | 6-F | 4-F-Ph | NHCHO | $CF_3$ | 6-F | 4-F-Ph | NHCHO |
| Br | 7-F | $CO_2Me$ | NHCHO | $CF_3$ | 7-F | $CO_2Me$ | NHCHO |
| Br | 7-F | $CO_2Et$ | NHCHO | $CF_3$ | 7-F | $CO_2Et$ | NHCHO |
| Br | 7-F | Me | NHCHO | $CF_3$ | 7-F | Me | NHCHO |
| Br | 7-F | n-Pr | NHCHO | $CF_3$ | 7-F | n-Pr | NHCHO |
| Br | 7-F | i-Pr | NHCHO | $CF_3$ | 7-F | i-Pr | NHCHO |
| Br | 7-F | 4-F-Ph | NHCHO | $CF_3$ | 7-F | 4-F-Ph | NHCHO |
| Br | 7-Cl | $CO_2Me$ | NHCHO | $CF_3$ | 7-Cl | $CO_2Me$ | NHCHO |
| Br | 7-Cl | $CO_2Et$ | NHCHO | $CF_3$ | 7-Cl | $CO_2Et$ | NHCHO |

TABLE 11-continued

| R¹ | R² | R³ | Y | R¹ | R² | R³ | Y |
|---|---|---|---|---|---|---|---|
| Br | 7-Cl | Me | NHCHO | CF₃ | 7-Cl | Me | NHCHO |
| Br | 7-Cl | n-Pr | NHCHO | CF₃ | 7-Cl | n-Pr | NHCHO |
| Br | 7-Cl | i-Pr | NHCHO | CF₃ | 7-Cl | i-Pr | NHCHO |
| Br | 7-Cl | 4-F-Ph | NHCHO | CF₃ | 7-Cl | 4-F-Ph | NHCHO |
| Br | 7-CF₃ | CO₂Me | NHCHO | CF₃ | 7-CF₃ | CO₂Me | NHCHO |
| Br | 7-CF₃ | CO₂Et | NHCHO | CF₃ | 7-CF₃ | CO₂Et | NHCHO |
| Br | 7-CF₃ | Me | NHCHO | CF₃ | 7-CF₃ | Me | NHCHO |
| Br | 7-CF₃ | n-Pr | NHCHO | CF₃ | 7-CF₃ | n-Pr | NHCHO |
| Br | 7-CF₃ | i-Pr | NHCHO | CF₃ | 7-CF₃ | i-Pr | NHCHO |
| Br | 7-CF₃ | 4-F-Ph | NHCHO | CF₃ | 7-CF₃ | 4-F-Ph | NHCHO |
| OCF₃ | 6-F | CO₂Me | NHCHO | Br | 6-F | CO₂Me | NH(CO)Me |
| OCF₃ | 6-F | CO₂Et | NHCHO | Br | 6-F | CO₂Et | NH(CO)Me |
| OCF₃ | 6-F | Me | NHCHO | Br | 6-F | Me | NH(CO)Me |
| OCF₃ | 6-F | n-Pr | NHCHO | Br | 6-F | n-Pr | NH(CO)Me |
| OCF₃ | 6-F | i-Pr | NHCHO | Br | 6-F | i-Pr | NH(CO)Me |
| OCF₃ | 6-F | 4-F-Ph | NHCHO | Br | 6-F | 4-F-Ph | NH(CO)Me |
| OCF₃ | 7-F | CO₂Me | NHCHO | Br | 7-F | CO₂Me | NH(CO)Me |
| OCF₃ | 7-F | CO₂Et | NHCHO | Br | 7-F | CO₂Et | NH(CO)Me |
| OCF₃ | 7-F | Me | NHCHO | Br | 7-F | Me | NH(CO)Me |
| OCF₃ | 7-F | n-Pr | NHCHO | Br | 7-F | n-Pr | NH(CO)Me |
| OCF₃ | 7-F | i-Pr | NHCHO | Br | 7-F | i-Pr | NH(CO)Me |
| OCF₃ | 7-F | 4-F-Ph | NHCHO | Br | 7-F | 4-F-Ph | NH(CO)Me |
| OCF₃ | 7-Cl | CO₂Me | NHCHO | Br | 7-Cl | CO₂Me | NH(CO)Me |
| OCF₃ | 7-Cl | CO₂Et | NHCHO | Br | 7-Cl | CO₂Et | NH(CO)Me |
| OCF₃ | 7-Cl | Me | NHCHO | Br | 7-Cl | Me | NH(CO)Me |
| OCF₃ | 7-Cl | n-Pr | NHCHO | Br | 7-Cl | n-Pr | NH(CO)Me |
| OCF₃ | 7-Cl | i-Pr | NHCHO | Br | 7-Cl | i-Pr | NH(CO)Me |
| OCF₃ | 7-Cl | 4-F-Ph | NHCHO | Br | 7-Cl | 4-F-Ph | NH(CO)Me |
| OCF₃ | 7-CF₃ | CO₂Me | NHCHO | Br | 7-CF₃ | CO₂Me | NH(CO)Me |
| OCF₃ | 7-CF₃ | CO₂Et | NHCHO | Br | 7-CF₃ | CO₂Et | NH(CO)Me |
| OCF₃ | 7-CF₃ | Me | NHCHO | Br | 7-CF₃ | Me | NH(CO)Me |
| OCF₃ | 7-CF₃ | n-Pr | NHCHO | Br | 7-CF₃ | n-Pr | NH(CO)Me |
| OCF₃ | 7-CF₃ | i-Pr | NHCHO | Br | 7-CF₃ | i-Pr | NH(CO)Me |
| OCF₃ | 7-CF₃ | 4-F-Ph | NHCHO | Br | 7-CF₃ | 4-F-Ph | NH(CO)Me |
| CF₃ | 6-F | CO₂Me | NH(CO)Me | OCF₃ | 6-F | CO₂Me | NH(CO)Me |
| CF₃ | 6-F | CO₂Et | NH(CO)Me | OCF₃ | 6-F | CO₂Et | NH(CO)Me |
| CF₃ | 6-F | Me | NH(CO)Me | OCF₃ | 6-F | Me | NH(CO)Me |
| CF₃ | 6-F | n-Pr | NH(CO)Me | OCF₃ | 6-F | n-Pr | NH(CO)Me |
| CF₃ | 6-F | i-Pr | NH(CO)Me | OCF₃ | 6-F | i-Pr | NH(CO)Me |
| CF₃ | 6-F | 4-F-Ph | NH(CO)Me | OCF₃ | 6-F | 4-F-Ph | NH(CO)Me |
| CF₃ | 7-F | CO₂Me | NH(CO)Me | OCF₃ | 7-F | CO₂Me | NH(CO)Me |
| CF₃ | 7-F | CO₂Et | NH(CO)Me | OCF₃ | 7-F | CO₂Et | NH(CO)Me |
| CF₃ | 7-F | Me | NH(CO)Me | OCF₃ | 7-F | Me | NH(CO)Me |
| CF₃ | 7-F | n-Pr | NH(CO)Me | OCF₃ | 7-F | n-Pr | NH(CO)Me |
| CF₃ | 7-F | i-Pr | NH(CO)Me | OCF₃ | 7-F | i-Pr | NH(CO)Me |
| CF₃ | 7-F | 4-F-Ph | NH(CO)Me | OCF₃ | 7-F | 4-F-Ph | NH(CO)Me |
| CF₃ | 7-Cl | CO₂Me | NH(CO)Me | OCF₃ | 7-Cl | CO₂Me | NH(CO)Me |
| CF₃ | 7-Cl | CO₂Et | NH(CO)Me | OCF₃ | 7-Cl | CO₂Et | NH(CO)Me |
| CF₃ | 7-Cl | Me | NH(CO)Me | OCF₃ | 7-Cl | Me | NH(CO)Me |
| CF₃ | 7-Cl | n-Pr | NH(CO)Me | OCF₃ | 7-Cl | n-Pr | NH(CO)Me |
| CF₃ | 7-Cl | i-Pr | NH(CO)Me | OCF₃ | 7-Cl | i-Pr | NH(CO)Me |
| CF₃ | 7-Cl | 4-F-Ph | NH(CO)Me | OCF₃ | 7-Cl | 4-F-Ph | NH(CO)Me |
| CF₃ | 7-CF₃ | CO₂Me | NH(CO)Me | OCF₃ | 7-CF₃ | CO₂Me | NH(CO)Me |
| CF₃ | 7-CF₃ | CO₂Et | NH(CO)Me | OCF₃ | 7-CF₃ | CO₂Et | NH(CO)Me |
| CF₃ | 7-CF₃ | Me | NH(CO)Me | OCF₃ | 7-CF₃ | Me | NH(CO)Me |
| CF₃ | 7-CF₃ | n-Pr | NH(CO)Me | OCF₃ | 7-CF₃ | n-Pr | NH(CO)Me |
| CF₃ | 7-CF₃ | i-Pr | NH(CO)Me | OCF₃ | 7-CF₃ | i-Pr | NH(CO)Me |
| CF₃ | 7-CF₃ | 4-F-Ph | NH(CO)Me | OCF₃ | 7-CF₃ | 4-F-Ph | NH(CO)Me |
| Br | 6-F | CO₂Me | OMe | CF₃ | 6-F | CO₂Me | OMe |
| Br | 6-F | CO₂Et | OMe | CF₃ | 6-F | CO₂Et | OMe |
| Br | 6-F | Me | OMe | CF₃ | 6-F | Me | OMe |
| Br | 6-F | n-Pr | OMe | CF₃ | 6-F | n-Pr | OMe |
| Br | 6-F | i-Pr | OMe | CF₃ | 6-F | i-Pr | OMe |
| Br | 6-F | 4-F-Ph | OMe | CF₃ | 6-F | 4-F-Ph | OMe |
| Br | 7-F | CO₂Me | OMe | CF₃ | 7-F | CO₂Me | OMe |
| Br | 7-F | CO₂Et | OMe | CF₃ | 7-F | CO₂Et | OMe |
| Br | 7-F | Me | OMe | CF₃ | 7-F | Me | OMe |
| Br | 7-F | n-Pr | OMe | CF₃ | 7-F | n-Pr | OMe |
| Br | 7-F | i-Pr | OMe | CF₃ | 7-F | i-Pr | OMe |
| Br | 7-F | 4-F-Ph | OMe | CF₃ | 7-F | 4-F-Ph | OMe |
| Br | 7-Cl | CO₂Me | OMe | CF₃ | 7-Cl | CO₂Me | OMe |
| Br | 7-Cl | CO₂Et | OMe | CF₃ | 7-Cl | CO₂Et | OMe |
| Br | 7-Cl | Me | OMe | CF₃ | 7-Cl | Me | OMe |
| Br | 7-Cl | n-Pr | OMe | CF₃ | 7-Cl | n-Pr | OMe |
| Br | 7-Cl | i-Pr | OMe | CF₃ | 7-Cl | i-Pr | OMe |
| Br | 7-Cl | 4-F-Ph | OMe | CF₃ | 7-Cl | 4-F-Ph | OMe |
| Br | 7-CF₃ | CO₂Me | OMe | CF₃ | 7-CF₃ | CO₂Me | OMe |

TABLE 11-continued

| R¹ | R² | R³ | Y | R¹ | R² | R³ | Y |
|---|---|---|---|---|---|---|---|
| Br | 7-CF₃ | CO₂Et | OMe | CF₃ | 7-CF₃ | CO₂Et | OMe |
| Br | 7-CF₃ | Me | OMe | CF₃ | 7-CF₃ | Me | OMe |
| Br | 7-CF₃ | n-Pr | OMe | CF₃ | 7-CF₃ | n-Pr | OMe |
| Br | 7-CF₃ | i-Pr | OMe | CF₃ | 7-CF₃ | i-Pr | OMe |
| Br | 7-CF₃ | 4-F-Ph | OMe | CF₃ | 7-CF₃ | 4-F-Ph | OMe |
| OCF₃ | 6-F | CO₂Me | OMe | Br | 6-F | CO₂Me | N=CHPh |
| OCF₃ | 6-F | CO₂Et | OMe | Br | 6-F | CO₂Et | N=CHPh |
| OCF₃ | 6-F | Me | OMe | Br | 6-F | Me | N=CHPh |
| OCF₃ | 6-F | n-Pr | OMe | Br | 6-F | n-Pr | N=CHPh |
| OCF₃ | 6-F | i-Pr | OMe | Br | 6-F | i-Pr | N=CHPh |
| OCF₃ | 6-F | 4-F-Ph | OMe | Br | 6-F | 4-F-Ph | N=CHPh |
| OCF₃ | 7-F | CO₂Me | OMe | Br | 7-F | CO₂Me | N=CHPh |
| OCF₃ | 7-F | CO₂Et | OMe | Br | 7-F | CO₂Et | N=CHPh |
| OCF₃ | 7-F | Me | OMe | Br | 7-F | Me | N=CHPh |
| OCF₃ | 7-F | n-Pr | OMe | Br | 7-F | n-Pr | N=CHPh |
| OCF₃ | 7-F | i-Pr | OMe | Br | 7-F | i-Pr | N=CHPh |
| OCF₃ | 7-F | 4-F-Ph | OMe | Br | 7-F | 4-F-Ph | N=CHPh |
| OCF₃ | 7-Cl | CO₂Me | OMe | Br | 7-Cl | CO₂Me | N=CHPh |
| OCF₃ | 7-Cl | CO₂Et | OMe | Br | 7-Cl | CO₂Et | N=CHPh |
| OCF₃ | 7-Cl | Me | OMe | Br | 7-Cl | Me | N=CHPh |
| OCF₃ | 7-Cl | n-Pr | OMe | Br | 7-Cl | n-Pr | N=CHPh |
| OCF₃ | 7-Cl | i-Pr | OMe | Br | 7-Cl | i-Pr | N=CHPh |
| OCF₃ | 7-Cl | 4-F-Ph | OMe | Br | 7-Cl | 4-F-Ph | N=CHPh |
| OCF₃ | 7-CF₃ | CO₂Me | OMe | Br | 7-CF₃ | CO₂Me | N=CHPh |
| OCF₃ | 7-CF₃ | CO₂Et | OMe | Br | 7-CF₃ | CO₂Et | N=CHPh |
| OCF₃ | 7-CF₃ | Me | OMe | Br | 7-CF₃ | Me | N=CHPh |
| OCF₃ | 7-CF₃ | n-Pr | OMe | Br | 7-CF₃ | n-Pr | N=CHPh |
| OCF₃ | 7-CF₃ | i-Pr | OMe | Br | 7-CF₃ | i-Pr | N=CHPh |
| OCF₃ | 7-CF₃ | 4-F-Ph | OMe | Br | 7-CF₃ | 4-F-Ph | N=CHPh |
| CF₃ | 6-F | CO₂Me | N=CHPh | OCF₃ | 6-F | CO₂Me | N=CHPh |
| CF₃ | 6-F | CO₂Et | N=CHPh | OCF₃ | 6-F | CO₂Et | N=CHPh |
| CF₃ | 6-F | Me | N=CHPh | OCF₃ | 6-F | Me | N=CHPh |
| CF₃ | 6-F | n-Pr | N=CHPh | OCF₃ | 6-F | n-Pr | N=CHPh |
| CF₃ | 6-F | i-Pr | N=CHPh | OCF₃ | 6-F | i-Pr | N=CHPh |
| CF₃ | 6-F | 4-F-Ph | N=CHPh | OCF₃ | 6-F | 4-F-Ph | N=CHPh |
| CF₃ | 7-F | CO₂Me | N=CHPh | OCF₃ | 7-F | CO₂Me | N=CHPh |
| CF₃ | 7-F | CO₂Et | N=CHPh | OCF₃ | 7-F | CO₂Et | N=CHPh |
| CF₃ | 7-F | Me | N=CHPh | OCF₃ | 7-F | Me | N=CHPh |
| CF₃ | 7-F | n-Pr | N=CHPh | OCF₃ | 7-F | n-Pr | N=CHPh |
| CF₃ | 7-F | i-Pr | N=CHPh | OCF₃ | 7-F | i-Pr | N=CHPh |
| CF₃ | 7-F | 4-F-Ph | N=CHPh | OCF₃ | 7-F | 4-F-Ph | N=CHPh |
| CF₃ | 7-Cl | CO₂Me | N=CHPh | OCF₃ | 7-Cl | CO₂Me | N=CHPh |
| CF₃ | 7-Cl | CO₂Et | N=CHPh | OCF₃ | 7-Cl | CO₂Et | N=CHPh |
| CF₃ | 7-Cl | Me | N=CHPh | OCF₃ | 7-Cl | Me | N=CHPh |
| CF₃ | 7-Cl | n-Pr | N=CHPh | OCF₃ | 7-Cl | n-Pr | N=CHPh |
| CF₃ | 7-Cl | i-Pr | N=CHPh | OCF₃ | 7-Cl | i-Pr | N=CHPh |
| CF₃ | 7-Cl | 4-F-Ph | N=CHPh | OCF₃ | 7-Cl | 4-F-Ph | N=CHPh |
| CF₃ | 7-CF₃ | CO₂Me | N=CHPh | OCF₃ | 7-CF₃ | CO₂Me | N=CHPh |
| CF₃ | 7-CF₃ | CO₂Et | N=CHPh | OCF₃ | 7-CF₃ | CO₂Et | N=CHPh |
| CF₃ | 7-CF₃ | Me | N=CHPh | OCF₃ | 7-CF₃ | Me | N=CHPh |
| CF₃ | 7-CF₃ | n-Pr | N=CHPh | OCF₃ | 7-CF₃ | n-Pr | N=CHPh |
| CF₃ | 7-CF₃ | i-Pr | N=CHPh | OCF₃ | 7-CF₃ | i-Pr | N=CHPh |
| CF₃ | 7-CF₃ | 4-F-Ph | N=CHPh | OCF₃ | 7-CF₃ | 4-F-Ph | N=CHPh |
| CF₃ | 6-F | CO₂Me | OH | OCF₃ | 6-F | CO₂Me | OH |
| CF₃ | 6-F | CO₂Et | OH | OCF₃ | 6-F | CO₂Et | OH |
| CF₃ | 6-F | Me | OH | OCF₃ | 6-F | Me | OH |
| CF₃ | 6-F | n-Pr | OH | OCF₃ | 6-F | n-Pr | OH |
| CF₃ | 6-F | i-Pr | OH | OCF₃ | 6-F | i-Pr | OH |
| CF₃ | 6-F | 4-F-Ph | OH | OCF₃ | 6-F | 4-F-Ph | OH |
| CF₃ | 7-F | CO₂Me | OH | OCF₃ | 7-F | CO₂Me | OH |
| CF₃ | 7-F | CO₂Et | OH | OCF₃ | 7-F | CO₂Et | OH |
| CF₃ | 7-F | Me | OH | OCF₃ | 7-F | Me | OH |
| CF₃ | 7-F | n-Pr | OH | OCF₃ | 7-F | n-Pr | OH |
| CF₃ | 7-F | i-Pr | OH | OCF₃ | 7-F | i-Pr | OH |
| CF₃ | 7-F | 4-F-Ph | OH | OCF₃ | 7-F | 4-F-Ph | OH |
| CF₃ | 7-Cl | CO₂Me | OH | OCF₃ | 7-Cl | CO₂Me | OH |
| CF₃ | 7-Cl | CO₂Et | OH | OCF₃ | 7-Cl | CO₂Et | OH |
| CF₃ | 7-Cl | Me | OH | OCF₃ | 7-Cl | Me | OH |
| CF₃ | 7-Cl | n-Pr | OH | OCF₃ | 7-Cl | n-Pr | OH |
| CF₃ | 7-Cl | i-Pr | OH | OCF₃ | 7-Cl | i-Pr | OH |
| CF₃ | 7-Cl | 4-F-Ph | OH | OCF₃ | 7-Cl | 4-F-Ph | OH |
| CF₃ | 7-CF₃ | CO₂Me | OH | OCF₃ | 7-CF₃ | CO₂Me | OH |
| CF₃ | 7-CF₃ | CO₂Et | OH | OCF₃ | 7-CF₃ | CO₂Et | OH |
| CF₃ | 7-CF₃ | Me | OH | OCF₃ | 7-CF₃ | Me | OH |
| CF₃ | 7-CF₃ | n-Pr | OH | OCF₃ | 7-CF₃ | n-Pr | OH |
| CF₃ | 7-CF₃ | i-Pr | OH | OCF₃ | 7-CF₃ | i-Pr | OH |
| CF₃ | 7-CF₃ | 4-F-Ph | OH | OCF₃ | 7-CF₃ | 4-F-Ph | OH |

TABLE 11-continued

| R¹ | R² | R³ | Y | R¹ | R² | R³ | Y |
| --- | --- | --- | --- | --- | --- | --- | --- |
| Br | 6-F | CO₂Me | OH | Br | 7-Cl | CO₂Me | OH |
| Br | 6-F | CO₂Et | OH | Br | 7-Cl | CO₂Et | OH |
| Br | 6-F | Me | OH | Br | 7-Cl | Me | OH |
| Br | 6-F | n-Pr | OH | Br | 7-Cl | n-Pr | OH |
| Br | 6-F | i-Pr | OH | Br | 7-Cl | i-Pr | OH |
| Br | 6-F | 4-F-Ph | OH | Br | 7-Cl | 4-F-Ph | OH |
| Br | 7-F | CO₂Me | OH | Br | 7-CF₃ | CO₂Me | OH |
| Br | 7-F | CO₂Et | OH | Br | 7-CF₃ | CO₂Et | OH |
| Br | 7-F | Me | OH | Br | 7-CF₃ | Me | OH |
| Br | 7-F | n-Pr | OH | Br | 7-CF₃ | n-Pr | OH |
| Br | 7-F | i-Pr | OH | Br | 7-CF₃ | i-Pr | OH |
| Br | 7-F | 4-F-Ph | OH | Br | 7-CF₃ | 4-F-Ph | OH |

TABLE 12

| R¹ | R² | R³ | Y | R¹ | R² | R³ | Y |
| --- | --- | --- | --- | --- | --- | --- | --- |
| Br | 6-F | CO₂Me | NH₂ | CF₃ | 6-F | CO₂Me | NH₂ |
| Br | 6-F | CO₂Et | NH₂ | CF₃ | 6-F | CO₂Et | NH₂ |
| Br | 6-F | Me | NH₂ | CF₃ | 6-F | Me | NH₂ |
| Br | 6-F | n-Pr | NH₂ | CF₃ | 6-F | n-Pr | NH₂ |
| Br | 6-F | i-Pr | NH₂ | CF₃ | 6-F | i-Pr | NH₂ |
| Br | 6-F | 4-F-Ph | NH₂ | CF₃ | 6-F | 4-F-Ph | NH₂ |
| Br | 7-F | CO₂Me | NH₂ | CF₃ | 7-F | CO₂Me | NH₂ |
| Br | 7-F | CO₂Et | NH₂ | CF₃ | 7-F | CO₂Et | NH₂ |
| Br | 7-F | Me | NH₂ | CF₃ | 7-F | Me | NH₂ |
| Br | 7-F | n-Pr | NH₂ | CF₃ | 7-F | n-Pr | NH₂ |
| Br | 7-F | i-Pr | NH₂ | CF₃ | 7-F | i-Pr | NH₂ |
| Br | 7-F | 4-F-Ph | NH₂ | CF₃ | 7-F | 4-F-Ph | NH₂ |
| Br | 7-Cl | CO₂Me | NH₂ | CF₃ | 7-Cl | CO₂Me | NH₂ |
| Br | 7-Cl | CO₂Et | NH₂ | CF₃ | 7-Cl | CO₂Et | NH₂ |
| Br | 7-Cl | Me | NH₂ | CF₃ | 7-Cl | Me | NH₂ |
| Br | 7-Cl | n-Pr | NH₂ | CF₃ | 7-Cl | n-Pr | NH₂ |
| Br | 7-Cl | i-Pr | NH₂ | CF₃ | 7-Cl | i-Pr | NH₂ |
| Br | 7-Cl | 4-F-Ph | NH₂ | CF₃ | 7-Cl | 4-F-Ph | NH₂ |
| Br | 7-CF₃ | CO₂Me | NH₂ | CF₃ | 7-CF₃ | CO₂Me | NH₂ |
| Br | 7-CF₃ | CO₂Et | NH₂ | CF₃ | 7-CF₃ | CO₂Et | NH₂ |
| Br | 7-CF₃ | Me | NH₂ | CF₃ | 7-CF₃ | Me | NH₂ |
| Br | 7-CF₃ | n-Pr | NH₂ | CF₃ | 7-CF₃ | n-Pr | NH₂ |
| Br | 7-CF₃ | i-Pr | NH₂ | CF₃ | 7-CF₃ | i-Pr | NH₂ |
| Br | 7-CF₃ | 4-F-Ph | NH₂ | CF₃ | 7-CF₃ | 4-F-Ph | NH₂ |
| OCF₃ | 6-F | CO₂Me | NH₂ | Br | 6-F | CO₂Me | NHMe |
| OCF₃ | 6-F | CO₂Et | NH₂ | Br | 6-F | CO₂Et | NHMe |
| OCF₃ | 6-F | Me | NH₂ | Br | 6-F | Me | NHMe |
| OCF₃ | 6-F | n-Pr | NH₂ | Br | 6-F | n-Pr | NHMe |
| OCF₃ | 6-F | i-Pr | NH₂ | Br | 6-F | i-Pr | NHMe |
| OCF₃ | 6-F | 4-F-Ph | NH₂ | Br | 6-F | 4-F-Ph | NHMe |
| OCF₃ | 7-F | CO₂Me | NH₂ | Br | 7-F | CO₂Me | NHMe |
| OCF₃ | 7-F | CO₂Et | NH₂ | Br | 7-F | CO₂Et | NHMe |
| OCF₃ | 7-F | Me | NH₂ | Br | 7-F | Me | NHMe |
| OCF₃ | 7-F | n-Pr | NH₂ | Br | 7-F | n-Pr | NHMe |
| OCF₃ | 7-F | i-Pr | NH₂ | Br | 7-F | i-Pr | NHMe |
| OCF₃ | 7-F | 4-F-Ph | NH₂ | Br | 7-F | 4-F-Ph | NHMe |
| OCF₃ | 7-Cl | CO₂Me | NH₂ | Br | 7-Cl | CO₂Me | NHMe |
| OCF₃ | 7-Cl | CO₂Et | NH₂ | Br | 7-Cl | CO₂Et | NHMe |
| OCF₃ | 7-Cl | Me | NH₂ | Br | 7-Cl | Me | NHMe |
| OCF₃ | 7-Cl | n-Pr | NH₂ | Br | 7-Cl | n-Pr | NHMe |
| OCF₃ | 7-Cl | i-Pr | NH₂ | Br | 7-Cl | i-Pr | NHMe |
| OCF₃ | 7-Cl | 4-F-Ph | NH₂ | Br | 7-Cl | 4-F-Ph | NHMe |
| OCF₃ | 7-CF₃ | CO₂Me | NH₂ | Br | 7-CF₃ | CO₂Me | NHMe |
| OCF₃ | 7-CF₃ | CO₂Et | NH₂ | Br | 7-CF₃ | CO₂Et | NHMe |
| OCF₃ | 7-CF₃ | Me | NH₂ | Br | 7-CF₃ | Me | NHMe |
| OCF₃ | 7-CF₃ | n-Pr | NH₂ | Br | 7-CF₃ | n-Pr | NHMe |
| OCF₃ | 7-CF₃ | i-Pr | NH₂ | Br | 7-CF₃ | i-Pr | NHMe |
| OCF₃ | 7-CF₃ | 4-F-Ph | NH₂ | Br | 7-CF₃ | 4-F-Ph | NHMe |
| CF₃ | 6-F | CO₂Me | NHMe | OCF₃ | 6-F | CO₂Me | NHMe |
| CF₃ | 6-F | CO₂Et | NHMe | OCF₃ | 6-F | CO₂Et | NHMe |
| CF₃ | 6-F | Me | NHMe | OCF₃ | 6-F | Me | NHMe |
| CF₃ | 6-F | n-Pr | NHMe | OCF₃ | 6-F | n-Pr | NHMe |
| CF₃ | 6-F | i-Pr | NHMe | OCF₃ | 6-F | i-Pr | NHMe |
| CF₃ | 6-F | 4-F-Ph | NHMe | OCF₃ | 6-F | 4-F-Ph | NHMe |
| CF₃ | 7-F | CO₂Me | NHMe | OCF₃ | 7-F | CO₂Me | NHMe |
| CF₃ | 7-F | CO₂Et | NHMe | OCF₃ | 7-F | CO₂Et | NHMe |
| CF₃ | 7-F | Me | NHMe | OCF₃ | 7-F | Me | NHMe |
| CF₃ | 7-F | n-Pr | NHMe | OCF₃ | 7-F | n-Pr | NHMe |

TABLE 12-continued

| R¹ | R² | R³ | Y | R¹ | R² | R³ | Y |
|---|---|---|---|---|---|---|---|
| CF₃ | 7-F | i-Pr | NHMe | OCF₃ | 7-F | i-Pr | NHMe |
| CF₃ | 7-F | 4-F-Ph | NHMe | OCF₃ | 7-F | 4-F-Ph | NHMe |
| CF₃ | 7-Cl | CO₂Me | NHMe | OCF₃ | 7-Cl | CO₂Me | NHMe |
| CF₃ | 7-Cl | CO₂Et | NHMe | OCF₃ | 7-Cl | CO₂Et | NHMe |
| CF₃ | 7-Cl | Me | NHMe | OCF₃ | 7-Cl | Me | NHMe |
| CF₃ | 7-Cl | n-Pr | NHMe | OCF₃ | 7-Cl | n-Pr | NHMe |
| CF₃ | 7-Cl | i-Pr | NHMe | OCF₃ | 7-Cl | i-Pr | NHMe |
| CF₃ | 7-Cl | 4-F-Ph | NHMe | OCF₃ | 7-Cl | 4-F-Ph | NHMe |
| CF₃ | 7-CF₃ | CO₂Me | NHMe | OCF₃ | 7-CF₃ | CO₂Me | NHMe |
| CF₃ | 7-CF₃ | CO₂Et | NHMe | OCF₃ | 7-CF₃ | CO₂Et | NHMe |
| CF₃ | 7-CF₃ | Me | NHMe | OCF₃ | 7-CF₃ | Me | NHMe |
| CF₃ | 7-CF₃ | n-Pr | NHMe | OCF₃ | 7-CF₃ | n-Pr | NHMe |
| CF₃ | 7-CF₃ | i-Pr | NHMe | OCF₃ | 7-CF₃ | i-Pr | NHMe |
| CF₃ | 7-CF₃ | 4-F-Ph | NHMe | OCF₃ | 7-CF₃ | 4-F-Ph | NHMe |
| Br | 6-F | CO₂Me | NHCHO | CF₃ | 6-F | CO₂Me | NHCHO |
| Br | 6-F | CO₂Et | NHCHO | CF₃ | 6-F | CO₂Et | NHCHO |
| Br | 6-F | Me | NHCHO | CF₃ | 6-F | Me | NHCHO |
| Br | 6-F | n-Pr | NHCHO | CF₃ | 6-F | n-Pr | NHCHO |
| Br | 6-F | i-Pr | NHCHO | CF₃ | 6-F | i-Pr | NHCHO |
| Br | 6-F | 4-F-Ph | NHCHO | CF₃ | 6-F | 4-F-Ph | NHCHO |
| Br | 7-F | CO₂Me | NHCHO | CF₃ | 7-F | CO₂Me | NHCHO |
| Br | 7-F | CO₂Et | NHCHO | CF₃ | 7-F | CO₂Et | NHCHO |
| Br | 7-F | Me | NHCHO | CF₃ | 7-F | Me | NHCHO |
| Br | 7-F | n-Pr | NHCHO | CF₃ | 7-F | n-Pr | NHCHO |
| Br | 7-F | i-Pr | NHCHO | CF₃ | 7-F | i-Pr | NHCHO |
| Br | 7-F | 4-F-Ph | NHCHO | CF₃ | 7-F | 4-F-Ph | NHCHO |
| Br | 7-Cl | CO₂Me | NHCHO | CF₃ | 7-Cl | CO₂Me | NHCHO |
| Br | 7-Cl | CO₂Et | NHCHO | CF₃ | 7-Cl | CO₂Et | NHCHO |
| Br | 7-Cl | Me | NHCHO | CF₃ | 7-Cl | Me | NHCHO |
| Br | 7-Cl | n-Pr | NHCHO | CF₃ | 7-Cl | n-Pr | NHCHO |
| Br | 7-Cl | i-Pr | NHCHO | CF₃ | 7-Cl | i-Pr | NHCHO |
| Br | 7-Cl | 4-F-Ph | NHCHO | CF₃ | 7-Cl | 4-F-Ph | NHCHO |
| Br | 7-CF₃ | CO₂Me | NHCHO | CF₃ | 7-CF₃ | CO₂Me | NHCHO |
| Br | 7-CF₃ | CO₂Et | NHCHO | CF₃ | 7-CF₃ | CO₂Et | NHCHO |
| Br | 7-CF₃ | Me | NHCHO | CF₃ | 7-CF₃ | Me | NHCHO |
| Br | 7-CF₃ | n-Pr | NHCHO | CF₃ | 7-CF₃ | n-Pr | NHCHO |
| Br | 7-CF₃ | i-Pr | NHCHO | CF₃ | 7-CF₃ | i-Pr | NHCHO |
| Br | 7-CF₃ | 4-F-Ph | NHCHO | CF₃ | 7-CF₃ | 4-F-Ph | NHCHO |
| OCF₃ | 6-F | CO₂Me | NHCHO | Br | 6-F | CO₂Me | NH(CO)Me |
| OCF₃ | 6-F | CO₂Et | NHCHO | Br | 6-F | CO₂Et | NH(CO)Me |
| OCF₃ | 6-F | Me | NHCHO | Br | 6-F | Me | NH(CO)Me |
| OCF₃ | 6-F | n-Pr | NHCHO | Br | 6-F | n-Pr | NH(CO)Me |
| OCF₃ | 6-F | i-Pr | NHCHO | Br | 6-F | i-Pr | NH(CO)Me |
| OCF₃ | 6-F | 4-F-Ph | NHCHO | Br | 6-F | 4-F-Ph | NH(CO)Me |
| OCF₃ | 7-F | CO₂Me | NHCHO | Br | 7-F | CO₂Me | NH(CO)Me |
| OCF₃ | 7-F | CO₂Et | NHCHO | Br | 7-F | CO₂Et | NH(CO)Me |
| OCF₃ | 7-F | Me | NHCHO | Br | 7-F | Me | NH(CO)Me |
| OCF₃ | 7-F | n-Pr | NHCHO | Br | 7-F | n-Pr | NH(CO)Me |
| OCF₃ | 7-F | i-Pr | NHCHO | Br | 7-F | i-Pr | NH(CO)Me |
| OCF₃ | 7-F | 4-F-Ph | NHCHO | Br | 7-F | 4-F-Ph | NH(CO)Me |
| OCF₃ | 7-Cl | CO₂Me | NHCHO | Br | 7-Cl | CO₂Me | NH(CO)Me |
| OCF₃ | 7-Cl | CO₂Et | NHCHO | Br | 7-Cl | CO₂Et | NE(CO)Me |
| OCF₃ | 7-Cl | Me | NHCHO | Br | 7-Cl | Me | NH(CO)Me |
| OCF₃ | 7-Cl | n-Pr | NHCHO | Br | 7-Cl | n-Pr | NH(CO)Me |
| OCF₃ | 7-Cl | i-Pr | NHCHO | Br | 7-Cl | i-Pr | NH(CO)Me |
| OCF₃ | 7-Cl | 4-F-Ph | NHCHO | Br | 7-Cl | 4-F-Ph | NH(CO)Me |
| OCF₃ | 7-CF₃ | CO₂Me | NHCHO | Br | 7-CF₃ | CO₂Me | NH(CO)Me |
| OCF₃ | 7-CF₃ | CO₂Et | NHCHO | Br | 7-CF₃ | CO₂Et | NH(CO)Me |
| OCF₃ | 7-CF₃ | Me | NHCHO | Br | 7-CF₃ | Me | NH(CO)Me |
| OCF₃ | 7-CF₃ | n-Pr | NHCHO | Br | 7-CF₃ | n-Pr | NH(CO)Me |
| OCF₃ | 7-CF₃ | i-Pr | NHCHO | Br | 7-CF₃ | i-Pr | NH(CO)Me |
| OCF₃ | 7-CF₃ | 4-F-Ph | NHCHO | Br | 7-CF₃ | 4-F-Ph | NH(CO)Me |
| Br | 7-F | CO₂Me | OMe | CF₃ | 7-F | CO₂Me | OMe |
| Br | 7-F | CO₂Et | OMe | CF₃ | 7-F | CO₂Et | OMe |
| Br | 7-F | Me | OMe | CF₃ | 7-F | Me | OMe |
| Br | 7-F | n-Pr | OMe | CF₃ | 7-F | n-Pr | OMe |
| Br | 7-F | i-Pr | OMe | CF₃ | 7-F | i-Pr | OMe |
| Br | 7-F | 4-F-Ph | OMe | CF₃ | 7-F | 4-F-Ph | OMe |
| Br | 7-Cl | CO₂Me | OMe | CF₃ | 7-Cl | CO₂Me | OMe |
| Br | 7-Cl | CO₂Et | OMe | CF₃ | 7-Cl | CO₂Et | OMe |
| Br | 7-Cl | Me | OMe | CF₃ | 7-Cl | Me | OMe |
| Br | 7-Cl | n-Pr | OMe | CF₃ | 7-Cl | n-Pr | OMe |
| Br | 7-Cl | i-Pr | OMe | CF₃ | 7-Cl | i-Pr | OMe |
| Br | 7-Cl | 4-F-Ph | OMe | CF₃ | 7-Cl | 4-F-Ph | OMe |
| Br | 7-CF₃ | CO₂Me | OMe | CF₃ | 7-CF₃ | CO₂Me | OMe |
| Br | 7-CF₃ | CO₂Et | OMe | CF₃ | 7-CF₃ | CO₂Et | OMe |
| Br | 7-CF₃ | Me | OMe | CF₃ | 7-CF₃ | Me | OMe |

TABLE 12-continued

| R$^1$ | R$^2$ | R$^3$ | Y | R$^1$ | R$^2$ | R$^3$ | Y |
|---|---|---|---|---|---|---|---|
| Br | 7-CF$_3$ | n-Pr | OMe | CF$_3$ | 7-CF$_3$ | n-Pr | OMe |
| Br | 7-CF$_3$ | i-Pr | OMe | CF$_3$ | 7-CF$_3$ | i-Pr | OMe |
| Br | 7-CF$_3$ | 4-F-Ph | OMe | CF$_3$ | 7-CF$_3$ | 4-F-Ph | OMe |
| OCF$_3$ | 6-F | CO$_2$Me | OMe | Br | 6-F | CO$_2$Me | N=CHPh |
| OCF$_3$ | 6-F | CO$_2$Et | OMe | Br | 6-F | CO$_2$Et | N=CHPh |
| OCF$_3$ | 6-F | Me | OMe | Br | 6-F | Me | N=CHPh |
| OCF$_3$ | 6-F | n-Pr | OMe | Br | 6-F | n-Pr | N=CHPh |
| OCF$_3$ | 6-F | i-Pr | OMe | Br | 6-F | i-Pr | N=CHPh |
| OCF$_3$ | 6-F | 4-F-Ph | OMe | Br | 6-F | 4-F-Ph | N=CHPh |
| OCF$_3$ | 7-F | CO$_2$Me | OMe | Br | 7-F | CO$_2$Me | N=CHPh |
| OCF$_3$ | 7-F | CO$_2$Et | OMe | Br | 7-F | CO$_2$Et | N=CHPh |
| OCF$_3$ | 7-F | Me | OMe | Br | 7-F | Me | N=CHPh |
| OCF$_3$ | 7-F | n-Pr | OMe | Br | 7-F | n-Pr | N=CHPh |
| OCF$_3$ | 7-F | i-Pr | OMe | Br | 7-F | i-Pr | N=CHPh |
| OCF$_3$ | 7-F | 4-F-Ph | OMe | Br | 7-F | 4-F-Ph | N=CHPh |
| OCF$_3$ | 7-Cl | CO$_2$Me | OMe | Br | 7-Cl | CO$_2$Me | N=CHPh |
| OCF$_3$ | 7-Cl | CO$_2$Et | OMe | Br | 7-Cl | CO$_2$Et | N=CHPh |
| OCF$_3$ | 7-Cl | Me | OMe | Br | 7-Cl | Me | N=CHPh |
| OCF$_3$ | 7-Cl | n-Pr | OMe | Br | 7-Cl | n-Pr | N=CHPh |
| OCF$_3$ | 7-Cl | i-Pr | OMe | Br | 7-Cl | i-Pr | N=CHPh |
| OCF$_3$ | 7-Cl | 4-F-Ph | OMe | Br | 7-Cl | 4-F-Ph | N=CHPh |
| OCF$_3$ | 7-CF$_3$ | CO$_2$Me | OMe | Br | 7-CF$_3$ | CO$_2$Me | N=CHPh |
| OCF$_3$ | 7-CF$_3$ | CO$_2$Et | OMe | Br | 7-CF$_3$ | CO$_2$Et | N=CHPh |
| OCF$_3$ | 7-CF$_3$ | Me | OMe | Br | 7-CF$_3$ | Me | N=CHPh |
| OCF$_3$ | 7-CF$_3$ | n-Pr | OMe | Br | 7-CF$_3$ | n-Pr | N=CHPh |
| OCF$_3$ | 7-CF$_3$ | i-Pr | OMe | Br | 7-CF$_3$ | i-Pr | N=CHPh |
| OCF$_3$ | 7-CF$_3$ | 4-F-Ph | OMe | Br | 7-CF$_3$ | 4-F-Ph | N=CHPh |
| CF$_3$ | 6-F | CO$_2$Me | N=CHPh | OCF$_3$ | 6-F | CO$_2$Me | N=CHPh |
| CF$_3$ | 6-F | CO$_2$Et | N=CHPh | OCF$_3$ | 6-F | CO$_2$Et | N=CHPh |
| CF$_3$ | 6-F | Me | N=CHPh | OCF$_3$ | 6-F | Me | N=CHPh |
| CF$_3$ | 6-F | n-Pr | N=CHPh | OCF$_3$ | 6-F | n-Pr | N=CHPh |
| CF$_3$ | 6-F | i-Pr | N=CHPh | OCF$_3$ | 6-F | i-Pr | N=CHPh |
| CF$_3$ | 6-F | 4-F-Ph | N=CHPh | OCF$_3$ | 6-F | 4-F-Ph | N=CHPh |
| CF$_3$ | 7-F | CO$_2$Me | N=CHPh | OCF$_3$ | 7-F | CO$_2$Me | N=CHPh |
| CF$_3$ | 7-F | CO$_2$Et | N=CHPh | OCF$_3$ | 7-F | CO$_2$Et | N=CHPh |
| CF$_3$ | 7-F | Me | N=CHPh | OCF$_3$ | 7-F | Me | N=CHPh |
| CF$_3$ | 7-F | n-Pr | N=CHPh | OCF$_3$ | 7-F | n-Pr | N=CHPh |
| CF$_3$ | 7-F | i-Pr | N=CHPh | OCF$_3$ | 7-F | i-Pr | N=CHPh |
| CF$_3$ | 7-F | 4-F-Ph | N=CHPh | OCF$_3$ | 7-F | 4-F-Ph | N=CHPh |
| CF$_3$ | 7-Cl | CO$_2$Me | N=CHPh | OCF$_3$ | 7-Cl | CO$_2$Me | N=CHPh |
| CF$_3$ | 7-Cl | CO$_2$Et | N=CHPh | OCF$_3$ | 7-Cl | CO$_2$Et | N=CHPh |
| CF$_3$ | 7-Cl | Me | N=CHPh | OCF$_3$ | 7-Cl | Me | N=CHPh |
| CF$_3$ | 7-Cl | n-Pr | N=CHPh | OCF$_3$ | 7-Cl | n-Pr | N=CHPh |
| CF$_3$ | 7-Cl | i-Pr | N=CHPh | OCF$_3$ | 7-Cl | i-Pr | N=CHPh |
| CF$_3$ | 7-Cl | 4-F-Ph | N=CHPh | OCF$_3$ | 7-Cl | 4-F-Ph | N=CHPh |
| CF$_3$ | 7-CF$_3$ | CO$_2$Me | N=CHPh | OCF$_3$ | 7-CF$_3$ | CO$_2$Me | N=CHPh |
| CF$_3$ | 7-CF$_3$ | CO$_2$Et | N=CHPh | OCF$_3$ | 7-CF$_3$ | CO$_2$Et | N=CHPh |
| CF$_3$ | 7-CF$_3$ | Me | N=CHPh | OCF$_3$ | 7-CF$_3$ | Me | N=CHPh |
| CF$_3$ | 7-CF$_3$ | n-Pr | N=CHPh | OCF$_3$ | 7-CF$_3$ | n-Pr | N=CHPh |
| CF$_3$ | 7-CF$_3$ | i-Pr | N=CHPh | OCF$_3$ | 7-CF$_3$ | i-Pr | N=CHPh |
| CF$_3$ | 7-CF$_3$ | 4-F-Ph | N=CHPh | OCF$_3$ | 7-CF$_3$ | 4-F-Ph | N=CHPh |
| CF$_3$ | 6-F | CO$_2$Me | OH | OCF$_3$ | 6-F | CO$_2$Me | OH |
| CF$_3$ | 6-F | CO$_2$Et | OH | OCF$_3$ | 6-F | CO$_2$Et | OH |
| CF$_3$ | 6-F | Me | OH | OCF$_3$ | 6-F | Me | OH |
| CF$_3$ | 6-F | n-Pr | OH | OCF$_3$ | 6-F | n-Pr | OH |
| CF$_3$ | 6-F | i-Pr | OH | OCF$_3$ | 6-F | i-Pr | OH |
| CF$_3$ | 6-F | 4-F-Ph | OH | OCF$_3$ | 6-F | 4-F-Ph | OH |
| CF$_3$ | 7-F | CO$_2$Me | OH | OCF$_3$ | 7-F | CO$_2$Me | OH |
| CF$_3$ | 7-F | CO$_2$Et | OH | OCF$_3$ | 7-F | CO$_2$Et | OH |
| CF$_3$ | 7-F | Me | OH | OCF$_3$ | 7-F | Me | OH |
| CF$_3$ | 7-F | n-Pr | OH | OCF$_3$ | 7-F | n-Pr | OH |
| CF$_3$ | 7-F | i-Pr | OH | OCF$_3$ | 7-F | i-Pr | OH |
| CF$_3$ | 7-F | 4-F-Ph | OH | OCF$_3$ | 7-F | 4-F-Ph | OH |
| CF$_3$ | 7-Cl | CO$_2$Me | OH | OCF$_3$ | 7-Cl | CO$_2$Me | OH |
| CF$_3$ | 7-Cl | CO$_2$Et | OH | OCF$_3$ | 7-Cl | CO$_2$Et | OH |
| CF$_3$ | 7-Cl | Me | OH | OCF$_3$ | 7-Cl | Me | OH |
| CF$_3$ | 7-Cl | n-Pr | OH | OCF$_3$ | 7-Cl | n-Pr | OH |
| CF$_3$ | 7-Cl | i-Pr | OH | OCF$_3$ | 7-Cl | i-Pr | OH |
| CF$_3$ | 7-Cl | 4-F-Ph | OH | OCF$_3$ | 7-Cl | 4-F-Ph | OH |
| CF$_3$ | 7-CF$_3$ | CO$_2$Me | OH | OCF$_3$ | 7-CF$_3$ | CO$_2$Me | OH |
| CF$_3$ | 7-CF$_3$ | CO$_2$Et | OH | OCF$_3$ | 7-CF$_3$ | CO$_2$Et | OH |
| CF$_3$ | 7-CF$_3$ | Me | OH | OCF$_3$ | 7-CF$_3$ | Me | OH |
| CF$_3$ | 7-CF$_3$ | n-Pr | OH | OCF$_3$ | 7-CF$_3$ | n-Pr | OH |
| CF$_3$ | 7-CF$_3$ | i-Pr | OH | OCF$_3$ | 7-CF$_3$ | i-Pr | OH |
| CF$_3$ | 7-CF$_3$ | 4-F-Ph | OH | OCF$_3$ | 7-CF$_3$ | 4-F-Ph | OH |
| Br | 6-F | CO$_2$Me | OH | Br | 7-Cl | CO$_2$Me | OH |
| Br | 6-F | CO$_2$Et | OH | Br | 7-Cl | CO$_2$Et | OH |

TABLE 12-continued

| R¹ | R² | R³ | Y | R¹ | R² | R³ | Y |
|---|---|---|---|---|---|---|---|
| Br | 6-F | Me | OH | Br | 7-Cl | Me | OH |
| Br | 6-F | n-Pr | OH | Br | 7-Cl | n-Pr | OH |
| Br | 6-F | i-Pr | OH | Br | 7-Cl | i-Pr | OH |
| Br | 6-F | 4-F-Ph | OH | Br | 7-Cl | 4-F-Ph | OH |
| Br | 7-F | CO₂Me | OH | Br | 7-CF₃ | CO₂Me | OH |
| Br | 7-F | CO₂Et | OH | Br | 7-CF₃ | CO₂Et | OH |
| Br | 7-F | Me | OH | Br | 7-CF₃ | Me | OH |
| Br | 7-F | n-Pr | OH | Br | 7-CF₃ | n-Pr | OH |
| Br | 7-F | i-Pr | ON | Br | 7-CF₃ | i-Pr | OH |
| Br | 7-F | 4-F-Ph | OH | Br | 7-CF₃ | 4-F-Ph | OH |

TABLE 13

| R¹ | R² | R³ | Y | R¹ | R² | R³ | Y |
|---|---|---|---|---|---|---|---|
| Br | 6-F | CO₂Me | Me | CF₃ | 6-F | CO₂Me | Me |
| Br | 6-F | CO₂Et | Me | CF₃ | 6-F | CO₂Et | Me |
| Br | 6-F | Me | Me | CF₃ | 6-F | Me | Me |
| Br | 6-F | n-Pr | Me | CF₃ | 6-F | n-Pr | Me |
| Br | 6-F | i-Pr | Me | CF₃ | 6-F | i-Pr | Me |
| Br | 6-F | 4-F-Ph | Me | CF₃ | 6-F | 4-F-Ph | Me |
| Br | 7-F | CO₂Me | Me | CF₃ | 7-F | CO₂Me | Me |
| Br | 7-F | CO₂Et | Me | CF₃ | 7-F | CO₂Et | Me |
| Br | 7-F | Me | Me | CF₃ | 7-F | Me | Me |
| Br | 7-F | n-Pr | Me | CF₃ | 7-F | n-Pr | Me |
| Br | 7-F | i-Pr | Me | CF₃ | 7-F | i-Pr | Me |
| Br | 7-F | 4-F-Ph | Me | CF₃ | 7-F | 4-F-Ph | Me |
| Br | 7-Cl | CO₂Me | Me | CF₃ | 7-Cl | CO₂Me | Me |
| Br | 7-Cl | CO₂Et | Me | CF₃ | 7-Cl | CO₂Et | Me |
| Br | 7-Cl | Me | Me | CF₃ | 7-Cl | Me | Me |
| Br | 7-Cl | n-Pr | Me | CF₃ | 7-Cl | n-Pr | Me |
| Br | 7-Cl | i-Pr | Me | CF₃ | 7-Cl | i-Pr | Me |
| Br | 7-Cl | 4-F-Ph | Me | CF₃ | 7-Cl | 4-F-Ph | Me |
| Br | 7-CF₃ | CO₂Me | Me | CF₃ | 7-CF₃ | CO₂Me | Me |
| Br | 7-CF₃ | CO₂Et | Me | CF₃ | 7-CF₃ | CO₂Et | Me |
| Br | 7-CF₃ | Me | Me | CF₃ | 7-CF₃ | Me | Me |
| Br | 7-CF₃ | n-Pr | Me | CF₃ | 7-CF₃ | n-Pr | Me |
| Br | 7-CF₃ | i-Pr | Me | CF₃ | 7-CF₃ | i-Pr | Me |
| Br | 7-CF₃ | 4-F-Ph | Me | CF₃ | 7-CF₃ | 4-F-Ph | Me |
| OCF₃ | 6-F | CO₂Me | Me | Br | 6-F | CO₂Me | Et |
| OCF₃ | 6-F | CO₂Et | Me | Br | 6-F | CO₂Et | Et |
| OCF₃ | 6-F | Me | Me | Br | 6-F | Me | Et |
| OCF₃ | 6-F | n-Pr | Me | Br | 6-F | n-Pr | Et |
| OCF₃ | 6-F | i-Pr | Me | Br | 6-F | i-Pr | Et |
| OCF₃ | 6-F | 4-F-Ph | Me | Br | 6-F | 4-F-Ph | Et |
| OCF₃ | 7-F | CO₂Me | Me | Br | 7-F | CO₂Me | Et |
| OCF₃ | 7-F | CO₂Et | Me | Br | 7-F | CO₂Et | Et |
| OCF₃ | 7-F | Me | Me | Br | 7-F | Me | Et |
| OCF₃ | 7-F | n-Pr | Me | Br | 7-F | n-Pr | Et |
| OCF₃ | 7-F | i-Pr | Me | Br | 7-F | i-Pr | Et |
| OCF₃ | 7-F | 4-F-Ph | Me | Br | 7-F | 4-F-Ph | Et |
| OCF₃ | 7-Cl | CO₂Me | Me | Br | 7-Cl | CO₂Me | Et |
| OCF₃ | 7-Cl | CO₂Et | Me | Br | 7-Cl | CO₂Et | Et |
| OCF₃ | 7-Cl | Me | Me | Br | 7-Cl | Me | Et |
| OCF₃ | 7-Cl | n-Pr | Me | Br | 7-Cl | n-Pr | Et |
| OCF₃ | 7-Cl | i-Pr | Me | Br | 7-Cl | i-Pr | Et |
| OCF₃ | 7-Cl | 4-F-Ph | Me | Br | 7-Cl | 4-F-Ph | Et |
| OCF₃ | 7-CF₃ | CO₂Me | Me | Br | 7-CF₃ | CO₂Me | Et |
| OCF₃ | 7-CF₃ | CO₂Et | Me | Br | 7-CF₃ | CO₂Et | Et |
| OCF₃ | 7-CF₃ | Me | Me | Br | 7-CF₃ | MO | Et |
| OCF₃ | 7-CF₃ | n-Pr | Me | Br | 7-CF₃ | n-Pr | Et |
| OCF₃ | 7-CF₃ | i-Pr | Me | Br | 7-CF₃ | i-Pr | Et |
| OCF₃ | 7-CF₃ | 4-F-Ph | Me | Br | 7-CF₃ | 4-F-Ph | Et |
| CF₃ | 6-F | CO₂Me | Et | OCF₃ | 6-F | CO₂Me | Et |
| CF₃ | 6-F | CO₂Et | Et | OCF₃ | 6-F | CO₂Et | Et |
| CF₃ | 6-F | Me | Et | OCF₃ | 6-F | Me | Et |
| CF₃ | 6-F | n-Pr | Et | OCF₃ | 6-F | n-Pr | Et |
| CF₃ | 6-F | i-Pr | Et | OCF₃ | 6-F | i-Pr | Et |
| CF₃ | 6-F | 4-F-Ph | Et | OCF₃ | 6-F | 4-F-Ph | Et |
| CF₃ | 7-F | CO₂Me | Et | OCF₃ | 7-F | CO₂Me | Et |
| CF₃ | 7-F | CO₂Et | Et | OCF₃ | 7-F | CO₂Et | Et |
| CF₃ | 7-F | Me | Et | OCF₃ | 7-F | Me | Et |
| CF₃ | 7-F | n-Pr | Et | OCF₃ | 7-F | n-Pr | Et |
| CF₃ | 7-F | i-Pr | Et | OCF₃ | 7-F | i-Pr | Et |
| CF₃ | 7-F | 4-F-Ph | Et | OCF₃ | 7-F | 4-F-Ph | Et |

TABLE 13-continued

| R¹ | R² | R³ | Y | R¹ | R² | R³ | Y |
|---|---|---|---|---|---|---|---|
| CF₃ | 7-Cl | CO₂Me | Et | OCF₃ | 7-Cl | CO₂Me | Et |
| CF₃ | 7-Cl | CO₂Et | Et | OCF₃ | 7-Cl | CO₂Et | Et |
| CF₃ | 7-Cl | Me | Et | OCF₃ | 7-Cl | Me | Et |
| CF₃ | 7-Cl | n-Pr | Et | OCF₃ | 7-Cl | n-Pr | Et |
| CF₃ | 7-Cl | i-Pr | Et | OCF₃ | 7-Cl | i-Pr | Et |
| CF₃ | 7-Cl | 4-F-Ph | Et | OCF₃ | 7-Cl | 4-F-Ph | Et |
| CF₃ | 7-CF₃ | CO₂Me | Et | OCF₃ | 7-CF₃ | CO₂Me | Et |
| CF₃ | 7-CF₃ | CO₂Et | Et | OCF₃ | 7-CF₃ | CO₂Et | Et |
| CF₃ | 7-CF₃ | Me | Et | OCF₃ | 7-CF₃ | Me | Et |
| CF₃ | 7-CF₃ | n-Pr | Et | OCF₃ | 7-CF₃ | n-Pr | Et |
| CF₃ | 7-CF₃ | i-Pr | Et | OCF₃ | 7-CF₃ | i-Pr | Et |
| CF₃ | 7-CF₃ | 4-F-Ph | Et | OCF₃ | 7-CF₃ | 4-F-Ph | Et |
| Br | 6-F | CO₂Me | —CH₂OCH₃ | CF₃ | 6-F | CO₂Me | —CH₂OCH₃ |
| Br | 6-F | CO₂Et | —CH₂OCH₃ | CF₃ | 6-F | CO₂Et | —CH₂OCH₃ |
| Br | 6-F | Me | —CH₂OCH₃ | CF₃ | 6-F | Me | —CH₂OCH₃ |
| Br | 6-F | n-Pr | —CH₂OCH₃ | CF₃ | 6-F | n-Pr | —CH₂OCH₃ |
| Br | 6-F | i-Pr | —CH₂OCH₃ | CF₃ | 6-F | i-Pr | —CH₂OCH₃ |
| Br | 6-F | 4-F-Ph | —CH₂OCH₃ | CF₃ | 6-F | 4-F-Ph | —CH₂OCH₃ |
| Br | 7-F | CO₂Me | —CH₂OCH₃ | CF₃ | 7-F | CO₂Me | —CH₂OCH₃ |
| Br | 7-F | CO₂Et | —CH₂OCH₃ | CF₃ | 7-F | CO₂Et | —CH₂OCH₃ |
| Br | 7-F | Me | —CH₂OCH₃ | CF₃ | 7-F | Me | —CH₂OCH₃ |
| Br | 7-F | n-Pr | —CH₂OCH₃ | CF₃ | 7-F | n-Pr | —CH₂OCH₃ |
| Br | 7-F | i-Pr | —CH₂OCH₃ | CF₃ | 7-F | i-Pr | —CH₂OCH₃ |
| Br | 7-F | 4-F-Ph | —CH₂OCH₃ | CF₃ | 7-F | 4-F-Ph | —CH₂OCH₃ |
| Br | 7-Cl | CO₂Me | —CH₂OCH₃ | CF₃ | 7-Cl | CO₂Me | —CH₂OCH₃ |
| Br | 7-Cl | CO₂Et | —CH₂OCH₃ | CF₃ | 7-Cl | CO₂Et | —CH₂OCH₃ |
| Br | 7-Cl | Me | —CH₂OCH₃ | CF₃ | 7-Cl | Me | —CH₂OCH₃ |
| Br | 7-Cl | n-Pr | —CH₂OCH₃ | CF₃ | 7-Cl | n-Pr | —CH₂OCH₃ |
| Br | 7-Cl | i-Pr | —CH₂OCH₃ | CF₃ | 7-Cl | i-Pr | —CH₂OCH₃ |
| Br | 7-Cl | 4-F-Ph | —CH₂OCH₃ | CF₃ | 7-Cl | 4-F-Ph | —CH₂OCH₃ |
| Br | 7-CF₃ | CO₂Me | —CH₂OCH₃ | CF₃ | 7-CF₃ | CO₂Me | —CH₂OCH₃ |
| Br | 7-CF₃ | CO₂Et | —CH₂OCH₃ | CF₃ | 7-CF₃ | CO₂Et | —CH₂OCH₃ |
| Br | 7-CF₃ | Me | —CH₂OCH₃ | CF₃ | 7-CF₃ | Me | —CH₂OCH₃ |
| Br | 7-CF₃ | n-Pr | —CH₂OCH₃ | CF₃ | 7-CF₃ | n-Pr | —CH₂OCH₃ |
| Br | 7-CF₃ | i-Pr | —CH₂OCH₃ | CF₃ | 7-CF₃ | i-Pr | —CH₂OCH₃ |
| Br | 7-CF₃ | 4-F-Ph | —CH₂OCH₃ | CF₃ | 7-CF₃ | 4-F-Ph | —CH₂OCH₃ |
| OCF₃ | 6-F | CO₂Me | —CH₂OCH₃ | Br | 6-F | CO₂Me | —CH₂C≡CH |
| OCF₃ | 6-F | CO₂Et | —CH₂OCH₃ | Br | 6-F | CO₂Et | —CH₂C≡CH |
| OCF₃ | 6-F | Me | —CH₂OCH₃ | Br | 6-F | Me | —CH₂C≡CH |
| OCF₃ | 6-F | n-Pr | —CH₂OCH₃ | Br | 6-F | n-Pr | —CH₂C≡CH |
| OCF₃ | 6-F | i-Pr | —CH₂OCH₃ | Br | 6-F | i-Pr | —CH₂C≡CH |
| OCF₃ | 6-F | 4-F-Ph | —CH₂OCH₃ | Br | 6-F | 4-F-Ph | —CH₂C≡CH |
| OCF₃ | 7-F | CO₂Me | —CH₂OCH₃ | CF₃ | 6-F | CO₂Me | —CH₂C≡CH |
| OCF₃ | 7-F | CO₂Et | —CH₂OCH₃ | CF₃ | 6-F | CO₂Et | —CH₂C≡CH |
| OCF₃ | 7-F | Me | —CH₂OCH₃ | CF₃ | 6-F | Me | —CH₂C≡CH |
| OCF₃ | 7-F | n-Pr | —CH₂OCH₃ | CF₃ | 6-F | n-Pr | —CH₂C≡CH |
| OCF₃ | 7-F | i-Pr | —CH₂OCH₃ | CF₃ | 6-F | i-Pr | —CH₂C≡CH |
| OCF₃ | 7-F | 4-F-Ph | —CH₂OCH₃ | CF₃ | 6-F | 4-F-Ph | —CH₂C≡CH |
| OCF₃ | 7-Cl | CO₂Me | —CH₂OCH₃ | Br | 7-F | CO₂Me | —CH₂C≡CH |
| OCF₃ | 7-Cl | CO₂Et | —CH₂OCH₃ | Br | 7-F | CO₂Et | —CH₂C≡CH |
| OCF₃ | 7-Cl | Me | —CH₂OCH₃ | Br | 7-F | Me | —CH₂C≡CH |
| OCF₃ | 7-Cl | n-Pr | —CH₂OCH₃ | Br | 7-F | n-Pr | —CH₂C≡CH |
| OCF₃ | 7-Cl | i-Pr | —CH₂OCH₃ | Br | 7-F | Pr | —CH₂C≡CH |
| OCF₃ | 7-Cl | 4-F-Ph | —CH₂OCH₃ | Br | 7-F | 4-F-Ph | —CH₂C≡CH |
| OCF₃ | 7-CF₃ | CO₂Me | —CH₂OCH₃ | Br | 7-Cl | CO₂Me | —CH₂C≡CH |
| OCF₃ | 7-CF₃ | CO₂Et | —CH₂OCH₃ | Br | 7-Cl | CO₂Et | —CH₂C≡CH |
| OCF₃ | 7-CF₃ | Me | —CH₂OCH₃ | Br | 7-Cl | Me | —CH₂C≡CH |
| OCF₃ | 7-CF₃ | n-Pr | —CH₂OCH₃ | Br | 7-Cl | n-Pr | —CH₂C≡CH |
| OCF₃ | 7-CF₃ | i-Pr | —CH₂OCH₃ | Br | 7-Cl | Pr | —CH₂C≡CH |
| OCF₃ | 7-CF₃ | 4-F-Ph | —CH₂OCH₃ | Br | 7-Cl | 4-F-Ph | —CH₂C≡CH |
| Br | 7-CF₃ | CO₂Me | —CH₂C≡CH | CF₃ | 7-CF₃ | CO₂Me | —CH₂C≡CH |
| Br | 7-CF₃ | CO₂Et | —CH₂C≡CH | CF₃ | 7-CF₃ | CO₂Et | —CH₂C≡CH |
| Br | 7-CF₃ | Me | —CH₂C≡CH | CF₃ | 7-CF₃ | Me | —CH₂C≡CH |
| Br | 7-CF₃ | n-Pr | —CH₂C≡CH | CF₃ | 7-CF₃ | n-Pr | —CH₂C≡CH |
| Br | 7-CF₃ | Pr | —CH₂C≡CH | CF₃ | 7-CF₃ | i-Pr | —CH₂C≡CH |
| Br | 7-CF₃ | 4-F-Ph | —CH₂C≡CH | CF₃ | 7-CF₃ | 4-F-Ph | —CH₂C≡CH |
| OCF₃ | 6-F | CO₂Me | —CH₂C≡CH | Br | 6-F | CO₂Me | —CH₂CH=CH₂ |
| OCF₃ | 6-F | CO₂Et | —CH₂C≡CH | Br | 6-F | CO₂Et | —CH₂CH=CH₂ |
| OCF₃ | 6-F | Me | —CH₂C≡CH | Br | 6-F | Me | —CH₂CH=CH₂ |
| OCF₃ | 6-F | n-Pr | —CH₂C≡CH | Br | 6-F | n-Pr | —CH₂CH=CH₂ |
| OCF₃ | 6-F | Pr | —CH₂C≡CH | Br | 6-F | Pr | —CH₂CH=CH₂ |
| OCF₃ | 6-F | 4-F-Ph | —CH₂C≡CH | Br | 6-F | 4-F-Ph | —CH₂CH=CH₂ |
| OCF₃ | 7-F | CO₂Me | —CH₂C≡CH | Br | 7-F | CO₂Me | —CH₂CH=CH₂ |
| OCF₃ | 7-F | CO₂Et | —CH₂C≡CH | Br | 7-F | CO₂Et | —CH₂CH=CH₂ |
| OCF₃ | 7-F | Me | —CH₂C≡CH | Br | 7-F | Me | —CH₂CH=CH₂ |
| OCF₃ | 7-F | n-Pr | —CH₂C≡CH | Br | 7-F | n-Pr | —CH₂CH=CH₂ |
| OCF₃ | 7-F | Pr | —CH₂C≡CH | Br | 7-F | Pr | —CH₂CH=CH₂ |

TABLE 13-continued

| R¹ | R² | R³ | Y | R¹ | R² | R³ | Y |
|---|---|---|---|---|---|---|---|
| OCF$_3$ | 7-F | 4-F-Ph | —CH$_2$C≡CH | Br | 7-F | 4-F-Ph | —CH$_2$CH=CH$_2$ |
| CF$_3$ | 7-F | CO$_2$Me | —CH$_2$C≡CH | OCF$_3$ | 7-Cl | CO$_2$Me | —CH$_2$C≡CH |
| CF$_3$ | 7-F | CO$_2$Et | —CH$_2$C≡CH | OCF$_3$ | 7-Cl | CO$_2$Et | —CH$_2$C≡CH |
| CF$_3$ | 7-F | Me | —CH$_2$C≡CH | OCF$_3$ | 7-Cl | Me | —CH$_2$C≡CH |
| CF$_3$ | 7-F | n-Pr | —CH$_2$C≡CH | OCF$_3$ | 7-Cl | n-Pr | —CH$_2$C≡CH |
| CF$_3$ | 7-F | i-Pr | —CH$_2$C≡CH | OCF$_3$ | 7-Cl | Pr | —CH$_2$C≡CH |
| CF$_3$ | 7-F | 4-F-Ph | —CH$_2$C≡CH | OCF$_3$ | 7-Cl | 4-F-Ph | —CH$_2$C≡CH |
| CF$_3$ | 7-Cl | CO$_2$Me | —CH$_2$C≡CH | OCF$_3$ | 7-CF$_3$ | CO$_2$Me | —CH$_2$C≡CH |
| CF$_3$ | 7-Cl | CO$_2$Et | —CH$_2$C≡CH | OCF$_3$ | 7-CF$_3$ | CO$_2$Et | —CH$_2$C≡CH |
| CF$_3$ | 7-Cl | Me | —CH$_2$C≡CH | OCF$_3$ | 7-CF$_3$ | Me | —CH$_2$C≡CH |
| CF$_3$ | 7-Cl | n-Pr | —CH$_2$C≡CH | OCF$_3$ | 7-CF$_3$ | n-Pr | —CH$_2$C≡CH |
| CF$_3$ | 7-Cl | i-Pr | —CH$_2$C≡CH | OCF$_3$ | 7-CF$_3$ | Pr | —CH$_2$C≡CH |
| CF$_3$ | 7-Cl | 4-F-Ph | —CH$_2$C≡CH | OCF$_3$ | 7-CF$_3$ | 4-F-Ph | —CH$_2$C≡CH |
| CF$_3$ | 6-F | CO$_2$Me | —CH$_2$CH=CH$_2$ | OCF$_3$ | 6-F | CO$_2$Me | —CH$_2$CH=CH$_2$ |
| CF$_3$ | 6-F | CO$_2$Et | —CH$_2$CH=CH$_2$ | OCF$_3$ | 6-F | CO$_2$Et | —CH$_2$CH=CH$_2$ |
| CF$_3$ | 6-F | Me | —CH$_2$CH=CH$_2$ | OCF$_3$ | 6-F | Me | —CH$_2$CH=CH$_2$ |
| CF$_3$ | 6-F | n-Pr | —CH$_2$CH=CH$_2$ | OCF$_3$ | 6-F | n-Pr | —CH$_2$CH=CH$_2$ |
| CF$_3$ | 6-F | Pr | —CH$_2$CH=CH$_2$ | OCF$_3$ | 6-F | Pr | —CH$_2$CH=CH$_2$ |
| CF$_3$ | 6-F | 4-F-Ph | —CH$_2$CH=CH$_2$ | OCF$_3$ | 6-F | 4-F-Ph | —CH$_2$CH=CH$_2$ |
| CF$_3$ | 7-F | CO$_2$Me | —CH$_2$CH=CH$_2$ | OCF$_3$ | 7-F | CO$_2$Me | —CH$_2$CH=CH$_2$ |
| CF$_3$ | 7-F | CO$_2$Et | —CH$_2$CH=CH$_2$ | OCF$_3$ | 7-F | CO$_2$Et | —CH$_2$CH=CH$_2$ |
| CF$_3$ | 7-F | Me | —CH$_2$CH=CH$_2$ | OCF$_3$ | 7-F | Me | —CH$_2$CH=CH$_2$ |
| CF$_3$ | 7-F | n-Pr | —CH$_2$CH=CH$_2$ | OCF$_3$ | 7-F | n-Pr | —CH$_2$CH=CH$_2$ |
| CF$_3$ | 7-F | Pr | —CH$_2$CH=CH$_2$ | OCF$_3$ | 7-F | Pr | —CH$_2$CH=CH$_2$ |
| CF$_3$ | 7-F | 4-F-Ph | —CH$_2$CH=CH$_2$ | OCF$_3$ | 7-F | 4-F-Ph | —CH$_2$CH=CH$_2$ |
| CF$_3$ | 7-Cl | CO$_2$Me | —CH$_2$CH=CH$_2$ | OCF$_3$ | 7-Cl | CO$_2$Me | —CH$_2$CH=CH$_2$ |
| CF$_3$ | 7-Cl | CO$_2$Et | —CH$_2$CH=CH$_2$ | OCF$_3$ | 7-Cl | CO$_2$Et | —CH$_2$CH=CH$_2$ |
| CF$_3$ | 7-Cl | Me | —CH$_2$CH=CH$_2$ | OCF$_3$ | 7-Cl | Me | —CH$_2$CH=CH$_2$ |
| CF$_3$ | 7-Cl | n-Pr | —CH$_2$CH=CH$_2$ | OCF$_3$ | 7-Cl | n-Pr | —CH$_2$CH=CH$_2$ |
| CF$_3$ | 7-Cl | Pr | —CH$_2$CH=CH$_2$ | OCF$_3$ | 7-Cl | Pr | —CH$_2$CH=CH$_2$ |
| CF$_3$ | 7-Cl | 4-F-Ph | —CH$_2$CH=CH$_2$ | OCF$_3$ | 7-Cl | 4-F-Ph | —CH$_2$CH=CH$_2$ |
| Br | 7-Cl | CO$_2$Me | —CH$_2$CH=CH$_2$ | CF$_3$ | 7-CF$_3$ | CO$_2$Me | —CH$_2$CH=CH$_2$ |
| Br | 7-Cl | CO$_2$Et | —CH$_2$CH=CH$_2$ | CF$_3$ | 7-CF$_3$ | CO$_2$Et | —CH$_2$CH=CH$_2$ |
| Br | 7-Cl | Me | —CH$_2$CH=CH$_2$ | CF$_3$ | 7-CF$_3$ | Me | —CH$_2$CH=CH$_2$ |
| Br | 7-Cl | n-Pr | —CH$_2$CH=CH$_2$ | CF$_3$ | 7-CF$_3$ | n-Pr | —CH$_2$CH=CH$_2$ |
| Br | 7-Cl | Pr | —CH$_2$CH=CH$_2$ | CF$_3$ | 7-CF$_3$ | Pr | —CH$_2$CH=CH$_2$ |
| Br | 7-Cl | 4-F-Ph | —CH$_2$CH=CH$_2$ | CF$_3$ | 7-CF$_3$ | 4-F-Ph | —CH$_2$CH=CH$_2$ |
| Br | 7-CF$_3$ | CO$_2$Me | —CH$_2$CH=CH$_2$ | OCF$_3$ | 7-CF$_3$ | CO$_2$Me | —CH$_2$CH=CH$_2$ |
| Br | 7-CF$_3$ | CO$_2$Et | —CH$_2$CH=CH$_2$ | OCF$_3$ | 7-CF$_3$ | CO$_2$Et | —CH$_2$CH=CH$_2$ |
| Br | 7-CF$_3$ | Me | —CH$_2$CH=CH$_2$ | OCF$_3$ | 7-CF$_3$ | Me | —CH$_2$CH=CH$_2$ |
| Br | 7-CF$_3$ | n-Pr | —CH$_2$CH=CH$_2$ | OCF$_3$ | 7-CF$_3$ | n-Pr | —CH$_2$CH=CH$_2$ |
| Br | 7-CF$_3$ | Pr | —CH$_2$CH=CH$_2$ | OCF$_3$ | 7-CF$_3$ | Pr | —CH$_2$CH=CH$_2$ |
| Br | 7-CF$_3$ | 4-F-Ph | —CH$_2$CH=CH$_2$ | OCF$_3$ | 7-CF$_3$ | 4-F-Ph | —CH$_2$CH=CH$_2$ |

TABLE 14

| R¹ | R² | R³ | Y | R¹ | R² | R³ | Y |
|---|---|---|---|---|---|---|---|
| Br | 6-F | CO$_2$Me | Me | CF$_3$ | 6-F | CO$_2$Me | Me |
| Br | 6-F | CO$_2$Et | Me | CF$_3$ | 6-F | CO$_2$Et | Me |
| Br | 6-F | Me | Me | CF$_3$ | 6-F | Me | Me |
| Br | 6-F | n-Pr | Me | CF$_3$ | 6-F | n-Pr | Me |
| Br | 6-F | i-Pr | Me | CF$_3$ | 6-F | i-Pr | Me |
| Br | 6-F | 4-F-Ph | Me | CF$_3$ | 6-F | 4-F-Ph | Me |
| Br | 7-F | CO$_2$Me | Me | CF$_3$ | 7-F | CO$_2$Me | Me |
| Br | 7-F | CO$_2$Et | Me | CF$_3$ | 7-F | CO$_2$Et | Me |
| Br | 7-F | Me | Me | CF$_3$ | 7-F | Me | Me |
| Br | 7-F | n-Pr | Me | CF$_3$ | 7-F | n-Pr | Me |
| Br | 7-F | i-Pr | Me | CF$_3$ | 7-F | i-Pr | Me |
| Br | 7-F | 4-F-Ph | Me | CF$_3$ | 7-F | 4-F-Ph | Me |
| Br | 7-Cl | CO$_2$Me | Me | CF$_3$ | 7-Cl | CO$_2$Me | Me |
| Br | 7-Cl | CO$_2$Et | Me | CF$_3$ | 7-Cl | CO$_2$Et | Me |
| Br | 7-Cl | Me | Me | CF$_3$ | 7-Cl | Me | Me |
| Br | 7-Cl | n-Pr | Me | CF$_3$ | 7-Cl | n-Pr | Me |
| Br | 7-Cl | i-Pr | Me | CF$_3$ | 7-Cl | i-Pr | Me |
| Br | 7-Cl | 4-F-Ph | Me | CF$_3$ | 7-Cl | 4-F-Ph | Me |
| Br | 7-CF$_3$ | CO$_2$Me | Me | CF$_3$ | 7-CF$_3$ | CO$_2$Me | Me |
| Br | 7-CF$_3$ | CO$_2$Et | Me | CF$_3$ | 7-CF$_3$ | CO$_2$Et | Me |
| Br | 7-CF$_3$ | Me | Me | CF$_3$ | 7-CF$_3$ | Me | Me |
| Br | 7-CF$_3$ | n-Pr | Me | CF$_3$ | 7-CF$_3$ | n-Pr | Me |
| Br | 7-CF$_3$ | i-Pr | Me | CF$_3$ | 7-CF$_3$ | i-Pr | Me |
| Br | 7-CF$_3$ | 4-F-Ph | Me | CF$_3$ | 7-CF$_3$ | 4-F-Ph | Me |
| OCF$_3$ | 6-F | CO$_2$Me | Me | Br | 6-F | CO$_2$Me | Et |
| OCF$_3$ | 6-F | CO$_2$Et | Me | Br | 6-F | CO$_2$Et | Et |
| OCF$_3$ | 6-F | Me | Me | Br | 6-F | Me | Et |

TABLE 14-continued

| R¹ | R² | R³ | Y | R¹ | R² | R³ | Y |
|---|---|---|---|---|---|---|---|
| OCF₃ | 6-F | n-Pr | Me | Br | 6-F | n-Pr | Et |
| OCF₃ | 6-F | i-Pr | Me | Br | 6-F | i-Pr | Et |
| OCF₃ | 6-F | 4-F-Ph | Me | Br | 6-F | 4-F-Ph | Et |
| OCF₃ | 7-F | CO₂Me | Me | Br | 7-F | CO₂Me | Et |
| OCF₃ | 7-F | CO₂Et | Me | Br | 7-F | CO₂Et | Et |
| OCF₃ | 7-F | Me | Me | Br | 7-F | Me | Et |
| OCF₃ | 7-F | n-Pr | Me | Br | 7-F | n-Pr | Et |
| OCF₃ | 7-F | i-Pr | Me | Br | 7-F | i-Pr | Et |
| OCF₃ | 7-F | 4-F-Ph | Me | Br | 7-F | 4-F-Ph | Et |
| OCF₃ | 7-Cl | CO₂Me | Me | Br | 7-Cl | CO₂Me | Et |
| OCF₃ | 7-Cl | CO₂Et | Me | Br | 7-Cl | CO₂Et | Et |
| OCF₃ | 7-Cl | Me | Me | Br | 7-Cl | Me | Et |
| OCF₃ | 7-Cl | n-Pr | Me | Br | 7-Cl | n-Pr | Et |
| OCF₃ | 7-Cl | i-Pr | Me | Br | 7-Cl | i-Pr | Et |
| OCF₃ | 7-Cl | 4-F-Ph | Me | Br | 7-Cl | 4-F-Ph | Et |
| OCF₃ | 7-CF₃ | CO₂Me | Me | Br | 7-CF₃ | CO₂Me | Et |
| OCF₃ | 7-CF₃ | CO₂Et | Me | Br | 7-CF₃ | CO₂Et | Et |
| OCF₃ | 7-CF₃ | Me | Me | Br | 7-CF₃ | Me | Et |
| OCF₃ | 7-CF₃ | n-Pr | Me | Br | 7-CF₃ | n-Pr | Et |
| OCF₃ | 7-CF₃ | i-Pr | Me | Br | 7-CF₃ | i-Pr | Et |
| OCF₃ | 7-CF3 | 4-F-Ph | Me | Br | 7-CF₃ | 4-F-Ph | Et |
| CF₃ | 6-F | CO₂Me | Et | OCF₃ | 6-F | CO₂Me | Et |
| CF₃ | 6-F | CO₂Et | Et | OCF₃ | 6-F | CO₂Et | Et |
| CF₃ | 6-F | Me | Et | OCF₃ | 6-F | Me | Et |
| CF₃ | 6-F | n-Pr | Et | OCF₃ | 6-F | n-Pr | Et |
| CF₃ | 6-F | i-Pr | Et | OCF₃ | 6-F | i-Pr | Et |
| CF₃ | 6-F | 4-F-Ph | Et | OCF₃ | 6-F | 4-F-Ph | Et |
| CF₃ | 7-F | CO₂Me | Et | OCF₃ | 7-F | CO₂Me | Et |
| CF₃ | 7-F | CO₂Et | Et | OCF₃ | 7-F | CO₂Et | Et |
| CF₃ | 7-F | Me | Et | OCF₃ | 7-F | Me | Et |
| CF₃ | 7-F | n-Pr | Et | OCF₃ | 7-F | n-Pr | Et |
| CF₃ | 7-F | i-Pr | Et | OCF₃ | 7-F | i-Pr | Et |
| CF₃ | 7-F | 4-F-Ph | Et | OCF₃ | 7-F | 4-F-Ph | Et |
| CF₃ | 7-Cl | CO₂Me | Et | OCF₃ | 7-Cl | CO₂Me | Et |
| CF₃ | 7-Cl | CO₂Et | Et | OCF₃ | 7-Cl | CO₂Et | Et |
| CF₃ | 7-Cl | Me | Et | OCF₃ | 7-Cl | Me | Et |
| CF₃ | 7-Cl | n-Pr | Et | OCF₃ | 7-Cl | n-Pr | Et |
| CF₃ | 7-Cl | i-Pr | Et | OCF₃ | 7-Cl | i-Pr | Et |
| CF₃ | 7-Cl | 4-F-Ph | Et | OCF₃ | 7-Cl | 4-F-Ph | Et |
| CF₃ | 7-CF₃ | CO₂Me | Et | OCF₃ | 7-CF₃ | CO₂Me | Et |
| CF₃ | 7-CF₃ | CO₂Et | Et | OCF₃ | 7-CF₃ | CO₂Et | Et |
| CF₃ | 7-CF₃ | Me | Et | OCF₃ | 7-CF₃ | Me | Et |
| CF₃ | 7-CF₃ | n-Pr | Et | OCF₃ | 7-CF₃ | n-Pr | Et |
| CF₃ | 7-CF₃ | i-Pr | Et | OCF₃ | 7-CF₃ | i-Pr | Et |
| CF₃ | 7-CF₃ | 4-F-Ph | Et | OCF₃ | 7-CF₃ | 4-F-Ph | Et |
| Br | 6-F | CO₂Me | —CH₂OCH₃ | CF₃ | 6-F | CO₂Me | —CH₂OCH₃ |
| Br | 6-F | CO₂Et | —CH₂OCH₃ | CF₃ | 6-F | CO₂Et | —CH₂OCH₃ |
| Br | 6-F | Me | —CH₂OCH₃ | CF₃ | 6-F | Me | —CH₂OCH₃ |
| Br | 6-F | n-Pr | —CH₂OCH₃ | CF₃ | 6-F | n-Pr | —CH₂OCH₃ |
| Br | 6-F | i-Pr | —CH₂OCH₃ | CF₃ | 6-F | i-Pr | —CH₂OCH₃ |
| Br | 6-F | 4-F-Ph | —CH₂OCH₃ | CF₃ | 6-F | 4-F-Ph | —CH₂OCH₃ |
| Br | 7-F | CO₂Me | —CH₂OCH₃ | CF₃ | 7-F | CO₂Me | —CH₂OCH₃ |
| Br | 7-F | CO₂Et | —CH₂OCH₃ | CF₃ | 7-F | CO₂Et | —CH₂OCH₃ |
| Br | 7-F | Me | —CH₂OCH₃ | CF₃ | 7-F | Me | —CH₂OCH₃ |
| Br | 7-F | n-Pr | —CH₂OCH₃ | CF₃ | 7-F | n-Pr | —CH₂OCH₃ |
| Br | 7-F | i-Pr | —CH₂OCH₃ | CF₃ | 7-F | i-Pr | —CH₂OCH₃ |
| Br | 7-F | 4-F-Ph | —CH₂OCH₃ | CF₃ | 7-F | 4-F-Ph | —CH₂OCH₃ |
| Br | 7-Cl | CO₂Me | —CH₂OCH₃ | CF₃ | 7-Cl | CO₂Me | —CH₂OCH₃ |
| Br | 7-Cl | CO₂Et | —CH₂OCH₃ | CF₃ | 7-Cl | CO₂Et | —CH₂OCH₃ |
| Br | 7-Cl | Me | —CH₂OCH₃ | CF₃ | 7-Cl | Me | —CH₂OCH₃ |
| Br | 7-Cl | n-Pr | —CH₂OCH₃ | CF₃ | 7-Cl | n-Pr | —CH₂OCH₃ |
| Br | 7-Cl | i-Pr | —CH₂OCH₃ | CF₃ | 7-Cl | i-Pr | —CH₂OCH₃ |
| Br | 7-Cl | 4-F-Ph | —CH₂OCH₃ | CF₃ | 7-Cl | 4-F-Ph | —CH₂OCH₃ |
| Br | 7-CF₃ | CO₂Me | —CH₂OCH₃ | CF₃ | 7-CF₃ | CO₂Me | —CH₂OCH₃ |
| Br | 7-CF₃ | CO₂Et | —CH₂OCH₃ | CF₃ | 7-CF₃ | CO₂Et | —CH₂OCH₃ |
| Br | 7-CF₃ | Me | —CH₂OCH₃ | CF₃ | 7-CF₃ | Me | —CH₂OCH₃ |
| Br | 7-CF₃ | n-Pr | —CH₂OCH₃ | CF₃ | 7-CF₃ | n-Pr | —CH₂OCH₃ |
| Br | 7-CF₃ | i-Pr | —CH₂OCH₃ | CF₃ | 7-CF₃ | i-Pr | —CH₂OCH₃ |
| Br | 7-CF₃ | 4-F-Ph | —CH₂OCH₃ | CF₃ | 7-CF₃ | 4-F-Ph | —CH₂OCH₃ |
| OCF₃ | 6-F | CO₂Me | —CH₂OCH₃ | Br | 6-F | CO₂Me | —CH₂C≡CH |
| OCF₃ | 6-F | CO₂Et | —CH₂OCH₃ | Br | 6-F | CO₂Et | —CH₂C≡CH |
| OCF₃ | 6-F | Me | —CH₂OCH₃ | Br | 6-F | Me | —CH₂C≡CH |
| OCF₃ | 6-F | n-Pr | —CH₂OCH₃ | Br | 6-F | n-Pr | —CH₂C≡CH |
| OCF₃ | 6-F | i-Pr | —CH₂OCH₃ | Br | 6-F | i-Pr | —CH₂C≡CH |
| OCF₃ | 6-F | 4-F-Ph | —CH₂OCH₃ | Br | 6-F | 4-F-Ph | —CH₂C≡CH |
| OCF₃ | 7-F | CO₂Me | —CH₂OCH₃ | CF₃ | 6-F | CO₂Me | —CH₂C≡CH |
| OCF₃ | 7-F | CO₂Et | —CH₂OCH₃ | CF₃ | 6-F | CO₂Et | —CH₂C≡CH |

TABLE 14-continued

| $R^1$ | $R^2$ | $R^3$ | Y | $R^1$ | $R^2$ | $R^3$ | Y |
|---|---|---|---|---|---|---|---|
| $OCF_3$ | 7-F | Me | —$CH_2OCH_3$ | $CF_3$ | 6-F | Me | —$CH_2C\equiv CH$ |
| $OCF_3$ | 7-F | n-Pr | —$CH_2OCH_3$ | $CF_3$ | 6-F | n-Pr | —$CH_2C\equiv CH$ |
| $OCF_3$ | 7-F | i-Pr | —$CH_2OCH_3$ | $CF_3$ | 6-F | i-Pr | —$CH_2C\equiv CH$ |
| $OCF_3$ | 7-F | 4-F-Ph | —$CH_2OCH_3$ | $CF_3$ | 6-F | 4-F-Ph | —$CH_2C\equiv CH$ |
| $OCF_3$ | 7-Cl | $CO_2Me$ | —$CH_2OCH_3$ | Br | 7-F | $CO_2Me$ | —$CH_2C\equiv CH$ |
| $OCF_3$ | 7-Cl | $CO_2Et$ | —$CH_2OCH_3$ | Br | 7-F | $CO_2Et$ | —$CH_2\equiv CH$ |
| $OCF_3$ | 7-Cl | Me | —$CH_2OCH_3$ | Br | 7-F | Me | —$CH_2C\equiv CH$ |
| $OCF_3$ | 7-Cl | n-Pr | —$CH_2OCH_3$ | Br | 7-F | n-Pr | —$CH_2C\equiv CH$ |
| $OCF_3$ | 7-Cl | i-Pr | —$CH_2OCH_3$ | Br | 7-F | Pr | —$CH_2C\equiv CH$ |
| $OCF_3$ | 7-Cl | 4-F-Ph | —$CH_2OCH_3$ | Br | 7-F | 4-F-Ph | —$CH_2C\equiv CH$ |
| $OCF_3$ | 7-$CF_3$ | $CO_2Me$ | —$CH_2OCH_3$ | Br | 7-Cl | $CO_2Me$ | —$CH_2C\equiv CH$ |
| $OCF_3$ | 7-$CF_3$ | $CO_2Et$ | —$CH_2OCH_3$ | Br | 7-Cl | $CO_2Et$ | —$CH_2C\equiv CH$ |
| $OCF_3$ | 7-$CF_3$ | Me | —$CH_2OCH_3$ | Br | 7-Cl | Me | —$CH_2C\equiv CH$ |
| $OCF_3$ | 7-$CF_3$ | n-Pr | —$CH_2OCH_3$ | Br | 7-Cl | n-Pr | —$CH_2C\equiv CH$ |
| $OCF_3$ | 7-$CF_3$ | i-Pr | —$CH_2OCH_3$ | Br | 7-Cl | Pr | —$CH_2C\equiv CH$ |
| $OCF_3$ | 7-$CF_3$ | 4-F-Ph | —$CH_2OCH_3$ | Br | 7-Cl | 4-F-Ph | —$CH_2C\equiv CH$ |
| Br | 7-$CF_3$ | $CO_2Me$ | —$CH_2C\equiv CH$ | $CF_3$ | 7-$CF_3$ | $CO_2Me$ | —$CH_2C\equiv CH$ |
| Br | 7-$CF_3$ | $CO_2Et$ | —$CH_2C\equiv CH$ | $CF_3$ | 7-$CF_3$ | $CO_2Et$ | —$CH_2C\equiv CH$ |
| Br | 7-$CF_3$ | Me | —$CH_2C\equiv CH$ | $CF_3$ | 7-$CF_3$ | Me | —$CH_2C\equiv CH$ |
| Br | 7-$CF_3$ | n-Pr | —$CH_2C\equiv CH$ | $CF_3$ | 7-$CF_3$ | n-Pr | —$CH_2C\equiv CH$ |
| Br | 7-$CF_3$ | Pr | —$CH_2C\equiv CH$ | $CF_3$ | 7-$CF_3$ | i-Pr | —$CH_2C\equiv CH$ |
| Br | 7-$CF_3$ | 4-F-Ph | —$CH_2C\equiv CH$ | $CF_3$ | 7-$CF_3$ | 4-F-Ph | —$CH_2C\equiv CH$ |
| $OCF_3$ | 6-F | $CO_2Me$ | —$CH_2C\equiv CH$ | Br | 6-F | $CO_2Me$ | —$CH_2CH=CH_2$ |
| $OCF_3$ | 6-F | $CO_2Et$ | —$CH_2C\equiv CH$ | Br | 6-F | $CO_2Et$ | —$CH_2CH=CH_2$ |
| $OCF_3$ | 6-F | Me | —$CH_2C\equiv CH$ | Br | 6-F | Me | —$CH_2CH=CH_2$ |
| $OCF_3$ | 6-F | n-Pr | —$CH_2C\equiv CH$ | Br | 6-F | n-Pr | —$CH_2CH=CH_2$ |
| $OCF_3$ | 6-F | Pr | —$CH_2C\equiv CH$ | Br | 6-F | Pr | —$CH_2CH=CH_2$ |
| $OCF_3$ | 6-F | 4-F-Ph | —$CH_2C\equiv CH$ | Br | 6-F | 4-F-Ph | —$CH_2CH=CH_2$ |
| $OCF_3$ | 7-F | $CO_2Me$ | —$CH_2C\equiv CH$ | Br | 7-F | $CO_2Me$ | —$CH_2CH=CH_2$ |
| $OCF_3$ | 7-F | $CO_2Et$ | —$CH_2C\equiv CH$ | Br | 7-F | $CO_2Et$ | —$CH_2CH=CH_2$ |
| $OCF_3$ | 7-F | Me | —$CH_2C\equiv CH$ | Br | 7-F | Me | —$CH_2CH=CH_2$ |
| $OCF_3$ | 7-F | n-Pr | —$CH_2C\equiv CH$ | Br | 7-F | n-Pr | —$CH_2CH=CH_2$ |
| $OCF_3$ | 7-F | Pr | —$CH_2C\equiv CH$ | Br | 7-F | Pr | —$CH_2CH=CH_2$ |
| $OCF_3$ | 7-F | 4-F-Ph | —$CH_2C\equiv CH$ | Br | 7-F | 4-F-Ph | —$CH_2CH=CH_2$ |
| $CF_3$ | 7-F | $CO_2Me$ | —$CH_2C\equiv CH$ | $OCF_3$ | 7-Cl | $CO_2Me$ | —$CH_2C\equiv CH$ |
| $CF_3$ | 7-F | $CO_2Et$ | —$CH_2C\equiv CH$ | $OCF_3$ | 7-Cl | $CO_2Et$ | —$CH_2C\equiv CH$ |
| $CF_3$ | 7-F | Me | —$CH_2C\equiv CH$ | $OCF_3$ | 7-Cl | Me | —$CH_2C\equiv CH$ |
| $CF_3$ | 7-F | n-Pr | —$CH_2C\equiv CH$ | $OCF_3$ | 7-Cl | n-Pr | —$CH_2C\equiv CH$ |
| $CF_3$ | 7-F | i-Pr | —$CH_2C\equiv CH$ | $OCF_3$ | 7-Cl | Pr | —$CH_2C\equiv CH$ |
| $CF_3$ | 7-F | 4-F-Ph | —$CH_2C\equiv CH$ | $OCF_3$ | 7-Cl | 4-F-Ph | —$CH_2C\equiv CH$ |
| $CF_3$ | 7-Cl | $CO_2Me$ | —$CH_2C\equiv CH$ | $OCF_3$ | 7-$CF_3$ | $CO_2Me$ | —$CH_2C\equiv CH$ |
| $CF_3$ | 7-Cl | $CO_2Et$ | —$CH_2C\equiv CH$ | $OCF_3$ | 7-$CF_3$ | $CO_2Et$ | —$CH_2C\equiv CH$ |
| $CF_3$ | 7-Cl | Me | —$CH_2C\equiv CH$ | $OCF_3$ | 7-$CF_3$ | Me | —$CH_2C\equiv CH$ |
| $CF_3$ | 7-Cl | n-Pr | —$CH_2C\equiv CH$ | $OCF_3$ | 7-$CF_3$ | n-Pr | —$CH_2C\equiv CH$ |
| $CF_3$ | 7-Cl | i-Pr | —$CH_2C\equiv CH$ | $OCF_3$ | 7-$CF_3$ | Pr | —$CH_2C\equiv CH$ |
| $CF_3$ | 7-Cl | 4-F-Ph | —$CH_2C\equiv CH$ | $OCF_3$ | 7-$CF_3$ | 4-F-Ph | —$CH_2C\equiv CH$ |
| $CF_3$ | 6-F | $CO_2Me$ | —$CH_2CH=CH_2$ | $OCF_3$ | 6-F | $CO_2Me$ | —$CH_2CH=CH_2$ |
| $CF_3$ | 6-F | $CO_2Et$ | —$CH_2CH=CH_2$ | $OCF_3$ | 6-F | $CO_2Et$ | —$CH_2CH=CH_2$ |
| $CF_3$ | 6-F | Me | —$CH_2CH=CH_2$ | $OCF_3$ | 6-F | Me | —$CH_2CH=CH_2$ |
| $CF_3$ | 6-F | n-Pr | —$CH_2CH=CH_2$ | $OCF_3$ | 6-F | n-Pr | —$CH_2CH=CH_2$ |
| $CF_3$ | 6-F | Pr | —$CH_2CH=CH_2$ | $OCF_3$ | 6-F | Pr | —$CH_2CH=CH_2$ |
| $CF_3$ | 6-F | 4-F-Ph | —$CH_2CH=CH_2$ | $OCF_3$ | 6-F | 4-F-Ph | —$CH_2CH=CH_2$ |
| $CF_3$ | 7-F | $CO_2Me$ | —$CH_2CH=CH_2$ | $OCF_3$ | 7-F | $CO_2Me$ | —$CH_2CH=CH_2$ |
| $CF_3$ | 7-F | $CO_2Et$ | —$CH_2CH=CH_2$ | $OCF_3$ | 7-F | $CO_2Et$ | —$CH_2CH=CH_2$ |
| $CF_3$ | 7-F | Me | —$CH_2CH=CH_2$ | $OCF_3$ | 7-F | Me | —$CH_2CH=CH_2$ |
| $CF_3$ | 7-F | n-Pr | —$CH_2CH=CH_2$ | $OCF_3$ | 7-F | n-Pr | —$CH_2CH=CH_2$ |
| $CF_3$ | 7-F | Pr | —$CH_2CH=CH_2$ | $OCF_3$ | 7-F | Pr | —$CH_2CH=CH_2$ |
| $CF_3$ | 7-F | 4-F-Ph | —$CH_2CH=CH_2$ | $OCF_3$ | 7-F | 4-F-Ph | —$CH_2CH=CH_2$ |
| $CF_3$ | 7-Cl | $CO_2Me$ | —$CH_2CH=CH_2$ | $OCF_3$ | 7-Cl | $CO_2Me$ | —$CH_2CH=CH_2$ |
| $CF_3$ | 7-Cl | $CO_2Et$ | —$CH_2CH=CH_2$ | $OCF_3$ | 7-Cl | $CO_2Et$ | —$CH_2CH=CH_2$ |
| $CF_3$ | 7-Cl | Me | —$CH_2CH=CH_2$ | $OCF_3$ | 7-Cl | Me | —$CH_2CH=CH_2$ |
| $CF_3$ | 7-Cl | n-Pr | —$CH_2CH=CH_2$ | $OCF_3$ | 7-Cl | n-Pr | —$CH_2CH=CH_2$ |
| $CF_3$ | 7-Cl | Pr | —$CH_2CH=CH_2$ | $OCF_3$ | 7-Cl | Pr | —$CH_2CH=CH_2$ |
| $CF_3$ | 7-Cl | 4-F-Ph | —$CH_2CH=CH_2$ | $OCF_3$ | 7-Cl | 4-F-Ph | —$CH_2CH=CH_2$ |
| Br | 7-Cl | $CO_2Me$ | —$CH_2CH=CH_2$ | $CF_3$ | 7-$CF_3$ | $CO_2Me$ | —$CH_2CH=CH_2$ |
| Br | 7-Cl | $CO_2Et$ | —$CH_2CH=CH_2$ | $CF_3$ | 7-$CF_3$ | $CO_2Et$ | —$CH_2CH=CH_2$ |
| Br | 7-Cl | Me | —$CH_2CH=CH_2$ | $CF_3$ | 7-$CF_3$ | Me | —$CH_2CH=CH_2$ |
| Br | 7-Cl | n-Pr | —$CH_2CH=CH_2$ | $CF_3$ | 7-$CF_3$ | n-Pr | —$CH_2CH=CH_2$ |
| Br | 7-Cl | Pr | —$CH_2CH=CH_2$ | $CF_3$ | 7-$CF_3$ | Pr | —$CH_2CH=CH_2$ |
| Br | 7-Cl | 4-F-Ph | —$CH_2CH=CH_2$ | $CF_3$ | 7-$CF_3$ | 4-F-Ph | —$CH_2CH=CH_2$ |
| Br | 7-$CF_3$ | $CO_2Me$ | —$CH_2CH=CH_2$ | $OCF_3$ | 7-$CF_3$ | $CO_2Me$ | —$CH_2CH=CH_2$ |
| Br | 7-$CF_3$ | $CO_2Et$ | —$CH_2CH=CH_2$ | $OCF_3$ | 7-$CF_3$ | $CO_2Et$ | —$CH_2CH=CH_2$ |
| Br | 7-$CF_3$ | Me | —$CH_2CH=CH_2$ | $OCF_3$ | 7-$CF_3$ | Me | —$CH_2CH=CH_2$ |
| Br | 7-$CF_3$ | n-Pr | —$CH_2CH=CH_2$ | $OCF_3$ | 7-$CF_3$ | n-Pr | —$CH_2CH=CH_2$ |
| Br | 7-$CF_3$ | Pr | —$CH_2CH=CH_2$ | $OCF_3$ | 7-$CF_3$ | Pr | —$CH_2CH=CH_2$ |
| Br | 7-$CF_3$ | 4-F-Ph | —$CH_2CH=CH_2$ | $OCF_3$ | 7-$CF_3$ | 4-F-Ph | —$CH_2CH=CH_2$ |

TABLE 15

| R¹ | R² | R³ | Y | R¹ | R² | R³ | Y |
|---|---|---|---|---|---|---|---|
| Br | 6-F | CO₂Me | NH₂ | CF₃ | 7-Cl | CO₂Me | NH₂ |
| Br | 6-F | CO₂Et | NH₂ | CF₃ | 7-Cl | CO₂Et | NH₂ |
| Br | 6-F | i-Pr | NH₂ | CF₃ | 7-Cl | i-Pr | NH₂ |
| Br | 6-F | Me | NH₂ | CF₃ | 7-Cl | Me | NH₂ |
| Br | 6-F | 4-F-Ph | NH₂ | CF₃ | 7-Cl | 4-F-Ph | NH₂ |
| Br | 7-F | CO₂Me | NH₂ | CF₃ | 7-CF₃ | CO₂Me | NH₂ |
| Br | 7-F | CO₂Et | NH₂ | CF₃ | 7-CF₃ | CO₂Et | NH₂ |
| Br | 7-F | i-Pr | NH₂ | CF₃ | 7-CF₃ | i-Pr | NH₂ |
| Br | 7-F | Me | NH₂ | CF₃ | 7-CF₃ | Me | NH₂ |
| Br | 7-F | 4-F-Ph | NH₂ | CF₃ | 7-CF₃ | 4-F-Ph | NH₂ |
| Br | 7-Cl | CO₂Me | NH₂ | OCF₃ | 6-F | CO₂Me | NH₂ |
| Br | 7-Cl | CO₂Et | NH₂ | OCF₃ | 6-F | CO₂Et | NH₂ |
| Br | 7-Cl | i-Pr | NH₂ | OCF₃ | 6-F | i-Pr | NH₂ |
| Br | 7-Cl | Me | NH₂ | OCF₃ | 6-F | Me | NH₂ |
| Br | 7-Cl | 4-F-Ph | NH₂ | OCF₃ | 6-F | 4-F-Ph | NH₂ |
| Br | 7-CF₃ | CO₂Me | NH₂ | OCF₃ | 7-F | CO₂Me | NH₂ |
| Br | 7-CF₃ | CO₂Et | NH₂ | OCF₃ | 7-F | CO₂Et | NH₂ |
| Br | 7-CF₃ | i-Pr | NH₂ | OCF₃ | 7-F | i-Pr | NH₂ |
| Br | 7-CF₃ | Me | NH₂ | OCF₃ | 7-F | Me | NH₂ |
| Br | 7-CF₃ | 4-F-Ph | NH₂ | OCF₃ | 7-F | 4-F-Ph | NH₂ |
| CF₃ | 6-F | CO₂Me | NH₂ | OCF₃ | 7-Cl | CO₂Me | NH₂ |
| CF₃ | 6-F | CO₂Et | NH₂ | OCF₃ | 7-Cl | CO₂Et | NH₂ |
| CF₃ | 6-F | i-Pr | NH₂ | OCF₃ | 7-Cl | i-Pr | NH₂ |
| CF₃ | 6-F | Me | NH₂ | OCF₃ | 7-Cl | Me | NH₂ |
| CF₃ | 6-F | 4-F-Ph | NH₂ | OCF₃ | 7-Cl | 4-F-Ph | NH₂ |
| CF₃ | 7-F | CO₂Me | NH₂ | OCF₃ | 7-CF₃ | CO₂Me | NH₂ |
| CF₃ | 7-F | CO₂Et | NH₂ | OCF₃ | 7-CF₃ | CO₂Et | NH₂ |
| CF₃ | 7-F | i-Pr | NH₂ | OCF₃ | 7-CF₃ | i-Pr | NH₂ |
| CF₃ | 7-F | Me | NH₂ | OCF₃ | 7-CF₃ | Me | NH₂ |
| CF₃ | 7-F | 4-F-Ph | NH₂ | OCF₃ | 7-CF₃ | 4-F-Ph | NH₂ |
| Br | 6-F | CO₂Me | NHMe | CF₃ | 7-Cl | CO₂Me | NHMe |
| Br | 6-F | CO₂Et | NHMe | CF₃ | 7-Cl | CO₂Et | NHMe |
| Br | 6-F | i-Pr | NHMe | CF₃ | 7-Cl | i-Pr | NHMe |
| Br | 6-F | Me | NHMe | CF₃ | 7-Cl | Me | NHMe |
| Br | 6-F | 4-F-Ph | NHMe | CF₃ | 7-Cl | 4-F-Ph | NHMe |
| Br | 7-F | CO₂Me | NHMe | CF₃ | 7-CF₃ | CO₂Me | NHMe |
| Br | 7-F | CO₂Et | NHMe | CF₃ | 7-CF₃ | CO₂Et | NHMe |
| Br | 7-F | i-Pr | NHMe | CF₃ | 7-CF₃ | i-Pr | NHMe |
| Br | 7-F | Me | NHMe | CF₃ | 7-CF₃ | Me | NHMe |
| Br | 7-F | 4-F-Ph | NHMe | CF₃ | 7-CF₃ | 4-F-Ph | NHMe |
| Br | 7-Cl | CO₂Me | NHMe | OCF₃ | 6-F | CO₂Me | NHMe |
| Br | 7-Cl | CO₂Et | NHMe | OCF₃ | 6-F | CO₂Et | NHMe |
| Br | 7-Cl | i-Pr | NHMe | OCF₃ | 6-F | i-Pr | NHMe |
| Br | 7-Cl | Me | NHMe | OCF₃ | 6-F | Me | NHMe |
| Br | 7-Cl | 4-F-Ph | NHMe | OCF₃ | 6-F | 4-F-Ph | NHMe |
| Br | 7-CF₃ | CO₂Me | NHMe | OCF₃ | 7-F | CO₂Me | NHMe |
| Br | 7-CF₃ | CO₂Et | NHMe | OCF₃ | 7-F | CO₂Et | NHMe |
| Br | 7-CF₃ | i-Pr | NHMe | OCF₃ | 7-F | i-Pr | NHMe |
| Br | 7-CF₃ | Me | NHMe | OCF₃ | 7-F | Me | NHMe |
| Br | 7-CF₃ | 4-F-Ph | NHMe | OCF₃ | 7-F | 4-F-Ph | NHMe |
| CF₃ | 6-F | CO₂Me | NHMe | OCF₃ | 7-Cl | CO₂Me | NHMe |
| CF₃ | 6-F | CO₂Et | NHMe | OCF₃ | 7-Cl | CO₂Et | NHMe |
| CF₃ | 6-F | i-Pr | NHMe | OCF₃ | 7-Cl | i-Pr | NHMe |
| CF₃ | 6-F | Me | NHMe | OCF₃ | 7-Cl | Me | NHMe |
| CF₃ | 6-F | 4-F-Ph | NHMe | OCF₃ | 7-Cl | 4-F-Ph | NHMe |
| CF₃ | 7-F | CO₂Me | NHMe | OCF₃ | 7-CF₃ | CO₂Me | NHMe |
| CF₃ | 7-F | CO₂Et | NHMe | OCF₃ | 7-CF₃ | CO₂Et | NHMe |
| CF₃ | 7-F | i-Pr | NHMe | OCF₃ | 7-CF₃ | i-Pr | NHMe |
| CF₃ | 7-F | Me | NHMe | OCF₃ | 7-CF₃ | Me | NHMe |
| CF₃ | 7-F | 4-F-Ph | NHMe | OCF₃ | 7-CF₃ | 4-F-Ph | NHMe |
| Br | 6-F | CO₂Me | NHCHO | CF₃ | 7-Cl | CO₂Me | NHCHO |
| Br | 6-F | CO₂Et | NHCHO | CF₃ | 7-Cl | CO₂Et | NHCHO |
| Br | 6-F | i-Pr | NHCHO | CF₃ | 7-Cl | i-Pr | NHCHO |
| Br | 6-F | Me | NHCHO | CF₃ | 7-Cl | Me | NHCHO |
| Br | 6-F | 4-F-Ph | NHCHO | CF₃ | 7-Cl | 4-F-Ph | NHCHO |
| Br | 7-F | CO₂Me | NHCHO | CF₃ | 7-CF₃ | CO₂Me | NHCHO |
| Br | 7-F | CO₂Et | NHCHO | CF₃ | 7-CF₃ | CO₂Et | NHCHO |
| Br | 7-F | i-Pr | NHCHO | CF₃ | 7-CF₃ | i-Pr | NHCHO |
| Br | 7-F | Me | NHCHO | CF₃ | 7-CF₃ | Me | NHCHO |
| Br | 7-F | 4-F-Ph | NHCHO | CF₃ | 7-CF₃ | 4-F-Ph | NHCHO |
| Br | 7-Cl | CO₂Me | NHCHO | OCF₃ | 6-F | CO₂Me | NHCHO |
| Br | 7-Cl | CO₂Et | NRCHO | OCF₃ | 6-F | CO₂Et | NHCHO |
| Br | 7-Cl | i-Pr | NHCHO | OCF₃ | 6-F | i-Pr | NHCHO |
| Br | 7-Cl | Me | NHCHO | OCF₃ | 6-F | Me | NHCHO |
| Br | 7-Cl | 4-F-Ph | NHCHO | OCF₃ | 6-F | 4-F-Ph | NHCHO |
| Br | 7-CF₃ | CO₂Me | NHCHO | OCF₃ | 7-F | CO₂Me | NHCHO |
| Br | 7-CF₃ | CO₂Et | NHCHO | OCF₃ | 7-F | CO₂Et | NHCHO |

TABLE 15-continued

| R¹ | R² | R³ | Y | R¹ | R² | R³ | Y |
|---|---|---|---|---|---|---|---|
| Br | 7-CF₃ | i-Pr | NHCHO | OCF₃ | 7-F | i-Pr | NHCHO |
| Br | 7-CF₃ | Me | NHCHO | OCF₃ | 7-F | Me | NHCHO |
| Br | 7-CF₃ | 4-F-Ph | NHCHO | OCF₃ | 7-F | 4-F-Ph | NHCHO |
| CF₃ | 6-F | CO₂Me | NHCHO | OCF₃ | 7-Cl | CO₂Me | NHCHO |
| CF₃ | 6-F | CO₂Et | NHCHO | OCF₃ | 7-Cl | CO₂Et | NHCHO |
| CF₃ | 6-F | i-Pr | NHCHO | OCF₃ | 7-Cl | i-Pr | NHCHO |
| CF₃ | 6-F | Me | NHCHO | OCF₃ | 7-Cl | Me | NHCHO |
| CF₃ | 6-F | 4-F-Ph | NHCHO | OCF₃ | 7-Cl | 4-F-Ph | NHCHO |
| CF₃ | 7-F | CO₂Me | NHCHO | OCF₃ | 7-CF₃ | CO₂Me | NHCHO |
| CF₃ | 7-F | CO₂Et | NHCHO | OCF₃ | 7-CF₃ | CO₂Et | NHCHO |
| CF₃ | 7-F | i-Pr | NHCHO | OCF₃ | 7-CF₃ | i-Pr | NHCHO |
| CF₃ | 7-F | Me | NHCHO | OCF₃ | 7-CF₃ | Me | NHCHO |
| CF₃ | 7-F | 4-F-Ph | NHCHO | OCF₃ | 7-CF₃ | 4-F-Ph | NHCHO |
| Br | 6-F | CO₂Me | NH(CO)Me | CF₃ | 7-Cl | CO₂Me | NH(CO)Me |
| Br | 6-F | CO₂Et | NH(CO)Me | CF₃ | 7-Cl | CO₂Et | NH(CO)Me |
| Br | 6-F | i-Pr | NH(CO)Me | CF₃ | 7-Cl | i-Pr | NH(CO)Me |
| Br | 6-F | Me | NH(CO)Me | CF₃ | 7-Cl | Me | NH(CO)Me |
| Br | 6-F | 4-F-Ph | NH(CO)Me | CF₃ | 7-Cl | 4-F-Ph | NH(CO)Me |
| Br | 7-F | CO₂Me | NH(CO)Me | CF₃ | 7-CF₃ | CO₂Me | NH(CO)Me |
| Br | 7-F | CO₂Et | NH(CO)Me | CF₃ | 7-CF₃ | CO₂Et | NH(CO)Me |
| Br | 7-F | i-Pr | NH(CO)Me | CF₃ | 7-CF₃ | i-Pr | NH(CO)Me |
| Br | 7-F | Me | NH(CO)Me | CF₃ | 7-CF₃ | Me | NH(CO)Me |
| Br | 7-F | 4-F-Ph | NH(CO)Me | CF₃ | 7-CF₃ | 4-F-Ph | NH(CO)Me |
| Br | 7-Cl | CO₂Me | NH(CO)Me | OCF₃ | 6-F | CO₂Me | NH(CO)Me |
| Br | 7-Cl | CO₂Et | NH(CO)Me | OCF₃ | 6-F | CO₂Et | NH(CO)Me |
| Br | 7-Cl | i-Pr | NH(CO)Me | OCF₃ | 6-F | i-Pr | NH(CO)Me |
| Br | 7-Cl | Me | NH(CO)Me | OCF₃ | 6-F | Me | NH(CO)Me |
| Br | 7-Cl | 4-F-Ph | NH(CO)Me | OCF₃ | 6-F | 4-F-Ph | NH(CO)Me |
| Br | 7-CF₃ | CO₂Me | NH(CO)Me | OCF₃ | 7-F | CO₂Me | NH(CO)Me |
| Br | 7-CF₃ | CO₂Et | NH(CO)Me | OCF₃ | 7-F | CO₂Et | NH(CO)Me |
| Br | 7-CF₃ | i-Pr | NH(CO)Me | OCF₃ | 7-F | i-Pr | NH(CO)Me |
| Br | 7-CF₃ | Me | NH(CO)Me | OCF₃ | 7-F | Me | NH(CO)Me |
| Br | 7-CF₃ | 4-F-Ph | NH(CO)Me | OCF₃ | 7-F | 4-F-Ph | NH(CO)Me |
| CF₃ | 6-F | CO₂Me | NH(CO)Me | OCF₃ | 7-Cl | CO₂Me | NH(CO)Me |
| CF₃ | 6-F | CO₂Et | NH(CO)Me | OCF₃ | 7-Cl | CO₂Et | NH(CO)Me |
| CF₃ | 6-F | i-Pr | NH(CO)Me | OCF₃ | 7-Cl | i-Pr | NH(CO)Me |
| CF₃ | 6-F | Me | NH(CO)Me | OCF₃ | 7-Cl | Me | NH(CO)Me |
| CF₃ | 6-F | 4-F-Ph | NH(CO)Me | OCF₃ | 7-Cl | 4-F-Ph | NH(CO)Me |
| CF₃ | 7-F | CO₂Me | NH(CO)Me | OCF₃ | 7-CF₃ | CO₂Me | NH(CO)Me |
| CF₃ | 7-F | CO₂Et | NH(CO)Me | OCF₃ | 7-CF₃ | CO₂Et | NH(CO)Me |
| CF₃ | 7-F | i-Pr | NH(CO)Me | OCF₃ | 7-CF₃ | i-Pr | NH(CO)Me |
| CF₃ | 7-F | Me | NH(CO)Me | OCF₃ | 7-CF₃ | Me | NH(CO)Me |
| CF₃ | 7-F | 4-F-Ph | NH(CO)Me | OCF₃ | 7-CF₃ | 4-F-Ph | NH(CO)Me |
| Br | 6-F | CO₂Me | NH(CO)NHMe | CF₃ | 7-Cl | CO₂Me | NH(CO)NHMe |
| Br | 6-F | CO₂Et | NH(CO)NHMe | CF₃ | 7-Cl | CO₂Et | NH(CO)NHMe |
| Br | 6-F | i-Pr | NH(CO)NHMe | CF₃ | 7-Cl | i-Pr | NH(CO)NHMe |
| Br | 6-F | Me | NH(CO)NHMe | CF₃ | 7-Cl | Me | NH(CO)NHMe |
| Br | 6-F | 4-F-Ph | NH(CO)NHMe | CF₃ | 7-Cl | 4-F-Ph | NH(CO)NHMe |
| Br | 7-F | CO₂Me | NH(CO)NHMe | CF₃ | 7-CF₃ | CO₂Me | NH(CO)NHMe |
| Br | 7-F | CO₂Et | NH(CO)NHMe | CF₃ | 7-CF₃ | CO₂Et | NH(CO)NHMe |
| Br | 7-F | i-Pr | NH(CO)NHMe | CF₃ | 7-CF₃ | i-Pr | NH(CO)NHMe |
| Br | 7-F | Me | NH(CO)NHMe | CF₃ | 7-CF₃ | Me | NH(CO)NHMe |
| Br | 7-F | 4-F-Ph | NH(CO)NHMe | CF₃ | 7-CF₃ | 4-F-Ph | NH(CO)NHMe |
| Br | 7-Cl | CO₂Me | NH(CO)NHMe | OCF₃ | 6-F | CO₂Me | NH(CO)NHMe |
| Br | 7-Cl | CO₂Et | NH(CO)NHMe | OCF₃ | 6-F | CO₂Et | NH(CO)NHMe |
| Br | 7-Cl | i-Pr | NH(CO)NHMe | OCF₃ | 6-F | i-Pr | NH(CO)NHMe |
| Br | 7-Cl | Me | NH(CO)NHMe | OCF₃ | 6-F | Me | NH(CO)NHMe |
| Br | 7-Cl | 4-F-Ph | NH(CO)NHMe | OCF₃ | 6-F | 4-F-Ph | NH(CO)NHMe |
| Br | 7-CF₃ | CO₂Me | NH(CO)NHMe | OCF₃ | 7-F | CO₂Me | NH(CO)NHMe |
| Br | 7-CF₃ | CO₂Et | NH(CO)NHMe | OCF₃ | 7-F | CO₂Et | NH(CO)NHMe |
| Br | 7-CF₃ | i-Pr | NH(CO)NHMe | OCF₃ | 7-F | i-Pr | NH(CO)NHMe |
| Br | 7-CF₃ | Me | NH(CO)NHMe | OCF₃ | 7-F | Me | NH(CO)NHMe |
| Br | 7-CF₃ | 4-F-Ph | NH(CO)NHMe | OCF₃ | 7-F | 4-F-Ph | NH(CO)NHMe |
| CF₃ | 6-F | CO₂Me | NH(CO)NHMe | OCF₃ | 7-Cl | CO₂Me | NH(CO)NHMe |
| CF₃ | 6-F | CO₂Et | NH(CO)NHMe | OCF₃ | 7-Cl | CO₂Et | NH(CO)NHMe |
| CF₃ | 6-F | i-Pr | NH(CO)NHMe | OCF₃ | 7-Cl | i-Pr | NH(CO)NHMe |
| CF₃ | 6-F | Me | NH(CO)NHMe | OCF₃ | 7-Cl | Me | NH(CO)NHMe |
| CF₃ | 6-F | 4-F-Ph | NH(CO)NHMe | OCF₃ | 7-Cl | 4-F-Ph | NH(CO)NHMe |
| CF₃ | 7-F | CO₂Me | NH(CO)NHMe | OCF₃ | 7-CF₃ | CO₂Me | NH(CO)NHMe |
| CF₃ | 7-F | CO₂Et | NH(CO)NHMe | OCF₃ | 7-CF₃ | CO₂Et | NH(CO)NHMe |
| CF₃ | 7-F | i-Pr | NH(CO)NHMe | OCF₃ | 7-CF₃ | i-Pr | NH(CO)NHMe |
| CF₃ | 7-F | Me | NH(CO)NHMe | OCF₃ | 7-CF₃ | Me | NH(CO)NHMe |
| CF₃ | 7-F | 4-F-Ph | NH(CO)NHMe | OCF₃ | 7-CF₃ | 4-F-Ph | NH(CO)NHMe |
| Br | 6-F | CO₂Me | N=CH₂ | CF₃ | 7-Cl | CO₂Me | N=CH₂ |
| Br | 6-F | CO₂Et | N=CH₂ | CF₃ | 7-Cl | CO₂Et | N=CH₂ |
| Br | 6-F | i-Pr | N=CH₂ | CF₃ | 7-Cl | i-Pr | N=CH₂ |
| Br | 6-F | Me | N=CH₂ | CF₃ | 7-Cl | Me | N=CH₂ |

TABLE 15-continued

| R¹ | R² | R³ | Y | R¹ | R² | R³ | Y |
|---|---|---|---|---|---|---|---|
| Br | 6-F | 4-F-Ph | N=CH₂ | CF₃ | 7-Cl | 4-F-Ph | N=CH₂ |
| Br | 7-F | CO₂Me | N=CH₂ | CF₃ | 7-CF₃ | CO₂Me | N=CH₂ |
| Br | 7-F | CO₂Et | N=CH₂ | CF₃ | 7-CF₃ | CO₂Et | N=CH₂ |
| Br | 7-F | i-Pr | N=CH₂ | CF₃ | 7-CF₃ | i-Pr | N=CH₂ |
| Br | 7-F | Me | N=CH₂ | CF₃ | 7-CF₃ | Me | N=CH₂ |
| Br | 7-F | 4-F-Ph | N=CH₂ | CF₃ | 7-CF₃ | 4-F-Ph | N=CH₂ |
| Br | 7-Cl | CO₂Me | N=CH₂ | OCF₃ | 6-F | CO₂Me | N=CH₂ |
| Br | 7-Cl | CO₂Et | N=CH₂ | OCF₃ | 6-F | CO₂Et | N=CH₂ |
| Br | 7-Cl | i-Pr | N=CH₂ | OCF₃ | 6-F | i-Pr | N=CH₂ |
| Br | 7-Cl | Me | N=CH₂ | OCF₃ | 6-F | Me | N=CH₂ |
| Br | 7-Cl | 4-F-Ph | N=CH₂ | OCF₃ | 6-F | 4-F-Ph | N=CH₂ |
| Br | 7-CF₃ | CO₂Me | N=CH₂ | OCF₃ | 7-F | CO₂Me | N=CH₂ |
| Br | 7-CF₃ | CO₂Et | N=CH₂ | OCF₃ | 7-F | CO₂Et | N=CH₂ |
| Br | 7-CF₃ | i-Pr | N=CH₂ | OCF₃ | 7-F | i-Pr | N=CH₂ |
| Br | 7-CF₃ | Me | N=CH₂ | OCF₃ | 7-F | Me | N=CH₂ |
| Br | 7-CF₃ | 4-F-Ph | N=CH₂ | OCF₃ | 7-F | 4-F-Ph | N=CH₂ |
| CF₃ | 6-F | CO₂Me | N=CH₂ | OCF₃ | 7-Cl | CO₂Me | N=CH₂ |
| CF₃ | 6-F | CO₂Et | N=CH₂ | OCF₃ | 7-Cl | CO₂Et | N=CH₂ |
| CF₃ | 6-F | i-Pr | N=CH₂ | OCF₃ | 7-Cl | i-Pr | N=CH₂ |
| CF₃ | 6-F | Me | N=CH₂ | OCF₃ | 7-Cl | Me | N=CH₂ |
| CF₃ | 6-F | 4-F-Ph | N=CH₂ | OCF₃ | 7-Cl | 4-F-Ph | N=CH₂ |
| CF₃ | 7-F | CO₂Me | N=CH₂ | OCF₃ | 7-CF₃ | CO₂Me | N=CH₂ |
| CF₃ | 7-F | CO₂Et | N=CH₂ | OCF₃ | 7-CF₃ | CO₂Et | N=CH₂ |
| CF₃ | 7-F | i-Pr | N=CH₂ | OCF₃ | 7-CF₃ | i-Pr | N=CH₂ |
| CF₃ | 7-F | Me | N=CH₂ | OCF₃ | 7-CF₃ | Me | N=CH₂ |
| CF₃ | 7-F | 4-F-Ph | N=CH₂ | OCF₃ | 7-CF₃ | 4-F-Ph | N=CH₂ |
| Br | 6-F | CO₂Me | N=CMe₂ | CF₃ | 7-Cl | CO₂Me | N=CMe₂ |
| Br | 6-F | CO₂Et | N=CMe₂ | CF₃ | 7-Cl | CO₂Et | N=CMe₂ |
| Br | 6-F | i-Pr | N=CMe₂ | CF₃ | 7-Cl | i-Pr | N=CMe₂ |
| Br | 6-F | Me | N=CMe₂ | CF₃ | 7-Cl | Me | N=CMe₂ |
| Br | 6-F | 4-F-Ph | N=CMe₂ | CF₃ | 7-Cl | 4-F-Ph | N=CMe₂ |
| Br | 7-F | CO₂Me | N=CMe₂ | CF₃ | 7-CF₃ | CO₂Me | N=CMe₂ |
| Br | 7-F | CO₂Et | N=CMe₂ | CF₃ | 7-CF₃ | CO₂Et | N=CMe₂ |
| Br | 7-F | i-Pr | N=CMe₂ | CF₃ | 7-CF₃ | i-Pr | N=CMe₂ |
| Br | 7-F | Me | N=CMe₂ | CF₃ | 7-CF₃ | Me | N=CMe₂ |
| Br | 7-F | 4-F-Ph | N=CMe₂ | CF₃ | 7-CF3 | 4-F-Ph | N=CMe₂ |
| Br | 7-Cl | CO₂Me | N=CMe₂ | OCF₃ | 6-F | CO₂Me | N=CMe₂ |
| Br | 7-Cl | CO₂Et | N=CMe₂ | OCF₃ | 6-F | CO₂Et | N=CMe₂ |
| Br | 7-Cl | i-Pr | N=CMe₂ | OCF₃ | 6-F | i-Pr | N=CMe₂ |
| Br | 7-Cl | Me | N=CMe₂ | OCF₃ | 6-F | Me | N=CMe₂ |
| Br | 7-Cl | 4-F-Ph | N=CMe₂ | OCF₃ | 6-F | 4-F-Ph | N=CMe₂ |
| Br | 7-CF₃ | CO₂Me | N=CMe₂ | OCF₃ | 7-F | CO₂Me | N=CMe₂ |
| Br | 7-CF₃ | CO₂Et | N=CMe₂ | OCF₃ | 7-F | CO₂Et | N=CMe₂ |
| Br | 7-CF₃ | i-Pr | N=CMe₂ | OCF₃ | 7-F | i-Pr | N=CMe₂ |
| Br | 7-CF₃ | Me | N=CMe₂ | OCF₃ | 7-F | Me | N=CMe₂ |
| Br | 7-CF₃ | 4-F-Ph | N=CMe₂ | OCF₃ | 7-F | 4-F-Ph | N=CMe₂ |
| CF₃ | 6-F | CO₂Me | N=CMe₂ | OCF₃ | 7-Cl | CO₂Me | N=CMe₂ |
| CF₃ | 6-F | CO₂Et | N=CMe₂ | OCF₃ | 7-Cl | CO₂Et | N=CMe₂ |
| CF₃ | 6-F | i-Pr | N=CMe₂ | OCF₃ | 7-Cl | i-Pr | N=CMe₂ |
| CF₃ | 6-F | Me | N=CMe₂ | OCF₃ | 7-Cl | Me | N=CMe₂ |
| CF₃ | 6-F | 4-F-Ph | N=CMe₂ | OCF₃ | 7-Cl | 4-F-Ph | N=CMe₂ |
| CF₃ | 7-F | CO₂Me | N=CMe₂ | OCF₃ | 7-CF₃ | CO₂Me | N=CMe₂ |
| CF₃ | 7-F | CO₂Et | N=CMe₂ | OCF₃ | 7-CF₃ | CO₂Et | N=CMe₂ |
| CF₃ | 7-F | i-Pr | N=CMe₂ | OCF₃ | 7-CF₃ | i-Pr | N=CMe₂ |
| CF₃ | 7-F | Me | N=CMe₂ | OCF₃ | 7-CF₃ | Me | N=CMe₂ |
| CF₃ | 7-F | 4-F-Ph | N=CMe₂ | OCF₃ | 7-CF₃ | 4-F-Ph | N=CMe₂ |
| Br | 6-F | CO₂Me | N=CHPh | CF₃ | 7-Cl | CO₂Me | N=CHPh |
| Br | 6-F | CO₂Et | N=CHPh | CF₃ | 7-Cl | CO₂Et | N=CHPh |
| Br | 6-F | i-Pr | N=CHPh | CF₃ | 7-Cl | i-Pr | N=CHPh |
| Br | 6-F | Me | N=CHPh | CF₃ | 7-Cl | Me | N=CHPh |
| Br | 6-F | 4-F-Ph | N=CHPh | CF₃ | 7-Cl | 4-F-Ph | N=CHPh |
| Br | 7-F | CO₂Me | N=CHPh | CF₃ | 7-CF₃ | CO₂Me | N=CHPh |
| Br | 7-F | CO₂Et | N=CHPh | CF₃ | 7-CF₃ | CO₂Et | N=CHPh |
| Br | 7-F | i-Pr | N=CHPh | CF₃ | 7-CF₃ | i-Pr | N=CHPh |
| Br | 7-F | Me | N=CHPh | CF₃ | 7-CF₃ | Me | N=CHPh |
| Br | 7-F | 4-F-Ph | N=CHPh | CF₃ | 7-CF₃ | 4-F-Ph | N=CHPh |
| Br | 7-Cl | CO₂Me | N=CHPh | OCF₃ | 6-F | CO₂Me | N=CHPh |
| Br | 7-Cl | CO₂Et | N=CHPh | OCF₃ | 6-F | CO₂Et | N=CHPh |
| Br | 7-Cl | i-Pr | N=CHPh | OCF₃ | 6-F | i-Pr | N=CHPh |
| Br | 7-Cl | Me | N=CHPh | OCF₃ | 6-F | Me | N=CHPh |
| Br | 7-Cl | 4-F-Ph | N=CHPh | OCF₃ | 6-F | 4-F-Ph | N=CHPh |
| Br | 7-CF₃ | CO₂Me | N=CHPh | OCF₃ | 7-F | CO₂Me | N=CHPh |
| Br | 7-CF₃ | CO₂Et | N=CHPh | OCF₃ | 7-F | CO₂Et | N=CHPh |
| Br | 7-CF₃ | i-Pr | N=CHPh | OCF₃ | 7-F | i-Pr | N=CHPh |
| Br | 7-CF₃ | Me | N=CHPh | OCF₃ | 7-F | Me | N=CHPh |
| Br | 7-CF₃ | 4-F-Ph | N=CHPh | OCF₃ | 7-F | 4-F-Ph | N=CHPh |
| CF₃ | 6-F | CO₂Me | N=CHPh | OCF₃ | 7-Cl | CO₂Me | N=CHPh |

TABLE 15-continued

| R¹ | R² | R³ | Y | R¹ | R² | R³ | Y |
|---|---|---|---|---|---|---|---|
| $CF_3$ | 6-F | $CO_2Et$ | N=CHPh | $OCF_3$ | 7-Cl | $CO_2Et$ | N=CHPh |
| $CF_3$ | 6-F | i-Pr | N=CHPh | $OCF_3$ | 7-Cl | i-Pr | N=CHPh |
| $CF_3$ | 6-F | Me | N=CHPh | $OCF_3$ | 7-Cl | Me | N=CHPh |
| $CF_3$ | 6-F | 4-F-Ph | N=CHPh | $OCF_3$ | 7-Cl | 4-F-Ph | N=CHPh |
| $CF_3$ | 7-F | $CO_2Me$ | N=CHPh | $OCF_3$ | 7-$CF_3$ | $CO_2Me$ | N=CHPh |
| $CF_3$ | 7-F | $CO_2Et$ | N=CHPh | $OCF_3$ | 7-$CF_3$ | $CO_2Et$ | N=CHPh |
| $CF_3$ | 7-F | i-Pr | N=CHPh | $OCF_3$ | 7-$CF_3$ | i-Pr | N=CHPh |
| $CF_3$ | 7-F | Me | N=CHPh | $OCF_3$ | 7-$CF_3$ | Me | N=CHPh |
| $CF_3$ | 7-F | 4-F-Ph | N=CHPh | $OCF_3$ | 7-$CF_3$ | 4-F-Ph | N=CHPh |
| Br | 6-F | $CO_2Me$ | $NH(CO)CF_3$ | $CF_3$ | 7-Cl | $CO_2Me$ | $NH(CO)CF_3$ |
| Br | 6-F | $CO_2Et$ | $NH(CO)CF_3$ | $CF_3$ | 7-Cl | $CO_2Et$ | $NH(CO)CF_3$ |
| Br | 6-F | i-Pr | $NH(CO)CF_3$ | $CF_3$ | 7-Cl | i-Pr | $NH(CO)CF_3$ |
| Br | 6-F | Me | $NH(CO)CF_3$ | $CF_3$ | 7-Cl | Me | $NH(CO)CF_3$ |
| Br | 6-F | 4-F-Ph | $NH(CO)CF_3$ | $CF_3$ | 7-Cl | 4-F-Ph | $NH(CO)CF_3$ |
| Br | 7-F | $CO_2Me$ | $NH(CO)CF_3$ | $CF_3$ | 7-$CF_3$ | $CO_2Me$ | $NH(CO)CF_3$ |
| Br | 7-F | $CO_2Et$ | $NH(CO)CF_3$ | $CF_3$ | 7-$CF_3$ | $CO_2Et$ | $NH(CO)CF_3$ |
| Br | 7-F | i-Pr | $NH(CO)CF_3$ | $CF_3$ | 7-$CF_3$ | i-Pr | $NH(CO)CF_3$ |
| Br | 7-F | Me | $NH(CO)CF_3$ | $CF_3$ | 7-$CF_3$ | Me | $NH(CO)CF_3$ |
| Br | 7-F | 4-F-Ph | $NH(CO)CF_3$ | $CF_3$ | 7-$CF_3$ | 4-F-Ph | $NH(CO)CF_3$ |
| Br | 7-Cl | $CO_2Me$ | $NH(CO)CF_3$ | $OCF_3$ | 6-F | $CO_2Me$ | $NH(CO)CF_3$ |
| Br | 7-Cl | $CO_2Et$ | $NH(CO)CF_3$ | $OCF_3$ | 6-F | $CO_2Et$ | $NH(CO)CF_3$ |
| Br | 7-Cl | i-Pr | $NH(CO)CF_3$ | $OCF_3$ | 6-F | i-Pr | $NH(CO)CF_3$ |
| Br | 7-Cl | Me | $NH(CO)CF_3$ | $OCF_3$ | 6-F | Me | $NH(CO)CF_3$ |
| Br | 7-Cl | 4-F-Ph | $NH(CO)CF_3$ | $OCF_3$ | 6-F | 4-F-Ph | $NH(CO)CF_3$ |
| Br | 7-$CF_3$ | $CO_2Me$ | $NH(CO)CF_3$ | $OCF_3$ | 7-F | $CO_2Me$ | $NH(CO)CF_3$ |
| Br | 7-$CF_3$ | $CO_2Et$ | $NH(CO)CF_3$ | $OCF_3$ | 7-F | $CO_2Et$ | $NH(CO)CF_3$ |
| Br | 7-$CF_3$ | i-Pr | $NH(CO)CF_3$ | $OCF_3$ | 7-F | i-Pr | $NH(CO)CF_3$ |
| Br | 7-$CF_3$ | Me | $NH(CO)CF_3$ | $OCF_3$ | 7-F | Me | $NH(CO)CF_3$ |
| Br | 7-$CF_3$ | 4-F-Ph | $NH(CO)CF_3$ | $OCF_3$ | 7-F | 4-F-Ph | $NH(CO)CF_3$ |
| $CF_3$ | 6-F | $CO_2Me$ | $NH(CO)CF_3$ | $OCF_3$ | 7-Cl | $CO_2Me$ | $NH(CO)CF_3$ |
| $CF_3$ | 6-F | $CO_2Et$ | $NH(CO)CF_3$ | $OCF_3$ | 7-Cl | $CO_2Et$ | $NH(CO)CF_3$ |
| $CF_3$ | 6-F | i-Pr | $NH(CO)CF_3$ | $OCF_3$ | 7-Cl | i-Pr | $NH(CO)CF_3$ |
| $CF_3$ | 6-F | Me | $NH(CO)CF_3$ | $OCF_3$ | 7-Cl | Me | $NH(CO)CF_3$ |
| $CF_3$ | 6-F | 4-F-Ph | $NH(CO)CF_3$ | $OCF_3$ | 7-Cl | 4-F-Ph | $NH(CO)CF_3$ |
| $CF_3$ | 7-F | $CO_2Me$ | $NH(CO)CF_3$ | $OCF_3$ | 7-$CF_3$ | $CO_2Me$ | $NH(CO)CF_3$ |
| $CF_3$ | 7-F | $CO_2Et$ | $NH(CO)CF_3$ | $OCF_3$ | 7-$CF_3$ | $CO_2Et$ | $NH(CO)CF_3$ |
| $CF_3$ | 7-F | i-Pr | $NH(CO)CF_3$ | $OCF_3$ | 7-$CF_3$ | i-Pr | $NH(CO)CF_3$ |
| $CF_3$ | 7-F | Me | $NH(CO)CF_3$ | $OCF_3$ | 7-$CF_3$ | Me | $NH(CO)CF_3$ |
| $CF_3$ | 7-F | 4-F-Ph | $NH(CO)CF_3$ | $OCF_3$ | 7-$CF_3$ | 4-F-Ph | $NH(CO)CF_3$ |
| Br | 6-F | $CO_2Me$ | OH | $CF_3$ | 7-Cl | $CO_2Me$ | OH |
| Br | 6-F | $CO_2Et$ | OH | $CF_3$ | 7-Cl | $CO_2Et$ | OH |
| Br | 6-F | i-Pr | OH | $CF_3$ | 7-Cl | i-Pr | OH |
| Br | 6-F | Me | OH | $CF_3$ | 7-Cl | Me | OH |
| Br | 6-F | 4-F-Ph | OH | $CF_3$ | 7-Cl | 4-F-Ph | OH |
| Br | 7-F | $CO_2Me$ | OH | $CF_3$ | 7-$CF_3$ | $CO_2Me$ | OH |
| Br | 7-F | $CO_2Et$ | OH | $CF_3$ | 7-$CF_3$ | $CO_2Et$ | OH |
| Br | 7-F | i-Pr | OH | $CF_3$ | 7-$CF_3$ | i-Pr | OH |
| Br | 7-F | Me | OH | $CF_3$ | 7-$CF_3$ | Me | OH |
| Br | 7-F | 4-F-Ph | OH | $CF_3$ | 7-$CF_3$ | 4-F-Ph | OH |
| Br | 7-Cl | $CO_2Me$ | OH | $OCF_3$ | 6-F | $CO_2Me$ | OH |
| Br | 7-Cl | $CO_2Et$ | OH | $OCF_3$ | 6-F | $CO_2Et$ | OH |
| Br | 7-Cl | i-Pr | OH | $OCF_3$ | 6-F | i-Pr | OH |
| Br | 7-Cl | Me | OH | $OCF_3$ | 6-F | Me | OH |
| Br | 7-Cl | 4-F-Ph | OH | $OCF_3$ | 6-F | 4-F-Ph | OH |
| Br | 7-$CF_3$ | $CO_2Me$ | OH | $OCF_3$ | 7-F | $CO_2Me$ | OH |
| Br | 7-$CF_3$ | $CO_2Et$ | OH | $OCF_3$ | 7-F | $CO_2Et$ | OH |
| Br | 7-$CF_3$ | i-Pr | OH | $OCF_3$ | 7-F | i-Pr | OH |
| Br | 7-$CF_3$ | Me | OH | $OCF_3$ | 7-F | Me | OH |
| Br | 7-$CF_3$ | 4-F-Ph | OH | $OCF_3$ | 7-F | 4-F-Ph | OH |
| $CF_3$ | 6-F | $CO_2Me$ | OH | $OCF_3$ | 7-Cl | $CO_2Me$ | OH |
| $CF_3$ | 6-F | $CO_2Et$ | OH | $OCF_3$ | 7-Cl | $CO_2Et$ | OH |
| $CF_3$ | 6-F | i-Pr | OH | $OCF_3$ | 7-Cl | i-Pr | OH |
| $CF_3$ | 6-F | Me | OH | $OCF_3$ | 7-Cl | Me | OH |
| $CF_3$ | 6-F | 4-F-Ph | OH | $OCF_3$ | 7-Cl | 4-F-Ph | OH |
| $CF_3$ | 7-F | $CO_2Me$ | OH | $OCF_3$ | 7-$CF_3$ | $CO_2Me$ | OH |
| $CF_3$ | 7-F | $CO_2Et$ | OH | $OCF_3$ | 7-$CF_3$ | $CO_2Et$ | OH |
| $CF_3$ | 7-F | i-Pr | OH | $OCF_3$ | 7-$CF_3$ | i-Pr | OH |
| $CF_3$ | 7-F | Me | OH | $OCF_3$ | 7-$CF_3$ | Me | OH |
| $CF_3$ | 7-F | 4-F-Ph | OH | $OCF_3$ | 7-$CF_3$ | 4-F-Ph | OH |
| Br | 6-F | $CO_2Me$ | OMe | $CF_3$ | 7-Cl | $CO_2Me$ | OMe |
| Br | 6-F | $CO_2Et$ | OMe | $CF_3$ | 7-Cl | $CO_2Et$ | OMe |
| Br | 6-F | i-Pr | OMe | $CF_3$ | 7-Cl | i-Pr | OMe |
| Br | 6-F | Me | OMe | $CF_3$ | 7-Cl | Me | OMe |
| Br | 6-F | 4-F-Ph | OMe | $CF_3$ | 7-Cl | 4-F-Ph | OMe |
| Br | 7-F | $CO_2Me$ | OMe | $CF_3$ | 7-$CF_3$ | $CO_2Me$ | OMe |
| Br | 7-F | $CO_2Et$ | OMe | $CF_3$ | 7-$CF_3$ | $CO_2Et$ | OMe |
| Br | 7-F | i-Pr | OMe | $CF_3$ | 7-$CF_3$ | i-Pr | OMe |

TABLE 15-continued

| R¹ | R² | R³ | Y | R¹ | R² | R³ | Y |
|---|---|---|---|---|---|---|---|
| Br | 7-F | Me | OMe | CF₃ | 7-CF₃ | Me | OMe |
| Br | 7-F | 4-F-Ph | OMe | CF₃ | 7-CF₃ | 4-F-Ph | OMe |
| Br | 7-Cl | CO₂Me | OMe | OCF₃ | 6-F | CO₂Me | OMe |
| Br | 7-Cl | CO₂Et | OMe | OCF₃ | 6-F | CO₂Et | OMe |
| Br | 7-Cl | i-Pr | OMe | OCF₃ | 6-F | i-Pr | OMe |
| Br | 7-Cl | Me | OMe | OCF₃ | 6-F | Me | OMe |
| Br | 7-Cl | 4-F-Ph | OMe | OCF₃ | 6-F | 4-F-Ph | OMe |
| Br | 7-CF₃ | CO₂Me | OMe | OCF₃ | 7-F | CO₂Me | OMe |
| Br | 7-CF₃ | CO₂Et | OMe | OCF₃ | 7-F | CO₂Et | OMe |
| Br | 7-CF₃ | i-Pr | OMe | OCF₃ | 7-F | i-Pr | OMe |
| Br | 7-CF₃ | Me | OMe | OCF₃ | 7-F | Me | OMe |
| Br | 7-CF₃ | 4-F-Ph | OMe | OCF₃ | 7-F | 4-F-Ph | OMe |
| CF₃ | 6-F | CO₂Me | OMe | OCF₃ | 7-Cl | CO₂Me | OMe |
| CF₃ | 6-F | CO₂Et | OMe | OCF₃ | 7-Cl | CO₂Et | OMe |
| CF₃ | 6-F | i-Pr | OMe | OCF₃ | 7-Cl | i-Pr | OMe |
| CF₃ | 6-F | Me | OMe | OCF₃ | 7-Cl | Me | OMe |
| CF₃ | 6-F | 4-F-Ph | OMe | OCF₃ | 7-Cl | 4-F-Ph | OMe |
| CF₃ | 7-F | CO₂Me | OMe | OCF₃ | 7-CF₃ | CO₂Me | OMe |
| CF₃ | 7-F | CO₂Et | OMe | OCF₃ | 7-CF₃ | CO₂Et | OMe |
| CF₃ | 7-F | i-Pr | OMe | OCF₃ | 7-CF₃ | i-Pr | OMe |
| CF₃ | 7-F | Me | OMe | OCF₃ | 7-CF₃ | Me | OMe |
| CF₃ | 7-F | 4-F-Ph | OMe | OCF₃ | 7-CF₃ | 4-F-Ph | OMe |
| Br | 6-F | CO₂Me | OCH₂Ph | CF₃ | 7-Cl | CO₂Me | OCH₂Ph |
| Br | 6-F | CO₂Et | OCH₂Ph | CF₃ | 7-Cl | CO₂Et | OCH₂Ph |
| Br | 6-F | i-Pr | OCH₂Ph | CF₃ | 7-Cl | i-Pr | OCH₂Ph |
| Br | 6-F | Me | OCH₂Ph | CF₃ | 7-Cl | Me | OCH₂Ph |
| Br | 6-F | 4-F-Ph | OCH₂Ph | CF₃ | 7-Cl | 4-F-Ph | OCH₂Ph |
| Br | 7-F | CO₂Me | OCH₂Ph | CF₃ | 7-CF₃ | CO₂Me | OCH₂Ph |
| Br | 7-F | CO₂Et | OCH₂Ph | CF₃ | 7-CF₃ | CO₂Et | OCH₂Ph |
| Br | 7-F | i-Pr | OCH₂Ph | CF₃ | 7-CF₃ | i-Pr | OCH₂Ph |
| Br | 7-F | Me | OCH₂Ph | CF₃ | 7-CF₃ | Me | OCH₂Ph |
| Br | 7-F | 4-F-Ph | OCH₂Ph | CF₃ | 7-CF₃ | 4-F-Ph | OCH₂Ph |
| Br | 7-Cl | CO₂Me | OCH₂Ph | OCF₃ | 6-F | CO₂Me | OCH₂Ph |
| Br | 7-Cl | CO₂Et | OCH₂Ph | OCF₃ | 6-F | CO₂Et | OCH₂Ph |
| Br | 7-Cl | i-Pr | OCH₂Ph | OCF₃ | 6-F | i-Pr | OCH₂Ph |
| Br | 7-Cl | Me | OCH₂Ph | OCF₃ | 6-F | Me | OCH₂Ph |
| Br | 7-Cl | 4-F-Ph | OCH₂Ph | OCF₃ | 6-F | 4-F-Ph | OCH₂Ph |
| Br | 7-CF₃ | CO₂Me | OCH₂Ph | OCF₃ | 7-F | CO₂Me | OCH₂Ph |
| Br | 7-CF₃ | CO₂Et | OCH₂Ph | OCF₃ | 7-F | CO₂Et | OCH₂Ph |
| Br | 7-CF₃ | i-Pr | OCH₂Ph | OCF₃ | 7-F | i-Pr | OCH₂Ph |
| Br | 7-CF₃ | Me | OCH₂Ph | OCF₃ | 7-F | Me | OCH₂Ph |
| Br | 7-CF₃ | 4-F-Ph | OCH₂Ph | OCF₃ | 7-F | 4-F-Ph | OCH₂Ph |
| CF₃ | 6-F | CO₂Me | OCH₂Ph | OCF₃ | 7-Cl | CO₂Me | OCH₂Ph |
| CF₃ | 6-F | CO₂Et | OCH₂Ph | OCF₃ | 7-Cl | CO₂Et | OCH₂Ph |
| CF₃ | 6-F | i-Pr | OCH₂Ph | OCF₃ | 7-Cl | i-Pr | OCH₂Ph |
| CF₃ | 6-F | Me | OCH₂Ph | OCF₃ | 7-Cl | Me | OCH₂Ph |
| CF₃ | 6-F | 4-F-Ph | OCH₂Ph | OCF₃ | 7-Cl | 4-F-Ph | OCH₂Ph |
| CF₃ | 7-F | CO₂Me | OCH₂Ph | OCF₃ | 7-CF₃ | CO₂Me | OCH₂Ph |
| CF₃ | 7-F | CO₂Et | OCH₂Ph | OCF₃ | 7-CF₃ | CO₂Et | OCH₂Ph |
| CF₃ | 7-F | i-Pr | OCH₂Ph | OCF₃ | 7-CF₃ | i-Pr | OCH₂Ph |
| CF₃ | 7-F | Me | OCH₂Ph | OCF₃ | 7-CF₃ | Me | OCH₂Ph |
| CF₃ | 7-F | 4-F-Ph | OCH₂Ph | OCF₃ | 7-CF₃ | 4-F-Ph | OCH₂Ph |

TABLE 16

| R¹ | R² | R³ | Y | R¹ | R² | R³ | Y |
|---|---|---|---|---|---|---|---|
| Br | 6-F | CO₂Me | NH₂ | CF₃ | 7-Cl | CO₂Me | NH₂ |
| Br | 6-F | CO₂Et | NH₂ | CF₃ | 7-Cl | CO₂Et | NH₂ |
| Br | 6-F | i-Pr | NH₂ | CF₃ | 7-Cl | i-Pr | NH₂ |
| Br | 6-F | Me | NH₂ | CF₃ | 7-Cl | Me | NH₂ |
| Br | 6-F | 4-F—Ph | NH₂ | CF₃ | 7-Cl | 4-F—Ph | NH₂ |
| Br | 7-F | CO₂Me | NH₂ | CF₃ | 7-CF₃ | CO₂Me | NH₂ |
| Br | 7-F | CO₂Et | NH₂ | CF₃ | 7-CF₃ | CO₂Et | NH₂ |
| Br | 7-F | i-Pr | NH₂ | CF₃ | 7-CF₃ | i-Pr | NH₂ |
| Br | 7-F | Me | NH₂ | CF₃ | 7-CF₃ | Me | NH₂ |
| Br | 7-F | 4-F—Ph | NH₂ | CF₃ | 7-CF₃ | 4-F—Ph | NH₂ |
| Br | 7-Cl | CO₂Me | NH₂ | OCF₃ | 6-F | CO₂Me | NH₂ |
| Br | 7-Cl | CO₂Et | NH₂ | OCF₃ | 6-F | CO₂Et | NH₂ |
| Br | 7-Cl | i-Pr | NH₂ | OCF₃ | 6-F | i-Pr | NH₂ |
| Br | 7-Cl | Me | NH₂ | OCF₃ | 6-F | Me | NH₂ |
| Br | 7-Cl | 4-F—Ph | NH₂ | OCF₃ | 6-F | 4-F—Ph | NH₂ |
| Br | 7-CF₃ | CO₂Me | NH₂ | OCF₃ | 7-F | CO₂Me | NH₂ |
| Br | 7-CF₃ | CO₂Et | NH₂ | OCF₃ | 7-F | CO₂Et | NH₂ |
| Br | 7-CF₃ | i-Pr | NH₂ | OCF₃ | 7-F | i-Pr | NH₂ |

TABLE 16-continued

| R¹ | R² | R³ | Y | R¹ | R² | R³ | Y |
|---|---|---|---|---|---|---|---|
| Br | 7-CF₃ | Me | NH₂ | OCF₃ | 7-F | Me | NH₂ |
| Br | 7-CF₃ | 4-F—Ph | NH₂ | OCF₃ | 7-F | 4-F—Ph | NH₂ |
| CF₃ | 6-F | CO₂Me | NH₂ | OCF₃ | 7-Cl | CO₂Me | NH₂ |
| CF₃ | 6-F | CO₂Et | NH₂ | OCF₃ | 7-Cl | CO₂Et | NH₂ |
| CF₃ | 6-F | i-Pr | NH₂ | OCF₃ | 7-Cl | i-Pr | NH₂ |
| CF₃ | 6-F | Me | NH₂ | OCF₃ | 7-Cl | Me | NH₂ |
| CF₃ | 6-F | 4-F—Ph | NH₂ | OCF₃ | 7-Cl | 4-F—Ph | NH₂ |
| CF₃ | 7-F | CO₂Me | NH₂ | OCF₃ | 7-CF₃ | CO₂Me | NH₂ |
| CF₃ | 7-F | CO₂Et | NH₂ | OCF₃ | 7-CF₃ | CO₂Et | NH₂ |
| CF₃ | 7-F | i-Pr | NH₂ | OCF₃ | 7-CF₃ | i-Pr | NH₂ |
| CF₃ | 7-F | Me | NH₂ | OCF₃ | 7-CF₃ | Me | NH₂ |
| CF₃ | 7-F | 4-F—Ph | NH₂ | OCF₃ | 7-CF₃ | 4-F—Ph | NH₂ |
| Br | 6-F | CO₂Me | NHMe | CF₃ | 7-Cl | CO₂Me | NHMe |
| Br | 6-F | CO₂Et | NHMe | CF₃ | 7-Cl | CO₂Et | NHMe |
| Br | 6-F | i-Pr | NHMe | CF₃ | 7-Cl | i-Pr | NHMe |
| Br | 6-F | Me | NHMe | CF₃ | 7-Cl | Me | NHMe |
| Br | 6-F | 4-F—Ph | NHMe | CF₃ | 7-Cl | 4-F—Ph | NHMe |
| Br | 7-F | CO₂Me | NHMe | CF₃ | 7-CF₃ | CO₂Me | NHMe |
| Br | 7-F | CO₂Et | NHMe | CF₃ | 7-CF₃ | CO₂Et | NHMe |
| Br | 7-F | i-Pr | NHMe | CF₃ | 7-CF₃ | i-Pr | NHMe |
| Br | 7-F | Me | NHMe | CF₃ | 7-CF₃ | Me | NHMe |
| Br | 7-F | 4-F—Ph | NHMe | CF₃ | 7-CF₃ | 4-F—Ph | NHMe |
| Br | 7-Cl | CO₂Me | NHMe | OCF₃ | 6-F | CO₂Me | NHMe |
| Br | 7-Cl | CO₂Et | NHMe | OCF₃ | 6-F | CO₂Et | NHMe |
| Br | 7-Cl | i-Pr | NHMe | OCF₃ | 6-F | i-Pr | NHMe |
| Br | 7-Cl | Me | NHMe | OCF₃ | 6-F | Me | NHMe |
| Br | 7-Cl | 4-F—Ph | NHMe | OCF₃ | 6-F | 4-F—Ph | NHMe |
| Br | 7-CF₃ | CO₂Me | NHMe | OCF₃ | 7-F | CO₂Me | NHMe |
| Br | 7-CF₃ | CO₂Et | NHMe | OCF₃ | 7-F | CO₂Et | NHMe |
| Br | 7-CF₃ | i-Pr | NHMe | OCF₃ | 7-F | i-Pr | NHMe |
| Br | 7-CF₃ | Me | NHMe | OCF₃ | 7-F | Me | NHMe |
| Br | 7-CF₃ | 4-F—Ph | NHMe | OCF₃ | 7-F | 4-F—Ph | NHMe |
| CF₃ | 6-F | CO₂Me | NHMe | OCF₃ | 7-Cl | CO₂Me | NHMe |
| CF₃ | 6-F | CO₂Et | NHMe | OCF₃ | 7-Cl | CO₂Et | NHMe |
| CF₃ | 6-F | i-Pr | NHMe | OCF₃ | 7-Cl | i-Pr | NMMe |
| CF₃ | 6-F | Me | NHMe | OCF₃ | 7-Cl | Me | NHMe |
| CF₃ | 6-F | 4-F—Ph | NHMe | OCF₃ | 7-Cl | 4-F—Ph | NHMe |
| CF₃ | 7-F | CO₂Me | NHMe | OCF₃ | 7-CF₃ | CO₂Me | NHMe |
| CF₃ | 7-F | CO₂Et | NHMe | OCF₃ | 7-CF₃ | CO₂Et | NHMe |
| CF₃ | 7-F | i-Pr | NHMe | OCF₃ | 7-CF₃ | i-Pr | NHMe |
| CF₃ | 7-F | Me | NHMe | OCF₃ | 7-CF₃ | Me | NHMe |
| CF₃ | 7-F | 4-F—Ph | NHMe | OCF₃ | 7-CF₃ | 4-F—Ph | NHMe |
| Br | 6-F | CO₂Me | NHCHO | CF₃ | 7-Cl | CO₂Me | NHCHO |
| Br | 6-F | CO₂Et | NHCHO | CF₃ | 7-Cl | CO₂Et | NHCHO |
| Br | 6-F | i-Pr | NHCHO | CF₃ | 7-Cl | i-Pr | NHCHO |
| Br | 6-F | Me | NHCHO | CF₃ | 7-Cl | Me | NHCHO |
| Br | 6-F | 4-F—Ph | NHCHO | CF₃ | 7-Cl | 4-F—Ph | NHCHO |
| Br | 7-F | CO₂Me | NHCHO | CF₃ | 7-CF₃ | CO₂Me | NHCHO |
| Br | 7-F | CO₂Et | NHCHO | CF₃ | 7-CF₃ | CO₂Et | NHCHO |
| Br | 7-F | i-Pr | NHCHO | CF₃ | 7-CF₃ | i-Pr | NHCHO |
| Br | 7-F | Me | NHCHO | CF₃ | 7-CF₃ | Me | NHCHO |
| Br | 7-F | 4-F—Ph | NHCHO | CF₃ | 7-CF₃ | 4-F—Ph | NHCHO |
| Br | 7-Cl | CO₂Me | NHCHO | OCF₃ | 6-F | CO₂Me | NHCHO |
| Br | 7-Cl | CO₂Et | NHCHO | OCF₃ | 6-F | CO₂Et | NHCHO |
| Br | 7-Cl | i-Pr | NHCHO | OCF₃ | 6-F | i-Pr | NHCHO |
| Br | 7-Cl | Me | NHCHO | OCF₃ | 6-F | Me | NHCHO |
| Br | 7-Cl | 4-F—Ph | NHCHO | OCF₃ | 6-F | 4-F—Ph | NHCHO |
| Br | 7-CF₃ | CO₂Me | NHCHO | OCF₃ | 7-F | CO₂Me | NHCHO |
| Br | 7-CF₃ | CO₂Et | NHCHO | OCF₃ | 7-F | CO₂Et | NHCHO |
| Br | 7-CF₃ | i-Pr | NHCHO | OCF₃ | 7-F | i-Pr | NHCHO |
| Br | 7-CF₃ | Me | NHCHO | OCF₃ | 7-F | Me | NHCHO |
| Br | 7-CF₃ | 4-F—Ph | NHCHO | OCF₃ | 7-F | 4-F—Ph | NHCHO |
| CF₃ | 6-F | CO₂Me | NHCHO | OCF₃ | 7-Cl | CO₂Me | NHCHO |
| CF₃ | 6-F | CO₂Et | NHCHO | OCF₃ | 7-Cl | CO₂Et | NHCHO |
| CF₃ | 6-F | i-Pr | NHCHO | OCF₃ | 7-Cl | i-Pr | NHCHO |
| CF₃ | 6-F | Me | NHCHO | OCF₃ | 7-Cl | Me | NHCHO |
| CF₃ | 6-F | 4-F—Ph | NHCHO | OCF₃ | 7-Cl | 4-F—Ph | NHCHO |
| CF₃ | 7-F | CO₂Me | NHCHO | OCF₃ | 7-CF₃ | CO₂Me | NHCHO |
| CF₃ | 7-F | CO₂Et | NHCHO | OCF₃ | 7-CF₃ | CO₂Et | NHCHO |
| CF₃ | 7-F | i-Pr | NHCHO | OCF₃ | 7-CF₃ | i-Pr | NHCHO |
| CF₃ | 7-F | Me | NHCHO | OCF₃ | 7-CF₃ | Me | NHCHO |
| CF₃ | 7-F | 4-F—Ph | NHCHO | OCF₃ | 7-CF₃ | 4-F—Ph | NHCHO |
| Br | 6-F | CO₂Me | NH(CO)Me | CF₃ | 7-Cl | CO₂Me | NH(CO)Me |
| Br | 6-F | CO₂Et | NH(CO)Me | CF₃ | 7-Cl | CO₂Et | NH(CO)Me |
| Br | 6-F | i-Pr | NH(CO)Me | CF₃ | 7-Cl | i-Pr | NH(CO)Me |
| Br | 6-F | Me | NH(CO)Me | CF₃ | 7-Cl | Me | NH(CO)Me |
| Br | 6-F | 4-F—Ph | NH(CO)Me | CF₃ | 7-Cl | 4-F—Ph | NH(CO)Me |

TABLE 16-continued

| R¹ | R² | R³ | Y | R¹ | R² | R³ | Y |
|---|---|---|---|---|---|---|---|
| Br | 7-F | CO₂Me | NH(CO)Me | CF₃ | 7-CF₃ | CO₂Me | NH(CO)Me |
| Br | 7-F | CO₂Et | NH(CO)Me | CF₃ | 7-CF₃ | CO₂Et | NH(CO)Me |
| Br | 7-F | i-Pr | NH(CO)Me | CF₃ | 7-CF₃ | i-Pr | NH(CO)Me |
| Br | 7-F | Me | NH(CO)Me | CF₃ | 7-CF₃ | Me | NH(CO)Me |
| Br | 7-F | 4-F—Ph | NH(CO)Me | CF₃ | 7-CF₃ | 4-F—Ph | NH(CO)Me |
| Br | 7-Cl | CO₂Me | NH(CO)Me | OCF₃ | 6-F | CO₂Me | NH(CO)Me |
| Br | 7-Cl | CO₂Et | NH(CO)Me | OCF₃ | 6-F | CO₂Et | NH(CO)Me |
| Br | 7-Cl | i-Pr | NH(CO)Me | OCF₃ | 6-F | i-Pr | NH(CO)Me |
| Br | 7-Cl | Me | NH(CO)Me | OCF₃ | 6-F | Me | NH(CO)Me |
| Br | 7-Cl | 4-F—Ph | NH(CO)Me | OCF₃ | 6-F | 4-F—Ph | NH(CO)Me |
| Br | 7-CF₃ | CO₂Me | NH(CO)Me | OCF₃ | 7-F | CO₂Me | NH(CO)Me |
| Br | 7-CF₃ | CO₂Et | NH(CO)Me | OCF₃ | 7-F | CO₂Et | NH(CO)Me |
| Br | 7-CF₃ | i-Pr | NH(CO)Me | OCF₃ | 7-F | i-Pr | NH(CO)Me |
| Br | 7-CF₃ | Me | NH(CO)Me | OCF₃ | 7-F | Me | NH(CO)Me |
| Br | 7-CF₃ | 4-F—Ph | NH(CO)Me | OCF₃ | 7-F | 4-F—Ph | NH(CO)Me |
| CF₃ | 6-F | CO₂Me | NH(CO)Me | OCF₃ | 7-Cl | CO₂Me | NH(CO)Me |
| CF₃ | 6-F | CO₂Et | NH(CO)Me | OCF₃ | 7-Cl | CO₂Et | NH(CO)Me |
| CF₃ | 6-F | i-Pr | NH(CO)Me | OCF₃ | 7-Cl | i-Pr | NH(CO)Me |
| CF₃ | 6-F | Me | NH(CO)Me | OCF₃ | 7-Cl | Me | NH(CO)Me |
| CF₃ | 6-F | 4-F—Ph | NH(CO)Me | OCF₃ | 7-Cl | 4-F—Ph | NH(CO)Me |
| CF₃ | 7-F | CO₂Me | NH(CO)Me | OCF₃ | 7-CF₃ | CO₂Me | NH(CO)Me |
| CF₃ | 7-F | CO₂Et | NH(CO)Me | OCF₃ | 7-CF₃ | CO₂Et | NH(CO)Me |
| CF₃ | 7-F | i-Pr | NH(CO)Me | OCF₃ | 7-CF₃ | i-Pr | NH(CO)Me |
| CF₃ | 7-F | Me | NH(CO)Me | OCF₃ | 7-CF₃ | Me | NH(CO)Me |
| CF₃ | 7-F | 4-F—Ph | NH(CO)Me | OCF₃ | 7-CF₃ | 4-F—Ph | NH(CO)Me |
| Br | 6-F | CO₂Me | NH(CO)NHMe | CF₃ | 7-Cl | CO₂Me | NH(CO)NHMe |
| Br | 6-F | CO₂Et | NH(CO)NHMe | CF₃ | 7-Cl | CO₂Et | NH(CO)NHMe |
| Br | 6-F | i-Pr | NH(CO)NHMe | CF₃ | 7-Cl | i-Pr | NH(CO)NHMe |
| Br | 6-F | Me | NH(CO)NHMe | CF₃ | 7-Cl | Me | NH(CO)NHMe |
| Br | 6-F | 4-F—Ph | NH(CO)NHMe | CF₃ | 7-Cl | 4-F—Ph | NH(CO)NHMe |
| Br | 7-F | CO₂Me | NH(CO)NHMe | CF₃ | 7-CF₃ | CO₂Me | NH(CO)NHMe |
| Br | 7-F | CO₂Et | NH(CO)NHMe | CF₃ | 7-CF₃ | CO₂Et | NH(CO)NHMe |
| Br | 7-F | i-Pr | NH(CO)NHMe | CF₃ | 7-CF₃ | i-Pr | NH(CO)NHMe |
| Br | 7-F | Me | NH(CO)NHMe | CF₃ | 7-CF₃ | Me | NH(CO)NHMe |
| Br | 7-F | 4-F—Ph | NH(CO)NHMe | CF₃ | 7-CF₃ | 4-F—Ph | NH(CO)NHMe |
| Br | 7-Cl | CO₂Me | NH(CO)NHMe | OCF₃ | 6-F | CO₂Me | NH(CO)NHMe |
| Br | 7-Cl | CO₂Et | NH(CO)NHMe | OCF₃ | 6-F | CO₂Et | NH(CO)NHMe |
| Br | 7-Cl | i-Pr | NH(CO)NHMe | OCF₃ | 6-F | i-Pr | NH(CO)NHMe |
| Br | 7-Cl | Me | NH(CO)NHMe | OCF₃ | 6-F | Me | NH(CO)NHMe |
| Br | 7-Cl | 4-F—Ph | NH(CO)NHMe | OCF₃ | 6-F | 4-F—Ph | NH(CO)NHMe |
| Br | 7-CF₃ | CO₂Me | NH(CO)NHMe | OCF₃ | 7-F | CO₂Me | NH(CO)NHMe |
| Br | 7-CF₃ | CO₂Et | NH(CO)NHMe | OCF₃ | 7-F | CO₂Et | NH(CO)NHMe |
| Br | 7-CF₃ | i-Pr | NH(CO)NHMe | OCF₃ | 7-F | i-Pr | NH(CO)NHMe |
| Br | 7-CF₃ | Me | NH(CO)NHMe | OCF₃ | 7-F | Me | NH(CO)NHMe |
| Br | 7-CF₃ | 4-F—Ph | NH(CO)NHMe | OCF₃ | 7-F | 4-F—Ph | NH(CO)NHMe |
| CF₃ | 6-F | CO₂Me | NH(CO)NHMe | OCF₃ | 7-Cl | CO₂Me | NH(CO)NHMe |
| CF₃ | 6-F | CO₂Et | NH(CO)NHMe | OCF₃ | 7-Cl | CO₂Et | NH(CO)NHMe |
| CF₃ | 6-F | i-Pr | NH(CO)NHMe | OCF₃ | 7-Cl | i-Pr | NH(CO)NHMe |
| CF₃ | 6-F | Me | NH(CO)NHMe | OCF₃ | 7-Cl | Me | NH(CO)NHMe |
| CF₃ | 6-F | 4-F—Ph | NH(CO)NHMe | OCF₃ | 7-Cl | 4-F—Ph | NH(CO)NHMe |
| CF₃ | 7-F | CO₂Me | NH(CO)NHMe | OCF₃ | 7-CF₃ | CO₂Me | NH(CO)NHMe |
| CF₃ | 7-F | CO₂Et | NH(CO)NHMe | OCF₃ | 7-CF₃ | CO₂Et | NH(CO)NHMe |
| CF₃ | 7-F | i-Pr | NH(CO)NHMe | OCF₃ | 7-CF₃ | i-Pr | NH(CO)NHMe |
| CF₃ | 7-F | Me | NH(CO)NHMe | OCF₃ | 7-CF₃ | Me | NH(CO)NHMe |
| CF₃ | 7-F | 4-F—Ph | NH(CO)NHMe | OCF₃ | 7-CF₃ | 4-F—Ph | NH(CO)NHMe |
| Br | 6-F | CO₂Me | N=CH₂ | CF₃ | 7-Cl | CO₂Me | N=CH₂ |
| Br | 6-F | CO₂Et | N=CH₂ | CF₃ | 7-Cl | CO₂Et | N=CH₂ |
| Br | 6-F | i-Pr | N=CH₂ | CF₃ | 7-Cl | i-Pr | N=CH₂ |
| Br | 6-F | Me | N=CH₂ | CF₃ | 7-Cl | Me | N=CH₂ |
| Br | 6-F | 4-F—Ph | N=CH₂ | CF₃ | 7-Cl | 4-F—Ph | N=CH₂ |
| Br | 7-F | CO₂Me | N=CH₂ | CF₃ | 7-CF₃ | CO₂Me | N=CH₂ |
| Br | 7-F | CO₂Et | N=CH₂ | CF₃ | 7-CF₃ | CO₂Et | N=CH₂ |
| Br | 7-F | i-Pr | N=CH₂ | CF₃ | 7-CF₃ | i-Pr | N=CH₂ |
| Br | 7-F | Me | N=CH₂ | CF₃ | 7-CF₃ | Me | N=CH₂ |
| Br | 7-F | 4-F—Ph | N=CH₂ | CF₃ | 7-CF₃ | 4-F—Ph | N=CH₂ |
| Br | 7-Cl | CO₂Me | N=CH₂ | OCF₃ | 6-F | CO₂Me | N=CH₂ |
| Br | 7-Cl | CO₂Et | N=CH₂ | OCF₃ | 6-F | CO₂Et | N=CH₂ |
| Br | 7-Cl | i-Pr | N=CH₂ | OCF₃ | 6-F | i-Pr | N=CH₂ |
| Br | 7-Cl | Me | N=CH₂ | OCF₃ | 6-F | Me | N=CH₂ |
| Br | 7-Cl | 4-F—Ph | N=CH₂ | OCF₃ | 6-F | 4-F—Ph | N=CH₂ |
| Br | 7-CF₃ | CO₂Me | N=CH₂ | OCF₃ | 7-F | CO₂Me | N=CH₂ |
| Br | 7-CF₃ | CO₂Et | N=CH₂ | OCF₃ | 7-F | CO₂Et | N=CH₂ |
| Br | 7-CF₃ | i-Pr | N=CH₂ | OCF₃ | 7-F | i-Pr | N=CH₂ |
| Br | 7-CF₃ | Me | N=CH₂ | OCF₃ | 7-F | Me | N=CH₂ |
| Br | 7-CF₃ | 4-F—Ph | N=CH₂ | OCF₃ | 7-F | 4-F—Ph | N=CH₂ |
| CF₃ | 6-F | CO₂Me | N=CH₂ | OCF₃ | 7-Cl | CO₂Me | N=CH₂ |
| CF₃ | 6-F | CO₂Et | N=CH₂ | OCF₃ | 7-Cl | CO₂Et | N=CH₂ |

TABLE 16-continued

| R¹ | R² | R³ | Y | R¹ | R² | R³ | Y |
|---|---|---|---|---|---|---|---|
| CF₃ | 6-F | i-Pr | N=CH₂ | OCF₃ | 7-Cl | i-Pr | N=CH₂ |
| CF₃ | 6-F | Me | N=CH₂ | OCF₃ | 7-Cl | Me | N=CH₂ |
| CF₃ | 6-F | 4-F—Ph | N=CH₂ | OCF₃ | 7-Cl | 4-F—Ph | N=CH₂ |
| CF₃ | 7-F | CO₂Me | N=CH₂ | OCF₃ | 7-CF₃ | CO₂Me | N=CH₂ |
| CF₃ | 7-F | CO₂Et | N=CH₂ | OCF₃ | 7-CF₃ | CO₂Et | N=CH₂ |
| CF₃ | 7-F | i-Pr | N=CH₂ | OCF₃ | 7-CF₃ | i-Pr | N=CH₂ |
| CF₃ | 7-F | Me | N=CH₂ | OCF₃ | 7-CF₃ | Me | N=CH₂ |
| CF₃ | 7-F | 4-F—Ph | N=CH₂ | OCF₃ | 7-CF₃ | 4-F—Ph | N=CH₂ |
| Br | 6-F | CO₂Me | N=CMe₂ | CF₃ | 7-Cl | CO₂Me | N=CMe₂ |
| Br | 6-F | CO₂Et | N=CMe₂ | CF₃ | 7-Cl | CO₂Et | N=CMe₂ |
| Br | 6-F | i-Pr | N=CMe₂ | CF₃ | 7-Cl | i-Pr | N=CMe₂ |
| Br | 6-F | Me | N=CMe₂ | CF₃ | 7-Cl | Me | N=CMe₂ |
| Br | 6-F | 4-F—Ph | N=CMe₂ | CF₃ | 7-Cl | 4-F—Ph | N=CMe₂ |
| Br | 7-F | CO₂Me | N=CMe₂ | CF₃ | 7-CF₃ | CO₂Me | N=CMe₂ |
| Br | 7-F | CO₂Et | N=CMe₂ | CF₃ | 7-CF₃ | CO₂Et | N=CMe₂ |
| Br | 7-F | i-Pr | N=CMe₂ | CF₃ | 7-CF₃ | i-Pr | N=CMe₂ |
| Br | 7-F | Me | N=CMe₂ | CF₃ | 7-CF₃ | Me | N=CMe₂ |
| Br | 7-F | 4-F—Ph | N=CMe₂ | CF₃ | 7-CF₃ | 4-F—Ph | N=CMe₂ |
| Br | 7-Cl | CO₂Me | N=CMe₂ | OCF₃ | 6-F | CO₂Me | N=CMe₂ |
| Br | 7-Cl | CO₂Et | N=CMe₂ | OCF₃ | 6-F | CO₂Et | N=CMe₂ |
| Br | 7-Cl | i-Pr | N=CMe₂ | OCF₃ | 6-F | i-Pr | N=CMe₂ |
| Br | 7-Cl | Me | N=CMe₂ | OCF₃ | 6-F | Me | N=CMe₂ |
| Br | 7-Cl | 4-F—Ph | N=CMe₂ | OCF₃ | 6-F | 4-F—Ph | N=CMe₂ |
| Br | 7-CF₃ | CO₂Me | N=CMe₂ | OCF₃ | 7-F | CO₂Me | N=CMe₂ |
| Br | 7-CF₃ | CO₂Et | N=CMe₂ | OCF₃ | 7-F | CO₂Et | N=CMe₂ |
| Br | 7-CF₃ | i-Pr | N=CMe₂ | OCF₃ | 7-F | i-Pr | N=CMe₂ |
| Br | 7-CF₃ | Me | N=CMe₂ | OCF₃ | 7-F | Me | N=CMe₂ |
| Br | 7-CF₃ | 4-F—Ph | N=CMe₂ | OCF₃ | 7-F | 4-F—Ph | N=CMe₂ |
| CF₃ | 6-F | CO₂Me | N=CMe₂ | OCF₃ | 7-Cl | CO₂Me | N=CMe₂ |
| CF₃ | 6-F | CO₂Et | N=CMe₂ | OCF₃ | 7-Cl | CO₂Et | N=CMe₂ |
| CF₃ | 6-F | i-Pr | N=CMe₂ | OCF₃ | 7-Cl | i-Pr | N=CMe₂ |
| CF₃ | 6-F | Me | N=CMe₂ | OCF₃ | 7-Cl | Me | N=CMe₂ |
| CF₃ | 6-F | 4-F—Ph | N=CMe₂ | OCF₃ | 7-Cl | 4-F—Ph | N=CMe₂ |
| CF₃ | 7-F | CO₂Me | N=CMe₂ | OCF₃ | 7-CF₃ | CO₂Me | N=CMe₂ |
| CF₃ | 7-F | CO₂Et | N=CMe₂ | OCF₃ | 7-CF₃ | CO₂Et | N=CMe₂ |
| CF₃ | 7-F | i-Pr | N=CMe₂ | OCF₃ | 7-CF₃ | i-Pr | N=CMe₂ |
| CF₃ | 7-F | Me | N=CMe₂ | OCF₃ | 7-CF₃ | Me | N=CMe₂ |
| CF₃ | 7-F | 4-F—Ph | N=CMe₂ | OCF₃ | 7-CF₃ | 4-F—Ph | N=CMe₂ |
| Br | 6-F | CO₂Me | N=CHPh | CF₃ | 7-Cl | CO₂Me | N=CHPh |
| Br | 6-F | CO₂Et | N=CHPh | CF₃ | 7-Cl | CO₂Et | N=CHPh |
| Br | 6-F | i-Pr | N=CHPh | CF₃ | 7-Cl | i-Pr | N=CHPh |
| Br | 6-F | Me | N=CHPh | CF₃ | 7-Cl | Me | N=CHPh |
| Br | 6-F | 4-F—Ph | N=CHPh | CF₃ | 7-Cl | 4-F—Ph | N=CHPh |
| Br | 7-F | CO₂Me | N=CHPh | CF₃ | 7-CF₃ | CO₂Me | N=CHPh |
| Br | 7-F | CO₂Et | N=CHPh | CF₃ | 7-CF₃ | CO₂Et | N=CHPh |
| Br | 7-F | i-Pr | N=CHPh | CF₃ | 7-CF₃ | i-Pr | N=CHPh |
| Br | 7-F | Me | N=CHPh | CF₃ | 7-CF₃ | Me | N=CHPh |
| Br | 7-F | 4-F—Ph | N=CHPh | CF₃ | 7-CF₃ | 4-F—Ph | N=CHPh |
| Br | 7-Cl | CO₂Me | N=CHPh | OCF₃ | 6-F | CO₂Me | N=CHPh |
| Br | 7-Cl | CO₂Et | N-CHPh | OCF₃ | 6-F | CO₂Et | N=CHPh |
| Br | 7-Cl | i-Pr | N=CHPh | OCF₃ | 6-F | i-Pr | N=CHPh |
| Br | 7-Cl | Me | N=CHPh | OCF₃ | 6-F | Me | N=CHPh |
| Br | 7-Cl | 4-F—Ph | N=CHPh | OCF₃ | 6-F | 4-F—Ph | N=CHPh |
| Br | 7-CF₃ | CO₂Me | N=CHPh | OCF₃ | 7-F | CO₂Me | N=CHPh |
| Br | 7-CF₃ | CO₂Et | N=CHPh | OCF₃ | 7-F | CO₂Et | N=CHPh |
| Br | 7-CF₃ | i-Pr | N=CHPh | OCF₃ | 7-F | i-Pr | N=CHPh |
| Br | 7-CF₃ | Me | N-CHPh | OCF₃ | 7-F | Me | N=CHPh |
| Br | 7-CF₃ | 4-F—Ph | N-CHPh | OCF₃ | 7-F | 4-F—Ph | N=CHPh |
| CF₃ | 6-F | CO₂Me | N=CHPh | OCF₃ | 7-Cl | CO₂Me | N=CHPh |
| CF₃ | 6-F | CO₂Et | N=CHPh | OCF₃ | 7-Cl | CO₂Et | N=CHPh |
| CF₃ | 6-F | i-Pr | N=CHPh | OCF₃ | 7-Cl | i-Pr | N=CHPh |
| CF₃ | 6-F | Me | N=CHPh | OCF₃ | 7-Cl | Me | N=CHPh |
| CF₃ | 6-F | 4-F—Ph | N=CHPh | OCF₃ | 7-Cl | 4-F—Ph | N=CHPh |
| CF₃ | 7-F | CO₂Me | N=CHPh | OCF₃ | 7-CF₃ | CO₂Me | N=CHPh |
| CF₃ | 7-F | CO₂Et | N=CHPh | OCF₃ | 7-CF₃ | CO₂Et | N=CHPh |
| CF₃ | 7-F | i-Pr | N=CHPh | OCF₃ | 7-CF₃ | i-Pr | N=CHPh |
| CF₃ | 7-F | Me | N=CHPh | OCF₃ | 7-CF₃ | Me | N=CHPh |
| CF₃ | 7-F | 4-F—Ph | N=CHPh | OCF₃ | 7-CF₃ | 4-F—Ph | N=CHPh |
| Br | 6-F | CO₂Me | NH(CO)CF₃ | CF₃ | 7-Cl | CO₂Me | NH(CO)CF₃ |
| Br | 6-F | CO₂Et | NH(CO)CF₃ | CF₃ | 7-Cl | CO₂Et | NH(CO)CF₃ |
| Br | 6-F | i-Pr | NH(CO)CF₃ | CF₃ | 7-Cl | i-Pr | NH(CO)CF₃ |
| Br | 6-F | Me | NH(CO)CF₃ | CF₃ | 7-Cl | Me | NH(CO)CF₃ |
| Br | 6-F | 4-F—Ph | NH(CO)CF₃ | CF₃ | 7-Cl | 4-F—Ph | NH(CO)CF₃ |
| Br | 7-F | CO₂Me | NH(CO)CF₃ | CF₃ | 7-CF₃ | CO₂Me | NH(CO)CF₃ |
| Br | 7-F | CO₂Et | NH(CO)CF₃ | CF₃ | 7-CF₃ | CO₂Et | NH(CO)CF₃ |
| Br | 7-F | i-Pr | NH(CO)CF₃ | CF₃ | 7-CF₃ | i-Pr | NH(CO)CF₃ |
| Br | 7-F | Me | NH(CO)CF₃ | CF₃ | 7-CF₃ | Me | NH(CO)CF₃ |

TABLE 16-continued

| R¹ | R² | R³ | Y | R¹ | R² | R³ | Y |
|---|---|---|---|---|---|---|---|
| Br | 7-F | 4-F—Ph | NH(CO)CF₃ | CF₃ | 7-CF₃ | 4-F—Ph | NH(CO)CF₃ |
| Br | 7-Cl | CO₂Me | NH(CO)CF₃ | OCF₃ | 6-F | CO₂Me | NH(CO)CF₃ |
| Br | 7-Cl | CO₂Et | NH(CO)CF₃ | OCF₃ | 6-F | CO₂Et | NH(CO)CF₃ |
| Br | 7-Cl | i-Pr | NH(CO)CF₃ | OCF₃ | 6-F | i-Pr | NH(CO)CF₃ |
| Br | 7-Cl | Me | NH(CO)CF₃ | OCF₃ | 6-F | Me | NH(CO)CF₃ |
| Br | 7-Cl | 4-F—Ph | NH(CO)CF₃ | OCF₃ | 6-F | 4-F—Ph | NH(CO)CF₃ |
| Br | 7-CF₃ | CO₂Me | NH(CO)CF₃ | OCF₃ | 7-F | CO₂Me | NH(CO)CF₃ |
| Br | 7-CF₃ | CO₂Et | NH(CO)CF₃ | OCF₃ | 7-F | CO₂Et | NH(CO)CF₃ |
| Br | 7-CF₃ | i-Pr | NH(CO)CF₃ | OCF₃ | 7-F | i-Pr | NH(CO)CF₃ |
| Br | 7-CF₃ | Me | NH(CO)CF₃ | OCF₃ | 7-F | Me | NH(CO)CF₃ |
| Br | 7-CF₃ | 4-F—Ph | NH(CO)CF₃ | OCF₃ | 7-F | 4-F—Ph | NH(CO)CF₃ |
| CF₃ | 6-F | CO₂Me | NH(CO)CF₃ | OCF₃ | 7-Cl | CO₂Me | NH(CO)CF₃ |
| CF₃ | 6-F | CO₂Et | NH(CO)CF₃ | OCF₃ | 7-Cl | CO₂Et | NH(CO)CF₃ |
| CF₃ | 6-F | i-Pr | NH(CO)CF₃ | OCF₃ | 7-Cl | i-Pr | NH(CO)CF₃ |
| CF₃ | 6-F | Me | NH(CO)CF₃ | OCF₃ | 7-Cl | Me | NH(CO)CF₃ |
| CF₃ | 6-F | 4-F—Ph | NH(CO)CF₃ | OCF₃ | 7-Cl | 4-F—Ph | NH(CO)CF₃ |
| CF₃ | 7-F | CO₂Me | NH(CO)CF₃ | OCF₃ | 7-CF₃ | CO₂Me | NH(CO)CF₃ |
| CF₃ | 7-F | CO₂Et | NH(CO)CF₃ | OCF₃ | 7-CF₃ | CO₂Et | NH(CO)CF₃ |
| CF₃ | 7-F | i-Pr | NH(CO)CF₃ | OCF₃ | 7-CF₃ | i-Pr | NH(CO)CF₃ |
| CF₃ | 7-F | Me | NH(CO)CF₃ | OCF₃ | 7-CF₃ | Me | NH(CO)CF₃ |
| CF₃ | 7-F | 4-F—Ph | NH(CO)CF₃ | OCF₃ | 7-CF₃ | 4-F—Ph | NH(CO)CF₃ |
| Br | 6-F | CO₂Me | OH | CF₃ | 7-Cl | CO₂Me | OH |
| Br | 6-F | CO₂Et | OH | CF₃ | 7-Cl | CO₂Et | OH |
| Br | 6-F | i-Pr | OH | CF₃ | 7-Cl | i-Pr | OH |
| Br | 6-F | Me | OH | CF₃ | 7-Cl | Me | OH |
| Br | 6-F | 4-F—Ph | OH | CF₃ | 7-Cl | 4-F—Ph | OH |
| Br | 7-F | CO₂Me | OH | CF₃ | 7-CF₃ | CO₂Me | OH |
| Br | 7-F | CO₂Et | OH | CF₃ | 7-CF₃ | CO₂Et | OH |
| Br | 7-F | i-Pr | OH | CF₃ | 7-CF₃ | i-Pr | OH |
| Br | 7-F | Me | OH | CF₃ | 7-CF₃ | Me | OH |
| Br | 7-F | 4-F—Ph | OH | CF₃ | 7-CF₃ | 4-F—Ph | OH |
| Br | 7-Cl | CO₂Me | OH | OCF₃ | 6-F | CO₂Me | OH |
| Br | 7-Cl | CO₂Et | OH | OCF₃ | 6-F | CO₂Et | OH |
| Br | 7-Cl | i-Pr | OH | OCF₃ | 6-F | i-Pr | OH |
| Br | 7-Cl | Me | OH | OCF₃ | 6-F | Me | OH |
| Br | 7-Cl | 4-F—Ph | OH | OCF₃ | 6-F | 4-F—Ph | OH |
| Br | 7-CF₃ | CO₂Me | OH | OCF₃ | 7-F | CO₂Me | OH |
| Br | 7-CF₃ | CO₂Et | OH | OCF₃ | 7-F | CO₂Et | OH |
| Br | 7-CF₃ | i-Pr | OH | OCF₃ | 7-F | i-Pr | OH |
| Br | 7-CF₃ | Me | OH | OCF₃ | 7-F | Me | OH |
| Br | 7-CF₃ | 4-F—Ph | OH | OCF₃ | 7-F | 4-F—Ph | OH |
| CF₃ | 6-F | CO₂Me | OH | OCF₃ | 7-Cl | CO₂Me | OH |
| CF₃ | 6-F | CO₂Et | OH | OCF₃ | 7-Cl | CO₂Et | OH |
| CF₃ | 6-F | i-Pr | OH | OCF₃ | 7-Cl | i-Pr | OH |
| CF₃ | 6-F | Me | OH | OCF₃ | 7-Cl | Me | OH |
| CF₃ | 6-F | 4-F—Ph | OH | OCF₃ | 7-Cl | 4-F—Ph | OH |
| CF₃ | 7-F | CO₂Me | OH | OCF₃ | 7-CF₃ | CO₂Me | OH |
| CF₃ | 7-F | CO₂Et | OH | OCF₃ | 7-CF₃ | CO₂Et | OH |
| CF₃ | 7-F | i-Pr | OH | OCF₃ | 7-CF₃ | i-Pr | OH |
| CF₃ | 7-F | Me | OH | OCF₃ | 7-CF₃ | Me | OH |
| CF₃ | 7-F | 4-F—Ph | OH | OCF₃ | 7-CF₃ | 4-F—Ph | OH |
| Br | 6-F | CO₂Me | OMe | CF₃ | 7-Cl | CO₂Me | OMe |
| Br | 6-F | CO₂Et | OMe | CF₃ | 7-Cl | CO₂Et | OMe |
| Br | 6-F | i-Pr | OMe | CF₃ | 7-Cl | i-Pr | OMe |
| Br | 6-F | Me | OMe | CF₃ | 7-Cl | Me | OMe |
| Br | 6-F | 4-F—Ph | OMe | CF₃ | 7-Cl | 4-F—Ph | OMe |
| Br | 7-F | CO₂Me | OMe | CF₃ | 7-CF₃ | CO₂Me | OMe |
| Br | 7-F | CO₂Et | OMe | CF₃ | 7-CF₃ | CO₂Et | OMe |
| Br | 7-F | i-Pr | OMe | CF₃ | 7-CF₃ | i-Pr | OMe |
| Br | 7-F | Me | OMe | CF₃ | 7-CF₃ | Me | OMe |
| Br | 7-F | 4-F—Ph | OMe | CF₃ | 7-CF₃ | 4-F—Ph | OMe |
| Br | 7-Cl | CO₂Me | OMe | OCF₃ | 6-F | CO₂Me | OMe |
| Br | 7-Cl | CO₂Et | OMe | OCF₃ | 6-F | CO₂Et | OMe |
| Br | 7-Cl | i-Pr | OMe | OCF₃ | 6-F | i-Pr | OMe |
| Br | 7-Cl | Me | OMe | OCF₃ | 6-F | Me | OMe |
| Br | 7-Cl | 4-F—Ph | OMe | OCF₃ | 6-F | 4-F—Ph | OMe |
| Br | 7-CF₃ | CO₂Me | OMe | OCF₃ | 7-F | CO₂Me | OMe |
| Br | 7-CF₃ | CO₂Et | OMe | OCF₃ | 7-F | CO₂Et | OMe |
| Br | 7-CF₃ | i-Pr | OMe | OCF₃ | 7-F | i-Pr | OMe |
| Br | 7-CF₃ | Me | OMe | OCF₃ | 7-F | Me | OMe |
| Br | 7-CF₃ | 4-F—Ph | OMe | OCF₃ | 7-F | 4-F—Ph | OMe |
| CF₃ | 6-F | CO₂Me | OMe | OCF₃ | 7-Cl | CO₂Me | OMe |
| CF₃ | 6-F | CO₂Et | OMe | OCF₃ | 7-Cl | CO₂Et | OMe |
| CF₃ | 6-F | i-Pr | OMe | OCF₃ | 7-Cl | i-Pr | OMe |
| CF₃ | 6-F | Me | OMe | OCF₃ | 7-Cl | Me | OMe |
| CF₃ | 6-F | 4-F—Ph | OMe | OCF₃ | 7-Cl | 4-F—Ph | OMe |
| CF₃ | 7-F | CO₂Me | OMe | OCF₃ | 7-CF₃ | CO₂Me | OMe |

TABLE 16-continued

| R¹ | R² | R³ | Y | R¹ | R² | R³ | Y |
|---|---|---|---|---|---|---|---|
| CF₃ | 7-F | CO₂Et | OMe | OCF₃ | 7-CF₃ | CO₂Et | OMe |
| CF₃ | 7-F | i-Pr | OMe | OCF₃ | 7-CF₃ | i-Pr | OMe |
| CF₃ | 7-F | Me | OMe | OCF₃ | 7-CF₃ | Me | OMe |
| CF₃ | 7-F | 4-F—Ph | OMe | OCF₃ | 7-CF₃ | 4-F—Ph | OMe |
| Br | 6-F | CO₂Me | OCH₂Ph | CF₃ | 7-Cl | CO₂Me | OCH₂Ph |
| Br | 6-F | CO₂Et | OCH₂Ph | CF₃ | 7-Cl | CO₂Et | OCH₂Ph |
| Br | 6-F | i-Pr | OCH₂Ph | CF₃ | 7-Cl | i-Pr | OCH₂Ph |
| Br | 6-F | Me | OCH₂Ph | CF₃ | 7-Cl | Me | OCH₂Ph |
| Br | 6-F | 4-F—Ph | OCH₂Ph | CF₃ | 7-Cl | 4-F—Ph | OCH₂Ph |
| Br | 7-F | CO₂Me | OCH₂Ph | CF₃ | 7-CF₃ | CO₂Me | OCH₂Ph |
| Br | 7-F | CO₂Et | OCH₂Ph | CF₃ | 7-CF₃ | CO₂Et | OCH₂Ph |
| Br | 7-F | i-Pr | OCH₂Ph | CF₃ | 7-CF₃ | i-Pr | OCH₂Ph |
| Br | 7-F | Me | OCH₂Ph | CF₃ | 7-CF₃ | Me | OCH₂Ph |
| Br | 7-F | 4-F—Ph | OCH₂Ph | CF₃ | 7-CF₃ | 4-F—Ph | OCH₂Ph |
| Br | 7-Cl | CO₂Me | OCH₂Ph | OCF₃ | 6-F | CO₂Me | OCH₂Ph |
| Br | 7-Cl | CO₂Et | OCH₂Ph | OCF₃ | 6-F | CO₂Et | OCH₂Ph |
| Br | 7-Cl | i-Pr | OCH₂Ph | OCF₃ | 6-F | i-Pr | OCH₂Ph |
| Br | 7-Cl | Me | OCH₂Ph | OCF₃ | 6-F | Me | OCH₂Ph |
| Br | 7-Cl | 4-F—Ph | OCH₂Ph | OCF₃ | 6-F | 4-F—Ph | OCH₂Ph |
| Br | 7-CF₃ | CO₂Me | OCH₂Ph | OCF₃ | 7-F | CO₂Me | OCH₂Ph |
| Br | 7-CF₃ | CO₂Et | OCH₂Ph | OCF₃ | 7-F | CO₂Et | OCH₂Ph |
| Br | 7-CF₃ | i-Pr | OCH₂Ph | OCF₃ | 7-F | i-Pr | OCH₂Ph |
| Br | 7-CF₃ | Me | OCH₂Ph | OCF₃ | 7-F | Me | OCH₂Ph |
| Br | 7-CF₃ | 4-F—Ph | OCH₂Ph | OCF₃ | 7-F | 4-F—Ph | OCH₂Ph |
| CF₃ | 6-F | CO₂Me | OCH₂Ph | OCF₃ | 7-Cl | CO₂Me | OCH₂Ph |
| CF₃ | 6-F | CO₂Et | OCH₂Ph | OCF₃ | 7-Cl | CO₂Et | OCH₂Ph |
| CF₃ | 6-F | i-Pr | OCH₂Ph | OCF₃ | 7-Cl | i-Pr | OCH₂Ph |
| CF₃ | 6-F | Me | OCH₂Ph | OCF₃ | 7-Cl | Me | OCH₂Ph |
| CF₃ | 6-F | 4-F—Ph | OCH₂Ph | OCF₃ | 7-Cl | 4-F—Ph | OCH₂Ph |
| CF₃ | 7-F | CO₂Me | OCH₂Ph | OCF₃ | 7-CF₃ | CO₂Me | OCH₂Ph |
| CF₃ | 7-F | CO₂Et | OCH₂Ph | OCF₃ | 7-CF₃ | CO₂Et | OCH₂Ph |
| CF₃ | 7-F | i-Pr | OCH₂Ph | OCF₃ | 7-CF₃ | i-Pr | OCH₂Ph |
| CF₃ | 7-F | Me | OCH₂Ph | OCF₃ | 7-CF₃ | Me | OCH₂Ph |
| CF₃ | 7-F | 4-F—Ph | OCH₂Ph | OCF₃ | 7-CF₃ | 4-F—Ph | OCH₂Ph |

TABLE 17

| R¹ | R² | R³ | Y | R¹ | R² | R³ | Y |
|---|---|---|---|---|---|---|---|
| Br | 6-F | CO₂Me | NH₂ | CF₃ | 7-Cl | CO₂Me | NH₂ |
| Br | 6-F | CO₂Et | NH₂ | CF₃ | 7-Cl | CO₂Et | NH₂ |
| Br | 6-F | i-Pr | NH₂ | CF₃ | 7-Cl | i-Pr | NH₂ |
| Br | 6-F | Me | NH₂ | CF₃ | 7-Cl | Me | NH₂ |
| Br | 6-F | 4-F—Ph | NH₂ | CF₃ | 7-Cl | 4-F—Ph | NH₂ |
| Br | 7-F | CO₂Me | NH₂ | CF₃ | 7-CF₃ | CO₂Me | NH₂ |
| Br | 7-F | CO₂Et | NH₂ | CF₃ | 7-CF₃ | CO₂Et | NH₂ |
| Br | 7-F | i-Pr | NH₂ | CF₃ | 7-CF₃ | i-Pr | NH₂ |
| Br | 7-F | Me | NH₂ | CF₃ | 7-CF₃ | Me | NH₂ |
| Br | 7-F | 4-F—Ph | NH₂ | CF₃ | 7-CF₃ | 4-F—Ph | NH₂ |
| Br | 7-Cl | CO₂Me | NH₂ | OCF₃ | 6-F | CO₂Me | NH₂ |
| Br | 7-Cl | CO₂Et | NH₂ | OCF₃ | 6-F | CO₂Et | NH₂ |
| Br | 7-Cl | i-Pr | NH₂ | OCF₃ | 6-F | i-Pr | NH₂ |
| Br | 7-Cl | Me | NH₂ | OCF₃ | 6-F | Me | NH₂ |
| Br | 7-Cl | 4-F—Ph | NH₂ | OCF₃ | 6-F | 4-F—Ph | NH₂ |
| Br | 7-CF₃ | CO₂Me | NH₂ | OCF₃ | 7-F | CO₂Me | NH₂ |
| Br | 7-CF₃ | CO₂Et | NH₂ | OCF₃ | 7-F | CO₂Et | NH₂ |
| Br | 7-CF₃ | i-Pr | NH₂ | OCF₃ | 7-F | i-Pr | NH₂ |
| Br | 7-CF₃ | Me | NH₂ | OCF₃ | 7-F | Me | NH₂ |
| Br | 7-CF₃ | 4-F—Ph | NH₂ | OCF₃ | 7-F | 4-F—Ph | NH₂ |
| CF₃ | 6-F | CO₂Me | NH₂ | OCF₃ | 7-Cl | CO₂Me | NH₂ |
| CF₃ | 6-F | CO₂Et | NH₂ | OCF₃ | 7-Cl | CO₂Et | NH₂ |
| CF₃ | 6-F | i-Pr | NH₂ | OCF₃ | 7-Cl | i-Pr | NH₂ |
| CF₃ | 6-F | Me | NH₂ | OCF₃ | 7-Cl | Me | NH₂ |
| CF₃ | 6-F | 4-F—Ph | NH₂ | OCF₃ | 7-Cl | 4-F—Ph | NH₂ |
| CF₃ | 7-F | CO₂Me | NH₂ | OCF₃ | 7-CF₃ | CO₂Me | NH₂ |
| CF₃ | 7-F | CO₂Et | NH₂ | OCF₃ | 7-CF₃ | CO₂Et | NH₂ |
| CF₃ | 7-F | i-Pr | NH₂ | OCF₃ | 7-CF₃ | i-Pr | NH₂ |
| CF₃ | 7-F | Me | NH₂ | OCF₃ | 7-CF₃ | Me | NH₂ |
| CF₃ | 7-F | 4-F—Ph | NH₂ | OCF₃ | 7-CF₃ | 4-F—Ph | NH₂ |
| Br | 6-F | CO₂Me | NHMe | CF₃ | 7-Cl | CO₂Me | NHMe |
| Br | 6-F | CO₂Et | NHMe | CF₃ | 7-Cl | CO₂Et | NHMe |
| Br | 6-F | i-Pr | NHMe | CF₃ | 7-Cl | i-Pr | NHMe |
| Br | 6-F | Me | NHMe | CF₃ | 7-Cl | Me | NHMe |
| Br | 6-F | 4-F—Ph | NHMe | CF₃ | 7-Cl | 4-F—Ph | NHMe |
| Br | 7-F | CO₂Me | NHMe | CF₃ | 7-CF₃ | CO₂Me | NHMe |

TABLE 17-continued

| R¹ | R² | R³ | Y | R¹ | R² | R³ | Y |
|---|---|---|---|---|---|---|---|
| Br | 7-F | CO₂Et | NHMe | CF₃ | 7-CF₃ | CO₂Et | NHMe |
| Br | 7-F | i-Pr | NHMe | CF₃ | 7-CF₃ | i-Pr | NHMe |
| Br | 7-F | Me | NHMe | CF₃ | 7-CF₃ | Me | NHMe |
| Br | 7-F | 4-F—Ph | NHMe | CF₃ | 7-CF₃ | 4-F—Ph | NHMe |
| Br | 7-Cl | CO₂Me | NHMe | OCF₃ | 6-F | CO₂Me | NHMe |
| Br | 7-Cl | CO₂Et | NHMe | OCF₃ | 6-F | CO₂Et | NHMe |
| Br | 7-Cl | i-Pr | NHMe | OCF₃ | 6-F | i-Pr | NHMe |
| Br | 7-Cl | Me | NHMe | OCF₃ | 6-F | Me | NHMe |
| Br | 7-Cl | 4-F—Ph | NHMe | OCF₃ | 6-F | 4-F—Ph | NHMe |
| Br | 7-CF₃ | CO₂Me | NHMe | OCF₃ | 7-F | CO₂Me | NHMe |
| Br | 7-CF₃ | CO₂Et | NHMe | OCF₃ | 7-F | CO₂Et | NHMe |
| Br | 7-CF₃ | i-Pr | NHMe | OCF₃ | 7-F | i-Pr | NHMe |
| Br | 7-CF₃ | Me | NHMe | OCF₃ | 7-F | Me | NHMe |
| Br | 7-CF₃ | 4-F—Ph | NHMe | OCF₃ | 7-F | 4-F—Ph | NHMe |
| CF₃ | 6-F | CO₂Me | NHMe | OCF₃ | 7-Cl | CO₂Me | NHMe |
| CF₃ | 6-F | CO₂Et | NHMe | OCF₃ | 7-Cl | CO₂Et | NHMe |
| CF₃ | 6-F | i-Pr | NHMe | OCF₃ | 7-Cl | i-Pr | NMMe |
| CF₃ | 6-F | Me | NHMe | OCF₃ | 7-Cl | Me | NHMe |
| CF₃ | 6-F | 4-F—Ph | NHMe | OCF₃ | 7-Cl | 4-F—Ph | NHMe |
| CF₃ | 7-F | CO₂Me | NHMe | OCF₃ | 7-CF₃ | CO₂Me | NHMe |
| CF₃ | 7-F | CO₂Et | NHMe | OCF₃ | 7-CF₃ | CO₂Et | NHMe |
| CF₃ | 7-F | i-Pr | NHMe | OCF₃ | 7-CF₃ | i-Pr | NHMe |
| CF₃ | 7-F | Me | NHMe | OCF₃ | 7-CF₃ | Me | NHMe |
| CF₃ | 7-F | 4-F—Ph | NHMe | OCF₃ | 7-CF₃ | 4-F—Ph | NHMe |
| Br | 6-F | CO₂Me | NHCHO | CF₃ | 7-Cl | CO₂Me | NHCHO |
| Br | 6-F | CO₂Et | NHCHO | CF₃ | 7-Cl | CO₂Et | NHCHO |
| Br | 6-F | i-Pr | NHCHO | CF₃ | 7-Cl | i-Pr | NHCHO |
| Br | 6-F | Me | NHCHO | CF₃ | 7-Cl | Me | NHCHO |
| Br | 6-F | 4-F—Ph | NHCHO | CF₃ | 7-Cl | 4-F—Ph | NHCHO |
| Br | 7-F | CO₂Me | NHCHO | CF₃ | 7-CF₃ | CO₂Me | NHCHO |
| Br | 7-F | CO₂Et | NHCHO | CF₃ | 7-CF₃ | CO₂Et | NHCHO |
| Br | 7-F | i-Pr | NHCHO | CF₃ | 7-CF₃ | i-Pr | NHCHO |
| Br | 7-F | Me | NHCHO | CF₃ | 7-CF₃ | Me | NHCHO |
| Br | 7-F | 4-F—Ph | NHCHO | CF₃ | 7-CF₃ | 4-F—Ph | NHCHO |
| Br | 7-Cl | CO₂Me | NHCHO | OCF₃ | 6-F | CO₂Me | NHCHO |
| Br | 7-Cl | CO₂Et | NHCHO | OCF₃ | 6-F | CO₂Et | NHCHO |
| Br | 7-Cl | i-Pr | NHCHO | OCF₃ | 6-F | i-Pr | NHCHO |
| Br | 7-Cl | Me | NHCHO | OCF₃ | 6-F | Me | NHCHO |
| Br | 7-Cl | 4-F—Ph | NHCHO | OCF₃ | 6-F | 4-F—Ph | NHCHO |
| Br | 7-CF₃ | CO₂Me | NHCHO | OCF₃ | 7-F | CO₂Me | NHCHO |
| Br | 7-CF₃ | CO₂Et | NHCHO | OCF₃ | 7-F | CO₂Et | NHCHO |
| Br | 7-CF₃ | i-Pr | NHCHO | OCF₃ | 7-F | i-Pr | NHCHO |
| Br | 7-CF₃ | Me | NHCHO | OCF₃ | 7-F | Me | NHCHO |
| Br | 7-CF₃ | 4-F—Ph | NHCHO | OCF₃ | 7-F | 4-F—Ph | NHCHO |
| CF₃ | 6-F | CO₂Me | NHCHO | OCF₃ | 7-Cl | CO₂Me | NHCHO |
| CF₃ | 6-F | CO₂Et | NHCHO | OCF₃ | 7-Cl | CO₂Et | NHCHO |
| CF₃ | 6-F | i-Pr | NHCHO | OCF₃ | 7-Cl | i-Pr | NHCHO |
| CF₃ | 6-F | Me | NHCHO | OCF₃ | 7-Cl | Me | NHCHO |
| CF₃ | 6-F | 4-F—Ph | NHCHO | OCF₃ | 7-Cl | 4-F—Ph | NHCHO |
| CF₃ | 7-F | CO₂Me | NHCHO | OCF₃ | 7-CF₃ | CO₂Me | NHCHO |
| CF₃ | 7-F | CO₂Et | NHCHO | OCF₃ | 7-CF₃ | CO₂Et | NHCHO |
| CF₃ | 7-F | i-Pr | NHCHO | OCF₃ | 7-CF₃ | i-Pr | NHCHO |
| CF₃ | 7-F | Me | NHCHO | OCF₃ | 7-CF₃ | Me | NHCHO |
| CF₃ | 7-F | 4-F—Ph | NHCHO | OCF₃ | 7-CF₃ | 4-F—Ph | NHCHO |
| Br | 6-F | CO₂Me | NH(CO)Me | CF₃ | 7-Cl | CO₂Me | NH(CO)Me |
| Br | 6-F | CO₂Et | NH(CO)Me | CF₃ | 7-Cl | CO₂Et | NH(CO)Me |
| Br | 6-F | i-Pr | NH(CO)Me | CF₃ | 7-Cl | i-Pr | NH(CO)Me |
| Br | 6-F | Me | NH(CO)Me | CF₃ | 7-Cl | Me | NH(CO)Me |
| Br | 6-F | 4-F—Ph | NH(CO)Me | CF₃ | 7-Cl | 4-F—Ph | NH(CO)Me |
| Br | 7-F | CO₂Me | NH(CO)Me | CF₃ | 7-CF₃ | CO₂Me | NH(CO)Me |
| Br | 7-F | CO₂Et | NH(CO)Me | CF₃ | 7-CF₃ | CO₂Et | NH(CO)Me |
| Br | 7-F | i-Pr | NH(CO)Me | CF₃ | 7-CF₃ | i-Pr | NH(CO)Me |
| Br | 7-F | Me | NH(CO)Me | CF₃ | 7-CF₃ | Me | NH(CO)Me |
| Br | 7-F | 4-F—Ph | NH(CO)Me | CF₃ | 7-CF₃ | 4-F—Ph | NH(CO)Me |
| Br | 7-Cl | CO₂Me | NH(CO)Me | OCF₃ | 6-F | CO₂Me | NH(CO)Me |
| Br | 7-Cl | CO₂Et | NH(CO)Me | OCF₃ | 6-F | CO₂Et | NH(CO)Me |
| Br | 7-Cl | i-Pr | NH(CO)Me | OCF₃ | 6-F | i-Pr | NH(CO)Me |
| Br | 7-Cl | Me | NH(CO)Me | OCF₃ | 6-F | Me | NH(CO)Me |
| Br | 7-Cl | 4-F—Ph | NH(CO)Me | OCF₃ | 6-F | 4-F—Ph | NH(CO)Me |
| Br | 7-CF₃ | CO₂Me | NH(CO)Me | OCF₃ | 7-F | CO₂Me | NH(CO)Me |
| Br | 7-CF₃ | CO₂Et | NH(CO)Me | OCF₃ | 7-F | CO₂Et | NH(CO)Me |
| Br | 7-CF₃ | i-Pr | NH(CO)Me | OCF₃ | 7-F | i-Pr | NH(CO)Me |
| Br | 7-CF₃ | Me | NH(CO)Me | OCF₃ | 7-F | Me | NH(CO)Me |
| Br | 7-CF₃ | 4-F—Ph | NH(CO)Me | OCF₃ | 7-F | 4-F—Ph | NH(CO)Me |
| CF₃ | 6-F | CO₂Me | NH(CO)Me | OCF₃ | 7-Cl | CO₂Me | NH(CO)Me |
| CF₃ | 6-F | CO₂Et | NH(CO)Me | OCF₃ | 7-Cl | CO₂Et | NH(CO)Me |
| CF₃ | 6-F | i-Pr | NH(CO)Me | OCF₃ | 7-Cl | i-Pr | NH(CO)Me |

TABLE 17-continued

| R¹ | R² | R³ | Y | R¹ | R² | R³ | Y |
|---|---|---|---|---|---|---|---|
| $CF_3$ | 6-F | Me | NH(CO)Me | $OCF_3$ | 7-Cl | Me | NH(CO)Me |
| $CF_3$ | 6-F | 4-F—Ph | NH(CO)Me | $OCF_3$ | 7-Cl | 4-F—Ph | NH(CO)Me |
| $CF_3$ | 7-F | $CO_2Me$ | NH(CO)Me | $OCF_3$ | 7-$CF_3$ | $CO_2Me$ | NH(CO)Me |
| $CF_3$ | 7-F | $CO_2Et$ | NH(CO)Me | $OCF_3$ | 7-$CF_3$ | $CO_2Et$ | NH(CO)Me |
| $CF_3$ | 7-F | i-Pr | NH(CO)Me | $OCF_3$ | 7-$CF_3$ | i-Pr | NH(CO)Me |
| $CF_3$ | 7-F | Me | NH(CO)Me | $OCF_3$ | 7-$CF_3$ | Me | NH(CO)Me |
| $CF_3$ | 7-F | 4-F—Ph | NH(CO)Me | $OCF_3$ | 7-$CF_3$ | 4-F—Ph | NH(CO)Me |
| Br | 6-F | $CO_2Me$ | NH(CO)NHMe | $CF_3$ | 7-Cl | $CO_2Me$ | NH(CO)NHMe |
| Br | 6-F | $CO_2Et$ | NH(CO)NHMe | $CF_3$ | 7-Cl | $CO_2Et$ | NH(CO)NHMe |
| Br | 6-F | i-Pr | NH(CO)NHMe | $CF_3$ | 7-Cl | i-Pr | NH(CO)NHMe |
| Br | 6-F | Me | NH(CO)NHMe | $CF_3$ | 7-Cl | Me | NH(CO)NHMe |
| Br | 6-F | 4-F—Ph | NH(CO)NHMe | $CF_3$ | 7-Cl | 4-F—Ph | NH(CO)NHMe |
| Br | 7-F | $CO_2Me$ | NH(CO)NHMe | $CF_3$ | 7-$CF_3$ | $CO_2Me$ | NH(CO)NHMe |
| Br | 7-F | $CO_2Et$ | NH(CO)NHMe | $CF_3$ | 7-$CF_3$ | $CO_2Et$ | NH(CO)NHMe |
| Br | 7-F | i-Pr | NH(CO)NHMe | $CF_3$ | 7-$CF_3$ | i-Pr | NH(CO)NHMe |
| Br | 7-F | Me | NH(CO)NHMe | $CF_3$ | 7-$CF_3$ | Me | NH(CO)NHMe |
| Br | 7-F | 4-F—Ph | NH(CO)NHMe | $CF_3$ | 7-$CF_3$ | 4-F—Ph | NH(CO)NHMe |
| Br | 7-Cl | $CO_2Me$ | NH(CO)NHMe | $OCF_3$ | 6-F | $CO_2Me$ | NH(CO)NHMe |
| Br | 7-Cl | $CO_2Et$ | NH(CO)NHMe | $OCF_3$ | 6-F | $CO_2Et$ | NH(CO)NHMe |
| Br | 7-Cl | i-Pr | NH(CO)NHMe | $OCF_3$ | 6-F | i-Pr | NH(CO)NHMe |
| Br | 7-Cl | Me | NH(CO)NHMe | $OCF_3$ | 6-F | Me | NH(CO)NHMe |
| Br | 7-Cl | 4-F—Ph | NH(CO)NHMe | $OCF_3$ | 6-F | 4-F—Ph | NH(CO)NHMe |
| Br | 7-$CF_3$ | $CO_2Me$ | NH(CO)NHMe | $OCF_3$ | 7-F | $CO_2Me$ | NH(CO)NHMe |
| Br | 7-$CF_3$ | $CO_2Et$ | NH(CO)NHMe | $OCF_3$ | 7-F | $CO_2Et$ | NH(CO)NHMe |
| Br | 7-$CF_3$ | i-Pr | NH(CO)NHMe | $OCF_3$ | 7-F | i-Pr | NH(CO)NHMe |
| Br | 7-$CF_3$ | Me | NH(CO)NHMe | $OCF_3$ | 7-F | Me | NH(CO)NHMe |
| Br | 7-$CF_3$ | 4-F—Ph | NH(CO)NHMe | $OCF_3$ | 7-F | 4-F—Ph | NH(CO)NHMe |
| $CF_3$ | 6-F | $CO_2Me$ | NH(CO)NHMe | $OCF_3$ | 7-Cl | $CO_2Me$ | NH(CO)NHMe |
| $CF_3$ | 6-F | $CO_2Et$ | NH(CO)NHMe | $OCF_3$ | 7-Cl | $CO_2Et$ | NH(CO)NHMe |
| $CF_3$ | 6-F | i-Pr | NH(CO)NHMe | $OCF_3$ | 7-Cl | i-Pr | NH(CO)NHMe |
| $CF_3$ | 6-F | Me | NH(CO)NHMe | $OCF_3$ | 7-Cl | Me | NH(CO)NHMe |
| $CF_3$ | 6-F | 4-F—Ph | NH(CO)NHMe | $OCF_3$ | 7-Cl | 4-F—Ph | NH(CO)NHMe |
| $CF_3$ | 7-F | $CO_2Me$ | NH(CO)NHMe | $OCF_3$ | 7-$CF_3$ | $CO_2Me$ | NH(CO)NHMe |
| $CF_3$ | 7-F | $CO_2Et$ | NH(CO)NHMe | $OCF_3$ | 7-$CF_3$ | $CO_2Et$ | NH(CO)NHMe |
| $CF_3$ | 7-F | i-Pr | NH(CO)NHMe | $OCF_3$ | 7-$CF_3$ | i-Pr | NH(CO)NHMe |
| $CF_3$ | 7-F | Me | NH(CO)NHMe | $OCF_3$ | 7-$CF_3$ | Me | NH(CO)NHMe |
| $CF_3$ | 7-F | 4-F—Ph | NH(CO)NHMe | $OCF_3$ | 7-$CF_3$ | 4-F—Ph | NH(CO)NHMe |
| Br | 6-F | $CO_2Me$ | $N=CH_2$ | $CF_3$ | 7-Cl | $CO_2Me$ | $N=CH_2$ |
| Br | 6-F | $CO_2Et$ | $N=CH_2$ | $CF_3$ | 7-Cl | $CO_2Et$ | $N=CH_2$ |
| Br | 6-F | i-Pr | $N=CH_2$ | $CF_3$ | 7-Cl | i-Pr | $N=CH_2$ |
| Br | 6-F | Me | $N=CH_2$ | $CF_3$ | 7-Cl | Me | $N=CH_2$ |
| Br | 6-F | 4-F—Ph | $N=CH_2$ | $CF_3$ | 7-Cl | 4-F—Ph | $N=CH_2$ |
| Br | 7-F | $CO_2Me$ | $N=CH_2$ | $CF_3$ | 7-$CF_3$ | $CO_2Me$ | $N=CH_2$ |
| Br | 7-F | $CO_2Et$ | $N=CH_2$ | $CF_3$ | 7-$CF_3$ | $CO_2Et$ | $N=CH_2$ |
| Br | 7-F | i-Pr | $N=CH_2$ | $CF_3$ | 7-$CF_3$ | i-Pr | $N=CH_2$ |
| Br | 7-F | Me | $N=CH_2$ | $CF_3$ | 7-$CF_3$ | Me | $N=CH_2$ |
| Br | 7-F | 4-F—Ph | $N=CH_2$ | $CF_3$ | 7-$CF_3$ | 4-F—Ph | $N=CH_2$ |
| Br | 7-Cl | $CO_2Me$ | $N=CH_2$ | $OCF_3$ | 6-F | $CO_2Me$ | $N=CH_2$ |
| Br | 7-Cl | $CO_2Et$ | $N=CH_2$ | $OCF_3$ | 6-F | $CO_2Et$ | $N=CH_2$ |
| Br | 7-Cl | i-Pr | $N=CH_2$ | $OCF_3$ | 6-F | i-Pr | $N=CH_2$ |
| Br | 7-Cl | Me | $N=CH_2$ | $OCF_3$ | 6-F | Me | $N=CH_2$ |
| Br | 7-Cl | 4-F—Ph | $N=CH_2$ | $OCF_3$ | 6-F | 4-F—Ph | $N=CH_2$ |
| Br | 7-$CF_3$ | $CO_2Me$ | $N=CH_2$ | $OCF_3$ | 7-F | $CO_2Me$ | $N=CH_2$ |
| Br | 7-$CF_3$ | $CO_2Et$ | $N=CH_2$ | $OCF_3$ | 7-F | $CO_2Et$ | $N=CH_2$ |
| Br | 7-$CF_3$ | i-Pr | $N=CH_2$ | $OCF_3$ | 7-F | i-Pr | $N=CH_2$ |
| Br | 7-$CF_3$ | Me | $N=CH_2$ | $OCF_3$ | 7-F | Me | $N=CH_2$ |
| Br | 7-$CF_3$ | 4-F—Ph | $N=CH_2$ | $OCF_3$ | 7-F | 4-F—Ph | $N=CH_2$ |
| $CF_3$ | 6-F | $CO_2Me$ | $N=CH_2$ | $OCF_3$ | 7-Cl | $CO_2Me$ | $N=CH_2$ |
| $CF_3$ | 6-F | $CO_2Et$ | $N=CH_2$ | $OCF_3$ | 7-Cl | $CO_2Et$ | $N=CH_2$ |
| $CF_3$ | 6-F | i-Pr | $N=CH_2$ | $OCF_3$ | 7-Cl | i-Pr | $N=CH_2$ |
| $CF_3$ | 6-F | Me | $N=CH_2$ | $OCF_3$ | 7-Cl | Me | $N=CH_2$ |
| $CF_3$ | 6-F | 4-F—Ph | $N=CH_2$ | $OCF_3$ | 7-Cl | 4-F—Ph | $N=CH_2$ |
| $CF_3$ | 7-F | $CO_2Me$ | $N=CH_2$ | $OCF_3$ | 7-$CF_3$ | $CO_2Me$ | $N=CH_2$ |
| $CF_3$ | 7-F | $CO_2Et$ | $N=CH_2$ | $OCF_3$ | 7-$CF_3$ | $CO_2Et$ | $N=CH_2$ |
| $CF_3$ | 7-F | i-Pr | $N=CH_2$ | $OCF_3$ | 7-$CF_3$ | i-Pr | $N=CH_2$ |
| $CF_3$ | 7-F | Me | $N=CH_2$ | $OCF_3$ | 7-$CF_3$ | Me | $N=CH_2$ |
| $CF_3$ | 7-F | 4-F—Ph | $N=CH_2$ | $OCF_3$ | 7-$CF_3$ | 4-F—Ph | $N=CH_2$ |
| Br | 6-F | $CO_2Me$ | $N=CMe_2$ | $CF_3$ | 7-Cl | $CO_2Me$ | $N=CMe_2$ |
| Br | 6-F | $CO_2Et$ | $N=CMe_2$ | $CF_3$ | 7-Cl | $CO_2Et$ | $N=CMe_2$ |
| Br | 6-F | i-Pr | $N=CMe_2$ | $CF_3$ | 7-Cl | i-Pr | $N=CMe_2$ |
| Br | 6-F | Me | $N=CMe_2$ | $CF_3$ | 7-Cl | Me | $N=CMe_2$ |
| Br | 6-F | 4-F—Ph | $N=CMe_2$ | $CF_3$ | 7-Cl | 4-F—Ph | $N=CMe_2$ |
| Br | 7-F | $CO_2Me$ | $N=CMe_2$ | $CF_3$ | 7-$CF_3$ | $CO_2Me$ | $N=CMe_2$ |
| Br | 7-F | $CO_2Et$ | $N=CMe_2$ | $CF_3$ | 7-$CF_3$ | $CO_2Et$ | $N=CMe_2$ |
| Br | 7-F | i-Pr | $N=CMe_2$ | $CF_3$ | 7-$CF_3$ | i-Pr | $N=CMe_2$ |
| Br | 7-F | Me | $N=CMe_2$ | $CF_3$ | 7-$CF_3$ | Me | $N=CMe_2$ |
| Br | 7-F | 4-F—Ph | $N=CMe_2$ | $CF_3$ | 7-$CF_3$ | 4-F—Ph | $N=CMe_2$ |

TABLE 17-continued

| R¹ | R² | R³ | Y | R¹ | R² | R³ | Y |
|---|---|---|---|---|---|---|---|
| Br | 7-Cl | CO₂Me | N=CMe₂ | OCF₃ | 6-F | CO₂Me | N=CMe₂ |
| Br | 7-Cl | CO₂Et | N=CMe₂ | OCF₃ | 6-F | CO₂Et | N=CMe₂ |
| Br | 7-Cl | i-Pr | N=CMe₂ | OCF₃ | 6-F | i-Pr | N=CMe₂ |
| Br | 7-Cl | Me | N=CMe₂ | OCF₃ | 6-F | Me | N=CMe₂ |
| Br | 7-Cl | 4-F—Ph | N=CMe₂ | OCF₃ | 6-F | 4-F—Ph | N=CMe₂ |
| Br | 7-CF₃ | CO₂Me | N=CMe₂ | OCF₃ | 7-F | CO₂Me | N=CMe₂ |
| Br | 7-CF₃ | CO₂Et | N=CMe₂ | OCF₃ | 7-F | CO₂Et | N=CMe₂ |
| Br | 7-CF₃ | i-Pr | N=CMe₂ | OCF₃ | 7-F | i-Pr | N=CMe₂ |
| Br | 7-CF₃ | Me | N=CMe₂ | OCF₃ | 7-F | Me | N=CMe₂ |
| Br | 7-CF₃ | 4-F—Ph | N=CMe₂ | OCF₃ | 7-F | 4-F—Ph | N=CMe₂ |
| CF₃ | 6-F | CO₂Me | N=CMe₂ | OCF₃ | 7-Cl | CO₂Me | N=CMe₂ |
| CF₃ | 6-F | CO₂Et | N=CMe₂ | OCF₃ | 7-Cl | CO₂Et | N=CMe₂ |
| CF₃ | 6-F | i-Pr | N=CMe₂ | OCF₃ | 7-Cl | i-Pr | N=CMe₂ |
| CF₃ | 6-F | Me | N=CMe₂ | OCF₃ | 7-Cl | Me | N=CMe₂ |
| CF₃ | 6-F | 4-F—Ph | N=CMe₂ | OCF₃ | 7-Cl | 4-F—Ph | N=CMe₂ |
| CF₃ | 7-F | CO₂Me | N=CMe₂ | OCF₃ | 7-CF₃ | CO₂Me | N=CMe₂ |
| CF₃ | 7-F | CO₂Et | N=CMe₂ | OCF₃ | 7-CF₃ | CO₂Et | N=CMe₂ |
| CF₃ | 7-F | i-Pr | N=CMe₂ | OCF₃ | 7-CF₃ | i-Pr | N=CMe₂ |
| CF₃ | 7-F | Me | N=CMe₂ | OCF₃ | 7-CF₃ | Me | N=CMe₂ |
| CF₃ | 7-F | 4-F—Ph | N=CMe₂ | OCF₃ | 7-CF₃ | 4-F—Ph | N=CMe₂ |
| Br | 6-F | CO₂Me | N=CHPh | CF₃ | 7-Cl | CO₂Me | N=CHPh |
| Br | 6-F | CO₂Et | N=CHPh | CF₃ | 7-Cl | CO₂Et | N=CHPh |
| Br | 6-F | i-Pr | N=CHPh | CF₃ | 7-Cl | i-Pr | N=CHPh |
| Br | 6-F | Me | N=CHPh | CF₃ | 7-Cl | Me | N=CHPh |
| Br | 6-F | 4-F—Ph | N=CHPh | CF₃ | 7-Cl | 4-F—Ph | N=CHPh |
| Br | 7-F | CO₂Me | N=CHPh | CF₃ | 7-CF₃ | CO₂Me | N=CHPh |
| Br | 7-F | CO₂Et | N=CHPh | CF₃ | 7-CF₃ | CO₂Et | N=CHPh |
| Br | 7-F | i-Pr | N=CHPh | CF₃ | 7-CF₃ | i-Pr | N=CHPh |
| Br | 7-F | Me | N=CHPh | CF₃ | 7-CF₃ | Me | N=CHPh |
| Br | 7-F | 4-F—Ph | N=CHPh | CF₃ | 7-CF₃ | 4-F—Ph | N=CHPh |
| Br | 7-Cl | CO₂Me | N=CHPh | OCF₃ | 6-F | CO₂Me | N=CHPh |
| Br | 7-Cl | CO₂Et | N-CHPh | OCF₃ | 6-F | CO₂Et | N=CHPh |
| Br | 7-Cl | i-Pr | N=CHPh | OCF₃ | 6-F | i-Pr | N=CHPh |
| Br | 7-Cl | Me | N=CHPh | OCF₃ | 6-F | Me | N=CHPh |
| Br | 7-Cl | 4-F—Ph | N=CHPh | OCF₃ | 6-F | 4-F—Ph | N=CHPh |
| Br | 7-CF₃ | CO₂Me | N=CHPh | OCF₃ | 7-F | CO₂Me | N=CHPh |
| Br | 7-CF₃ | CO₂Et | N=CHPh | OCF₃ | 7-F | CO₂Et | N=CHPh |
| Br | 7-CF₃ | i-Pr | N=CHPh | OCF₃ | 7-F | i-Pr | N=CHPh |
| Br | 7-CF₃ | Me | N-CHPh | OCF₃ | 7-F | Me | N=CHPh |
| Br | 7-CF₃ | 4-F—Ph | N-CHPh | OCF₃ | 7-F | 4-F—Ph | N=CHPh |
| CF₃ | 6-F | CO₂Me | N=CHPh | OCF₃ | 7-Cl | CO₂Me | N=CHPh |
| CF₃ | 6-F | CO₂Et | N=CHPh | OCF₃ | 7-Cl | CO₂Et | N=CHPh |
| CF₃ | 6-F | i-Pr | N=CHPh | OCF₃ | 7-Cl | i-Pr | N=CHPh |
| CF₃ | 6-F | Me | N=CHPh | OCF₃ | 7-Cl | Me | N=CHPh |
| CF₃ | 6-F | 4-F—Ph | N=CHPh | OCF₃ | 7-Cl | 4-F—Ph | N=CHPh |
| CF₃ | 7-F | CO₂Me | N=CHPh | OCF₃ | 7-CF₃ | CO₂Me | N=CHPh |
| CF₃ | 7-F | CO₂Et | N=CHPh | OCF₃ | 7-CF₃ | CO₂Et | N=CHPh |
| CF₃ | 7-F | i-Pr | N=CHPh | OCF₃ | 7-CF₃ | i-Pr | N=CHPh |
| CF₃ | 7-F | Me | N=CHPh | OCF₃ | 7-CF₃ | Me | N=CHPh |
| CF₃ | 7-F | 4-F—Ph | N=CHPh | OCF₃ | 7-CF₃ | 4-F—Ph | N=CHPh |
| Br | 6-F | CO₂Me | NH(CO)CF₃ | CF₃ | 7-Cl | CO₂Me | NH(CO)CF₃ |
| Br | 6-F | CO₂Et | NH(CO)CF₃ | CF₃ | 7-Cl | CO₂Et | NH(CO)CF₃ |
| Br | 6-F | i-Pr | NH(CO)CF₃ | CF₃ | 7-Cl | i-Pr | NH(CO)CF₃ |
| Br | 6-F | Me | NH(CO)CF₃ | CF₃ | 7-Cl | Me | NH(CO)CF₃ |
| Br | 6-F | 4-F—Ph | NH(CO)CF₃ | CF₃ | 7-Cl | 4-F—Ph | NH(CO)CF₃ |
| Br | 7-F | CO₂Me | NH(CO)CF₃ | CF₃ | 7-CF₃ | CO₂Me | NH(CO)CF₃ |
| Br | 7-F | CO₂Et | NH(CO)CF₃ | CF₃ | 7-CF₃ | CO₂Et | NH(CO)CF₃ |
| Br | 7-F | i-Pr | NH(CO)CF₃ | CF₃ | 7-CF₃ | i-Pr | NH(CO)CF₃ |
| Br | 7-F | Me | NH(CO)CF₃ | CF₃ | 7-CF₃ | Me | NH(CO)CF₃ |
| Br | 7-F | 4-F—Ph | NH(CO)CF₃ | CF₃ | 7-CF₃ | 4-F—Ph | NH(CO)CF₃ |
| Br | 7-Cl | CO₂Me | NH(CO)CF₃ | OCF₃ | 6-F | CO₂Me | NH(CO)CF₃ |
| Br | 7-Cl | CO₂Et | NH(CO)CF₃ | OCF₃ | 6-F | CO₂Et | NH(CO)CF₃ |
| Br | 7-Cl | i-Pr | NH(CO)CF₃ | OCF₃ | 6-F | i-Pr | NH(CO)CF₃ |
| Br | 7-Cl | Me | NH(CO)CF₃ | OCF₃ | 6-F | Me | NH(CO)CF₃ |
| Br | 7-Cl | 4-F—Ph | NH(CO)CF₃ | OCF₃ | 6-F | 4-F—Ph | NH(CO)CF₃ |
| Br | 7-CF₃ | CO₂Me | NH(CO)CF₃ | OCF₃ | 7-F | CO₂Me | NH(CO)CF₃ |
| Br | 7-CF₃ | CO₂Et | NH(CO)CF₃ | OCF₃ | 7-F | CO₂Et | NH(CO)CF₃ |
| Br | 7-CF₃ | i-Pr | NH(CO)CF₃ | OCF₃ | 7-F | i-Pr | NH(CO)CF₃ |
| Br | 7-CF₃ | Me | NH(CO)CF₃ | OCF₃ | 7-F | Me | NH(CO)CF₃ |
| Br | 7-CF₃ | 4-F—Ph | NH(CO)CF₃ | OCF₃ | 7-F | 4-F—Ph | NH(CO)CF₃ |
| CF₃ | 6-F | CO₂Me | NH(CO)CF₃ | OCF₃ | 7-Cl | CO₂Me | NH(CO)CF₃ |
| CF₃ | 6-F | CO₂Et | NH(CO)CF₃ | OCF₃ | 7-Cl | CO₂Et | NH(CO)CF₃ |
| CF₃ | 6-F | i-Pr | NH(CO)CF₃ | OCF₃ | 7-Cl | i-Pr | NH(CO)CF₃ |
| CF₃ | 6-F | Me | NH(CO)CF₃ | OCF₃ | 7-Cl | Me | NH(CO)CF₃ |
| CF₃ | 6-F | 4-F—Ph | NH(CO)CF₃ | OCF₃ | 7-Cl | 4-F—Ph | NH(CO)CF₃ |
| CF₃ | 7-F | CO₂Me | NH(CO)CF₃ | OCF₃ | 7-CF₃ | CO₂Me | NH(CO)CF₃ |
| CF₃ | 7-F | CO₂Et | NH(CO)CF₃ | OCF₃ | 7-CF₃ | CO₂Et | NH(CO)CF₃ |

TABLE 17-continued

| R¹ | R² | R³ | Y | R¹ | R² | R³ | Y |
|---|---|---|---|---|---|---|---|
| CF₃ | 7-F | i-Pr | NH(CO)CF₃ | OCF₃ | 7-CF₃ | i-Pr | NH(CO)CF₃ |
| CF₃ | 7-F | Me | NH(CO)CF₃ | OCF₃ | 7-CF₃ | Me | NH(CO)CF₃ |
| CF₃ | 7-F | 4-F—Ph | NH(CO)CF₃ | OCF₃ | 7-CF₃ | 4-F—Ph | NH(CO)CF₃ |
| Br | 6-F | CO₂Me | OH | CF₃ | 7-Cl | CO₂Me | OH |
| Br | 6-F | CO₂Et | OH | CF₃ | 7-Cl | CO₂Et | OH |
| Br | 6-F | i-Pr | OH | CF₃ | 7-Cl | i-Pr | OH |
| Br | 6-F | Me | OH | CF₃ | 7-Cl | Me | OH |
| Br | 6-F | 4-F—Ph | OH | CF₃ | 7-Cl | 4-F—Ph | OH |
| Br | 7-F | CO₂Me | OH | CF₃ | 7-CF₃ | CO₂Me | OH |
| Br | 7-F | CO₂Et | OH | CF₃ | 7-CF₃ | CO₂Et | OH |
| Br | 7-F | i-Pr | OH | CF₃ | 7-CF₃ | i-Pr | OH |
| Br | 7-F | Me | OH | CF₃ | 7-CF₃ | Me | OH |
| Br | 7-F | 4-F—Ph | OH | CF₃ | 7-CF₃ | 4-F—Ph | OH |
| Br | 7-Cl | CO₂Me | OH | OCF₃ | 6-F | CO₂Me | OH |
| Br | 7-Cl | CO₂Et | OH | OCF₃ | 6-F | CO₂Et | OH |
| Br | 7-Cl | i-Pr | OH | OCF₃ | 6-F | i-Pr | OH |
| Br | 7-Cl | Me | OH | OCF₃ | 6-F | Me | OH |
| Br | 7-Cl | 4-F—Ph | OH | OCF₃ | 6-F | 4-F—Ph | OH |
| Br | 7-CF₃ | CO₂Me | OH | OCF₃ | 7-F | CO₂Me | OH |
| Br | 7-CF₃ | CO₂Et | OH | OCF₃ | 7-F | CO₂Et | OH |
| Br | 7-CF₃ | i-Pr | OH | OCF₃ | 7-F | i-Pr | OH |
| Br | 7-CF₃ | Me | OH | OCF₃ | 7-F | Me | OH |
| Br | 7-CF₃ | 4-F—Ph | OH | OCF₃ | 7-F | 4-F—Ph | OH |
| CF₃ | 6-F | CO₂Me | OH | OCF₃ | 7-Cl | CO₂Me | OH |
| CF₃ | 6-F | CO₂Et | OH | OCF₃ | 7-Cl | CO₂Et | OH |
| CF₃ | 6-F | i-Pr | OH | OCF₃ | 7-Cl | i-Pr | OH |
| CF₃ | 6-F | Me | OH | OCF₃ | 7-Cl | Me | OH |
| CF₃ | 6-F | 4-F—Ph | OH | OCF₃ | 7-Cl | 4-F—Ph | OH |
| CF₃ | 7-F | CO₂Me | OH | OCF₃ | 7-CF₃ | CO₂Me | OH |
| CF₃ | 7-F | CO₂Et | OH | OCF₃ | 7-CF₃ | CO₂Et | OH |
| CF₃ | 7-F | i-Pr | OH | OCF₃ | 7-CF₃ | i-Pr | OH |
| CF₃ | 7-F | Me | OH | OCF₃ | 7-CF₃ | Me | OH |
| CF₃ | 7-F | 4-F—Ph | OH | OCF₃ | 7-CF₃ | 4-F—Ph | OH |
| Br | 6-F | CO₂Me | OMe | CF₃ | 7-Cl | CO₂Me | OMe |
| Br | 6-F | CO₂Et | OMe | CF₃ | 7-Cl | CO₂Et | OMe |
| Br | 6-F | i-Pr | OMe | CF₃ | 7-Cl | i-Pr | OMe |
| Br | 6-F | Me | OMe | CF₃ | 7-Cl | Me | OMe |
| Br | 6-F | 4-F—Ph | OMe | CF₃ | 7-Cl | 4-F—Ph | OMe |
| Br | 7-F | CO₂Me | OMe | CF₃ | 7-CF₃ | CO₂Me | OMe |
| Br | 7-F | CO₂Et | OMe | CF₃ | 7-CF₃ | CO₂Et | OMe |
| Br | 7-F | i-Pr | OMe | CF₃ | 7-CF₃ | i-Pr | OMe |
| Br | 7-F | Me | OMe | CF₃ | 7-CF₃ | Me | OMe |
| Br | 7-F | 4-F—Ph | OMe | CF₃ | 7-CF₃ | 4-F—Ph | OMe |
| Br | 7-Cl | CO₂Me | OMe | OCF₃ | 6-F | CO₂Me | OMe |
| Br | 7-Cl | CO₂Et | OMe | OCF₃ | 6-F | CO₂Et | OMe |
| Br | 7-Cl | i-Pr | OMe | OCF₃ | 6-F | i-Pr | OMe |
| Br | 7-Cl | Me | OMe | OCF₃ | 6-F | Me | OMe |
| Br | 7-Cl | 4-F—Ph | OMe | OCF₃ | 6-F | 4-F—Ph | OMe |
| Br | 7-CF₃ | CO₂Me | OMe | OCF₃ | 7-F | CO₂Me | OMe |
| Br | 7-CF₃ | CO₂Et | OMe | OCF₃ | 7-F | CO₂Et | OMe |
| Br | 7-CF₃ | i-Pr | OMe | OCF₃ | 7-F | i-Pr | OMe |
| Br | 7-CF₃ | Me | OMe | OCF₃ | 7-F | Me | OMe |
| Br | 7-CF₃ | 4-F—Ph | OMe | OCF₃ | 7-F | 4-F—Ph | OMe |
| CF₃ | 6-F | CO₂Me | OMe | OCF₃ | 7-Cl | CO₂Me | OMe |
| CF₃ | 6-F | CO₂Et | OMe | OCF₃ | 7-Cl | CO₂Et | OMe |
| CF₃ | 6-F | i-Pr | OMe | OCF₃ | 7-Cl | i-Pr | OMe |
| CF₃ | 6-F | Me | OMe | OCF₃ | 7-Cl | Me | OMe |
| CF₃ | 6-F | 4-F—Ph | OMe | OCF₃ | 7-Cl | 4-F—Ph | OMe |
| CF₃ | 7-F | CO₂Me | OMe | OCF₃ | 7-CF₃ | CO₂Me | OMe |
| CF₃ | 7-F | CO₂Et | OMe | OCF₃ | 7-CF₃ | CO₂Et | OMe |
| CF₃ | 7-F | i-Pr | OMe | OCF₃ | 7-CF₃ | i-Pr | OMe |
| CF₃ | 7-F | Me | OMe | OCF₃ | 7-CF₃ | Me | OMe |
| CF₃ | 7-F | 4-F—Ph | OMe | OCF₃ | 7-CF₃ | 4-F—Ph | OMe |
| Br | 6-F | CO₂Me | OCH₂Ph | CF₃ | 7-Cl | CO₂Me | OCH₂Ph |
| Br | 6-F | CO₂Et | OCH₂Ph | CF₃ | 7-Cl | CO₂Et | OCH₂Ph |
| Br | 6-F | i-Pr | OCH₂Ph | CF₃ | 7-Cl | i-Pr | OCH₂Ph |
| Br | 6-F | Me | OCH₂Ph | CF₃ | 7-Cl | Me | OCH₂Ph |
| Br | 6-F | 4-F—Ph | OCH₂Ph | CF₃ | 7-Cl | 4-F—Ph | OCH₂Ph |
| Br | 7-F | CO₂Me | OCH₂Ph | CF₃ | 7-CF₃ | CO₂Me | OCH₂Ph |
| Br | 7-F | CO₂Et | OCH₂Ph | CF₃ | 7-CF₃ | CO₂Et | OCH₂Ph |
| Br | 7-F | i-Pr | OCH₂Ph | CF₃ | 7-CF₃ | i-Pr | OCH₂Ph |
| Br | 7-F | Me | OCH₂Ph | CF₃ | 7-CF₃ | Me | OCH₂Ph |
| Br | 7-F | 4-F—Ph | OCH₂Ph | CF₃ | 7-CF₃ | 4-F—Ph | OCH₂Ph |
| Br | 7-Cl | CO₂Me | OCH₂Ph | OCF₃ | 6-F | CO₂Me | OCH₂Ph |
| Br | 7-Cl | CO₂Et | OCH₂Ph | OCF₃ | 6-F | CO₂Et | OCH₂Ph |
| Br | 7-Cl | i-Pr | OCH₂Ph | OCF₃ | 6-F | i-Pr | OCH₂Ph |
| Br | 7-Cl | Me | OCH₂Ph | OCF₃ | 6-F | Me | OCH₂Ph |

TABLE 17-continued

| R¹ | R² | R³ | Y | R¹ | R² | R³ | Y |
|---|---|---|---|---|---|---|---|
| Br | 7-Cl | 4-F—Ph | OCH₂Ph | OCF₃ | 6-F | 4-F—Ph | OCH₂Ph |
| Br | 7-CF₃ | CO₂Me | OCH₂Ph | OCF₃ | 7-F | CO₂Me | OCH₂Ph |
| Br | 7-CF₃ | CO₂Et | OCH₂Ph | OCF₃ | 7-F | CO₂Et | OCH₂Ph |
| Br | 7-CF₃ | i-Pr | OCH₂Ph | OCF₃ | 7-F | i-Pr | OCH₂Ph |
| Br | 7-CF₃ | Me | OCH₂Ph | OCF₃ | 7-F | Me | OCH₂Ph |
| Br | 7-CF₃ | 4-F—Ph | OCH₂Ph | OCF₃ | 7-F | 4-F—Ph | OCH₂Ph |
| CF₃ | 6-F | CO₂Me | OCH₂Ph | OCF₃ | 7-Cl | CO₂Me | OCH₂Ph |
| CF₃ | 6-F | CO₂Et | OCH₂Ph | OCF₃ | 7-Cl | CO₂Et | OCH₂Ph |
| CF₃ | 6-F | i-Pr | OCH₂Ph | OCF₃ | 7-Cl | i-Pr | OCH₂Ph |
| CF₃ | 6-F | Me | OCH₂Ph | OCF₃ | 7-Cl | Me | OCH₂Ph |
| CF₃ | 6-F | 4-F—Ph | OCH₂Ph | OCF₃ | 7-Cl | 4-F—Ph | OCH₂Ph |
| CF₃ | 7-F | CO₂Me | OCH₂Ph | OCF₃ | 7-CF₃ | CO₂Me | OCH₂Ph |
| CF₃ | 7-F | CO₂Et | OCH₂Ph | OCF₃ | 7-CF₃ | CO₂Et | OCH₂Ph |
| CF₃ | 7-F | i-Pr | OCH₂Ph | OCF₃ | 7-CF₃ | i-Pr | OCH₂Ph |
| CF₃ | 7-F | Me | OCH₂Ph | OCF₃ | 7-CF₃ | Me | OCH₂Ph |
| CF₃ | 7-F | 4-F—Ph | OCH₂Ph | OCF₃ | 7-CF₃ | 4-F—Ph | OCH₂Ph |

TABLE 18

| R¹ | R² | R³ | Y | R¹ | R² | R³ | Y |
|---|---|---|---|---|---|---|---|
| Br | 6-F | CO₂Me | NH₂ | CF₃ | 7-Cl | CO₂Me | NH₂ |
| Br | 6-F | CO₂Et | NH₂ | CF₃ | 7-Cl | CO₂Et | NH₂ |
| Br | 6-F | i-Pr | NH₂ | CF₃ | 7-Cl | i-Pr | NH₂ |
| Br | 6-F | Me | NH₂ | CF₃ | 7-Cl | Me | NH₂ |
| Br | 6-F | 4-F—Ph | NH₂ | CF₃ | 7-Cl | 4-F—Ph | NH₂ |
| Br | 7-F | CO₂Me | NH₂ | CF₃ | 7-CF₃ | CO₂Me | NH₂ |
| Br | 7-F | CO₂Et | NH₂ | CF₃ | 7-CF₃ | CO₂Et | NH₂ |
| Br | 7-F | i-Pr | NH₂ | CF₃ | 7-CF₃ | i-Pr | NH₂ |
| Br | 7-F | Me | NH₂ | CF₃ | 7-CF₃ | Me | NH₂ |
| Br | 7-F | 4-F—Ph | NH₂ | CF₃ | 7-CF₃ | 4-F—Ph | NH₂ |
| Br | 7-Cl | CO₂Me | NH₂ | OCF₃ | 6-F | CO₂Me | NH₂ |
| Br | 7-Cl | CO₂Et | NH₂ | OCF₃ | 6-F | CO₂Et | NH₂ |
| Br | 7-Cl | i-Pr | NH₂ | OCF₃ | 6-F | i-Pr | NH₂ |
| Br | 7-Cl | Me | NH₂ | OCF₃ | 6-F | Me | NH₂ |
| Br | 7-Cl | 4-F—Ph | NH₂ | OCF₃ | 6-F | 4-F—Ph | NH₂ |
| Br | 7-CF₃ | CO₂Me | NH₂ | OCF₃ | 7-F | CO₂Me | NH₂ |
| Br | 7-CF₃ | CO₂Et | NH₂ | OCF₃ | 7-F | CO₂Et | NH₂ |
| Br | 7-CF₃ | i-Pr | NH₂ | OCF₃ | 7-F | i-Pr | NH₂ |
| Br | 7-CF₃ | Me | NH₂ | OCF₃ | 7-F | Me | NH₂ |
| Br | 7-CF₃ | 4-F—Ph | NH₂ | OCF₃ | 7-F | 4-F—Ph | NH₂ |
| CF₃ | 6-F | CO₂Me | NH₂ | OCF₃ | 7-Cl | CO₂Me | NH₂ |
| CF₃ | 6-F | CO₂Et | NH₂ | OCF₃ | 7-Cl | CO₂Et | NH₂ |
| CF₃ | 6-F | i-Pr | NH₂ | OCF₃ | 7-Cl | i-Pr | NH₂ |
| CF₃ | 6-F | Me | NH₂ | OCF₃ | 7-Cl | Me | NH₂ |
| CF₃ | 6-F | 4-F—Ph | NH₂ | OCF₃ | 7-Cl | 4-F—Ph | NH₂ |
| CF₃ | 7-F | CO₂Me | NH₂ | OCF₃ | 7-CF₃ | CO₂Me | NH₂ |
| CF₃ | 7-F | CO₂Et | NH₂ | OCF₃ | 7-CF₃ | CO₂Et | NH₂ |
| CF₃ | 7-F | i-Pr | NH₂ | OCF₃ | 7-CF₃ | i-Pr | NH₂ |
| CF₃ | 7-F | Me | NH₂ | OCF₃ | 7-CF₃ | Me | NH₂ |
| CF₃ | 7-F | 4-F—Ph | NH₂ | OCF₃ | 7-CF₃ | 4-F—Ph | NH₂ |
| Br | 6-F | CO₂Me | NHMe | CF₃ | 7-Cl | CO₂Me | NHMe |
| Br | 6-F | CO₂Et | NHMe | CF₃ | 7-Cl | CO₂Et | NHMe |
| Br | 6-F | i-Pr | NHMe | CF₃ | 7-Cl | i-Pr | NHMe |
| Br | 6-F | Me | NHMe | CF₃ | 7-Cl | Me | NHMe |
| Br | 6-F | 4-F—Ph | NHMe | CF₃ | 7-Cl | 4-F—Ph | NHMe |
| Br | 7-F | CO₂Me | NHMe | CF₃ | 7-CF₃ | CO₂Me | NHMe |
| Br | 7-F | CO₂Et | NHMe | CF₃ | 7-CF₃ | CO₂Et | NHMe |
| Br | 7-F | i-Pr | NHMe | CF₃ | 7-CF₃ | i-Pr | NHMe |
| Br | 7-F | Me | NHMe | CF₃ | 7-CF₃ | Me | NHMe |
| Br | 7-F | 4-F—Ph | NHMe | CF₃ | 7-CF₃ | 4-F—Ph | NHMe |
| Br | 7-Cl | CO₂Me | NHMe | OCF₃ | 6-F | CO₂Me | NHMe |
| Br | 7-Cl | CO₂Et | NHMe | OCF₃ | 6-F | CO₂Et | NHMe |
| Br | 7-Cl | i-Pr | NHMe | OCF₃ | 6-F | i-Pr | NHMe |
| Br | 7-Cl | Me | NHMe | OCF₃ | 6-F | Me | NHMe |
| Br | 7-Cl | 4-F—Ph | NHMe | OCF₃ | 6-F | 4-F—Ph | NHMe |
| Br | 7-CF₃ | CO₂Me | NHMe | OCF₃ | 7-F | CO₂Me | NHMe |
| Br | 7-CF₃ | CO₂Et | NHMe | OCF₃ | 7-F | CO₂Et | NHMe |
| Br | 7-CF₃ | i-Pr | NHMe | OCF₃ | 7-F | i-Pr | NHMe |
| Br | 7-CF₃ | Me | NHMe | OCF₃ | 7-F | Me | NHMe |
| Br | 7-CF₃ | 4-F—Ph | NHMe | OCF₃ | 7-F | 4-F—Ph | NHMe |
| CF₃ | 6-F | CO₂Me | NHMe | OCF₃ | 7-Cl | CO₂Me | NHMe |
| CF₃ | 6-F | CO₂Et | NHMe | OCF₃ | 7-Cl | CO₂Et | NHMe |
| CF₃ | 6-F | i-Pr | NHMe | OCF₃ | 7-Cl | i-Pr | NMMe |
| CF₃ | 6-F | Me | NHMe | OCF₃ | 7-Cl | Me | NHMe |

TABLE 18-continued

| R¹ | R² | R³ | Y | R¹ | R² | R³ | Y |
|---|---|---|---|---|---|---|---|
| CF₃ | 6-F | 4-F—Ph | NHMe | OCF₃ | 7-Cl | 4-F—Ph | NHMe |
| CF₃ | 7-F | CO₂Me | NHMe | OCF₃ | 7-CF₃ | CO₂Me | NHMe |
| CF₃ | 7-F | CO₂Et | NHMe | OCF₃ | 7-CF₃ | CO₂Et | NHMe |
| CF₃ | 7-F | i-Pr | NHMe | OCF₃ | 7-CF₃ | i-Pr | NHMe |
| CF₃ | 7-F | Me | NHMe | OCF₃ | 7-CF₃ | Me | NHMe |
| CF₃ | 7-F | 4-F—Ph | NHMe | OCF₃ | 7-CF₃ | 4-F—Ph | NHMe |
| Br | 6-F | CO₂Me | NHCHO | CF₃ | 7-Cl | CO₂Me | NHCHO |
| Br | 6-F | CO₂Et | NHCHO | CF₃ | 7-Cl | CO₂Et | NHCHO |
| Br | 6-F | i-Pr | NHCHO | CF₃ | 7-Cl | i-Pr | NHCHO |
| Br | 6-F | Me | NHCHO | CF₃ | 7-Cl | Me | NHCHO |
| Br | 6-F | 4-F—Ph | NHCHO | CF₃ | 7-Cl | 4-F—Ph | NHCHO |
| Br | 7-F | CO₂Me | NHCHO | CF₃ | 7-CF₃ | CO₂Me | NHCHO |
| Br | 7-F | CO₂Et | NHCHO | CF₃ | 7-CF₃ | CO₂Et | NHCHO |
| Br | 7-F | i-Pr | NHCHO | CF₃ | 7-CF₃ | i-Pr | NHCHO |
| Br | 7-F | Me | NHCHO | CF₃ | 7-CF₃ | Me | NHCHO |
| Br | 7-F | 4-F—Ph | NHCHO | CF₃ | 7-CF₃ | 4-F—Ph | NHCHO |
| Br | 7-Cl | CO₂Me | NHCHO | OCF₃ | 6-F | CO₂Me | NHCHO |
| Br | 7-Cl | CO₂Et | NHCHO | OCF₃ | 6-F | CO₂Et | NHCHO |
| Br | 7-Cl | i-Pr | NHCHO | OCF₃ | 6-F | i-Pr | NHCHO |
| Br | 7-Cl | Me | NHCHO | OCF₃ | 6-F | Me | NHCHO |
| Br | 7-Cl | 4-F—Ph | NHCHO | OCF₃ | 6-F | 4-F—Ph | NHCHO |
| Br | 7-CF₃ | CO₂Me | NHCHO | OCF₃ | 7-F | CO₂Me | NHCHO |
| Br | 7-CF₃ | CO₂Et | NHCHO | OCF₃ | 7-F | CO₂Et | NHCHO |
| Br | 7-CF₃ | i-Pr | NHCHO | OCF₃ | 7-F | i-Pr | NHCHO |
| Br | 7-CF₃ | Me | NHCHO | OCF₃ | 7-F | Me | NHCHO |
| Br | 7-CF₃ | 4-F—Ph | NHCHO | OCF₃ | 7-F | 4-F—Ph | NHCHO |
| CF₃ | 6-F | CO₂Me | NHCHO | OCF₃ | 7-Cl | CO₂Me | NHCHO |
| CF₃ | 6-F | CO₂Et | NHCHO | OCF₃ | 7-Cl | CO₂Et | NHCHO |
| CF₃ | 6-F | i-Pr | NHCHO | OCF₃ | 7-Cl | i-Pr | NHCHO |
| CF₃ | 6-F | Me | NHCHO | OCF₃ | 7-Cl | Me | NHCHO |
| CF₃ | 6-F | 4-F—Ph | NHCHO | OCF₃ | 7-Cl | 4-F—Ph | NHCHO |
| CF₃ | 7-F | CO₂Me | NHCHO | OCF₃ | 7-CF₃ | CO₂Me | NHCHO |
| CF₃ | 7-F | CO₂Et | NHCHO | OCF₃ | 7-CF₃ | CO₂Et | NHCHO |
| CF₃ | 7-F | i-Pr | NHCHO | OCF₃ | 7-CF₃ | i-Pr | NHCHO |
| CF₃ | 7-F | Me | NHCHO | OCF₃ | 7-CF₃ | Me | NHCHO |
| CF₃ | 7-F | 4-F—Ph | NHCHO | OCF₃ | 7-CF₃ | 4-F—Ph | NHCHO |
| Br | 6-F | CO₂Me | NH(CO)Me | CF₃ | 7-Cl | CO₂Me | NH(CO)Me |
| Br | 6-F | CO₂Et | NH(CO)Me | CF₃ | 7-Cl | CO₂Et | NH(CO)Me |
| Br | 6-F | i-Pr | NH(CO)Me | CF₃ | 7-Cl | i-Pr | NH(CO)Me |
| Br | 6-F | Me | NH(CO)Me | CF₃ | 7-Cl | Me | NH(CO)Me |
| Br | 6-F | 4-F—Ph | NH(CO)Me | CF₃ | 7-Cl | 4-F—Ph | NH(CO)Me |
| Br | 7-F | CO₂Me | NH(CO)Me | CF₃ | 7-CF₃ | CO₂Me | NH(CO)Me |
| Br | 7-F | CO₂Et | NH(CO)Me | CF₃ | 7-CF₃ | CO₂Et | NH(CO)Me |
| Br | 7-F | i-Pr | NH(CO)Me | CF₃ | 7-CF₃ | i-Pr | NH(CO)Me |
| Br | 7-F | Me | NH(CO)Me | CF₃ | 7-CF₃ | Me | NH(CO)Me |
| Br | 7-F | 4-F—Ph | NH(CO)Me | CF₃ | 7-CF₃ | 4-F—Ph | NH(CO)Me |
| Br | 7-Cl | CO₂Me | NH(CO)Me | OCF₃ | 6-F | CO₂Me | NH(CO)Me |
| Br | 7-Cl | CO₂Et | NH(CO)Me | OCF₃ | 6-F | CO₂Et | NH(CO)Me |
| Br | 7-Cl | i-Pr | NH(CO)Me | OCF₃ | 6-F | i-Pr | NH(CO)Me |
| Br | 7-Cl | Me | NH(CO)Me | OCF₃ | 6-F | Me | NH(CO)Me |
| Br | 7-Cl | 4-F—Ph | NH(CO)Me | OCF₃ | 6-F | 4-F—Ph | NH(CO)Me |
| Br | 7-CF₃ | CO₂Me | NH(CO)Me | OCF₃ | 7-F | CO₂Me | NH(CO)Me |
| Br | 7-CF₃ | CO₂Et | NH(CO)Me | OCF₃ | 7-F | CO₂Et | NH(CO)Me |
| Br | 7-CF₃ | i-Pr | NH(CO)Me | OCF₃ | 7-F | i-Pr | NH(CO)Me |
| Br | 7-CF₃ | Me | NH(CO)Me | OCF₃ | 7-F | Me | NH(CO)Me |
| Br | 7-CF₃ | 4-F—Ph | NH(CO)Me | OCF₃ | 7-F | 4-F—Ph | NH(CO)Me |
| CF₃ | 6-F | CO₂Me | NH(CO)Me | OCF₃ | 7-Cl | CO₂Me | NH(CO)Me |
| CF₃ | 6-F | CO₂Et | NH(CO)Me | OCF₃ | 7-Cl | CO₂Et | NH(CO)Me |
| CF₃ | 6-F | i-Pr | NH(CO)Me | OCF₃ | 7-Cl | i-Pr | NH(CO)Me |
| CF₃ | 6-F | Me | NH(CO)Me | OCF₃ | 7-Cl | Me | NH(CO)Me |
| CF₃ | 6-F | 4-F—Ph | NH(CO)Me | OCF₃ | 7-Cl | 4-F—Ph | NH(CO)Me |
| CF₃ | 7-F | CO₂Me | NH(CO)Me | OCF₃ | 7-CF₃ | CO₂Me | NH(CO)Me |
| CF₃ | 7-F | CO₂Et | NH(CO)Me | OCF₃ | 7-CF₃ | CO₂Et | NH(CO)Me |
| CF₃ | 7-F | i-Pr | NH(CO)Me | OCF₃ | 7-CF₃ | i-Pr | NH(CO)Me |
| CF₃ | 7-F | Me | NH(CO)Me | OCF₃ | 7-CF₃ | Me | NH(CO)Me |
| CF₃ | 7-F | 4-F—Ph | NH(CO)Me | OCF₃ | 7-CF₃ | 4-F—Ph | NH(CO)Me |
| Br | 6-F | CO₂Me | NH(CO)NHMe | CF₃ | 7-Cl | CO₂Me | NH(CO)NHMe |
| Br | 6-F | CO₂Et | NH(CO)NHMe | CF₃ | 7-Cl | CO₂Et | NH(CO)NHMe |
| Br | 6-F | i-Pr | NH(CO)NHMe | CF₃ | 7-Cl | i-Pr | NH(CO)NHMe |
| Br | 6-F | Me | NH(CO)NHMe | CF₃ | 7-Cl | Me | NH(CO)NHMe |
| Br | 6-F | 4-F—Ph | NH(CO)NHMe | CF₃ | 7-Cl | 4-F—Ph | NH(CO)NHMe |
| Br | 7-F | CO₂Me | NH(CO)NHMe | CF₃ | 7-CF₃ | CO₂Me | NH(CO)NHMe |
| Br | 7-F | CO₂Et | NH(CO)NHMe | CF₃ | 7-CF₃ | CO₂Et | NH(CO)NHMe |
| Br | 7-F | i-Pr | NH(CO)NHMe | CF₃ | 7-CF₃ | i-Pr | NH(CO)NHMe |
| Br | 7-F | Me | NH(CO)NHMe | CF₃ | 7-CF₃ | Me | NH(CO)NHMe |
| Br | 7-F | 4-F—Ph | NH(CO)NHMe | CF₃ | 7-CF₃ | 4-F—Ph | NH(CO)NHMe |
| Br | 7-Cl | CO₂Me | NH(CO)NHMe | OCF₃ | 6-F | CO₂Me | NH(CO)NHMe |

TABLE 18-continued

| R¹ | R² | R³ | Y | R¹ | R² | R³ | Y |
|---|---|---|---|---|---|---|---|
| Br | 7-Cl | CO₂Et | NH(CO)NHMe | OCF₃ | 6-F | CO₂Et | NH(CO)NHMe |
| Br | 7-Cl | i-Pr | NH(CO)NHMe | OCF₃ | 6-F | i-Pr | NH(CO)NHMe |
| Br | 7-Cl | Me | NH(CO)NHMe | OCF₃ | 6-F | Me | NH(CO)NHMe |
| Br | 7-Cl | 4-F—Ph | NH(CO)NHMe | OCF₃ | 6-F | 4-F—Ph | NH(CO)NHMe |
| Br | 7-CF₃ | CO₂Me | NH(CO)NHMe | OCF₃ | 7-F | CO₂Me | NH(CO)NHMe |
| Br | 7-CF₃ | CO₂Et | NH(CO)NHMe | OCF₃ | 7-F | CO₂Et | NH(CO)NHMe |
| Br | 7-CF₃ | i-Pr | NH(CO)NHMe | OCF₃ | 7-F | i-Pr | NH(CO)NHMe |
| Br | 7-CF₃ | Me | NH(CO)NHMe | OCF₃ | 7-F | Me | NH(CO)NHMe |
| Br | 7-CF₃ | 4-F—Ph | NH(CO)NHMe | OCF₃ | 7-F | 4-F—Ph | NH(CO)NHMe |
| CF₃ | 6-F | CO₂Me | NH(CO)NHMe | OCF₃ | 7-Cl | CO₂Me | NH(CO)NHMe |
| CF₃ | 6-F | CO₂Et | NH(CO)NHMe | OCF₃ | 7-Cl | CO₂Et | NH(CO)NHMe |
| CF₃ | 6-F | i-Pr | NH(CO)NHMe | OCF₃ | 7-Cl | i-Pr | NH(CO)NHMe |
| CF₃ | 6-F | Me | NH(CO)NHMe | OCF₃ | 7-Cl | Me | NH(CO)NHMe |
| CF₃ | 6-F | 4-F—Ph | NH(CO)NHMe | OCF₃ | 7-Cl | 4-F—Ph | NH(CO)NHMe |
| CF₃ | 7-F | CO₂Me | NH(CO)NHMe | OCF₃ | 7-CF₃ | CO₂Me | NH(CO)NHMe |
| CF₃ | 7-F | CO₂Et | NH(CO)NHMe | OCF₃ | 7-CF₃ | CO₂Et | NH(CO)NHMe |
| CF₃ | 7-F | i-Pr | NH(CO)NHMe | OCF₃ | 7-CF₃ | i-Pr | NH(CO)NHMe |
| CF₃ | 7-F | Me | NH(CO)NHMe | OCF₃ | 7-CF₃ | Me | NH(CO)NHMe |
| CF₃ | 7-F | 4-F—Ph | NH(CO)NHMe | OCF₃ | 7-CF₃ | 4-F—Ph | NH(CO)NHMe |
| Br | 6-F | CO₂Me | N=CH₂ | CF₃ | 7-Cl | CO₂Me | N=CH₂ |
| Br | 6-F | CO₂Et | N=CH₂ | CF₃ | 7-Cl | CO₂Et | N=CH₂ |
| Br | 6-F | i-Pr | N=CH₂ | CF₃ | 7-Cl | i-Pr | N=CH₂ |
| Br | 6-F | Me | N=CH₂ | CF₃ | 7-Cl | Me | N=CH₂ |
| Br | 6-F | 4-F—Ph | N=CH₂ | CF₃ | 7-Cl | 4-F—Ph | N=CH₂ |
| Br | 7-F | CO₂Me | N=CH₂ | CF₃ | 7-CF₃ | CO₂Me | N=CH₂ |
| Br | 7-F | CO₂Et | N=CH₂ | CF₃ | 7-CF₃ | CO₂Et | N=CH₂ |
| Br | 7-F | i-Pr | N=CH₂ | CF₃ | 7-CF₃ | i-Pr | N=CH₂ |
| Br | 7-F | Me | N=CH₂ | CF₃ | 7-CF₃ | Me | N=CH₂ |
| Br | 7-F | 4-F—Ph | N=CH₂ | CF₃ | 7-CF₃ | 4-F—Ph | N=CH₂ |
| Br | 7-Cl | CO₂Me | N=CH₂ | OCF₃ | 6-F | CO₂Me | N=CH₂ |
| Br | 7-Cl | CO₂Et | N=CH₂ | OCF₃ | 6-F | CO₂Et | N=CH₂ |
| Br | 7-Cl | i-Pr | N=CH₂ | OCF₃ | 6-F | i-Pr | N=CH₂ |
| Br | 7-Cl | Me | N=CH₂ | OCF₃ | 6-F | Me | N=CH₂ |
| Br | 7-Cl | 4-F—Ph | N=CH₂ | OCF₃ | 6-F | 4-F—Ph | N=CH₂ |
| Br | 7-CF₃ | CO₂Me | N=CH₂ | OCF₃ | 7-F | CO₂Me | N=CH₂ |
| Br | 7-CF₃ | CO₂Et | N=CH₂ | OCF₃ | 7-F | CO₂Et | N=CH₂ |
| Br | 7-CF₃ | i-Pr | N=CH₂ | OCF₃ | 7-F | i-Pr | N=CH₂ |
| Br | 7-CF₃ | Me | N=CH₂ | OCF₃ | 7-F | Me | N=CH₂ |
| Br | 7-CF₃ | 4-F—Ph | N=CH₂ | OCF₃ | 7-F | 4-F—Ph | N=CH₂ |
| CF₃ | 6-F | CO₂Me | N=CH₂ | OCF₃ | 7-Cl | CO₂Me | N=CH₂ |
| CF₃ | 6-F | CO₂Et | N=CH₂ | OCF₃ | 7-Cl | CO₂Et | N=CH₂ |
| CF₃ | 6-F | i-Pr | N=CH₂ | OCF₃ | 7-Cl | i-Pr | N=CH₂ |
| CF₃ | 6-F | Me | N=CH₂ | OCF₃ | 7-Cl | Me | N=CH₂ |
| CF₃ | 6-F | 4-F—Ph | N=CH₂ | OCF₃ | 7-Cl | 4-F—Ph | N=CH₂ |
| CF₃ | 7-F | CO₂Me | N=CH₂ | OCF₃ | 7-CF₃ | CO₂Me | N=CH₂ |
| CF₃ | 7-F | CO₂Et | N=CH₂ | OCF₃ | 7-CF₃ | CO₂Et | N=CH₂ |
| CF₃ | 7-F | i-Pr | N=CH₂ | OCF₃ | 7-CF₃ | i-Pr | N=CH₂ |
| CF₃ | 7-F | Me | N=CH₂ | OCF₃ | 7-CF₃ | Me | N=CH₂ |
| CF₃ | 7-F | 4-F—Ph | N=CH₂ | OCF₃ | 7-CF₃ | 4-F—Ph | N=CH₂ |
| Br | 6-F | CO₂Me | N=CMe₂ | CF₃ | 7-Cl | CO₂Me | N=CMe₂ |
| Br | 6-F | CO₂Et | N=CMe₂ | CF₃ | 7-Cl | CO₂Et | N=CMe₂ |
| Br | 6-F | i-Pr | N=CMe₂ | CF₃ | 7-Cl | i-Pr | N=CMe₂ |
| Br | 6-F | Me | N=CMe₂ | CF₃ | 7-Cl | Me | N=CMe₂ |
| Br | 6-F | 4-F—Ph | N=CMe₂ | CF₃ | 7-Cl | 4-F—Ph | N=CMe₂ |
| Br | 7-F | CO₂Me | N=CMe₂ | CF₃ | 7-CF₃ | CO₂Me | N=CMe₂ |
| Br | 7-F | CO₂Et | N=CMe₂ | CF₃ | 7-CF₃ | CO₂Et | N=CMe₂ |
| Br | 7-F | i-Pr | N=CMe₂ | CF₃ | 7-CF₃ | i-Pr | N=CMe₂ |
| Br | 7-F | Me | N=CMe₂ | CF₃ | 7-CF₃ | Me | N=CMe₂ |
| Br | 7-F | 4-F—Ph | N=CMe₂ | CF₃ | 7-CF₃ | 4-F—Ph | N=CMe₂ |
| Br | 7-Cl | CO₂Me | N=CMe₂ | OCF₃ | 6-F | CO₂Me | N=CMe₂ |
| Br | 7-Cl | CO₂Et | N=CMe₂ | OCF₃ | 6-F | CO₂Et | N=CMe₂ |
| Br | 7-Cl | i-Pr | N=CMe₂ | OCF₃ | 6-F | i-Pr | N=CMe₂ |
| Br | 7-Cl | Me | N=CMe₂ | OCF₃ | 6-F | Me | N=CMe₂ |
| Br | 7-Cl | 4-F—Ph | N=CMe₂ | OCF₃ | 6-F | 4-F—Ph | N=CMe₂ |
| Br | 7-CF₃ | CO₂Me | N=CMe₂ | OCF₃ | 7-F | CO₂Me | N=CMe₂ |
| Br | 7-CF₃ | CO₂Et | N=CMe₂ | OCF₃ | 7-F | CO₂Et | N=CMe₂ |
| Br | 7-CF₃ | i-Pr | N=CMe₂ | OCF₃ | 7-F | i-Pr | N=CMe₂ |
| Br | 7-CF₃ | Me | N=CMe₂ | OCF₃ | 7-F | Me | N=CMe₂ |
| Br | 7-CF₃ | 4-F—Ph | N=CMe₂ | OCF₃ | 7-F | 4-F—Ph | N=CMe₂ |
| CF₃ | 6-F | CO₂Me | N=CMe₂ | OCF₃ | 7-Cl | CO₂Me | N=CMe₂ |
| CF₃ | 6-F | CO₂Et | N=CMe₂ | OCF₃ | 7-Cl | CO₂Et | N=CMe₂ |
| CF₃ | 6-F | i-Pr | N=CMe₂ | OCF₃ | 7-Cl | i-Pr | N=CMe₂ |
| CF₃ | 6-F | Me | N=CMe₂ | OCF₃ | 7-Cl | Me | N=CMe₂ |
| CF₃ | 6-F | 4-F—Ph | N=CMe₂ | OCF₃ | 7-Cl | 4-F—Ph | N=CMe₂ |
| CF₃ | 7-F | CO₂Me | N=CMe₂ | OCF₃ | 7-CF₃ | CO₂Me | N=CMe₂ |
| CF₃ | 7-F | CO₂Et | N=CMe₂ | OCF₃ | 7-CF₃ | CO₂Et | N=CMe₂ |
| CF₃ | 7-F | i-Pr | N=CMe₂ | OCF₃ | 7-CF₃ | i-Pr | N=CMe₂ |

TABLE 18-continued

| R¹ | R² | R³ | Y | R¹ | R² | R³ | Y |
|---|---|---|---|---|---|---|---|
| CF₃ | 7-F | Me | N=CMe₂ | OCF₃ | 7-CF₃ | Me | N=CMe₂ |
| CF₃ | 7-F | 4-F—Ph | N=CMe₂ | OCF₃ | 7-CF₃ | 4-F—Ph | N=CMe₂ |
| Br | 6-F | CO₂Me | N=CHPh | CF₃ | 7-Cl | CO₂Me | N=CHPh |
| Br | 6-F | CO₂Et | N=CHPh | CF₃ | 7-Cl | CO₂Et | N=CHPh |
| Br | 6-F | i-Pr | N=CHPh | CF₃ | 7-Cl | i-Pr | N=CHPh |
| Br | 6-F | Me | N=CHPh | CF₃ | 7-Cl | Me | N=CHPh |
| Br | 6-F | 4-F—Ph | N=CHPh | CF₃ | 7-Cl | 4-F—Ph | N=CHPh |
| Br | 7-F | CO₂Me | N=CHPh | CF₃ | 7-CF₃ | CO₂Me | N=CHPh |
| Br | 7-F | CO₂Et | N=CHPh | CF₃ | 7-CF₃ | CO₂Et | N=CHPh |
| Br | 7-F | i-Pr | N=CHPh | CF₃ | 7-CF₃ | i-Pr | N=CHPh |
| Br | 7-F | Me | N=CHPh | CF₃ | 7-CF₃ | Me | N=CHPh |
| Br | 7-F | 4-F—Ph | N=CHPh | CF₃ | 7-CF₃ | 4-F—Ph | N=CHPh |
| Br | 7-Cl | CO₂Me | N=CHPh | OCF₃ | 6-F | CO₂Me | N=CHPh |
| Br | 7-Cl | CO₂Et | N-CHPh | OCF₃ | 6-F | CO₂Et | N=CHPh |
| Br | 7-Cl | i-Pr | N=CHPh | OCF₃ | 6-F | i-Pr | N=CHPh |
| Br | 7-Cl | Me | N=CHPh | OCF₃ | 6-F | Me | N=CHPh |
| Br | 7-Cl | 4-F—Ph | N=CHPh | OCF₃ | 6-F | 4-F—Ph | N=CHPh |
| Br | 7-CF₃ | CO₂Me | N=CHPh | OCF₃ | 7-F | CO₂Me | N=CHPh |
| Br | 7-CF₃ | CO₂Et | N=CHPh | OCF₃ | 7-F | CO₂Et | N=CHPh |
| Br | 7-CF₃ | i-Pr | N=CHPh | OCF₃ | 7-F | i-Pr | N=CHPh |
| Br | 7-CF₃ | Me | N-CHPh | OCF₃ | 7-F | Me | N=CHPh |
| Br | 7-CF₃ | 4-F—Ph | N-CHPh | OCF₃ | 7-F | 4-F—Ph | N=CHPh |
| CF₃ | 6-F | CO₂Me | N=CHPh | OCF₃ | 7-Cl | CO₂Me | N=CHPh |
| CF₃ | 6-F | CO₂Et | N=CHPh | OCF₃ | 7-Cl | CO₂Et | N=CHPh |
| CF₃ | 6-F | i-Pr | N=CHPh | OCF₃ | 7-Cl | i-Pr | N=CHPh |
| CF₃ | 6-F | Me | N=CHPh | OCF₃ | 7-Cl | Me | N=CHPh |
| CF₃ | 6-F | 4-F—Ph | N=CHPh | OCF₃ | 7-Cl | 4-F—Ph | N=CHPh |
| CF₃ | 7-F | CO₂Me | N=CHPh | OCF₃ | 7-CF₃ | CO₂Me | N=CHPh |
| CF₃ | 7-F | CO₂Et | N=CHPh | OCF₃ | 7-CF₃ | CO₂Et | N=CHPh |
| CF₃ | 7-F | i-Pr | N=CHPh | OCF₃ | 7-CF₃ | i-Pr | N=CHPh |
| CF₃ | 7-F | Me | N=CHPh | OCF₃ | 7-CF₃ | Me | N=CHPh |
| CF₃ | 7-F | 4-F—Ph | N=CHPh | OCF₃ | 7-CF₃ | 4-F—Ph | N=CHPh |
| Br | 6-F | CO₂Me | NH(CO)CF₃ | CF₃ | 7-Cl | CO₂Me | NH(CO)CF₃ |
| Br | 6-F | CO₂Et | NH(CO)CF₃ | CF₃ | 7-Cl | CO₂Et | NH(CO)CF₃ |
| Br | 6-F | i-Pr | NH(CO)CF₃ | CF₃ | 7-Cl | i-Pr | NH(CO)CF₃ |
| Br | 6-F | Me | NH(CO)CF₃ | CF₃ | 7-Cl | Me | NH(CO)CF₃ |
| Br | 6-F | 4-F—Ph | NH(CO)CF₃ | CF₃ | 7-Cl | 4-F—Ph | NH(CO)CF₃ |
| Br | 7-F | CO₂Me | NH(CO)CF₃ | CF₃ | 7-CF₃ | CO₂Me | NH(CO)CF₃ |
| Br | 7-F | CO₂Et | NH(CO)CF₃ | CF₃ | 7-CF₃ | CO₂Et | NH(CO)CF₃ |
| Br | 7-F | i-Pr | NH(CO)CF₃ | CF₃ | 7-CF₃ | i-Pr | NH(CO)CF₃ |
| Br | 7-F | Me | NH(CO)CF₃ | CF₃ | 7-CF₃ | Me | NH(CO)CF₃ |
| Br | 7-F | 4-F—Ph | NH(CO)CF₃ | CF₃ | 7-CF₃ | 4-F—Ph | NH(CO)CF₃ |
| Br | 7-Cl | CO₂Me | NH(CO)CF₃ | OCF₃ | 6-F | CO₂Me | NH(CO)CF₃ |
| Br | 7-Cl | CO₂Et | NH(CO)CF₃ | OCF₃ | 6-F | CO₂Et | NH(CO)CF₃ |
| Br | 7-Cl | i-Pr | NH(CO)CF₃ | OCF₃ | 6-F | i-Pr | NH(CO)CF₃ |
| Br | 7-Cl | Me | NH(CO)CF₃ | OCF₃ | 6-F | Me | NH(CO)CF₃ |
| Br | 7-Cl | 4-F—Ph | NH(CO)CF₃ | OCF₃ | 6-F | 4-F—Ph | NH(CO)CF₃ |
| Br | 7-CF₃ | CO₂Me | NH(CO)CF₃ | OCF₃ | 7-F | CO₂Me | NH(CO)CF₃ |
| Br | 7-CF₃ | CO₂Et | NH(CO)CF₃ | OCF₃ | 7-F | CO₂Et | NH(CO)CF₃ |
| Br | 7-CF₃ | i-Pr | NH(CO)CF₃ | OCF₃ | 7-F | i-Pr | NH(CO)CF₃ |
| Br | 7-CF₃ | Me | NH(CO)CF₃ | OCF₃ | 7-F | Me | NH(CO)CF₃ |
| Br | 7-CF₃ | 4-F—Ph | NH(CO)CF₃ | OCF₃ | 7-F | 4-F—Ph | NH(CO)CF₃ |
| CF₃ | 6-F | CO₂Me | NH(CO)CF₃ | OCF₃ | 7-Cl | CO₂Me | NH(CO)CF₃ |
| CF₃ | 6-F | CO₂Et | NH(CO)CF₃ | OCF₃ | 7-Cl | CO₂Et | NH(CO)CF₃ |
| CF₃ | 6-F | i-Pr | NH(CO)CF₃ | OCF₃ | 7-Cl | i-Pr | NH(CO)CF₃ |
| CF₃ | 6-F | Me | NH(CO)CF₃ | OCF₃ | 7-Cl | Me | NH(CO)CF₃ |
| CF₃ | 6-F | 4-F—Ph | NH(CO)CF₃ | OCF₃ | 7-Cl | 4-F—Ph | NH(CO)CF₃ |
| CF₃ | 7-F | CO₂Me | NH(CO)CF₃ | OCF₃ | 7-CF₃ | CO₂Me | NH(CO)CF₃ |
| CF₃ | 7-F | CO₂Et | NH(CO)CF₃ | OCF₃ | 7-CF₃ | CO₂Et | NH(CO)CF₃ |
| CF₃ | 7-F | i-Pr | NH(CO)CF₃ | OCF₃ | 7-CF₃ | i-Pr | NH(CO)CF₃ |
| CF₃ | 7-F | Me | NH(CO)CF₃ | OCF₃ | 7-CF₃ | Me | NH(CO)CF₃ |
| CF₃ | 7-F | 4-F—Ph | NH(CO)CF₃ | OCF₃ | 7-CF₃ | 4-F—Ph | NH(CO)CF₃ |
| Br | 6-F | CO₂Me | OH | CF₃ | 7-Cl | CO₂Me | OH |
| Br | 6-F | CO₂Et | OH | CF₃ | 7-Cl | CO₂Et | OH |
| Br | 6-F | i-Pr | OH | CF₃ | 7-Cl | i-Pr | OH |
| Br | 6-F | Me | OH | CF₃ | 7-Cl | Me | OH |
| Br | 6-F | 4-F—Ph | OH | CF₃ | 7-Cl | 4-F—Ph | OH |
| Br | 7-F | CO₂Me | OH | CF₃ | 7-CF₃ | CO₂Me | OH |
| Br | 7-F | CO₂Et | OH | CF₃ | 7-CF₃ | CO₂Et | OH |
| Br | 7-F | i-Pr | OH | CF₃ | 7-CF₃ | i-Pr | OH |
| Br | 7-F | Me | OH | CF₃ | 7-CF₃ | Me | OH |
| Br | 7-F | 4-F—Ph | OH | CF₃ | 7-CF₃ | 4-F—Ph | OH |
| Br | 7-Cl | CO₂Me | OH | OCF₃ | 6-F | CO₂Me | OH |
| Br | 7-Cl | CO₂Et | OH | OCF₃ | 6-F | CO₂Et | OH |
| Br | 7-Cl | i-Pr | OH | OCF₃ | 6-F | i-Pr | OH |
| Br | 7-Cl | Me | OH | OCF₃ | 6-F | Me | OH |
| Br | 7-Cl | 4-F—Ph | OH | OCF₃ | 6-F | 4-F—Ph | OH |

TABLE 18-continued

| R¹ | R² | R³ | Y | R¹ | R² | R³ | Y |
|---|---|---|---|---|---|---|---|
| Br | 7-CF₃ | CO₂Me | OH | OCF₃ | 7-F | CO₂Me | OH |
| Br | 7-CF₃ | CO₂Et | OH | OCF₃ | 7-F | CO₂Et | OH |
| Br | 7-CF₃ | i-Pr | OH | OCF₃ | 7-F | i-Pr | OH |
| Br | 7-CF₃ | Me | OH | OCF₃ | 7-F | Me | OH |
| Br | 7-CF₃ | 4-F—Ph | OH | OCF₃ | 7-F | 4-F—Ph | OH |
| CF₃ | 6-F | CO₂Me | OH | OCF₃ | 7-Cl | CO₂Me | OH |
| CF₃ | 6-F | CO₂Et | OH | OCF₃ | 7-Cl | CO₂Et | OH |
| CF₃ | 6-F | i-Pr | OH | OCF₃ | 7-Cl | i-Pr | OH |
| CF₃ | 6-F | Me | OH | OCF₃ | 7-Cl | Me | OH |
| CF₃ | 6-F | 4-F—Ph | OH | OCF₃ | 7-Cl | 4-F—Ph | OH |
| CF₃ | 7-F | CO₂Me | OH | OCF₃ | 7-CF₃ | CO₂Me | OH |
| CF₃ | 7-F | CO₂Et | OH | OCF₃ | 7-CF₃ | CO₂Et | OH |
| CF₃ | 7-F | i-Pr | OH | OCF₃ | 7-CF₃ | i-Pr | OH |
| CF₃ | 7-F | Me | OH | OCF₃ | 7-CF₃ | Me | OH |
| CF₃ | 7-F | 4-F—Ph | OH | OCF₃ | 7-CF₃ | 4-F—Ph | OH |
| Br | 6-F | CO₂Me | OMe | CF₃ | 7-Cl | CO₂Me | OMe |
| Br | 6-F | CO₂Et | OMe | CF₃ | 7-Cl | CO₂Et | OMe |
| Br | 6-F | i-Pr | OMe | CF₃ | 7-Cl | i-Pr | OMe |
| Br | 6-F | Me | OMe | CF₃ | 7-Cl | Me | OMe |
| Br | 6-F | 4-F—Ph | OMe | CF₃ | 7-Cl | 4-F—Ph | OMe |
| Br | 7-F | CO₂Me | OMe | CF₃ | 7-CF₃ | CO₂Me | OMe |
| Br | 7-F | CO₂Et | OMe | CF₃ | 7-CF₃ | CO₂Et | OMe |
| Br | 7-F | i-Pr | OMe | CF₃ | 7-CF₃ | i-Pr | OMe |
| Br | 7-F | Me | OMe | CF₃ | 7-CF₃ | Me | OMe |
| Br | 7-F | 4-F—Ph | OMe | CF₃ | 7-CF₃ | 4-F—Ph | OMe |
| Br | 7-Cl | CO₂Me | OMe | OCF₃ | 6-F | CO₂Me | OMe |
| Br | 7-Cl | CO₂Et | OMe | OCF₃ | 6-F | CO₂Et | OMe |
| Br | 7-Cl | i-Pr | OMe | OCF₃ | 6-F | i-Pr | OMe |
| Br | 7-Cl | Me | OMe | OCF₃ | 6-F | Me | OMe |
| Br | 7-Cl | 4-F—Ph | OMe | OCF₃ | 6-F | 4-F—Ph | OMe |
| Br | 7-CF₃ | CO₂Me | OMe | OCF₃ | 7-F | CO₂Me | OMe |
| Br | 7-CF₃ | CO₂Et | OMe | OCF₃ | 7-F | CO₂Et | OMe |
| Br | 7-CF₃ | i-Pr | OMe | OCF₃ | 7-F | i-Pr | OMe |
| Br | 7-CF₃ | Me | OMe | OCF₃ | 7-F | Me | OMe |
| Br | 7-CF₃ | 4-F—Ph | OMe | OCF₃ | 7-F | 4-F—Ph | OMe |
| CF₃ | 6-F | CO₂Me | OMe | OCF₃ | 7-Cl | CO₂Me | OMe |
| CF₃ | 6-F | CO₂Et | OMe | OCF₃ | 7-Cl | CO₂Et | OMe |
| CF₃ | 6-F | i-Pr | OMe | OCF₃ | 7-Cl | i-Pr | OMe |
| CF₃ | 6-F | Me | OMe | OCF₃ | 7-Cl | Me | OMe |
| CF₃ | 6-F | 4-F—Ph | OMe | OCF₃ | 7-Cl | 4-F—Ph | OMe |
| CF₃ | 7-F | CO₂Me | OMe | OCF₃ | 7-CF₃ | CO₂Me | OMe |
| CF₃ | 7-F | CO₂Et | OMe | OCF₃ | 7-CF₃ | CO₂Et | OMe |
| CF₃ | 7-F | i-Pr | OMe | OCF₃ | 7-CF₃ | i-Pr | OMe |
| CF₃ | 7-F | Me | OMe | OCF₃ | 7-CF₃ | Me | OMe |
| CF₃ | 7-F | 4-F—Ph | OMe | OCF₃ | 7-CF₃ | 4-F—Ph | OMe |
| Br | 6-F | CO₂Me | OCH₂Ph | CF₃ | 7-Cl | CO₂Me | OCH₂Ph |
| Br | 6-F | CO₂Et | OCH₂Ph | CF₃ | 7-Cl | CO₂Et | OCH₂Ph |
| Br | 6-F | i-Pr | OCH₂Ph | CF₃ | 7-Cl | i-Pr | OCH₂Ph |
| Br | 6-F | Me | OCH₂Ph | CF₃ | 7-Cl | Me | OCH₂Ph |
| Br | 6-F | 4-F—Ph | OCH₂Ph | CF₃ | 7-Cl | 4-F—Ph | OCH₂Ph |
| Br | 7-F | CO₂Me | OCH₂Ph | CF₃ | 7-CF₃ | CO₂Me | OCH₂Ph |
| Br | 7-F | CO₂Et | OCH₂Ph | CF₃ | 7-CF₃ | CO₂Et | OCH₂Ph |
| Br | 7-F | i-Pr | OCH₂Ph | CF₃ | 7-CF₃ | i-Pr | OCH₂Ph |
| Br | 7-F | Me | OCH₂Ph | CF₃ | 7-CF₃ | Me | OCH₂Ph |
| Br | 7-F | 4-F—Ph | OCH₂Ph | CF₃ | 7-CF₃ | 4-F—Ph | OCH₂Ph |
| Br | 7-Cl | CO₂Me | OCH₂Ph | OCF₃ | 6-F | CO₂Me | OCH₂Ph |
| Br | 7-Cl | CO₂Et | OCH₂Ph | OCF₃ | 6-F | CO₂Et | OCH₂Ph |
| Br | 7-Cl | i-Pr | OCH₂Ph | OCF₃ | 6-F | i-Pr | OCH₂Ph |
| Br | 7-Cl | Me | OCH₂Ph | OCF₃ | 6-F | Me | OCH₂Ph |
| Br | 7-Cl | 4-F—Ph | OCH₂Ph | OCF₃ | 6-F | 4-F—Ph | OCH₂Ph |
| Br | 7-CF₃ | CO₂Me | OCH₂Ph | OCF₃ | 7-F | CO₂Me | OCH₂Ph |
| Br | 7-CF₃ | CO₂Et | OCH₂Ph | OCF₃ | 7-F | CO₂Et | OCH₂Ph |
| Br | 7-CF₃ | i-Pr | OCH₂Ph | OCF₃ | 7-F | i-Pr | OCH₂Ph |
| Br | 7-CF₃ | Me | OCH₂Ph | OCF₃ | 7-F | Me | OCH₂Ph |
| Br | 7-CF₃ | 4-F—Ph | OCH₂Ph | OCF₃ | 7-F | 4-F—Ph | OCH₂Ph |
| CF₃ | 6-F | CO₂Me | OCH₂Ph | OCF₃ | 7-Cl | CO₂Me | OCH₂Ph |
| CF₃ | 6-F | CO₂Et | OCH₂Ph | OCF₃ | 7-Cl | CO₂Et | OCH₂Ph |
| CF₃ | 6-F | i-Pr | OCH₂Ph | OCF₃ | 7-Cl | i-Pr | OCH₂Ph |
| CF₃ | 6-F | Me | OCH₂Ph | OCF₃ | 7-Cl | Me | OCH₂Ph |
| CF₃ | 6-F | 4-F—Ph | OCH₂Ph | OCF₃ | 7-Cl | 4-F—Ph | OCH₂Ph |
| CF₃ | 7-F | CO₂Me | OCH₂Ph | OCF₃ | 7-CF₃ | CO₂Me | OCH₂Ph |
| CF₃ | 7-F | CO₂Et | OCH₂Ph | OCF₃ | 7-CF₃ | CO₂Et | OCH₂Ph |
| CF₃ | 7-F | i-Pr | OCH₂Ph | OCF₃ | 7-CF₃ | i-Pr | OCH₂Ph |
| CF₃ | 7-F | Me | OCH₂Ph | OCF₃ | 7-CF₃ | Me | OCH₂Ph |
| CF₃ | 7-F | 4-F—Ph | OCH₂Ph | OCF₃ | 7-CF₃ | 4-F—Ph | OCH₂Ph |

TABLE 19

| R¹ | R² | R³ | Y | R¹ | R² | R³ | Y |
|---|---|---|---|---|---|---|---|
| Br | 7-F | 4-F—Ph | NHSO₂Me | Br | 7-F | 4-F—Ph | NMe(CHO) |
| CF₃ | 7-F | 4-F—Ph | NHSO₂Me | CF₃ | 7-F | 4-F—Ph | NMe(CHO) |
| OCF₃ | 7-F | 4-F—Ph | NHSO₂Me | OCF₃ | 7-F | 4-F—Ph | NMe(CHO) |
| CF₃ | 7-Cl | CO₂Me | NHSO₂Me | CF₃ | 7-Cl | CO₂Me | NMe(CHO) |
| OCF₃ | 7-Cl | CO₂Me | NHSO₂Me | OCF₃ | 7-Cl | CO₂Me | NMe(CHO) |
| OCF₃ | 7-Cl | CO₂Et | NHSO₂Me | OCF₃ | 7-Cl | CO₂Et | NMe(CHO) |
| Br | 7-F | 4-F—Ph | NHSO₂Ph | Br | 7-F | 4-F—Ph | NMe(CO)Me |
| CF₃ | 7-F | 4-F—Ph | NHSO₂Ph | CF₃ | 7-F | 4-F—Ph | NMe(CO)Me |
| OCF₃ | 7-F | 4-F—Ph | NHSO₂Ph | OCF₃ | 7-F | 4-F—Ph | NMe(CO)Me |
| CF₃ | 7-Cl | CO₂Me | NHSO₂Ph | CF₃ | 7-Cl | CO₂Me | NMe(CO)Me |
| OCF₃ | 7-Cl | CO₂Me | NHSO₂Ph | OCF₃ | 7-Cl | CO₂Me | NMe(CO)Me |
| OCF₃ | 7-Cl | CO₂Et | NHSO₂Ph | OCF₃ | 7-Cl | CO₂Et | NMe(CO)Me |
| Br | 7-F | 4-F—Ph | NH(CO)NHPh | Br | 7-F | 4-F—Ph | O(CO)Me |
| CF₃ | 7-F | 4-F—Ph | NH(CO)NHPh | CF₃ | 7-F | 4-F—Ph | O(CO)Me |
| OCF₃ | 7-F | 4-F—Ph | NH(CO)NHPh | OCF₃ | 7-F | 4-F—Ph | O(CO)Me |
| CF₃ | 7-Cl | CO₂Me | NH(CO)NHPh | CF₃ | 7-Cl | CO₂Me | O(CO)Me |
| OCF₃ | 7-Cl | CO₂Me | NH(CO)NHPh | OCF₃ | 7-Cl | CO₂Me | O(CO)Me |
| OCF₃ | 7-Cl | CO₂Et | NH(CO)NHPh | OCF₃ | 7-Cl | CO₂Et | O(CO)Me |
| Br | 7-F | 4-F—Ph | N=CHMe | Br | 7-F | 4-F—Ph | O(CO)OMe |
| CF₃ | 7-F | 4-F—Ph | N=CHMe | CF₃ | 7-F | 4-F—Ph | O(CO)OMe |
| OCF₃ | 7-F | 4-F—Ph | N=CHMe | OCF₃ | 7-F | 4-F—Ph | O(CO)OMe |
| CF₃ | 7-Cl | CO₂Me | N=CHMe | CF₃ | 7-Cl | CO₂Me | O(CO)OMe |
| OCF₃ | 7-Cl | CO₂Me | N=CHMe | OCF₃ | 7-Cl | CO₂Me | O(CO)OMe |
| OCF₃ | 7-Cl | CO₂Et | N=CHMe | OCF₃ | 7-Cl | CO₂Et | O(CO)OMe |
| Br | 7-F | 4-F—Ph | O(CO)NHMe | Br | 7-F | 4-F—Ph | NHCH₂Ph |
| CF₃ | 7-F | 4-F—Ph | O(CO)NHMe | CF₃ | 7-F | 4-F—Ph | NHCH₂Ph |
| OCF₃ | 7-F | 4-F—Ph | O(CO)NHMe | OCF₃ | 7-F | 4-F—Ph | NHCH₂Ph |
| CF₃ | 7-Cl | CO₂Me | O(CO)NHMe | CF₃ | 7-Cl | CO₂Me | NHCH₂Ph |
| OCF₃ | 7-Cl | CO₂Me | O(CO)NHMe | OCF₃ | 7-Cl | CO₂Me | NHCH₂Ph |
| OCF₃ | 7-Cl | CO₂Et | O(CO)NHMe | OCF₃ | 7-Cl | CO₂Et | NHCH₂Ph |
| Br | 7-F | 4-F—Ph | NMe₂ | Br | 7-F | 4-F—Ph | NHPh |
| CF₃ | 7-F | 4-F—Ph | NMe₂ | CF₃ | 7-F | 4-F—Ph | NHPh |
| OCF₃ | 7-F | 4-F—Ph | NMe₂ | OCF₃ | 7-F | 4-F—Ph | NHPh |
| CF₃ | 7-Cl | CO₂Me | NMe₂ | CF₃ | 7-Cl | CO₂Me | NHPh |
| OCF₃ | 7-Cl | CO₂Me | NMe₂ | OCF₃ | 7-Cl | CO₂Me | NHPh |
| OCF₃ | 7-Cl | CO₂Et | NMe₂ | OCF₃ | 7-Cl | CO₂Et | NHPh |
| Br | 7-F | 4-F—Ph | NHEt | Br | 7-F | 4-F—Ph | NH(CO)Et |
| CF₃ | 7-F | 4-F—Ph | NHEt | CF₃ | 7-F | 4-F—Ph | NH(CO)Et |
| OCF₃ | 7-F | 4-F—Ph | NHEt | OCF₃ | 7-F | 4-F—Ph | NH(CO)Et |
| CF₃ | 7-Cl | CO₂Me | NHEt | CF₃ | 7-Cl | CO₂Me | NH(CO)Et |
| OCF₃ | 7-Cl | CO₂Me | NHEt | OCF₃ | 7-Cl | CO₂Me | NH(CO)Et |
| OCF₃ | 7-Cl | CO₂Et | NHEt | OCF₃ | 7-Cl | CO₂Et | NH(CO)Et |
| Br | 7-F | 4-F—Ph | NHi—Pr | Br | 7-F | 4-F—Ph | NH(CO)Ph |
| CF₃ | 7-F | 4-F—Ph | NHi—Pr | CF₃ | 7-F | 4-F—Ph | NH(CO)Ph |
| OCF₃ | 7-F | 4-F—Ph | NHi—Pr | OCF₃ | 7-F | 4-F—Ph | NH(CO)Ph |
| CF₃ | 7-Cl | CO₂Me | NHi—Pr | CF₃ | 7-Cl | CO₂Me | NH(CO)Ph |
| OCF₃ | 7-Cl | CO₂Me | NHi—Pr | OCF₃ | 7-Cl | CO₂Me | NH(CO)Ph |
| OCF₃ | 7-Cl | CO₂Et | NHi—Pr | OCF₃ | 7-Cl | CO₂Et | NH(CO)Ph |
| Br | 7-F | 4-F—Ph | NHCO₂Me | Br | 7-F | 4-F—Ph | NHSO₂NHMe |
| CF₃ | 7-F | 4-F—Ph | NHCO₂Me | CF₃ | 7-F | 4-F—Ph | NHSO₂NHMe |
| OCF₃ | 7-F | 4-F—Ph | NHCO₂Me | OCF₃ | 7-F | 4-F—Ph | NHSO₂NHMe |
| CF₃ | 7-Cl | CO₂Me | NHCO₂Me | CF₃ | 7-Cl | CO₂Me | NHSO₂NHMe |
| OCF₃ | 7-Cl | CO₂Me | NHCO₂Me | OCF₃ | 7-Cl | CO₂Me | NHSO₂NHMe |
| OCF₃ | 7-Cl | CO₂Et | NHCO₂Me | OCF₃ | 7-Cl | CO₂Et | NHSO₂NHMe |
| Br | 7-F | 4-F—Ph | NHCO₂Et | Br | 7-F | 4-F—Ph | NH(4-F—Ph) |
| CF₃ | 7-F | 4-F—Ph | NHCO₂Et | CF₃ | 7-F | 4-F—Ph | NH(4-F—Ph) |
| OCF₃ | 7-F | 4-F—Ph | NHCO₂Et | OCF₃ | 7-F | 4-F—Ph | NH(4-F—Ph) |
| CF₃ | 7-Cl | CO₂Me | NHCO₂Et | CF₃ | 7-Cl | CO₂Me | NH(4-F—Ph) |
| OCF₃ | 7-Cl | CO₂Me | NHCO₂Et | OCF₃ | 7-Cl | CO₂Me | NH(4-F—Ph) |
| OCF₃ | 7-Cl | CO₂Et | NHCO₂Et | OCF₃ | 7-Cl | CO₂Et | NH(4-F—Ph) |
| Br | 7-F | 4-F—Ph | NHSO₂NH₂ | Br | 7-F | 4-F—Ph | NH(4-MeO—Ph) |
| CF₃ | 7-F | 4-F—Ph | NHSO₂NH₂ | CF₃ | 7-F | 4-F—Ph | NH(4-MeO—Ph) |
| OCF₃ | 7-F | 4-F—Ph | NHSO₂NH₂ | OCF₃ | 7-F | 4-F—Ph | NH(4-MeO—Ph) |
| CF₃ | 7-Cl | CO₂Me | NHSO₂NH₂ | CF₃ | 7-Cl | CO₂Me | NH(4-MeO—Ph) |
| OCF₃ | 7-Cl | CO₂Me | NHSO₂NH₂ | OCF₃ | 7-Cl | CO₂Me | NH(4-MeO—Ph) |
| OCF₃ | 7-Cl | CO₂Et | NHSO₂NH₂ | OCF₃ | 7-Cl | CO₂Et | NH(4-MeO—Ph) |
| Br | 7-F | 4-F—Ph | NHSO₂NHPh | Br | 7-F | 4-F—Ph | NHCH₂C=CH |
| CF₃ | 7-F | 4-F—Ph | NHSO₂NHPh | CF₃ | 7-F | 4-F—Ph | NHCH₂C=CH |
| OCF₃ | 7-F | 4-F—Ph | NHSO₂NHPh | OCF₃ | 7-F | 4-F—Ph | NHCH₂C=CH |
| CF₃ | 7-Cl | CO₂Me | NHSO₂NHPh | CF₃ | 7-Cl | CO₂Me | NHCH₂C=CH |
| OCF₃ | 7-Cl | CO₂Me | NHSO₂NHPh | OCF₃ | 7-Cl | CO₂Me | NHCH₂C=CH |
| OCF₃ | 7-Cl | CO₂Et | NHSO₂NHPh | OCF₃ | 7-Cl | CO₂Et | NHCH₂C=CH |

TABLE 20

| R¹ | R² | R³ | Y | R¹ | R² | R³ | Y |
|---|---|---|---|---|---|---|---|
| CF₃ | 6-F | 4-F—Ph | NH₂ | CF₃ | 6-F | 4-F—Ph | NHMe |
| CF₃ | 6-F | Me | NH₂ | CF₃ | 6-F | Me | NHMe |
| CF₃ | 6-F | Et | NH₂ | CF₃ | 6-F | Et | NHMe |
| CF₃ | 6-F | i-Pr | NH₂ | CF₃ | 6-F | i-Pr | NHMe |
| CF₃ | 7-F | 4-F—Ph | NH₂ | CF₃ | 7-F | 4-F—Ph | NHMe |
| CF₃ | 7-F | Me | NH₂ | CF₃ | 7-F | Me | NHMe |
| CF₃ | 7-F | Et | NH₂ | CF₃ | 7-F | Et | NHMe |
| CF₃ | 7-F | i-Pr | NH₂ | CF₃ | 7-F | i-Pr | NHMe |
| CF₃ | 7-Cl | 4-F—Ph | NH₂ | CF₃ | 7-Cl | 4-F—Ph | NHMe |
| CF₃ | 7-Cl | Me | NH₂ | CF₃ | 7-Cl | Me | NHMe |
| CF₃ | 7-Cl | Et | NH₂ | CF₃ | 7-Cl | Et | NHMe |
| CF₃ | 7-Cl | i-Pr | NH₂ | CF₃ | 7-Cl | i-Pr | NHMe |
| OCF₃ | 6-F | 4-F—Ph | NH₂ | OCF₃ | 6-F | 4-F—Ph | NHMe |
| OCF₃ | 6-F | Me | NH₂ | OCF₃ | 6-F | Me | NHMe |
| OCF₃ | 6-F | Et | NH₂ | OCF₃ | 6-F | Et | NHMe |
| OCF₃ | 6-F | i-Pr | NH₂ | OCF₃ | 6-F | i-Pr | NHMe |
| OCF₃ | 7-F | 4-F—Ph | NH₂ | OCF₃ | 7-F | 4-F—Ph | NHMe |
| OCF₃ | 7-F | Me | NH₂ | OCF₃ | 7-F | Me | NHMe |
| OCF₃ | 7-F | Et | NH₂ | OCF₃ | 7-F | Et | NHMe |
| OCF₃ | 7-F | i-Pr | NH₂ | OCF₃ | 7-F | i-Pr | NHMe |
| OCF₃ | 7-Cl | 4-F—Ph | NH₂ | OCF₃ | 7-Cl | 4-F—Ph | NHMe |
| OCF₃ | 7-Cl | Me | NH₂ | OCF₃ | 7-Cl | Me | NHMe |
| OCF₃ | 7-Cl | Et | NH₂ | OCF₃ | 7-Cl | Et | NHMe |
| OCF₃ | 7-Cl | i-Pr | NH₂ | OCF₃ | 7-Cl | i-Pr | NHMe |
| CF₃ | 6-F | 4-F—Ph | NH(CO)Me | CF₃ | 6-F | 4-F—Ph | NHCHO |
| CF₃ | 6-F | Me | NH(CO)Me | CF₃ | 6-F | Me | NHCHO |
| CF₃ | 6-F | Et | NH(CO)Me | CF₃ | 6-F | Et | NHCHO |
| CF₃ | 6-F | i-Pr | NH(CO)Me | CF₃ | 6-F | i-Pr | NHCHO |
| CF₃ | 7-F | 4-F—Ph | NH(CO)Me | CF₃ | 7-F | 4-F—Ph | NHCHO |
| CF₃ | 7-F | Me | NH(CO)Me | CF₃ | 7-F | Me | NHCHO |
| CF₃ | 7-F | Et | NH(CO)Me | CF₃ | 7-F | Et | NHCHO |
| CF₃ | 7-F | i-Pr | NH(CO)Me | CF₃ | 7-F | i-Pr | NHCHO |
| CF₃ | 7-Cl | 4-F—Ph | NH(CO)Me | CF₃ | 7-Cl | 4-F—Ph | NHCHO |
| CF₃ | 7-Cl | Me | NH(CO)Me | CF₃ | 7-Cl | Me | NHCHO |
| CF₃ | 7-Cl | Et | NH(CO)Me | CF₃ | 7-Cl | Et | NHCHO |
| CF₃ | 7-Cl | i-Pr | NH(CO)Me | CF₃ | 7-Cl | i-Pr | NHCHO |
| OCF₃ | 6-F | 4-F—Ph | NH(CO)Me | OCF₃ | 6-F | 4-F—Ph | NHCHO |
| OCF₃ | 6-F | Me | NH(CO)Me | OCF₃ | 6-F | Me | NHCHO |
| OCF₃ | 6-F | Et | NH(CO)Me | OCF₃ | 6-F | Et | NHCHO |
| OCF₃ | 6-F | i-Pr | NH(CO)Me | OCF₃ | 6-F | i-Pr | NHCHO |
| OCF₃ | 7-F | 4-F—Ph | NH(CO)Me | OCF₃ | 7-F | 4-F—Ph | NHCHO |
| OCF₃ | 7-F | Me | NH(CO)Me | OCF₃ | 7-F | Me | NHCHO |
| OCF₃ | 7-F | Et | NH(CO)Me | OCF₃ | 7-F | Et | NHCHO |
| OCF₃ | 7-F | i-Pr | NH(CO)Me | OCF₃ | 7-F | i-Pr | NHCHO |
| OCF₃ | 7-Cl | 4-F—Ph | NH(CO)Me | OCF₃ | 7-Cl | 4-F—Ph | NHCHO |
| OCF₃ | 7-Cl | Me | NH(CO)Me | OCF₃ | 7-Cl | Me | NHCHO |
| OCF₃ | 7-Cl | Et | NH(CO)Me | OCF₃ | 7-Cl | Et | NHCHO |
| OCF₃ | 7-Cl | i-Pr | NH(CO)Me | OCF₃ | 7-Cl | i-Pr | NHCHO |
| CF₃ | 6-F | 4-F—Ph | NH(CO)NHMe | CF₃ | 6-F | 4-F—Ph | NHCO₂Me |
| CF₃ | 6-F | Me | NH(CO)NHMe | CF₃ | 6-F | Me | NHCO₂Me |
| CF₃ | 6-F | Et | NH(CO)NHMe | CF₃ | 6-F | Et | NHCO₂Me |
| CF₃ | 6-F | i-Pr | NH(CO)NHMe | CF₃ | 6-F | i-Pr | NHCO₂Me |
| CF₃ | 7-F | 4-F—Ph | NH(CO)NHMe | CF₃ | 7-F | 4-F—Ph | NHCO₂Me |
| CF₃ | 7-F | Me | NH(CO)NHMe | CF₃ | 7-F | Me | NHCO₂Me |
| CF₃ | 7-F | Et | NH(CO)NHMe | CF₃ | 7-F | Et | NHCO₂Me |
| CF₃ | 7-F | i-Pr | NH(CO)NHMe | CF₃ | 7-F | i-Pr | NHCO₂Me |
| CF₃ | 7-Cl | 4-F—Ph | NH(CO)NHMe | CF₃ | 7-Cl | 4-F—Ph | NHCO₂Me |
| CF₃ | 7-Cl | Me | NH(CO)NHMe | CF₃ | 7-Cl | Me | NHCO₂Me |
| CF₃ | 7-Cl | Et | NH(CO)NHMe | CF₃ | 7-Cl | Et | NHCO₂Me |
| CF₃ | 7-Cl | i-Pr | NH(CO)NHMe | CF₃ | 7-Cl | i-Pr | NHCO₂Me |
| OCF₃ | 6-F | 4-F—Ph | NH(CO)NHMe | OCF₃ | 6-F | 4-F—Ph | NHCO₂Me |
| OCF₃ | 6-F | Me | NH(CO)NHMe | OCF₃ | 6-F | Me | NHCO₂Me |
| OCF₃ | 6-F | Et | NH(CO)NHMe | OCF₃ | 6-F | Et | NHCO₂Me |
| OCF₃ | 6-F | i-Pr | NH(CO)NHMe | OCF₃ | 6-F | i-Pr | NHCO₂Me |
| OCF₃ | 7-F | 4-F—Ph | NH(CO)NHMe | OCF₃ | 7-F | 4-F—Ph | NHCO₂Me |
| OCF₃ | 7-F | Me | NH(CO)NHMe | OCF₃ | 7-F | Me | NHCO₂Me |
| OCF₃ | 7-F | Et | NH(CO)NHMe | OCF₃ | 7-F | Et | NHCO₂Me |
| OCF₃ | 7-F | i-Pr | NH(CO)NHMe | OCF₃ | 7-F | i-Pr | NHCO₂Me |
| OCF₃ | 7-Cl | 4-F—Ph | NH(CO)NHMe | OCF₃ | 7-Cl | 4-F—Ph | NHCO₂Me |
| OCF₃ | 7-Cl | Me | NH(CO)NHMe | OCF₃ | 7-Cl | Me | NHCO₂Me |
| OCF₃ | 7-Cl | Et | NH(CO)NHMe | OCF₃ | 7-Cl | Et | NHCO₂Me |
| OCF₃ | 7-Cl | i-Pr | NH(CO)NHMe | OCF₃ | 7-Cl | i-Pr | NHCO₂Me |
| CF₃ | 6-F | 4-F—Ph | N=CH₂ | CF₃ | 6-F | 4-F—Ph | N=CMe₂ |
| CF₃ | 6-F | Me | N=CH₂ | CF₃ | 6-F | Me | N=CMe₂ |
| CF₃ | 6-F | Et | N=CH₂ | CF₃ | 6-F | Et | N=CMe₂ |
| CF₃ | 6-F | i-Pr | N=CH₂ | CF₃ | 6-F | i-Pr | N=CMe₂ |
| CF₃ | 7-F | 4-F—Ph | N=CH₂ | CF₃ | 7-F | 4-F—Ph | N=CMe₂ |

TABLE 20-continued

| R¹ | R² | R³ | Y | R¹ | R² | R³ | Y |
|---|---|---|---|---|---|---|---|
| CF₃ | 7-F | Me | N=CH₂ | CF₃ | 7-F | Me | N=CMe₂ |
| CF₃ | 7-F | Et | N=CH₂ | CF₃ | 7-F | Et | N=CMe₂ |
| CF₃ | 7-F | i-Pr | N=CH₂ | CF₃ | 7-F | i-Pr | N=CMe₂ |
| CF₃ | 7-Cl | 4-F—Ph | N=CH₂ | CF₃ | 7-Cl | 4-F—Ph | N=CMe₂ |
| CF₃ | 7-Cl | Me | N=CH₂ | CF₃ | 7-Cl | Me | N=CMe₂ |
| CF₃ | 7-Cl | Et | N=CH₂ | CF₃ | 7-Cl | Et | N=CMe₂ |
| CF₃ | 7-Cl | i-Pr | N=CH₂ | CF₃ | 7-Cl | i-Pr | N=CMe₂ |
| OCF₃ | 6-F | 4-F—Ph | N=CH₂ | OCF₃ | 6-F | 4-F—Ph | N=CMe₂ |
| OCF₃ | 6-F | Me | N=CH₂ | OCF₃ | 6-F | Me | N=CMe₂ |
| OCF₃ | 6-F | Et | N=CH₂ | OCF₃ | 6-F | Et | N=CMe₂ |
| OCF₃ | 6-F | i-Pr | N=CH₂ | OCF₃ | 6-F | i-Pr | N=CMe₂ |
| OCF₃ | 7-F | 4-F—Ph | N=CH₂ | OCF₃ | 7-F | 4-F—Ph | N=CMe₂ |
| OCF₃ | 7-F | Me | N=CH₂ | OCF₃ | 7-F | Me | N=CMe₂ |
| OCF₃ | 7-F | Et | N=CH₂ | OCF₃ | 7-F | Et | N=CMe₂ |
| OCF₃ | 7-F | i-Pr | N=CH₂ | OCF₃ | 7-F | i-Pr | N=CMe₂ |
| OCF₃ | 7-Cl | 4-F—Ph | N=CH₂ | OCF₃ | 7-Cl | 4-F—Ph | N=CMe₂ |
| OCF₃ | 7-Cl | Me | N=CH₂ | OCF₃ | 7-Cl | Me | N=CMe₂ |
| OCF₃ | 7-Cl | Et | N=CH₂ | OCF₃ | 7-Cl | Et | N=CMe₂ |
| OCF₃ | 7-Cl | i-Pr | N=CH₂ | OCF₃ | 7-Cl | i-Pr | N=CMe₂ |
| CF₃ | 6-F | 4-F—Ph | N=CHPh | CF₃ | 6-F | 4-F—Ph | OH |
| CF₃ | 6-F | Me | N=CHPh | CF₃ | 6-F | Me | OH |
| CF₃ | 6-F | Et | N=CHPh | CF₃ | 6-F | Et | OH |
| CF₃ | 6-F | i-Pr | N=CHPh | CF₃ | 6-F | i-Pr | OH |
| CF₃ | 7-F | 4-F—Ph | N=CHPh | CF₃ | 7-F | 4-F—Ph | OH |
| CF₃ | 7-F | Me | N=CHPh | CF₃ | 7-F | Me | OH |
| CF₃ | 7-F | Et | N=CHPh | CF₃ | 7-F | Et | OH |
| CF₃ | 7-F | i-Pr | N=CHPh | CF₃ | 7-F | i-Pr | OH |
| CF₃ | 7-Cl | 4-F—Ph | N=CHPh | CF₃ | 7-Cl | 4-F—Ph | OH |
| CF₃ | 7-Cl | Me | N=CHPh | CF₃ | 7-Cl | Me | OH |
| CF₃ | 7-Cl | Et | N=CHPh | CF₃ | 7-Cl | Et | OH |
| CF₃ | 7-Cl | i-Pr | N=CHPh | CF₃ | 7-Cl | i-Pr | OH |
| OCF₃ | 6-F | 4-F—Ph | N=CHPh | OCF₃ | 6-F | 4-F—Ph | OH |
| OCF₃ | 6-F | Me | N=CHPh | OCF₃ | 6-F | Me | OH |
| OCF₃ | 6-F | Et | N=CHPh | OCF₃ | 6-F | Et | OH |
| OCF₃ | 6-F | i-Pr | N=CHPh | OCF₃ | 6-F | i-Pr | OH |
| OCF₃ | 7-F | 4-F—Ph | N=CHPh | OCF₃ | 7-F | 4-F—Ph | OH |
| OCF₃ | 7-F | Me | N=CHPh | OCF₃ | 7-F | Me | OH |
| OCF₃ | 7-F | Et | N=CHPh | OCF₃ | 7-F | Et | OH |
| OCF₃ | 7-F | i-Pr | N=CHPh | OCF₃ | 7-F | i-Pr | OH |
| OCF₃ | 7-Cl | 4-F—Ph | N=CHPh | OCF₃ | 7-Cl | 4-F—Ph | OH |
| OCF₃ | 7-Cl | Me | N=CHPh | OCF₃ | 7-Cl | Me | OH |
| OCF₃ | 7-Cl | Et | N=CHPh | OCF₃ | 7-Cl | Et | OH |
| OCF₃ | 7-Cl | i-Pr | N=CHPh | OCF₃ | 7-Cl | i-Pr | OH |
| CF₃ | 6-F | 4-F—Ph | OMe | CF₃ | 6-F | 4-F—Ph | OCH₂Ph |
| CF₃ | 6-F | Me | OMe | CF₃ | 6-F | Me | OCH₂Ph |
| CF₃ | 6-F | Et | OMe | CF₃ | 6-F | Et | OCH₂Ph |
| CF₃ | 6-F | i-Pr | OMe | CF₃ | 6-F | i-Pr | OCH₂Ph |
| CF₃ | 7-F | 4-F—Ph | OMe | CF₃ | 7-F | 4-F—Ph | OCH₂Ph |
| CF₃ | 7-F | Me | OMe | CF₃ | 7-F | Me | OCH₂Ph |
| CF₃ | 7-F | Et | OMe | CF₃ | 7-F | Et | OCH₂Ph |
| CF₃ | 7-F | i-Pr | OMe | CF₃ | 7-F | i-Pr | OCH₂Ph |
| CF₃ | 7-Cl | 4-F—Ph | OMe | CF₃ | 7-Cl | 4-F—Ph | OCH₂Ph |
| CF₃ | 7-Cl | Me | OMe | CF₃ | 7-Cl | Me | OCH₂Ph |
| CF₃ | 7-Cl | Et | OMe | CF₃ | 7-Cl | Et | OCH₂Ph |
| CF₃ | 7-Cl | i-Pr | OMe | CF₃ | 7-Cl | i-Pr | OCH₂Ph |
| OCF₃ | 6-F | 4-F—Ph | OMe | OCF₃ | 6-F | 4-F—Ph | OCH₂Ph |
| OCF₃ | 6-F | Me | OMe | OCF₃ | 6-F | Me | OCH₂Ph |
| OCF₃ | 6-F | Et | OMe | OCF₃ | 6-F | Et | OCH₂Ph |
| OCF₃ | 6-F | i-Pr | OMe | OCF₃ | 6-F | i-Pr | OCH₂Ph |
| OCF₃ | 7-F | 4-F—Ph | OMe | OCF₃ | 7-F | 4-F—Ph | OCH₂Ph |
| OCF₃ | 7-F | Me | OMe | OCF₃ | 7-F | Me | OCH₂Ph |
| OCF₃ | 7-F | Et | OMe | OCF₃ | 7-F | Et | OCH₂Ph |
| OCF₃ | 7-F | i-Pr | OMe | OCF₃ | 7-F | i-Pr | OCH₂Ph |
| OCF₃ | 7-Cl | 4-F—Ph | OMe | OCF₃ | 7-Cl | 4-F—Ph | OCH₂Ph |
| OCF₃ | 7-Cl | Me | OMe | OCF₃ | 7-Cl | Me | OCH₂Ph |
| OCF₃ | 7-Cl | Et | OMe | OCF₃ | 7-Cl | Et | OCH₂Ph |
| OCF₃ | 7-Cl | i-Pr | OMe | OCF₃ | 7-Cl | i-Pr | OCH₂Ph |

TABLE 21

| R¹ | R² | R³ | Y | R¹ | R² | R³ | Y |
|---|---|---|---|---|---|---|---|
| CF₃ | 6-F | 4-F-Ph | NH₂ | CF₃ | 6-F | 4-F-Ph | NHMe |
| CF₃ | 6-F | Me | NH₂ | CF₃ | 6-F | Me | NHMe |
| CF₃ | 6-F | Et | NH₂ | CF₃ | 6-F | Et | NHMe |

TABLE 21-continued

| R¹ | R² | R³ | Y | R¹ | R² | R³ | Y |
|---|---|---|---|---|---|---|---|
| CF₃ | 6-F | i-Pr | NH₂ | CF₃ | 6-F | i-Pr | NHMe |
| CF₃ | 7-F | 4-F-Ph | NH₂ | CF₃ | 7-F | 4-F-Ph | NHMe |
| CF₃ | 7-F | Me | NH₂ | CF₃ | 7-F | Me | NHMe |
| CF₃ | 7-F | Et | NH₂ | CF₃ | 7-F | Et | NHMe |
| CF₃ | 7-F | i-Pr | NH₂ | CF₃ | 7-F | i-Pr | NHMe |
| CF₃ | 7-Cl | 4-F-Ph | NH₂ | CF₃ | 7-Cl | 4-F-Ph | NHMe |
| CF₃ | 7-Cl | Me | NH₂ | CF₃ | 7-Cl | Me | NHMe |
| CF₃ | 7-Cl | Et | NH₂ | CF₃ | 7-Cl | Et | NHMe |
| CF₃ | 7-Cl | i-Pr | NH₂ | CF₃ | 7-Cl | i-Pr | NHMe |
| OCF₃ | 6-F | 4-F-Ph | NH₂ | OCF₃ | 6-F | 4-F-Ph | NHMe |
| OCF₃ | 6-F | Me | NH₂ | OCF₃ | 6-F | Me | NHMe |
| OCF₃ | 6-F | Et | NH₂ | OCF₃ | 6-F | Et | NHMe |
| OCF₃ | 6-F | i-Pr | NH₂ | OCF₃ | 6-F | i-Pr | NHMe |
| OCF₃ | 7-F | 4-F-Ph | NH₂ | OCF₃ | 7-F | 4-F-Ph | NHMe |
| OCF₃ | 7-F | Me | NH₂ | OCF₃ | 7-F | Me | NHMe |
| OCF₃ | 7-F | Et | NH₂ | OCF₃ | 7-F | Et | NHMe |
| OCF₃ | 7-F | i-Pr | NH₂ | OCF₃ | 7-F | i-Pr | NHMe |
| OCF₃ | 7-Cl | 4-F-Ph | NH₂ | OCF₃ | 7-Cl | 4-F-Ph | NHMe |
| OCF₃ | 7-Cl | Me | NH₂ | OCF₃ | 7-Cl | Me | NHMe |
| OCF₃ | 7-Cl | Et | NH₂ | OCF₃ | 7-Cl | Et | NHMe |
| OCF₃ | 7-Cl | i-Pr | NH₂ | OCF₃ | 7-Cl | i-Pr | NHMe |
| CF₃ | 6-F | 4-F-Ph | NH(CO)Me | CF₃ | 6-F | 4-F-Ph | NHCHO |
| CF₃ | 6-F | Me | NH(CO)Me | CF₃ | 6-F | Me | NHCHO |
| CF₃ | 6-F | Et | NH(CO)Me | CF₃ | 6-F | Et | NHCHO |
| CF₃ | 6-F | i-Pr | NH(CO)Me | CF₃ | 6-F | i-Pr | NHCHO |
| CF₃ | 7-F | 4-F-Ph | NH(CO)Me | CF₃ | 7-F | 4-F-Ph | NHCHO |
| CF₃ | 7-F | Me | NH(CO)Me | CF₃ | 7-F | Me | NHCHO |
| CF₃ | 7-F | Et | NH(CO)Me | CF₃ | 7-F | Et | NHCHO |
| CF₃ | 7-F | i-Pr | NH(CO)Me | CF₃ | 7-F | i-Pr | NHCHO |
| CF₃ | 7-Cl | 4-F-Ph | NH(CO)Me | CF₃ | 7-Cl | 4-F-Ph | NHCHO |
| CF₃ | 7-Cl | Me | NH(CO)Me | CF₃ | 7-Cl | Me | NHCHO |
| CF₃ | 7-Cl | Et | NH(CO)Me | CF₃ | 7-Cl | Et | NHCHO |
| CF₃ | 7-Cl | i-Pr | NH(CO)Me | CF₃ | 7-Cl | i-Pr | NHCHO |
| OCF₃ | 6-F | 4-F-Ph | NH(CO)Me | OCF₃ | 6-F | 4-F-Ph | NHCHO |
| OCF₃ | 6-F | Me | NH(CO)Me | OCF₃ | 6-F | Me | NHCHO |
| OCF₃ | 6-F | Et | NH(CO)Me | OCF₃ | 6-F | Et | NHCHO |
| OCF₃ | 6-F | i-Pr | NH(CO)Me | OCF₃ | 6-F | i-Pr | NHCHO |
| OCF₃ | 7-F | 4-F-Ph | NH(CO)Me | OCF₃ | 7-F | 4-F-Ph | NHCHO |
| OCF₃ | 7-F | Me | NH(CO)Me | OCF₃ | 7-F | Me | NHCHO |
| OCF₃ | 7-F | Et | NH(CO)Me | OCF₃ | 7-F | Et | NHCHO |
| OCF₃ | 7-F | i-Pr | NH(CO)Me | OCF₃ | 7-F | i-Pr | NHCHO |
| OCF₃ | 7-Cl | 4-F-Ph | NH(CO)Me | OCF₃ | 7-Cl | 4-F-Ph | NHCHO |
| OCF₃ | 7-Cl | Me | NH(CO)Me | OCF₃ | 7-Cl | Me | NHCHO |
| OCF₃ | 7-Cl | Et | NH(CO)Me | OCF₃ | 7-Cl | Et | NHCHO |
| OCF₃ | 7-Cl | i-Pr | NH(CO)Me | OCF₃ | 7-Cl | i-Pr | NHCHO |
| CF₃ | 6-F | 4-F-Ph | NH(CO)NHMe | CF₃ | 6-F | 4-F-Ph | NHCO₂Me |
| CF₃ | 6-F | Me | NH(CO)NHMe | CF₃ | 6-F | Me | NHCO₂Me |
| CF₃ | 6-F | Et | NH(CO)NHMe | CF₃ | 6-F | Et | NHCO₂Me |
| CF₃ | 6-F | i-Pr | NH(CO)NHMe | CF₃ | 6-F | i-Pr | NRCO₂Me |
| CF₃ | 7-F | 4-F-Ph | NH(CO)NHMe | CF₃ | 7-F | 4-F-Ph | NHCO₂Me |
| CF₃ | 7-F | Me | NH(CO)NHMe | CF₃ | 7-F | Me | NHCO₂Me |
| CF₃ | 7-F | Et | NH(CO)NHMe | CF₃ | 7-F | Et | NHCO₂Me |
| CF₃ | 7-F | i-Pr | NH(CO)NHMe | CF₃ | 7-F | i-Pr | NHCO₂Me |
| CF₃ | 7-Cl | 4-F-Ph | NH(CO)NHMe | CF₃ | 7-Cl | 4-F-Ph | NHCO₂Me |
| CF₃ | 7-Cl | Me | NH(CO)NHMe | CF₃ | 7-Cl | Me | NHCO₂Me |
| CF₃ | 7-Cl | Et | NH(CO)NHMe | CF₃ | 7-Cl | Et | NHCO₂Me |
| CF₃ | 7-Cl | i-Pr | NH(CO)NHMe | CF₃ | 7-Cl | i-Pr | NHCO₂Me |
| OCF₃ | 6-F | 4-F-Ph | NH(CO)NHMe | OCF₃ | 6-F | 4-F-Ph | NHCO₂Me |
| OCF₃ | 6-F | Me | NH(CO)NHMe | OCF₃ | 6-F | Me | NHCO₂Me |
| OCF₃ | 6-F | Et | NH(CO)NHMe | OCF₃ | 6-F | Et | NHCO₂Me |
| OCF₃ | 6-F | i-Pr | NH(CO)NNMe | OCF₃ | 6-F | i-Pr | NHCO₂Me |
| OCF₃ | 7-F | 4-F-Ph | NH(CO)NHMe | OCF₃ | 7-F | 4-F-Ph | NHCO₂Me |
| OCF₃ | 7-F | Me | NH(CO)NHMe | OCF₃ | 7-F | Me | NHCO₂Me |
| OCF₃ | 7-F | Et | NH(CO)NHMe | OCF₃ | 7-F | Et | NHCO₂Me |
| OCF₃ | 7-F | i-Pr | NH(CO)NHMe | OCF₃ | 7-F | i-Pr | NHCO₂Me |
| OCF₃ | 7-Cl | 4-F-Ph | NH(CO)NHMe | OCF₃ | 7-Cl | 4-F-Ph | NHCO₂Me |
| OCF₃ | 7-Cl | Me | NH(CO)NHMe | OCF₃ | 7-Cl | Me | NHCO₂Me |
| OCF₃ | 7-Cl | Et | NH(CO)NHMe | OCF3 | 7-Cl | Et | NHCO₂Me |
| OCF₃ | 7-Cl | i-Pr | NH(CO)NHMe | OCF₃ | 7-Cl | i-Pr | NHCO₂Me |
| CF₃ | 6-F | 4-F-Ph | N=CH₂ | CF₃ | 6-F | 4-F-Ph | N=CMe₂ |
| CF₃ | 6-F | Me | N=CH₂ | CF₃ | 6-F | Me | N=CMe₂ |
| CF₃ | 6-F | Et | N=CH₂ | CF₃ | 6-F | Et | N=CMe₂ |
| CF₃ | 6-F | i-Pr | N=CH₂ | CF₃ | 6-F | i-Pr | N=CMe₂ |
| CF₃ | 7-F | 4-F-Ph | N=CH₂ | CF₃ | 7-F | 4-F-Ph | N=CMe₂ |
| CF₃ | 7-F | Me | N=CH₂ | CF₃ | 7-F | Me | N=CMe₂ |
| CF₃ | 7-F | Et | N=CH₂ | CF₃ | 7-F | Et | N=CMe₂ |
| CF₃ | 7-F | i-Pr | N=CH₂ | CF₃ | 7-F | i-Pr | N=CMe₂ |

TABLE 21-continued

| R¹ | R² | R³ | Y | R¹ | R² | R³ | Y |
|---|---|---|---|---|---|---|---|
| CF₃ | 7-Cl | 4-F-Ph | N=CH₂ | CF₃ | 7-Cl | 4-F-Ph | N=CMe₂ |
| CF₃ | 7-Cl | Me | N=CH₂ | CF₃ | 7-Cl | Me | N=CMe₂ |
| CF₃ | 7-Cl | Et | N=CH₂ | CF₃ | 7-Cl | Et | N=CMe₂ |
| CF₃ | 7-Cl | i-Pr | N=CH₂ | CF₃ | 7-Cl | i-Pr | N=CMe₂ |
| OCF₃ | 6-F | 4-F-Ph | N=CH₂ | OCF₃ | 6-F | 4-F-Ph | N=CMe₂ |
| OCF₃ | 6-F | Me | N=CH₂ | OCF₃ | 6-F | Me | N=CMe₂ |
| OCF₃ | 6-F | Et | N=CH₂ | OCF₃ | 6-F | Et | N=CMe₂ |
| OCF₃ | 6-F | i-Pr | N=CH₂ | OCF₃ | 6-F | i-Pr | N=CMe₂ |
| OCF₃ | 7-F | 4-F-Ph | N=CH₂ | OCF₃ | 7-F | 4-F-Ph | N=CMe₂ |
| OCF₃ | 7-F | Me | N=CH₂ | OCF₃ | 7-F | Me | N=CMe₂ |
| OCF₃ | 7-F | Et | N=CH₂ | OCF₃ | 7-F | Et | N=CMe₂ |
| OCF₃ | 7-F | i-Pr | N=CH₂ | OCF₃ | 7-F | i-Pr | N=CMe₂ |
| OCF₃ | 7-Cl | 4-F-Ph | N=CH₂ | OCF₃ | 7-Cl | 4-F-Ph | N=CMe₂ |
| OCF₃ | 7-Cl | Me | N=CH₂ | OCF₃ | 7-Cl | Me | N=CMe₂ |
| OCF₃ | 7-Cl | Et | N=CH₂ | OCF₃ | 7-Cl | Et | N=CMe₂ |
| OCF₃ | 7-Cl | i-Pr | N=CH₂ | OCF₃ | 7-Cl | i-Pr | N=CMe₂ |
| CF₃ | 6-F | 4-F-Ph | N=CHPh | CF₃ | 6-F | 4-F-Ph | OH |
| CF₃ | 6-F | Me | N=CHPh | CF₃ | 6-F | Me | OH |
| CF₃ | 6-F | Et | N=CHPh | CF₃ | 6-F | Et | OH |
| CF₃ | 6-F | i-Pr | N=CHPh | CF₃ | 6-F | i-Pr | OH |
| CF₃ | 7-F | 4-F-Ph | N=CHPh | CF₃ | 7-F | 4-F-Ph | OH |
| CF₃ | 7-F | Me | N=CHPh | CF₃ | 7-F | Me | OH |
| CF₃ | 7-F | Et | N=CHPh | CF₃ | 7-F | Et | OH |
| CF₃ | 7-F | i-Pr | N=CHPh | CF₃ | 7-F | i-Pr | OH |
| CF₃ | 7-Cl | 4-F-Ph | N=CHPh | CF₃ | 7-Cl | 4-F-Ph | OH |
| CF₃ | 7-Cl | Me | N=CHPh | CF₃ | 7-Cl | Me | OH |
| CF₃ | 7-Cl | Et | N=CHPh | CF₃ | 7-Cl | Et | OH |
| CF₃ | 7-Cl | i-Pr | N=CHPh | CF₃ | 7-Cl | i-Pr | OH |
| OCF₃ | 6-F | 4-F-Ph | N=CHPh | OCF₃ | 6-F | 4-F-Ph | OH |
| OCF₃ | 6-F | Me | N=CHPh | OCF₃ | 6-F | Me | OH |
| OCF₃ | 6-F | Et | N=CHPh | OCF₃ | 6-F | Et | OH |
| OCF₃ | 6-F | i-Pr | N=CHPh | OCF₃ | 6-F | i-Pr | OH |
| OCF₃ | 7-F | 4-F-Ph | N=CHPh | OCF₃ | 7-F | 4-F-Ph | OH |
| OCF₃ | 7-F | Me | N=CHPh | OCF₃ | 7-F | Me | OH |
| OCF₃ | 7-F | Et | N=CHPh | OCF₃ | 7-F | Et | OH |
| OCF₃ | 7-F | i-Pr | N=CHPh | OCF₃ | 7-F | i-Pr | OH |
| OCF₃ | 7-Cl | 4-F-Ph | N=CHPh | OCF₃ | 7-Cl | 4-F-Ph | OH |
| OCF₃ | 7-Cl | Me | N=CHPh | OCF₃ | 7-Cl | Me | OH |
| OCF₃ | 7-Cl | Et | N=CHPh | OCF₃ | 7-Cl | Et | OH |
| OCF₃ | 7-Cl | i-Pr | N=CHPh | OCF₃ | 7-Cl | i-Pr | OH |
| CF₃ | 6-F | 4-F-Ph | OMe | CF₃ | 6-F | 4-F-Ph | OCH₂Ph |
| CF₃ | 6-F | Me | OMe | CF₃ | 6-F | Me | OCH₂Ph |
| CF₃ | 6-F | Et | OMe | CF₃ | 6-F | Et | OCH₂Ph |
| CF₃ | 6-F | i-Pr | OMe | CF₃ | 6-F | i-Pr | OCH₂Ph |
| CF₃ | 7-F | 4-F-Ph | OMe | CF₃ | 7-F | 4-F-Ph | OCH₂Ph |
| CF₃ | 7-F | Me | OMe | CF₃ | 7-F | Me | OCH₂Ph |
| CF₃ | 7-F | Et | OMe | CF₃ | 7-F | Et | OCH₂Ph |
| CF₃ | 7-F | i-Pr | OMe | CF₃ | 7-F | i-Pr | OCH₂Ph |
| CF₃ | 7-Cl | 4-F-Ph | OMe | CF₃ | 7-Cl | 4-F-Ph | OCH₂Ph |
| CF₃ | 7-Cl | Me | OMe | CF₃ | 7-Cl | Me | OCH₂Ph |
| CF₃ | 7-Cl | Et | OMe | CF₃ | 7-Cl | Et | OCH₂Ph |
| CF₃ | 7-Cl | i-Pr | OMe | CF₃ | 7-Cl | i-Pr | OCH₂Ph |
| OCF₃ | 6-F | 4-F-Ph | OMe | OCF₃ | 6-F | 4-F-Ph | OCH₂Ph |
| OCF₃ | 6-F | Me | OMe | OCF₃ | 6-F | Me | OCH₂Ph |
| OCF₃ | 6-F | Et | OMe | OCF₃ | 6-F | Et | OCH₂Ph |
| OCF₃ | 6-F | i-Pr | OMe | OCF₃ | 6-F | i-Pr | OCH₂Ph |
| OCF₃ | 7-F | 4-F-Ph | OMe | OCF₃ | 7-F | 4-F-Ph | OCH₂Ph |
| OCF₃ | 7-F | Me | OMe | OCF₃ | 7-F | Me | OCH₂Ph |
| OCF₃ | 7-F | Et | OMe | OCF₃ | 7-F | Et | OCH₂Ph |
| OCF₃ | 7-F | i-Pr | OMe | OCF₃ | 7-F | i-Pr | OCH₂Ph |
| OCF₃ | 7-Cl | 4-F-Ph | CMe | OCF₃ | 7-Cl | 4-F-Ph | OCH₂Ph |
| OCF₃ | 7-Cl | Me | OMe | OCF₃ | 7-Cl | Me | OCH₂Ph |
| OCF₃ | 7-Cl | Et | OMe | OCF₃ | 7-Cl | Et | OCH₂Ph |
| OCF₃ | 7-Cl | i-Pr | OMe | OCF₃ | 7-Cl | i-Pr | OCH₂Ph |

TABLE 22

| R¹ | R² | R³ | Y | R¹ | R² | R³ | Y |
|---|---|---|---|---|---|---|---|
| OCF₃ | 6-F | 4-F-Ph | Me | CF₃ | 7-F | Et | Et |
| OCF₃ | 6-F | Me | Me | CF₃ | 7-F | i-Pr | Et |
| OCF₃ | 6-F | Et | Me | CF₃ | 7-Cl | 4-F-Ph | Et |
| OCF₃ | 6-F | i-Pr | Me | CF₃ | 7-Cl | Me | Et |
| OCF₃ | 7-F | 4-F-Ph | Me | CF₃ | 7-Cl | Et | Et |
| OCF₃ | 7-F | Me | Me | CF₃ | 7-Cl | i-Pr | Et |

TABLE 22-continued

| R¹ | R² | R³ | Y | R¹ | R² | R³ | Y |
| --- | --- | --- | --- | --- | --- | --- | --- |
| OCF₃ | 7-F | Et | Me | OCF₃ | 6-F | 4-F-Ph | Et |
| OCF₃ | 7-F | i-Pr | Me | OCF₃ | 6-F | Me | Et |
| OCF₃ | 7-Cl | 4-F-Ph | Me | OCF₃ | 6-F | Et | Et |
| OCF₃ | 7-Cl | Me | Me | OCF₃ | 6-F | i-Pr | Et |
| OCF₃ | 7-Cl | Et | Me | OCF₃ | 7-F | 4-F-Ph | Et |
| OCF₃ | 7-Cl | i-Pr | Me | OCF₃ | 7-F | Me | Et |
| CF₃ | 6-F | 4-F-Ph | Et | OCF₃ | 7-F | Et | Et |
| CF₃ | 6-F | Me | Et | OCF₃ | 7-F | i-Pr | Et |
| CF₃ | 6-F | Et | Et | OCF₃ | 7-Cl | 4-F-Ph | Et |
| CF₃ | 6-F | i-Pr | Et | OCF₃ | 7-Cl | Me | Et |
| CF₃ | 7-F | 4-F-Ph | Et | OCF₃ | 7-Cl | Et | Et |
| CF₃ | 7-F | Me | Et | OCF₃ | 7-Cl | i-Pr | Et |
| CF₃ | 6-F | 4-F-Ph | —CH₂OCH₃ | CF₃ | 6-F | 4-F-Ph | —CH₂CO₂Me |
| CF₃ | 6-F | Me | —CH₂OCH₃ | CF₃ | 6-F | Me | —CH₂CO₂Me |
| CF₃ | 6-F | Et | —CH₂OCH₃ | CF₃ | 6-F | Et | —CH₂CO₂Me |
| CF₃ | 6-F | i-Pr | —CH₂OCH₃ | CF₃ | 6-F | i-Pr | —CH₂CO₂Me |
| CF₃ | 7-F | 4-F-Ph | —CH₂OCH₃ | CF₃ | 7-F | 4-F-Ph | —CH₂CO₂Me |
| CF₃ | 7-F | Me | —CH₂OCH₃ | CF₃ | 7-F | Me | —CH₂CO₂Me |
| CF₃ | 7-F | Et | —CH₂OCH₃ | CF₃ | 7-F | Et | —CH₂CO₂Me |
| CF₃ | 7-F | i-Pr | —CH₂OCH₃ | CF₃ | 7-F | i-Pr | —CH₂CO₂Me |
| CF₃ | 7-Cl | 4-F-Ph | —CH₂OCH₃ | CF₃ | 7-Cl | 4-F-Ph | —CK₂CO₂Me |
| CF₃ | 7-Cl | Me | —CH₂OCH₃ | CF₃ | 7-Cl | Me | —CH₂CO₂Me |
| CF₃ | 7-Cl | Et | —CH₂OCH₃ | CF₃ | 7-Cl | Et | —CH₂CO₂Me |
| CF₃ | 7-Cl | i-Pr | —CH₂OCH₃ | CF₃ | 7-Cl | i-Pr | —CH₂CO₂Me |
| OCF₃ | 6-F | 4-F-Ph | —CH₂OCH₃ | OCF₃ | 6-F | 4-F-Ph | —CH₂CO₂Me |
| OCF₃ | 6-F | Me | —CH₂OCH₃ | OCF₃ | 6-F | Me | —CH₂CO₂Me |
| OCF₃ | 6-F | Et | —CH₂OCH₃ | OCF₃ | 6-F | Et | —CH₂CO₂Me |
| OCF₃ | 6-F | i-Pr | —CH₂OCH₃ | OCF₃ | 6-F | i-Pr | —CH₂CO₂Me |
| OCF₃ | 7-F | 4-F-Ph | —CH₂OCH₃ | OCF₃ | 7-F | 4-F-Ph | —CH₂CO₂Me |
| OCF₃ | 7-F | Me | —CH₂OCH₃ | OCF₃ | 7-F | Me | —CH₂CO₂Me |
| OCF₃ | 7-F | Et | —CH₂OCH₃ | OCF₃ | 7-F | Et | —CH₂CO₂Me |
| OCF₃ | 7-F | i-Pr | —CH₂OCH₃ | OCF₃ | 7-F | i-Pr | —CH₂CO₂Me |
| OCF₃ | 7-Cl | 4-F-Ph | —CH₂OCH₃ | OCF₃ | 7-Cl | 4-F-Ph | —CH₂CO2Me |
| OCF₃ | 7-Cl | Me | —CH₂OCH₃ | OCF₃ | 7-Cl | Me | —CH₂CO₂Me |
| OCF₃ | 7-Cl | Et | —CH₂OCH₃ | OCF₃ | 7-Cl | Et | —CH₂CO₂Me |
| OCF₃ | 7-Cl | i-Pr | —CH₂OCH₃ | OCF₃ | 7-Cl | i-Pr | —CH₂CO₂Me |
| CF₃ | 6-F | 4-F-Ph | —CH₂C≡CH | CF₃ | 6-F | 4-F-Ph | —CH₂CH=CH₂ |
| CF₃ | 6-F | Me | —CH₂C≡CH | CF₃ | 6-F | Me | —CH₂CH=CH₂ |
| CF₃ | 6-F | Et | —CH₂C≡CH | CF₃ | 6-F | Et | —CH₂CH=CH₂ |
| CF₃ | 6-F | i-Pr | —CH₂C≡CH | CF₃ | 6-F | i-Pr | —CH₂CH=CH₂ |
| CF₃ | 7-F | 4-F-Ph | —CH₂C≡CH | CF₃ | 7-F | 4-F-Ph | —CH₂CH=CH₂ |
| CF₃ | 7-F | Me | —CH₂C≡CH | CF₃ | 7-F | Me | —CH₂CH=CH₂ |
| CF₃ | 7-F | Et | —CH₂C≡CH | CF₃ | 7-F | Et | —CH₂CH=CH₂ |
| CF₃ | 7-F | i-Pr | —CH₂C≡CH | CF₃ | 7-F | i-Pr | —CH₂CH=CH₂ |
| CF₃ | 7-Cl | 4-F-Ph | —CH₂C≡CH | CF₃ | 7-Cl | 4-F-Ph | —CH₂CH=CH₂ |
| CF₃ | 7-Cl | Me | —CH₂C≡CH | CF₃ | 7-Cl | Me | —CH₂CH=CH₂ |
| CF₃ | 7-Cl | Et | —CH₂C≡CH | CF₃ | 7-Cl | Et | —CH₂CH=CH₂ |
| CF₃ | 7-Cl | i-Pr | —CH₂C≡CH | CF₃ | 7-Cl | i-Pr | —CH₂CH=CH₂ |
| OCF₃ | 6-F | 4-F-Ph | —CH₂C≡CH | OCF₃ | 6-F | 4-F-Ph | —CH₂CH=CH₂ |
| OCF₃ | 6-F | Me | —CH₂C≡CH | OCF₃ | 6-F | Me | —CH₂CH=CH₂ |
| OCF₃ | 6-F | Et | —CH₂C≡CH | OCF₃ | 6-F | Et | —CH₂CH=CH₂ |
| OCF₃ | 6-F | i-Pr | —CH₂C≡CH | OCF₃ | 6-F | i-Pr | —CH₂CH=CH₂ |
| OCF₃ | 7-F | 4-F-Ph | —CH₂C≡CH | OCF₃ | 7-F | 4-F-Ph | —CH₂CH=CH₂ |
| OCF₃ | 7-F | Me | —CH₂C≡CH | OCF₃ | 7-F | Me | —CH₂CH=CH₂ |
| OCF₃ | 7-F | Et | —CH₂C≡CH | OCF₃ | 7-F | Et | —CH₂CH=CH₂ |
| OCF₃ | 7-F | i-Pr | —CH₂C≡CH | OCF₃ | 7-F | i-Pr | —CH₂CH=CH₂ |
| OCF₃ | 7-Cl | 4-F-Ph | —CH₂C≡CH | OCF₃ | 7-Cl | 4-F-Ph | —CH₂CH=CH₂ |
| OCF₃ | 7-Cl | Me | —CH₂C≡CH | OCF₃ | 7-Cl | Me | —CH₂CH=CH₂ |
| OCF₃ | 7-Cl | Et | —CH₂C≡CH | OCF₃ | 7-Cl | Et | —CH₂CH=CH₂ |
| OCF₃ | 7-Cl | i-Pr | —CH₂C≡CH | OCF₃ | 7-Cl | i-Pr | —CH₂CH=CH₂ |

TABLE 23

| R¹ | R² | R³ | Y | R¹ | R² | R³ | Y |
| --- | --- | --- | --- | --- | --- | --- | --- |
| CF₃ | 6-F | 4-F-Ph | Me | CF₃ | 6-F | 4-F-Ph | Et |
| CF₃ | 6-F | Me | Me | CF₃ | 6-F | Me | Et |
| CF₃ | 6-F | Et | Me | CF₃ | 6-F | Et | Et |
| CF₃ | 6-F | i-Pr | Me | CF₃ | 6-F | i-Pr | Et |
| CF₃ | 7-F | 4-F-Ph | Me | CF₃ | 7-F | 4-F-Ph | Et |
| CF₃ | 7-F | Me | Me | CF₃ | 7-F | Me | Et |
| CF₃ | 7-F | Et | Me | CF₃ | 7-F | Et | Et |
| CF₃ | 7-F | i-Pr | Me | CF₃ | 7-F | i-Pr | Et |
| CF₃ | 7-Cl | 4-F-Ph | Me | CF₃ | 7-Cl | 4-F-Ph | Et |
| CF₃ | 7-Cl | Me | Me | CF₃ | 7-Cl | Me | Et |

TABLE 23-continued

| R¹ | R² | R³ | Y | R¹ | R² | R³ | Y |
|---|---|---|---|---|---|---|---|
| CF₃ | 7-Cl | Et | Me | CF₃ | 7-Cl | Et | Et |
| CF₃ | 7-Cl | i-Pr | Me | CF₃ | 7-Cl | i-Pr | Et |
| OCF₃ | 6-F | 4-F-Ph | Me | OCF₃ | 6-F | 4-F-Ph | Et |
| OCF₃ | 6-F | Me | Me | OCF₃ | 6-F | Me | Et |
| OCF₃ | 6-F | Et | Me | OCF₃ | 6-F | Et | Et |
| OCF₃ | 6-F | i-Pr | Me | OCF₃ | 6-F | i-Pr | Et |
| OCF₃ | 7-F | 4-F-Ph | Me | OCF₃ | 7-F | 4-F-Ph | Et |
| OCF₃ | 7-F | Me | Me | OCF₃ | 7-F | Me | Et |
| OCF₃ | 7-F | Et | Me | OCF₃ | 7-F | Et | Et |
| OCF₃ | 7-F | i-Pr | Me | OCF₃ | 7-F | i-Pr | Et |
| OCF₃ | 7-Cl | 4-F-Ph | Me | OCF₃ | 7-Cl | 4-F-Ph | Et |
| OCF₃ | 7-Cl | Me | Me | OCF₃ | 7-Cl | Me | Et |
| OCF₃ | 7-Cl | Et | Me | OCF₃ | 7-Cl | Et | Et |
| OCF₃ | 7-Cl | i-Pr | Me | OCF₃ | 7-Cl | i-Pr | Et |
| CF₃ | 6-F | 4-F-Ph | —CH₂OCH₃ | CF₃ | 6-F | 4-F-Ph | —CH₂CO₂Me |
| CF₃ | 6-F | Me | —CH₂OCH₃ | CF₃ | 6-F | Me | —CH₂CO₂Me |
| CF₃ | 6-F | Et | —CH₂OCH₃ | CF₃ | 6-F | Et | —CH₂CO₂Me |
| CF₃ | 6-F | i-Pr | —CH₂OCH₃ | CF₃ | 6-F | i-Pr | —CH₂CO₂Me |
| CF₃ | 7-F | 4-F-Ph | —CH₂OCH₃ | CF₃ | 7-F | 4-F-Ph | —CH₂CO₂Me |
| CF₃ | 7-F | Me | —CH₂OCH₃ | CF₃ | 7-F | Me | —CH₂CO₂Me |
| CF₃ | 7-F | Et | —CH₂OCH₃ | CF₃ | 7-F | Et | —CH₂CO₂Me |
| CF₃ | 7-F | i-Pr | —CH₂OCH₃ | CF₃ | 7-F | i-Pr | —CH₂CO₂Me |
| CF₃ | 7-Cl | 4-F-Ph | —CH₂OCH₃ | CF₃ | 7-Cl | 4-F-Ph | —CH₂CO₂Me |
| CF₃ | 7-Cl | Me | —CH₂OCH₃ | CF₃ | 7-Cl | Me | —CH₂CO₂Me |
| CF₃ | 7-Cl | Et | —CH₂OCH₃ | CF₃ | 7-Cl | Et | —CH₂CO₂Me |
| CF₃ | 7-Cl | i-Pr | —CH₂OCH₃ | CF₃ | 7-Cl | i-Pr | —CH₂CO₂Me |
| OCF₃ | 6-F | 4-F-Ph | —CH₂OCH₃ | OCF₃ | 6-F | 4-F-Ph | —CH₂CO₂Me |
| OCF₃ | 6-F | Me | —CH₂OCH₃ | OCF₃ | 6-F | Me | —CH₂CO₂Me |
| OCF₃ | 6-F | Et | —CH₂OCH₃ | OCF₃ | 6-F | Et | —CH₂CO₂Me |
| OCF₃ | 6-F | i-Pr | —CH₂OCH₃ | OCF₃ | 6-F | i-Pr | —CH₂CO₂Me |
| OCF₃ | 7-F | 4-F-Ph | —CH₂OCH₃ | OCF₃ | 7-F | 4-F-Ph | —CH₂CO₂Me |
| OCF₃ | 7-F | Me | —CH₂OCH₃ | OCF₃ | 7-F | Me | —CH₂CO₂Me |
| OCF₃ | 7-F | Et | —CH₂OCH₃ | OCF₃ | 7-F | Et | —CH₂CO₂Me |
| OCF₃ | 7-F | i-Pr | —CH₂OCH₃ | OCF₃ | 7-F | i-Pr | —CH₂CO₂Me |
| OCF₃ | 7-Cl | 4-F-Ph | —CH₂OCH₃ | OCF₃ | 7-Cl | 4-F-Ph | —CH₂CO₂Me |
| OCF₃ | 7-Cl | Me | —CH₂OCH₃ | OCF₃ | 7-Cl | Me | —CH₂CO₂Me |
| OCF₃ | 7-Cl | Et | —CH₂OCH₃ | OCF₃ | 7-Cl | Et | —CH₂CO₂Me |
| OCF₃ | 7-Cl | i-Pr | —CH₂OCH₃ | OCF₃ | 7-Cl | i-Pr | —CH₂CO₂Me |
| CF₃ | 6-F | 4-F-Ph | —CH₂C≡CH | CF₃ | 6-F | 4-F-Ph | —CH₂CH=CH₂ |
| CF₃ | 6-F | Me | —CH₂C≡CH | CF₃ | 6-F | Me | —CH₂CH=CH₂ |
| CF₃ | 6-F | Et | —CH₂C≡CH | CF₃ | 6-F | Et | —CH₂CH=CH₂ |
| CF₃ | 6-F | i-Pr | —CH₂C≡CH | CF₃ | 6-F | i-Pr | —CH₂CH=CH₂ |
| CF₃ | 7-F | 4-F-Ph | —CH₂C≡CH | CF₃ | 7-F | 4-F-Ph | —CH₂CH=CH₂ |
| CF₃ | 7-F | Me | —CH₂C≡CH | CF₃ | 7-F | Me | —CH₂CH=CH₂ |
| CF₃ | 7-F | Et | —CH₂C≡CH | CF₃ | 7-F | Et | —CH₂CH=CH₂ |
| CF₃ | 7-F | i-Pr | —CH₂C≡CH | CF₃ | 7-F | i-Pr | —CH₂CH=CH₂ |
| CF₃ | 7-Cl | 4-F-Ph | —CH₂C≡CH | CF₃ | 7-Cl | 4-F-Ph | —CH₂CH=CH₂ |
| CF₃ | 7-Cl | Me | —CH₂C≡CH | CF₃ | 7-Cl | Me | —CH₂CH=CH₂ |
| CF₃ | 7-Cl | Et | —CH₂C≡CH | CF₃ | 7-Cl | Et | —CH₂CH=CH₂ |
| CF₃ | 7-Cl | i-Pr | —CH₂C≡CH | CF₃ | 7-Cl | i-Pr | —CH₂CH=CH₂ |
| OCF₃ | 6-F | 4-F-Ph | —CH₂C≡CH | OCF₃ | 6-F | 4-F-Ph | —CH₂CH=CH₂ |
| OCF₃ | 6-F | Me | —CH₂C≡CH | OCF₃ | 6-F | Me | —CH₂CH=CH₂ |
| OCF₃ | 6-F | Et | —CH₂C≡CH | OCF₃ | 6-F | Et | —CH₂CH=CH₂ |
| OCF₃ | 6-F | i-Pr | —CH₂C≡CH | OCF₃ | 6-F | i-Pr | —CH₂CH=CH₂ |
| OCF₃ | 7-F | 4-F-Ph | —CH₂C≡CH | OCF₃ | 7-F | 4-F-Ph | —CH₂CH=CH₂ |
| OCF₃ | 7-F | Me | —CH₂C≡CH | OCF₃ | 7-F | Me | —CH₂CH=CH₂ |
| OCF₃ | 7-F | Et | —CH₂C≡CH | OCF₃ | 7-F | Et | —CH₂CH=CH₂ |
| OCF₃ | 7-F | i-Pr | —CH₂C≡CH | OCF₃ | 7-F | i-Pr | —CH₂CH=CH₂ |
| OCF₃ | 7-Cl | 4-F-Ph | —CH₂C≡CH | OCF₃ | 7-Cl | 4-F-Ph | —CH₂CH=CH₂ |
| OCF₃ | 7-Cl | Me | —CH₂C≡CH | OCF₃ | 7-Cl | Me | —CH₂CH=CH₂ |
| OCF₃ | 7-Cl | Et | —CH₂C≡CH | OCF₃ | 7-Cl | Et | —CH₂CH=CH₂ |
| OCF₃ | 7-Cl | i-Pr | —CH₂C≡CH | OCF₃ | 7-Cl | i-Pr | —CH₂CH=CH₂ |

Formulation and Use

The compounds of this invention will generally be used in formulation with an agriculturally suitable carrier comprising a liquid or solid diluent or an organic solvent. Useful formulations of the compounds of Formula I can be prepared in conventional ways. They include dusts, granules, baits, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain from less than about 1% to 99% by weight of active ingredient(s) and at least one of a) about 0.1%. to 20% surfactant(s) cud b) about 5% to 99% solid or liquid diluent(s). More specifically, they will contain effective amounts of these ingredients in the following approximate proportions:

|  | Percent by Weight | | |
| --- | --- | --- | --- |
|  | Active Ingredient | Diluent(s) | Surfactant(s) |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed Dorland Books, Caldwell, N.J. The more absorptive diluents are preferred for wettable powders and the denser ones for dusts. Typical liquid diluents and solvents are described in Marsden, "Solvents Guide," 2nd Ed , Interscience, New York, 1950. Solubility under 0.1% is preferred for suspension concentrates; solution concentrates are preferably stable against phase separation at 0° C. "McCutcheon's Detergents and Emulsifiers Annual", Allured Publ Corp., Ridgewood, N.J., as well as Sisely and Wood, "Encyclopedia of Surface Active Agents", Chemical Publ. Co., Inc., New York, 1964, list surfactants and recommended uses. All formulations can-contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See J. E. Browning, "Agglomeration", *Chemical Engineering*, Dec. 4, 1967, pages 147 and following, and "Perry's Chemical Engineer's Handbook", 4th Ed., McGraw-Hill, New York, 1963, pages 8 to 59 and following.

Example A

| Emulsifiable Concentrate | |
| --- | --- |
| Methyl 2,3-dihydro-2-[[N-methyl-N-[4-(trifluoromethyl)phenyl]amino]carbonyl]-7-(trifluoromethyl)[1]benzopyrano-[4,3-c]pyrazole-3a(4H)-carboxylate | 20% |
| blend of oil soluble sulfonates and polyoxyethylene ethers | 10% |
| isophorone | 70% |

The ingredients are combined and stirred with gentle warming to speed solution. A fine screen filter is included in the packaging operation to insure the absence of any extraneous undissolved material in the product.

Example B

| Wettable Powder | |
| --- | --- |
| Methyl 7-chloro-2,3-dihydro-2-[[N-methyl-N-[4-(trifluoromethyl)phenyl]amino]carbonyl]-[1]benzopyrano[4,3-c]pyrazole-3a(4H)-carboxylate | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammer-mill, the material is re-blended and sifted through a 50 mesh screen.

Example C

| Dust | |
| --- | --- |
| Wettable powder of Example B | 10% |
| pyrophyllite (powder) | 90% |

The wettable powder and the pyrophyllite diluent are thoroughly blended and then packaged. The product is suitable for use as a dust.

Example D

| Granule | |
| --- | --- |
| Methyl 2-[[N-(4-chlorophenyl)-N-methylamino]-carbonyl]2,3-dihydro-7-(trifluoromethyl)[1]-benzopyrano[4,3-c]-pyrazole-3a(4H)-carboxylate | 10% |
| attapulgite granules (low volative matter, 0.71/0.30 mm; U.S.S. No. 25–50 sieves) | 90% |

The active ingredient is dissolved in a volatile solvent such as acetone and sprayed upon dedusted and pre-warmed attapulgite granules in a double cone blender. The acetone is then driven off by heating. The granules are then allowed to cool and are packaged.

Example E

| Granule | |
| --- | --- |
| Wettable powder of Example B | 15% |
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

Example F

| Solution | |
| --- | --- |
| Methyl 2-[[N-(4-bromophenyl)-N-methylamino]-carbonyl]2,3-dihydro-7-(trifluoromethyl)-[1]-benzopyrano[4,3-c]pyrazole-3a(4H)-carboxylate | 25% |

-continued

| Solution | |
|---|---|
| N-methyl-pyrrolidone | 75% |

The ingredients are combined and stirred to produce solution suitable for direct, low volume application.

Example G

| Aqueous Suspension | |
|---|---|
| Methyl 2,3-dihydro-2-[[N-methyl-N-[4-(trifluoromethoxy)phenyl]amino]carbonyl]-7-(trifluoromethyl)[1]benzopyrano[4,3-c]pyrazole-3a(4H)-carboxylate | 40% |
| polyacrylic acid thickener | 0.3% |
| dodecyclophenol polyethylene glycol | 0.5% |
| disodium phosphate | 1.0% |
| monosodium phosphate | 0.5% |
| polyvinyl alcohol | 1.0% |
| water | 56.7% |

The ingredients are blended and ground together in sand mill to produce particles substantially all under 5 microns in size.

Example H

| Oil Suspension | |
|---|---|
| Methyl 2,3-dihydro-2-[[N-methyl-N-[4-(trifluoromethyl)phenyl]amino]carbonyl]-7-(trifluoromethyl)[1]benzopyrano[4,3-c]-pyrazole-3a(4H)-carboxylate | 35.0% |
| blend of polyalcohol carboxylic esters and oil soluble petroleum sulfonates | 6.0% |
| xylene range solvent | 59.0% |

The ingredients are combined and ground together in a sand mill to produce particles substantially all below 5 microns. The product can be used directly, extended with oils, or emulsified in water.

Example I

| Bait Granules | |
|---|---|
| Methyl 2,3-dihydro-2-[[N-methyl-N-[4(trifluoromethyl)phenyl]amino]carbonyl]-7-(trifluoromethyl)[1]benzopyrano[4,3-c]-pyrazole-3a(4H)-carboxylate | 3.0% |
| blend of polyethoxylated nonylphenols and sodium dodecylbenzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged.

Compounds of Formula I can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of this invention can be formulated are:
Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl) benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with a-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-2-isopropyl-4-methyl-6-pyrimidylphosphorothioate (diazinon)
octachlorocamphene (toxaphene)
O-ethyl-O-p-nitrophenyl phenylphosphonothioate (EPN)
(S)-α-cyano-m-phenoxybenzyl (1R, 3R)-3-(2,2-dibromovinyl)- 2,2-dimethylcyclopropanecarboxylate (deltamethrin)
Methyl-N', N'-dimethyl-N-[(methylcarbamoyl)oxy]-1-thioox amimidate (oxamyl)
cyano (3-phenoxyphenyl)-methyl-4-chloro-α-(1-methylethyl)benzeneacetate (fenvalerate)
(3-phenoxyphenyl)methyl(+)-cis, trans-3-(2,2-dichloro ethenyl)-2,2-dimethylcyclopropanecarboxylate (permethrin)
α-cyano-3-phenoxybenzyl 3-(2,2-dichlorovinyl)-2,2-dimethylcyclopropane carboxylate (cypermethrin)
O-ethyl-S-(p-chlorophenyl)ethylphosphonodithioate (profenofos)
O-ethyl-O-[4-(methylthio)-phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotphos, phosmet, phosphamidon, phosalone, pirimicarb, phorate, terbufos, trichlorfon, methoxychlor, bifenthrin, biphenate, cyfluthrin, fenpropathrin, fluvalinate, flucythrinate, tralomethrin, metaldehyde and rotenone.
Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-ylmethyl]- 1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1-yl)- 2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl]methyl]-1H-1,2,4-triazole (flusilazol)
Nematocides:
S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid O-ethyl O'-[4-(methylthio)-m-tolyl]diester (fenamiphos)

Bactericides:
tribasic copper sulfate
streptomycin sulfate

Acaricides:
senecioic acid, ester with 2-sec-butyl-4,6-dinitro-phenol (binapacryl)
6-methyl-1,3-cithiolo[4,5-β]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxo-thiazolidine-3-carboxamide (hexythiazox)
amitraz
propargite
fenbutatin-oxide Biological
Bacillus thuringiensis
Avermectin B.

Utility

The compounds of this invention are characterized by favorable metabolic and soil residual patterns and exhibit activity against a wide spectrum of foliar and soil-inhabiting arthropods which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests but the compounds of this invention display activity against economically important agronomic, forestry, greenhouse, ornamental food and fiber product, stored product, domestic structure, and nursery pests, such as:

larvae of the order Lepidoptera including fall and beet armyworm and other Spodoptera spp., tobacco budworm, corn earworm and other Heliothis spp., European corn borer, navel orangeworm, stalk/stem borers and other pyralids, cabbage and soybean loopers and other loopers, codling moth, grape berry moth and other tortricids, black cutworm, spotted cutworm, other cutworms and other noctuids, diamondback moth, green cloverworm, velvetbean caterpillar, green cloverworm, pink bollworm, gypsy moth, and spruce budworm;

foliar feeding larvae and adults of the order Coleoptera including Colorado potato beetle, Mexican bean beetle, flea beetle, Japanese beetles, and other leaf beetles, boll weevil, rice water weevil, granary weevil, rice weevil and other weevil pests, and soil inhabiting insects such as Western corn rootworm and other Diabrotica spp., Japanese beetle, European chafer and other coleopteran grubs, and wireworms;

adults and larvae of the orders Hemiptera and Homoptera including tarnished plant bug and other plant bugs (miridae), aster leafhopper and other leafhoppers (cicadellidae), rice planthopper, brown planthopper, and other planthoppers (fulgoroidea), psylids, whiteflies (aleurodidae), aphids (aphidae), scales (coccidae and diaspididae), lace bugs (tingidae), stink bugs (pentatomidae), cinch bugs and other seed bugs (lygaeidae), cicadas (cicadidae), spittlebugs (cercopids), squash bugs (coredia), red bugs and cotton stainers (pyrrhocoridae);

adults and larvae of the order acari (mites) including European red mite, two spotted spider mite, rust mites, McDaniel mite, and foliar feeding mites;

adults and immatures of the order Orthoptera including grasshoppers;

adults and immatures of the order Diptera including leafminers, midges, fruit flies (tephritidae), and soil maggots;

adults and immatures of the order Thysanoptera including onion thrips and other foliar feeding thrips.

The compounds are also active against economically important livestock, household, public and animal health pests such as:

insect pests of the order Hymenoptera including carpenter ants, bees, hornets, and wasps;

insect pests of the order including house flies, stable flies, face flies, horn flies, blow flies, and other muscoid fly pests, horse flies, deer flies and other Brachycera, mosquitoes, black flies, biting midges, sand flies, sciarids, and other Nematocera;

insect pests of the order Orthoptera including cockroaches and crickets;

insect pests of the order Isoptera including the Eastern subterranean termite and other termites;

insect pests of the order Mallophaga and Anoplura including the head louse, body louse, chicken head louse and other sucking and chewing parasitic lice that attack man and animals;

insect pests of the order Siphonoptera including the cat flea, dog flea and other fleas.

The specific species for which control is exemplified are: fall armyworm, *Spodoptera fruigiperda*; tobacco budworm, *Heliothis virescens*; boll weevil, *Anthonomus grandis*; aster leafhopper, *Macrosteles fascifrons*; black bean aphid, (*Aphis Fabae*); southern corn rootworm, *Diabrotica undecimpunctata*. The pest control protection afforded by the compounds of the present invention is not limited, however, to these species. The compounds of this invention may also be utilized as rodenticides.

Application

Arthropod pests are controlled and protection of agronomic crops, animal and human health is achieved by applying one or more of the compounds of this invention, in an effective amount, to the environment of the pests including the agronomic and/or nonagronomic locus of infestation, to the area to be protected, or directly on the pests to be controlled. Because of the diversity of habitat and behavior of these arthropod pest species, many different methods of application are employed. A preferred method of application is by spraying with equipment that distributes the compound in the environment of the pests, on the foliage, animal, person, or premise, in the soil or animal, to the plant part that is infested or needs to be protected. Alternatively, granular formulations of these toxicant compounds can be applied to or incorporated into the soil. Other methods of application can also be employed including direct and residual sprays, aerial sprays, baits, eartags, boluses, foggers, aerosols, and many others. The compounds can be incorporated into baits that are consumed by the arthropods or in devices such as traps and the like which entice them to ingest or otherwise contact the compounds.

The compounds of this invention can be applied in their pure state, but most often application will be of a formulation comprising one or more compounds with suitable carriers (including diluents and surfactants) and possibly in combination with a food depending on the contemplated end use. A preferred method of application involves spraying a water dispersion or refined oil solution of the compounds. Combinations with spray oils, spray oil concentrations, and synergists such as piperonyl butoxide often enhance the efficacy of the compounds of this invention.

The rate of application of the compounds required for effective control will depend on such factors as the species of arthropod to be controlled, the pest's life cycle, life stage, its size, location, time of year, host crop or animal, feeding behavior, mating behavior, ambient moisture, temperature, etc. In general, application rates of 0.01 to 2 kg of active ingredient per hectare are sufficient to provide large-scale effective control of pests in agronomic ecosystems under normal circumstances, but as little as 0.001 kg/hectare or as much as 8 kg hectare may be required. For nonagronomic applications, effective use rates will range from about 1.0 to 50 mg/square meter but as little as about 0.1 mg/square meter or as much as 150 mg/square meter may be required.

The following Tests demonstrate the control efficacy of compounds of Formula I on specific pests; see Index Tables A and B for compound descriptions.

INDEX TABLE A

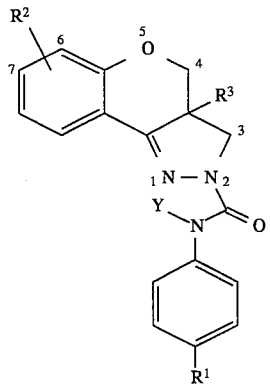

| Cmpd | $R^1$ | $R^2$ | $R^3$ | Y | mp (°C.) |
|---|---|---|---|---|---|
| 1 | $CF_3$ | 7-$CF_3$ | $CO_2CH_3$ | $CH_3$ | 107–110 |
| 2 | $CF_3$ | 7-Cl | $CH_3$ | $CH_3$ | 171–182 |
| 3 | $CF_3$ | 7-Cl | $CH(CH_3)_2$ | $CH_3$ | 138–142 |
| 4 | $CF_3$ | 6-F | 4-F—Ph | $CH_3$ | 180–186 |
| 5 | $CF_3$ | 7-Cl | $CO_2CH_3$ | $CH_3$ | 122–125 |
| 6 | $OCF_3$ | 7-$CF_3$ | $CO_2CH_3$ | $CH_3$ | 147–150 |
| 7 | Br | 7-$CF_3$ | $CO_2CH_3$ | $CH_3$ | 132–135 |
| 8 | $CF_3$ | H | $CO_2CH_3$ | $CH_3$ | 167–171 |
| 9 | $CF_3$ | 7-$CF_3$ | $CO_2CH_3$ | $CH_2OCH_3$ | 103–106 |
| 10 | $CF_3$ | 7-$CF_3$ | $CO_2CH_3$ | $CH_2CO_2CH_3$ | 111–115 |
| 11 | $CF_3$ | 7-$CF_3$ | $CO_2CH_3$ | $CH_2Ph$ | 68–70 |
| 12 | $CF_3$ | 7-$CF_3$ | $CO_2CH_3$ | $CH_2CH=CH_2$ | 88–90 |
| 13 | $CF_3$ | 7-$CF_3$ | $CO_2CH_3$ | $CH_2C\equiv CH$ | 98–100 |
| 14 | $CF_3$ | 7-$CF_3$ | $CO_2CH_3$ | $CH_2CH_3$ | 121–123 |
| 15 | $CF_3$ | 7-Cl | $CH(CH_3)_2$ | $CH_2CH=CH_2$ | oil |
| 16 | $CF_3$ | 7-$CF_3$ | $CO_2CH_3$ | $CH_2CN$ | 158–161 |
| 17 | Br | 7-$CF_3$ | $CO_2CH_3$ | $CH_2OCH_3$ | 128–130 |
| 18 | $CF_3$ | 7-Cl | $CH(CH_3)_2$ | $CH_2Ph$ | 161–164 |
| 19 | Br | 7-$CF_3$ | $CO_2CH_3$ | $CH_2Ph$ | 138–140 |
| 20 | $CF_3$ | 7-Cl | $CH(CH_3)_2$ | $CH_2C\equiv CH$ | 102–106 |
| 21 | $CF_3$ | 7-Cl | $CH(CH_3)_2$ | $CH_2CO_2CH_3$ | 165–167 |
| 22 | $CF_3$ | 7-$CF_3$ | $CO_2CH_3$ | $CH_2CO_2CH_2CH_3$ | 131–134 |
| 23 | $CF_3$ | 7-$CF_3$ | $CO_2CH_3$ | $CH_2CO_2C(CH_3)_3$ | 111–113 |
| 24 | $CF_3$ | 7-$CF_3$ | $CO_2CH_3$ | $CH_2$-Ph-4-$CF_3$ | 128–131 |
| 25 | $CF_3$ | 7-Cl | $CH_3$ | $CH_2CH=CH_2$ | 186–188 |
| 26 | $CF_3$ | 7-Cl | $CH_3$ | $CH_2Ph$ | 165–169 |
| 27 | $CF_3$ | 7-Cl | $CH_3$ | $CH_2CO_2CH_3$ | 89–94 |
| 28 | $CF_3$ | 7-Cl | $CH_3$ | $CH_2C\equiv CH$ | 112–115 |
| 29 | $CF_3$ | 7-Cl | $CH(CH_3)_2$ | $CH_2OCH_3$ | 68–70 |
| 30 | Br | 7-$CF_3$ | $CO_2CH_3$ | $CH_2CH=CH_2$ | 86–90 |
| 31 | Br | 7-$CF_3$ | $CO_2CH_3$ | $CH_2C\equiv CH$ | 85–90 |
| 32 | Br | 7-$CF_3$ | $CO_2CH_3$ | $CH_2CO_2CH_3$ | 120–122 |
| 33 | $CF_3$ | 7-Cl | $CH_3$ | $CH_2OCH_3$ | 140–142 |
| 34 | $CF_3$ | 7-$CF_3$ | $CO_2CH_3$ | $CH_2$—Ph-4-$OCH_3$ | 60–69 |
| 35 | $CF_3$ | 7-$CF_3$ | $CO_2CH_3$ | $CH_2CH_2CH_3$ | 55–60 |
| 36 | $CF_3$ | 7-$CF_3$ | $CO_2CH_3$ | $NH_2$ | 118–121 |
| 37 | $CF_3$ | 7-F | $CO_2CH_3$ | $CH_3$ | 155–160 |
| 38 | $CF_3$ | 7-F | $CO_2CH_3$ | $CH_2OCH_3$ | 95–101 |
| 39 | $CF_3$ | 7-F | $CO_2CH_3$ | $CH_2CO_2CH_3$ | 70–75 |
| 40 | $CF_3$ | 7-$CF_3$ | $CO_2CH_2CH_3$ | $CH_2CH_3$ | 120–122 |
| 41 | $CF_3$ | 7-$CF_3$ | $CO_2CH_3$ | $N(COMe)_2$ | 139–142 |
| 42 | $CF_3$ | 7-$CF_3$ | $CO_2CH_3$ | $NH(COMe)$ | 159–160 |
| 43 | $CF_3$ | 7-$CF_3$ | $CO_2CH_3$ | $N=CMe_2$ | 80–84 |

INDEX TABLE A

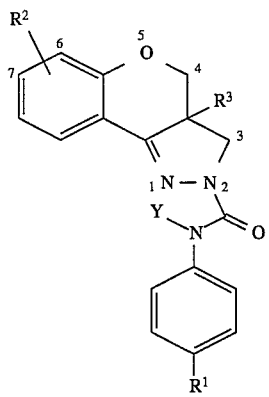

| Cmpd | R¹ | R² | R³ | Y | mp (°C.) |
|---|---|---|---|---|---|
| 44 | CF₃ | 7-CF₃ | CO₂CH₃ | N=CHPh | 85–94 |
| 45 | CF₃ | 7-CF₃ | CO₂CH₃ | CH₂CHO | 138–140 |

INDEX TABLE B

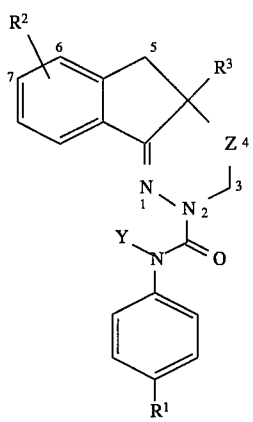

| Cmpd | R¹ | R² | R³ | Y | Z | mp (°C.) |
|---|---|---|---|---|---|---|
| 46 | Br | 7-F | 4-F—Ph | NH₂ | O | 175–180 |
| 47 | OCF₃ | 7-F | 4-F—Ph | NH₂ | O | 130–131 |
| 48 | OCF₃ | 7-F | 4-F—Ph | N(COMe)₂ | O | 108–111 |
| 49 | OCF₃ | 7-Cl | CO₂CH₃ | NH₂ | O | 146–150 |

TEST A

Fall Armyworm

Test units, each consisting of an 8-ounce (230 mL) plastic cup containing a layer of wheat germ diet, approximately 0.5 cm thick, were prepared. Ten third-instar larvae of fall armyworm (*Spodoptera frugiperda*) were placed into a cup. Solutions of each of the test compounds (acetone/distilled water 75/25 solvent) were sprayed into the cup. Spraying was accomplished by passing the cup, on a conveyer belt, directly beneath a flat fan hydraulic nozzle which discharged the spray at a rate of 0.5 pounds of active ingredient per acre (about 0.55 kg/ha) at 30 p.s.i. (207 kPa). The cup was then covered and held at 27° C. and 50% relative humidity for 48 hours, after which time readings were taken. Of the compounds tested, the following resulted in greater than or equal to 80% mortality: 1, 2, 3, 4, 5, 6, 7, 8, 9*, 10*, 11 , 12 , 13, 14**, 15, 16, 17, 18, 19, 20, 21, 22, 23, 25, 26, 2, 28, 29, 30, 31, 32, 33, 34, 35, 36, 40, 41, 43, 44, 45* and 46*.

*Tested at 250 ppm
**Tested at 50 ppm

TEST B

Tobacco Budworm

The test procedure of Test 1 was repeated for efficacy against third-instar larvae of the tobacco budworm (*Heliothis virescens*). Of the compounds tested, the following resulted in greater than or equal to 80% mortality: 1, 2, 3, 4, 5, 6, 7, 8, 9*, 10*, 11*, 12*, 13, 14**, 15, 17, 19, 20, 21, 25, 28, 29, 30, 31, 32, 33, 34, 35, 36, 40, 41, 42, 43, 44, 45*, 46 and 47*.

*Tested at 250 ppm
**Tested at 50 ppm

TEST C

Southern Corn Rootworm

Test units, each consisting of an 8-ounce (230 mL) plastic cup containing 1 sprouted corn seed, were prepared. The test unit was sprayed as described in Test A with individual solutions of the test compounds. After the spray on the cup had dried, five third-instar larvae of the southern corn rootworm (*Diabrotica undecimpunctata howardi*) were placed into the cup. A moistened dental wick was inserted into the cup to prevent drying and the cup was then covered. The cup was then held at 27° C. and 50% relative humidity for 48 hours, after which time mortality readings were taken. Of the compounds tested, the following resulted in greater than or equal to 80% mortality: 1, 2, 3, 4, 5, 6, 7, 8, 9*, 10*, 11*, 12*, 13, 15, 16, 19, 20, 21, 23, 24, 25, 27, 28, 30, 31, 32, 33, 35, 36, 40, 41, 42, 43, 44, 46 and 47*.

*Tested at 250 ppm

TEST D

Aster Leafhopper

Test units were prepared from a 12-ounce (350 mL) cup containing oat (*Avena sativa*) seedlings in a 1-inch (2.54 cm) layer of sterilized soil. The test unit was sprayed as described in Test A with individual solutions of the below-listed compounds. After the oats had dried from the spraying, between 10 and 15 adult aster leafhoppers (*Mascrosteles fascifrons*) were aspirated into the covered cup. The cup was held at 27° C. and 50% relative humidity for 48 hours, after which time mortality readings were taken. Of the compounds tested, the following resulted in greater than or equal to 80% mortality: 1, 2, 3, 4, 5, 6, 7, 8, 9*, 10*, 11, 12, 13, 14**, 15, 16, 17, 20, 21, 27, 28, 29, 30, 31, 32, 33, 35, 36, 40, 43 and 45*.

*Tested at 250 ppm
**Tested at 50 ppm

TEST E

Boll Weevil

Five adult boll weevils (*Anthonomus grandis grandis*) were placed into each of a 9 ounce (260 mL) cup. The test procedure employed was then otherwise the same as in Test A with one cup per treatment. Mortality readings were taken 48 hours after treatment. Of the compounds tested, the following resulted in greater than or equal to 80% mortality: 1, 2, 3, 4, 5, 6, 7, 8, 9*, 11*, 12*, 13, 16, 17, 20, 25, 27, 28, 29, 31, 33, 36, 40, 41, 42, 43, 44, 46 and 47*.

*Tested at 250 ppm
**Tested at 50 ppm

We claim:

1. A compound of the formula

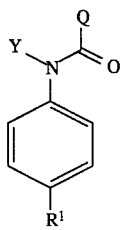

wherein

Q is

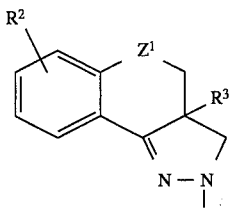

Q-1 wherein $R^1$ is selected from the group Cl, Br, $CF_3$, $OCF_3$, $OCF_2H$ and $OSO_2CF_3$;

$R^2$ is selected from the group H, F, Cl, Br, $CF_3$, $OCF_3$, $OCF_2H$ and $OCH_2CF_3$;

Y is selected from the group $NR^6R^7$, $N=CR^8R^9$, and $OR^6$;

$R^3$ is selected from the group $CO_2Me$, $CO_2Et$, Ph, 4-F-Ph, 4-Cl-Ph and $C_1$–$C_3$ alkyl;

$R^4$ is $C_1$–$C_3$ alkyl;

$R^6$ is selected from the group H, $C_1$–$C_4$ alkyl, $C_1$–$C_4$ haloalkyl, $C_2$–$C_4$ alkenyl, $C_2$–$C_4$ alkynyl, $SO_2NR^8R^9$ $SO_2R^{10}$, $COR^8$, $CONR^8R^9$, $CO_2^{R8}$, phenyl optionally substituted with halogen or $C_1$–$C_4$ alkoxy, and benzyl optionally substituted with halogen;

$R^7$ is selected from the group H, $C_1$–$C_4$ alkyl and $COR^8$;

$R^8$ is selected from the group H, $C_1$–$C_4$ alkyl, $C_1$–$C_4$ haloalkyl and phenyl optionally substituted by a group selected from halogen, CN, $NO_2$, $CF_3$ and $OCF_3$;

$R^9$ is selected from the group H and $C_1$–$C_4$ alkyl;

$R^8$ and $R^9$ can be taken together as —$CH_2CH_2CH_2$—, —$CH_2CH_2CH_2CH_2$— and —$CH_2CH_2CH_2CH_2CH_2$—;

R10 is selected from the group $C_1$–$C_4$ alkyl and $C_1$–$C_4$ haloalkyl; and $Z^1$ is O.

2. A compound according to claim 1 wherein $R^6$ is H or $C_1$–$C_3$ alkyl.

3. A compound according to claim 2 wherein $R^7$ is H, $C_1$–$C_3$ alkyl, or $COR^8$, and $R^8$ is $C_1$–$C_3$ alkyl.

4. A compound according to claim 1 wherein $R^3$ is $CO_2Me$.

5. A compound according to claim 2:
methyl 2-[[-1-[4(trifluoromethyl)phenyl]hydrazino] carbonyl]-2,3-dihydro-7-(trifluoromethyl)[ 1]benzopyrano[4,3-C] pyrazole-3a (4H)-carboxylate.

6. An arthropodicidal composition comprising an arthropodicidally effective amount of a compound according to any one of claims 1 or 2–5 and a carrier therefor.

7. A method for controlling arthropods comprising applying to them or to their environment an arthropodicidally effective amount of a compound according to any one of claims 1 or 2–5.

* * * * *